US011701422B2

(12) United States Patent
Vitelli et al.

(10) Patent No.: US 11,701,422 B2
(45) Date of Patent: Jul. 18, 2023

(54) EXPRESSION SYSTEMS

(71) Applicant: GLAXOSMITHKLINE BIOLOGICALS SA, Rixensart (BE)

(72) Inventors: Alessandra Vitelli, Rome (IT); Alfredo Nicosia, Naples (IT); Riccardo Cortese, Basel (CH)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 16/800,384

(22) Filed: Feb. 25, 2020

(65) Prior Publication Data

US 2020/0360509 A1  Nov. 19, 2020

Related U.S. Application Data

(63) Continuation of application No. 15/068,115, filed on Mar. 11, 2016, now abandoned, which is a
(Continued)

(30) Foreign Application Priority Data

Dec. 30, 2010   (WO) ................. PCT/EP2010/007995

(51) Int. Cl.
*A61K 39/155* (2006.01)
*A61K 39/145* (2006.01)
(Continued)

(52) U.S. Cl.
CPC ............ *A61K 39/145* (2013.01); *A61K 39/12* (2013.01); *A61K 39/155* (2013.01);
(Continued)

(58) Field of Classification Search
None
See application file for complete search history.

(56) References Cited

U.S. PATENT DOCUMENTS 7,247,472 B2 * 7/2007 Wilson ................... A61P 31/12
                                                435/320.1
8,715,692 B2 * 5/2014 Pushko ................... A61P 31/12
                                                435/325
(Continued)

FOREIGN PATENT DOCUMENTS

JP   2010-168288 A    8/2010
WO   2003/028759 A1   4/2003
(Continued)

OTHER PUBLICATIONS

Armengol, et al., "Identification of T-cell epitopes in the structural and non-structural proteins of classical swine fever virus", J Gen Virol.; Mar. 2002; vol. 83(3); pp. 551-560.
(Continued)

*Primary Examiner* — M Franco G Salvoza
(74) *Attorney, Agent, or Firm* — Birch, Stewart, Kolasch & Birch, LLP

(57) ABSTRACT

The invention relates to an expression system comprising polynucleotides encoding proteins, wherein the expression system comprises a first polynucleotide encoding at least one protein, peptide or variant thereof, which induces a T cell response, and a second polynucleotide encoding at least one protein, peptide or variant thereof, which induces an anti-pathogenic B cell response. The invention further relates to protein mixtures encoded by the expression system and cells comprising the expression system or the protein mixture and pharmaceutical compositions comprising the expression system or the protein mixture.

16 Claims, 7 Drawing Sheets

Specification includes a Sequence Listing.

Related U.S. Application Data continuation of application No. 13/976,873, filed as application No. PCT/EP2011/074307 on Dec. 30, 2011, now abandoned.

(51) Int. Cl.
*A61K 39/12* (2006.01)
*C07K 14/005* (2006.01)
*C12N 15/85* (2006.01)
*C12N 15/86* (2006.01)
*A61K 39/00* (2006.01)

(52) U.S. Cl.
CPC ............ *C07K 14/005* (2013.01); *C12N 15/85* (2013.01); *C12N 15/86* (2013.01); *A61K 2039/53* (2013.01); *C12N 2710/10343* (2013.01); *C12N 2760/18522* (2013.01); *C12N 2760/18534* (2013.01); *C12N 2800/22* (2013.01); *C12N 2840/20* (2013.01)

(56) References Cited

U.S. PATENT DOCUMENTS

| | | | |
|---|---|---|---|
| 2003/0087241 A1* | 5/2003 | Kool | C12Q 1/6853 435/6.11 |
| 2005/0136035 A1* | 6/2005 | Ko | A61K 38/162 435/456 |
| 2006/0252132 A1 | 11/2006 | Yang et al. | |
| 2009/0246855 A1* | 10/2009 | Fouchier | A61P 31/16 435/235.1 |
| 2010/0040650 A1 | 2/2010 | Crowe, Jr. et al. | |
| 2010/0203081 A1 | 8/2010 | Rabadan et al. | |
| 2011/0091496 A1* | 4/2011 | Graham | A61P 37/00 424/229.1 |
| 2011/0129498 A1 | 6/2011 | Cortese et al. | |

FOREIGN PATENT DOCUMENTS

| | | |
|---|---|---|
| WO | 2007/126887 A2 | 11/2007 |
| WO | 2008/028759 A1 | 3/2008 |
| WO | 2008/133663 A2 | 11/2008 |
| WO | 2009/146902 A1 | 12/2009 |
| WO | WO-2009146902 A1 * | 12/2009 ............ A61P 37/04 |
| WO | 2010/009277 A2 | 1/2010 |

OTHER PUBLICATIONS

Bogs, e al., "Highly Pathogenic H5N1 Influenza Viruses Carry Virulence Determinants beyond the Polybasic Hemagglutinin Cleavage Site" PLOSone Jul. 2010; vol. 5 (2); e11826.
Chen, et al., "Structure of the hemagglutinin precursor cleavage site, a determinant of influenza pathogenicity and the origin of the labile conformation", Cell; Oct. 30, 1998; vol. 95(3):pp. 409-417.
Hebeis, et al., "Activation of virus-specific memory B cells in the absence of T cell help", J Exp Med. Feb. 16, 2004; vol. 199(4); pp. 593-602.
Horimoto, et al., "Biologic effects of introducing additional basic amino acid residues into the hemagglutinin cleavage site of a virulent avian influenza virus", Virus Res.; Jul. 1997; vol. 50(1); pp. 35-40.
Hsu, et al., "Synergistic effect of immunization with a peptide cocktail inducing antibody, helper and cytotoxic T-cell responses on protection against respiratory syncytial virus" J. Gen Virol. ; 1999 vol. 80 (6); pp. 1401-1405.
Lee, et al., "Pathogenic potential of North American H7N2 avian influenza virus: a mutagenesis study using reverse genetics", Virology; Sep. 30, 2006; vol. 353(2); pp. 388-395.
Lelievre, et al., "Structural Properties of chimeric peptides containing a T0cell epitope linked to a fusion peptide and their importance for in vivo induction of cytotoxic T-cell responses" Eur. J. Biochem; 1997; vol. 249; pp. 895-904.
Munster, et al., "Insertion of a Multibasic Cleavage Motif into the Hemagglutinin of a Low-Pathogenic Avian Influenza H6N1 Virus Induces a Highly Pathogenic Phenotype" J. Virology; Aug. 2010; vol. 84; pp. 7953-7960.
Nayak, et al., "Molecular characterization and complete genome sequence of avian paramyxovirus type 4 prototype strain duck/Hong Kong/D3/75", Virol J.; Oct. 20, 2008; vol. 5 (124); pp. 1-11.
Ohuchi, et al., "Human Influenza Virus Hemagglutinin with High Sensitivity to Proteolytic Activation" J. Virology; Jul. 1991; vol. 65 (7); pp. 3530-3537.
Racaniello, "Influenza RNA Virus RNA genome", found at http://www.virology.ws/2009/05/01/influenza-virus-rna-genome/ (2009).
Steinhauer, "Role of hemagglutinin cleavage for the pathogenicity of influenza virus", Virology; May 25, 1999; vol. 258(1); pp. 1-20.
Srikiatkhachorn and Braciale "Virus-specific CD8+ t Lymphocytes Downregulate T Helper Cell Type 2 Cytokine Secretion and Pulmonary Eosiophilia during Experimental Murine Respiratory Syncytial Virus Infection" J. Exp. Med.; 1997; vol. 186(3); pp. 421-432.
Subarrayan, et al "Expression and Characterisation of a Multivalent Human Respiratory Syncytial Virus Protein" Molecular Biology; 2010; vol. 44 (3); pp. 420-430.
Zeng, et al., "Induction of balanced Immunity in BALB/c mice by vaccination with a recombinant fusion protein containing a respiratory syncytial virus G protein fragment and a CTL epitope" Vaccine; 2006; vol. 24; pp. 941-947.
Boxus, M. et al., "DNA immunization with plasmids encoding fusions and nucleocapsid proteins of bovine respiratory synctial virus induces a strong cell-mediated immunity and protects calves against challenge" J. Virol.; Jul. 2007; pp. 6879-6889; vol. 81(13).
Connors, M, et al. "Respiratory synctial virus (RSV) F, G, M2 (22K), and N proteins each induce resistance to RSV challenge, but resistance induced by M2 and N proteins is relatively short-lived" J. Virol.; Mar. 1991; pp. 1634-1637 vol. 65(3).
Zeng, R., et al., "Protective effect of a RSV subunit vaccine candidate G1F/M2 was enhanced by a HSP70-Like protein in mice" Biochem Biophys Res Commun.; Dec. 2008; pp. 498-499; vol. 377(2).
Nayak et al., "Molecular characterization and complete genome sequence of avian paramyxovirus type 4 prototype strain duck/Hong Kong/03/75," Virology Journal 5:124 (2008).
Maecker et al., "Cytotoxic T Cell Responses to DNA Vaccination: Dependence on Antigen Presentation via Class II MHC," The Journal of Immunology, 161: 6532-6536 (1998).
Rodriguez et al., "CD4+ T Cells Induced by a DNA Vaccine: Immunological Consequences of Epitope-Specific Lysosomal Targeting," Journal of Virology, vol. 75, No. 21:10421-10430 (2001).
Radcliffe et al., "Multiple gene products from a single vector: 'self-cleaving' 2A peptides," Gene Therapy, 11: 1673-1674 (2004).

\* cited by examiner

WB on HeLa total cell lysates

Anti-H1 serum

A

B

Serum Testing
Neut Virus: 2009 H1N1 MEX

EXPRESSION SYSTEMS

CROSS-REFERENCE TO RELATED APPLICATIONS

This application is filed pursuant to 35 U.S.C. § 111(a) as a United States Continuation Application of U.S. application Ser. No. 15/068,115, filed Mar. 11, 2016, which is a Continuation of abandoned U.S. patent application Ser. No. 13/976,873 filed Jan. 28, 2014 pursuant to 35 U.S.C. § 371 as a U.S. National Phase Application of International Application Serial No. PCT/EP2011/074307 filed Dec. 30, 2011, and also claiming priority to International Application Serial No. PCT/EP2010/007995 filed Dec. 30, 2010, and the entire contents of each of the foregoing applications are hereby incorporated by reference.

FIELD OF THE INVENTION

The invention relates to an expression system comprising polynucleotides encoding proteins, wherein the expression system comprises a first polynucleotide encoding at least one protein, peptide or variant thereof, which induces a T cell response, and a second polynucleotide encoding at least one protein peptide or variant thereof, which induces an anti-pathogenic B cell response. The invention further relates to protein mixtures encoded by the expression system and cells comprising the expression system or the protein mixture and pharmaceutical compositions comprising the expression system or the protein mixture. The expression system, polynucleotides, proteins, cells, and pharmaceutical compositions are useful in the prophylaxis or treatment of infections. The invention further relates to nucleotide constructs and expression systems encoding a modified influenza hemagglutinin (HA).

BACKGROUND OF THE INVENTION

Infectious diseases are still a major thread of mankind. One way for preventing or treating infectious diseases is the artificial induction of an immune response by vaccination which is the administration of antigenic material to an individual such that an adaptive immune response against the respective antigen is developed. The antigenic material may be pathogens (e.g. microorganisms or viruses) which are structurally intact but inactivated (i.e. non-infective) or which are attenuated (i.e. with reduced infectivity), or purified components of the pathogen that have been found to be highly immunogenic. Another approach for inducing an immune response against a pathogen is the provision of expression systems comprising one or more vector encoding immunogenic proteins or peptides of the pathogen. Such vector may be in the form of naked plasmid DNA, or the immunogenic proteins or peptides are delivered by using viral vectors, for example on the basis of modified vaccinia viruses (e.g. Modified Vaccinia Ankara; MVA) or adenoviral vectors. Such expression systems have the advantage of comprising well-characterized components having a low sensitivity against environmental conditions.

It is a particular aim when developing vector based expression systems that the application of these expression systems to a patient elicits an immune response which is protective against the infection by the respective pathogen. However, although inducing an immunogenic response against the pathogen, some expression systems are not able to elicit an immune response which is strong enough to fully protect against infections by the pathogen. Accordingly, there is still a need for expressions systems which are capable of inducing a protective immune response against a pathogen, e.g. an infectious agent like a virus.

Viruses

Viruses are a group of pathogens/infectious agents which have no own metabolism and can be considered as obligatory endoparasites of the respective host cells using at least parts of host's cell facilities for conducting viral protein expression and virus replication. Viruses can be classified on the basis of the type (DNA/RNA), the strandedness (single-stranded (ss) or double-stranded (ds)), the sense (negative sense or positive sense) of the nucleic acid constituting their genome and their replication (Baltimore classification). Accordingly, viruses are generally classified in DNA and RNA viruses. Viruses can be further classified into single-stranded (ss) or double-stranded (ds) DNA or RNA viruses, which genome is a single-stranded or double-stranded nucleic acid. Some viruses have a genome which is partially double-stranded and partially single-stranded (e.g. hepadnaviruses). The orientation or "sense" of the genome and/or in the manufacturing of medicament for use in the prophylaxis or treatment of a pathogen and/or for use in methods of prophylaxis or treatment of of a pathogen, wherein the pathogen plays an important role for the viral life cycle of viruses, in particular in the life cycle of ssRNA viruses or ssDNA viruses. A positive sense ssRNA (+) genome has the same orientation as a cellular mRNA and can be directly translated into viral proteins. In the life cycle of viruses having a negative sense single-stranded RNA genome (ssRNA (−)), it is necessary that the genomic sequences are transcribed into positive sense mRNA which can be translated into viral proteins by the host cell. A single-stranded genome that contains both positive-sense and negative-sense is called "ambisense" (e.g. ssRNA (+/−), ssDNA(+/−)).

Although the genome of viruses may be quite large (e.g. in the case of DNA viruses), in particular small RNA viruses have evolutionary developed strategies for expressing their gene products (e.g. proteins and peptides) in a very efficient manner. One of these strategies is the expression of one or more polyprotein encoded by the viral genome, which is co- or posttranslationally processed into single proteins and/or peptides. This strategy is adapted, for example, by some double-stranded (ds) RNA viruses or single-stranded (ss) RNA viruses having a positive sense genome. "Enveloped viruses", such as orthomyxoviruses, paramyxoviruses, retroviruses, flaviviruses, rhabdoviruses and alphaviruses, are surrounded by a lipid bilayer originating from the host plasma membrane (1).

Attachment glycoproteins are found in all enveloped viruses and mediate the initial interaction between the viral envelope and the plasma membrane of the host cell via their binding to carbohydrate moieties or cell adhesion domains of proteins or other molecules on the plasma membrane of the host cell. Thereby, attachment glycoproteins bridge the gap between the virus and the membrane of the host cell. Attachment glycoproteins designated as "H" possess hemagglutinin activity, glycoproteins designated as "HN possesses hemagglutinin and neuraminidase activities. Attachment glycoproteins are designated as "G" when they have neither haemagglutination nor neuraminidase activity.

Paramyxoviruses

Paramyxoviruses are a family of animal viruses which comprises a single stranded non-segmented negative-sense RNA. Paramyxoviruses are responsible for a number of animal and human diseases. The RNA genome of paramyxoviruses is 15-19 kilo bases (kb) in length and encodes 6-10 genes. Each gene contains transcription start/stop signals at the beginning and end, which are transcribed as part of the gene. The gene sequence is conserved across the paramyxoviruses due to a phenomenon known as transcriptional polarity in which genes closest to the 3' end of the genome are transcribed in greater abundance than those towards the 5' end. After each gene is transcribed, the RNA-Dependent RNA polymerase pauses to release the new mRNA when it encounters an intergenic sequence. When the RNA polymerase is paused, there is a chance that it will dissociate from the RNA genome. If it dissociates, it must reenter the genome at the leader sequence, rather than continuing to transcribe the length of the genome. As a result, the further downstream genes are from the leader sequence, the less they will be transcribed by the RNA polymerase. The genes of paramyxoviruses are arranged in relative order of protein needed for successful infection. The conserved gene sequence is Nucleocapsid-Phosphoprotein-Matrix-Fusion-Attachment-Large (polymerase).

Many Paramyxovirus genomes follow the so-called "Rule of Six". According to this rule, the total length of the genome is almost always a multiple of six. However, the members of the sub-family Pneumovirinae comprising the Respiratory Syncytial Virus (RSV) do not follow this rule.

Respiratory Syncytial Virus (RSV)

The enveloped virus designated as respiratory syncytial virus (RSV) is the most important cause of viral lower respiratory tract illness (LRTI) in infants and children worldwide (2). In the United States, it is estimated that 70,000-126,000 infants are hospitalized annually with RSV pneumonia or bronchiolitis and that the rate of hospitalization for bronchiolitis has increased since 1980 (3). Children are infected by 2 years of age and the WHO has estimated that RSV causes disease in approximately 64 million children each year and 160,000 deaths. In industrialised countries, RSV is responsible for at least 50% of hospitalisations for respiratory disease in children, and up to 6% of all RSV infections in children result in hospitalisation (4). RSV infection does not provoke lasting immunity, so that human hosts experience lifelong cycles of infection and re-infection. Although it is traditionally regarded as a pediatric pathogen, RSV also causes severe disease in the elderly and immuno-compromised individuals (5). The burden of RSV disease in the elderly is comparable to that of seasonal influenza and the economic impact of RSV-related disease in adults is estimated to be greater than that of influenza in relation to numbers of days lost from work (6, 7). Monoclonal antibody prophylaxis is effective in reducing RSV hospitalisations by 50% in infants at high risk of severe disease (8). However, there is currently no effective RSV vaccine or anti-viral therapy.

The disastrous effect of a formalin-inactivated (FI) RSV vaccine in infants in the 1960s has hampered vaccine development. The vaccine failed to protect against RSV infection and induced exacerbated respiratory disease (9) which has been attributed to induction of high titre, poorly neutralising, low affinity antibodies, lack of CD8+ T cell priming and induction of a Th2-biased immune response (10, 11, and 12). There is evidence that RSV impairs the induction of an adequate adaptive T cell immune response (13).

There is, therefore, a clear need for an effective vaccine not only to protect infants, but also to boost immunity in the elderly and to reduce the circulation of RSV in siblings and adults, who are the main source of RSV infection for infants. A RSV vaccine capable of inducing neutralizing antibody response and potent and broad T cell response for priming a T cell responses in individuals who have not yet been infected with RSV (infants) or for boosting a pre-existing T cell response in individuals who need to 'reset' the memory response to higher levels (elderly) is especially desirable.

Orthomyxoviruses

Orthomyxoviruses are a family of RNA viruses that includes five genera: Influenzavirus A, Influenzavirus B, Influenzavirus C, Isavirus and Thogotovirus. A sixth genus has recently been described. The first three genera contain viruses that cause influenza in vertebrates, including birds, humans, and other mammals. The three genera of influenza virus have antigenic differences in their nucleoprotein and matrix protein. Influenzavirus A infects humans, other mammals, and birds, and causes all influenza pandemics. Influenzavirus B infects humans and seals. Influenzavirus C infects humans and pigs.

Viruses of the Orthomyxovirus family contain 6 to 8 segments of linear negative-sense single stranded RNA. The total genome length is 12000-15000 nucleotides (nt). The largest segment 2300-2500 nt; of second largest 2300-2500 nt; of third 2200-2300 nt; of fourth 1700-1800 nt; of fifth 1500-1600 nt; of sixth 1400-1500 nt; of seventh 1000-1100 nt; of eighth 800-900 nt. Genome sequence has terminal repeated sequences; repeated at both ends. Terminal repeats at the 5'-end are 12-13 nucleotides long. The nucleotide sequences of 3'-terminus are identical the same in genera of same family; most on RNA (segments), or on all RNA species. Terminal repeats at the 3'-end 9-11 nucleotides long.

Influenza virus is one of the most important respiratory pathogens. In the US alone, influenza infection is responsible for 20,000-40,000 deaths and over 100,000 hospitalizations annually (1). Infants, the elderly, and individuals with compromised cardiac, pulmonary, or immune systems are at great risk of serious complications following flu infection.

Immunization proves to be the most effective measure in preventing the disease. One of the common features shared by all current influenza vaccines consists in targeting primarily the induction of neutralizing antibodies directed against the major viral envelope protein, hemagglutinin (HA).

SUMMARY OF THE INVENTION

The invention provides in a first aspect an expression system comprising a first polynucleotide encoding at least one protein, peptide or variant thereof, which induces a T cell response and a second polynucleotide encoding at least one protein, peptide or variant thereof, which induces an anti-pathogenic B cell response.

In a second aspect, the invention provides an isolated protein mixture encoded by the expression system of the first aspect.

In a third aspect, the invention provides an isolated host cell containing the expression system of the first aspect and/or the protein mixture of the second aspect.

In a fourth aspect, the present invention provides a composition comprising the expression system of the first aspect, or the protein mixture of the second aspect, and a pharmaceutical acceptable carrier and/or excipient.

In a fifth aspect, the present invention provides the expression system of the first aspect, the protein mixture of the second aspect, the cell of the third aspect and the composition of the fourth aspect, for the use in medicine in particular in the treatment or prevention of infectious diseases, preferably a viral disease.

In a sixth aspect, the present invention provides for a method of treatment or prevention of a viral disease comprising the administration of an effective amount of the expression system of the first aspect, the protein mixture of the second aspect, the cell of the third aspect and the composition of the fourth aspect.

In a seventh aspect, the present invention provides for a method of enhancing an immune response comprising the administration of the expression system of the first aspect, the protein mixture of the second aspect, the cell of the third aspect and the composition of the fourth aspect.

In an eighth aspect, the present invention provides nucleotide constructs encoding influenza hemagglutinin (HA), an expression system comprising these nucleotide constructs, and proteins or polyproteins encoded by the nucleotide constructs or the expression system, wherein the HA0 cleavage site has a multibasic sequence.

In a ninth aspect, the present invention provides the use of the multibasic HA0 cleavage site for constructing expression systems capable for expressing influenza hemagglutinin (HA) in vitro and/or in vivo.

In a tenth aspect, the invention provides an isolated protein mixture encoded by the expression system of the eighth aspect.

In an eleventh aspect, the invention provides an isolated host cell containing the nucleotide constructs, the expression system or the proteins or polyproteins of the eighth aspect and/or the protein mixture of the tenth aspect.

In a twelfth aspect, the present invention provides a composition comprising the nucleotide constructs, the expression system or the proteins or polyproteins of the eighth aspect, or the protein mixture of the tenth aspect, and a pharmaceutical acceptable carrier and/or excipient.

In a thirteenth aspect, the present invention provides the nucleotide constructs, the expression system or the proteins or polyproteins of the eighth aspect, the protein mixture of the tenth aspect, the cell of the eleventh aspect and the composition of the twelfth aspect, for the use in medicine in particular in the treatment or prevention of influenza virus infections.

In a fourteenth aspect, the present invention provides for a method of treatment or prevention of an influenza virus infections comprising the administration of an effective amount of the nucleotide constructs, the expression system or the proteins or polyproteins of the eighth aspect, the protein mixture of the tenth aspect, the cell of the eleventh aspect and the composition of the twelfth aspect.

In a fifteenth aspect, the present invention provides for a method of enhancing an immune response comprising the administration of the nucleotide constructs, the expression system or the proteins or polyproteins of the eighth aspect, the protein mixture of the tenth aspect, the cell of the eleventh aspect and the composition of the twelfth aspect.

The above summary does not necessarily describe all aspects of the present invention.

DETAILED DESCRIPTION OF THE INVENTION

Figure 1:
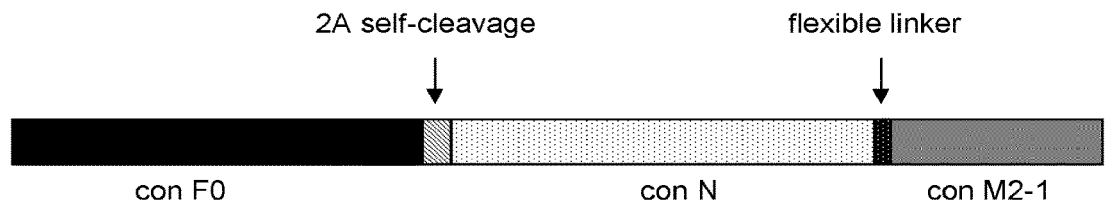
FIG. 1: Schematic Diagram of the RSV vaccine polyprotein. conF0=consensus sequence of the F protein, 2A=translational cleavage site of the Foot and Mouth Disease virus, conN=consensus sequence of the N protein, conM2-1=consensus of the M2-1 protein.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

Definitions

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The abbreviations "F" or "F0" are used interchangeably herein and refer to the Fusion protein of paramyxoviruses, preferably of RSV.

The abbreviation "G" refers to the Glycoprotein of paramyxoviruses, preferably of pneumovirinae, more preferably of RSV.

The abbreviation "H" refers to the Hemagglutinin Protein of paramyxoviruses, preferably of morbilliviruses.

The abbreviation "HN" refers to the Hemagglutinin-Neuraminidase Protein of paramyxoviruses, particularly of Respirovirus, Avulavirus and Rubulavirus.

The abbreviation "N" refers to the Nucleocapsid protein of paramyxoviruses, preferably of RSV.

The abbreviation "M" refers to the glycosylated Matrix protein of paramyxoviruses, preferably of RSV.

With respect to paramyxoviruses, the abbreviation "M2" or "M2-1" refers to the non-glycosylated Matrix protein of paramyxoviruses, preferably of RSV.

The abbreviation "P" refers to the Phosphoprotein of paramyxoviruses, preferably of RSV.

With respect to paramyxoviruses, the abbreviation "NS1" and "NS2" refer to the non-structural proteins 1 and 2 of paramyxoviruses, preferably of RSV.

The abbreviation "L" refers to the catalytic subunit of the polymerase of paramyxoviruses, preferably of RSV.

The abbreviation "HA" refers to the hemagglutinin of orthomyxovirus, preferably influenzaviruses, more preferably of influenza A virus.

The abbreviation "HA0" refers to the precursor protein of hemagglutinin subunits HA1 and HA2 of orthomyxovirus, preferably influenzaviruses, more preferably of influenza A virus The abbreviation "H1p" refers to the modified hemagglutinin of orthomyxovirus, preferably influenzaviruses, more preferably of influenza A virus.

The abbreviation "NA" refers to the neuraminidase of orthomyxovirus, preferably influenzaviruses, more preferably of influenza A virus.

The abbreviation "NP" refers to the nucleoprotein of orthomyxoviruses, preferably influenzaviruses, more preferably of influenza A virus.

The abbreviation "M1" refers to the matrixprotein 1 of orthomyxoviruses, preferably influenzaviruses, more preferably of influenza A virus.

With respect to orthomyxoviruses, the abbreviation "M2" refers to the Matrix protein M2 of orthomyxoviruses, preferably influenzaviruses, more preferably of influenza A virus.

With respect to orthomyxovirus, the abbreviation "NS1" refers to the non-structural protein 1 of orthomyxoviruses, preferably influenzaviruses, more preferably of influenza A virus.

The abbreviation "NS2/NEP" refers to the non-structural protein 2 (also referred to as NEP, nuclear export protein) of orthomyxoviruses, preferably influenzaviruses, more preferably influenza A virus.

The abbreviation "PA" refers to a polymerase subunit protein of orthomyxoviruses, preferably influenzaviruses, more preferably influenza A virus.

The abbreviation "PB1" refers to a polymerase subunit protein of orthomyxoviruses, preferably influenzaviruses, more preferably influenza A virus.

The abbreviation "PB2" refers to a polymerase subunit protein of orthomyxoviruses, preferably influenzaviruses, more preferably influenza A virus.

The abbreviation "PB1-F2" or "PB1F2" refers to a protein encoded by an alternate reading frame in the PB1 Gene segment of orthomyxoviruses, preferably influenzaviruses, more preferably influenza A virus.

The term "expression system" as used herein refers to a system designed to produce one or more gene products of interest. Typically, such system is designed "artificially", i.e. by gene-technological means usable to produce the gene product of interest either in vitro in cell-free systems or in vivo in cell-based systems. It is understood that naturally occurring expression systems such as for instance native viruses are not encompassed by the expression system of the present invention.

The "gene product of interest" typically refers to a macromolecule such as but not limited to RNA, peptide, polypeptide, or protein, or segment, epitope, or fragment thereof.

In an expression system the gene product of interest is encoded for by one or more nucleic acid molecules. Nucleic acid molecules are understood as a polymeric macromolecules made from nucleotide monomers. Nucleotide monomers are composed of a nucleobase, a five-carbon sugar (such as but not limited to ribose or 2'-deoxyribose), and one to three phosphate groups. Typically, a polynucleotide is formed through phosphodiester bonds between the individual nucleotide monomers. In the context of the present invention referred to nucleic acid molecules include but are not limited to ribonucleic acid (RNA) and deoxyribonucleic acid (DNA). The terms "polynucleotide" and "nucleic acid" are used interchangeably herein.

In cell-free expression systems isolated polynucleotides are used as template for in vitro translation reactions. In cell-based expression systems polynucleotides are comprised on one or more vectors. As used herein, the term "vector" refers to a protein or a polynucleotide or a mixture thereof which is capable of being introduced or of introducing the proteins and/or nucleic acid comprised therein into a cell. In the context of the present invention it is preferred that the genes of interest encoded by the introduced polynucleotide are expressed within the cell upon introduction of the vector or vectors. Examples of suitable vectors include but are not limited to plasmids, cosmids, phages, viruses or artificial chromosomes.

The phrase "induction of T cell response" refers to the generation or the re-stimulation of virus specific CD4+ or CD8+ T cells. The expression system of the invention can induce or re-stimulate a T cell mediated adaptive response directed to the MHC class I or class II epitopes present in the viral proteins expressed by the polynucleotide. Such T cell response can be measured by art known methods, preferably by ex-vivo re-stimulation of T cells with synthetic peptides spanning the entire viral proteins and analysis of proliferation or Interferon-gamma production.

The phrase "induction of B cell response" refers to the generation or the re-stimulation of virus specific B cells producing immunoglobulins of class IgG or IgA. The expression system of the invention can induce or re-stimulate B cells producing antibodies specific for pathogenic, e.g. viral, antigens expressed by the polynucleotide. Such B cell response can be measured by ELISA (Enzyme Linked Immuno Stained Assay) assay with the synthetic antigen of serum or mucosal immunoglobulin. Alternatively the induced antibody titer can be measured by virus neutralization assays.

The phrase "induction of an anti-pathogenic B cell response" refers to the generation or the re-stimulation of virus specific B cells producing immunoglobulins of class IgG or IgA which inactivates, eliminates, blocks and/or neutralizes the respective pathogen such that the disease caused by the pathogen does not break out and/or the symptoms are alleviated. This is also called a "protective immune response" against the pathogen. The expression system of the invention can induce or re-stimulate B cells producing antibodies specific for pathogenic, e.g. viral, antigens expressed by the polynucleotide. Such B cell response can be measured by ELISA (Enzyme Linked Immuno Stained Assay) assay with the synthetic antigen of serum or mucosal immunoglobulin. Alternatively the induced antibody titer can be measured by virus neutralization assays.

The phrase "enhancing an immune response" refers to the strengthening or intensification of the humoral and/or cellular immune response against an immunogen, preferably pathogens, more preferably viruses. The enhancement of the immune response can be measured by comparing the immune response elicited by an expression system of the invention with the immune response of an expression system expressing the same antigen/immunogen alone by using tests described herein and/or tests well known in the present technical field.

In an expression system, a gene of interest may be encoded by a single polynucleotide or by several separate polynucleotides. In cell-based expression systems one or more polynucleotides may be comprised on a single or on several separate vectors. Each of these polynucleotides may encode the whole or a part of the gene product of interest.

Furthermore, expression systems may encompass "expression control sequences" that regulate the expression of the gene of interest. Typically, expression control sequences are polypeptides or polynucleotides such as but not limited to promoters, enhancers, silencers, insulators, or repressors.

Accordingly, a vector comprising one or more polynucleotides encoding for one or more gene products of interest may comprise further expression control sequences. In a vector comprising more than one polynucleotide encoding for one or more gene products of interest, the expression may be controlled together or separately by one or more expression control sequences. More specifically, each polynucleotide comprised on the vector may be control by a separate expression control sequence or all polynucleotides comprised on the vector may be controlled by a single expression control sequence. Polynucleotides comprised on a single vector controlled by a single expression control sequences preferably form an open reading frame.

The term "expression system" further encompasses the expression of the gene product of interest comprising the transcription of the polynucleotides, RNA splicing, translation into a polypeptide, and post-translational modification of a polypeptide or protein.

The term "open reading frame" (ORF) refers to a sequence of nucleotides, that can be translated into amino acids. Typically, such an ORF contains a start codon, a subsequent region usually having a length which is a multiple of 3 nucleotides, but does not contain a stop codon (TAG, TAA, TGA, UAG, UAA, or UGA) in the given reading frame. Typically, ORFs occur naturally or are constructed artificially, i.e. by gene-technological means. An ORF codes for a protein where the amino acids into which it can be translated form a peptide-linked chain.

The terms "protein", "polypeptide" and "peptide" are used interchangeably herein and refer to any peptide-linked chain of amino acids, regardless of length or post-translational modification.

The term "post-translational" used herein refers to events that occur after the translation of a nucleotide triplet into an amino acid and the formation of a peptide bond to the proceeding amino acid in the sequence. Such post-translational events may occur after the entire polypeptide was formed or already during the translation process on those parts of the polypeptide that have already been translated. Post-translational events typically alter or modify the chemical or structural properties of the resultant polypeptide. Examples of post-translational events include but are not limited to events such as glycosylation or phosphorylation of amino acids, or cleavage of the peptide chain, e.g. by an endopeptidase.

The term "co-translational" used herein refers to events that occur during the translation process of a nucleotide triplet into an amino acid chain. Those events typically alter or modify the chemical or structural properties of the resultant amino acid chain. Examples of co-translational events include but are not limited to events that may stop the translation process entirely or interrupted the peptide bond formation resulting in two discreet translation products.

As used herein, the terms "polyprotein" or "artificial polyprotein" refer to an amino acid chain that comprises, or essentially consists of or consists of two amino acid chains that are not naturally connected to each other. The polyprotein may comprise one or more further amino acid chains. Each amino acid chain is preferably a complete protein, i.e. spanning an entire ORF, or a fragment, domain or epitope thereof. The individual parts of a polyprotein may either be permanently or temporarily connected to each other. Parts of a polyprotein that are permanently connected are translated from a single ORF and are not later separated co- or post-translationally. Parts of polyproteins that are connected temporarily may also derive from a single ORF but are divided co-translationally due to separation during the translation process or post-translationally due to cleavage of the peptide chain, e.g. by an endopeptidase. Additionally or alternatively, parts of a polyprotein may also be derived from two different ORF and are connected post-translationally, for instance through covalent bonds.

Proteins or polyproteins usable in the present invention (including protein derivatives, protein variants, protein fragments, protein segments, protein epitops and protein domains) can be further modified by chemical modification. This means such a chemically modified polypeptide comprises other chemical groups than the 20 naturally occurring amino acids. Examples of such other chemical groups include without limitation glycosylated amino acids and phosphorylated amino acids. Chemical modifications of a polypeptide may provide advantageous properties as compared to the parent polypeptide, e.g. one or more of enhanced stability, increased biological half-life, or increased water solubility. Chemical modifications applicable to the variants usable in the present invention include without limitation: PEGylation, glycosylation of non-glycosylated parent polypeptides, or the modification of the glycosylation pattern present in the parent polypeptide. Such chemical modifications applicable to the variants usable in the present invention may occur co- or post-translational.

The term "segment" refers to any part of a macromolecule (e.g. a polypeptide, protein or polyprotein) into which this macromolecule can be divided. A macromolecule may consist of one or more segments. Such segmentation may exist due to functional (e.g. having immunoreactive features or membrane attachment functions) or structural (e.g. nucleotide or amino acid sequence, or secondary or tertiary structure) properties of the macromolecule and/or the individual segment. In the context of the present invention it is preferred that the term "segment" refers to a part of a protein or polyprotein. It is particularly preferred that such segment folds and/or functions independently of the rest of the protein or polyprotein.

An "epitope", also known as antigenic determinant, is the segment of a macromolecule that is recognized by the immune system, specifically by antibodies, B cells, or T cells. Such epitope is that part or segment of a macromolecule capable of binding to an antibody or antigen-binding fragment thereof. In this context, the term "binding" preferably relates to a specific binding. In the context of the present invention it is preferred that the term "epitope" refers to the segment of protein or polyprotein that is recognized by the immune system. Epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents.

As used herein, the term "domain" refers to the segment of a protein or polyprotein sequence or structure (or corresponding nucleotide sequence) that can evolve, function, and/or exist independently of the rest of the protein chain. Typically, a protein consists of one or several domains with each of them being three-dimensional structure that are stable and folded independently of the rest of the protein chain. Such domain typically forms an independent functional unit within the protein (e.g. transmembrane-domains, immunoglobulin-like domains, or DNA-binding domains).

As used herein, the term protein or segment "variant" is to be understood as a polypeptide (or segment) which differs in comparison to the polypeptide (or segment, epitop, or domain) from which it is derived by one or more changes in the amino acid sequence. The polypeptide from which a protein variant is derived is also known as the parent polypeptide. Likewise, the segment from which a segment variant is derived from is known as the parent segment. Typically, a variant is constructed artificially, preferably by gene-technological means. Typically, the parent polypeptide is a wild-type protein or wild-type protein domain. In the context of the present invention it is further preferred that a parent polypeptide (or parent segment) is the consensus sequence of two or more wild-type polypeptides (or wild-type segments). Further, the variants usable in the present invention may also be derived from homologs, orthologs, or paralogs of the parent polypeptide or from artificially constructed variant, provided that the variant exhibits at least one biological activity of the parent polypeptide. The changes in the amino acid sequence may be amino acid exchanges, insertions, deletions, N-terminal truncations, or C-terminal truncations, or any combination of these changes, which may occur at one or several sites. In preferred embodiments, a variant usable in the present invention exhibits a total number of up to 200 (up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200) changes in the amino acid sequence (i.e. exchanges, insertions, deletions, N-terminal truncations, and/or C-terminal truncations). The amino acid exchanges may be conservative and/or non-conservative. In preferred embodiments, a variant usable in the present invention differs from the protein or domain from which it is derived by up to 1, 2, 3, 4, 5, 6, 7, 8, 9, 10, 15, 20, 25, 30, 35, 40, 45, 50, 55, 60, 65, 70, 75, 80, 85, 90, 95, or 100 amino acid exchanges, preferably conservative amino acid changes.

Alternatively or additionally, a "variant" as used herein, can be characterized by a certain degree of sequence identity to the parent polypeptide or parent polynucleotide from which it is derived. More precisely, a protein variant in the context of the present invention exhibits at least 80% sequence identity to its parent polypeptide. A polynucleotide variant in the context of the present invention exhibits at least 80% sequence identity to its parent polynucleotide. Preferably, the sequence identity of protein variants is over a continuous stretch of 20, 30, 40, 45, 50, 60, 70, 80, 90, 100 or more amino acids. Preferably, the sequence identity of polynucleotide variants is over a continuous stretch of 60, 90, 120, 135, 150, 180, 210, 240, 270, 300 or more nucleotides.

The term "at least 80% sequence identity" is used throughout the specification with regard to polypeptide and polynucleotide sequence comparisons. This expression preferably refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide. Preferably, the polypeptide in question and the reference polypeptide exhibit the indicated sequence identity over a continuous stretch of 20, 30, 40, 45, 50, 60, 70, 80, 90, 100 or more amino acids or over the entire length of the reference polypeptide. Preferably, the polynucleotide in question and the reference polynucleotide exhibit the indicated sequence identity over a continuous stretch of 60, 90, 120, 135, 150, 180, 210, 240, 270, 300 or more nucleotides or over the entire length of the reference polypeptide.

Variants may additionally or alternatively comprise deletions of amino acids, which may be N-terminal truncations, C-terminal truncations or internal deletions or any combination of these. Such variants comprising N-terminal truncations, C-terminal truncations and/or internal deletions are referred to as "deletion variant" or "fragments" in the context of the present application. The terms "deletion variant" and "fragment" are used interchangeably herein. A fragment may be naturally occurring (e.g. splice variants) or it may be constructed artificially, preferably by gene-technological means. Preferably, a fragment (or deletion variant) has a deletion of up to 1, 2, 3, 4, 5, 6, 7, 8, 9, 10, 15, 20, 25, 30, 35, 40, 45, 50, 55, 60, 65, 70, 75, 80, 85, 90, 95, or 100 amino acids at its N-terminus and/or at its C-terminus and/or internally as compared to the parent polypeptide, preferably at its N-terminus, at its N- and C-terminus, or at its C-terminus. In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by SEQ ID, if not specifically indicated otherwise. For example, a peptide sequence consisting of 50 amino acids compared to the amino acid sequence of protein F according to SEQ ID NO: 1 may exhibit a maximum sequence identity percentage of 10.04% (50/498) while a sequence with a length of 249 amino acids may exhibit a maximum sequence identity percentage of 50.00% (249/498).

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) *Proc. Natl. Acad. Sci. USA* 90: 5873-5877), with hmmalign (HMMER package, http://hmmer.wustl.edu/) or with the CLUSTAL algorithm (Thompson, J. D., Higgins, D. G. & Gibson, T. J. (1994) *Nucleic Acids Res.* 22, 4673-80) available e.g. on the world wide web at ebi.ac.uk/Tools/clustalw/ or on the world wide web at ebi.ac.uk/Tools/clustalw2/index.html or on the world wide web at npsa-pbil.ibcp.fr/cgi-bin/npsa_automat.pl?page=/NPSA/npsa_clustalw.html. Preferred parameters used are the default parameters as they are set on the world wide web at ebi.ac.uk/Tools/clustalw/ or the world wide web at ebi.ac.uk/Tools/clustalw2/index.html. The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215: 403-410. BLAST polynucleotide searches are performed with the BLASTN program, score=100, word length=12, to obtain polynucleotide sequences that are homologous to those nucleic acids which encode F, N, or M2-1. BLAST protein searches are performed with the BLASTP program, score=50, word length=3, to obtain amino acid sequences homologous to the F polypeptide, N polypeptide, or M2-1 polypeptide. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields. When percentages of sequence identity are referred to in the present application, these percentages are calculated in relation to the full length of the longer sequence, if not specifically indicated otherwise.

The polynucleotides of the invention encodes proteins, peptides or variants thereof which comprise amino acids which are designated following the standard one- or three-letter code according to WIPO standard ST.25 unless otherwise indicated. if not indicated otherwise, the one- or three letter code is directed at the naturally occurring L-amino acids and the amino acid sequence is indicated in the direction from the N-terminus to the C-terminus of the respective protein, peptide or variant thereof.

"Hybridization" can also be used as a measure of sequence identity or homology between two nucleic acid sequences. A nucleic acid sequence encoding a protein of the invention, or a portion of any of these can be used as a hybridization probe according to standard hybridization techniques. The hybridization of a respective probe to DNA or RNA from a test source is an indication of the presence of the target DNA or RNA, respectively, in the test source. Hybridization conditions are known to those skilled in the art and can be found, for example, in Current Protocols in Molecular Biology, John Wiley & Sons, N. Y., 6.3.1-6.3.6, 1991. "Moderate hybridization conditions" are defined as equivalent to hybridization in 2× sodium chloride/sodium citrate (SSC) at 30° C., followed by a wash in IX SSC, 0.1% SDS at 50° C. "Highly stringent conditions" are defined as equivalent to hybridization in 6× sodium chloride/sodium citrate (SSC) at 45° C., followed by a wash in 0.2×SSC, 0.1% SDS at 65° C.

Additionally or alternatively a deletion variant may occur not due to structural deletions of the respective amino acids as described above, but due to these amino acids being inhibited or otherwise not able to fulfill their biological function. Typically, such functional deletion occurs due to the insertions to or exchanges in the amino acid sequence that changes the functional properties of the resultant protein, such as but not limited to alterations in the chemical properties of the resultant protein (i.e. exchange of hydrophobic amino acids to hydrophilic amino acids), alterations in the post-translational modifications of the resultant protein (e.g. post-translational cleavage or glycosylation pattern), or alterations in the secondary or tertiary protein structure. Additionally or alternatively, a functional deletion may also occur due to transcriptional or post-transcriptional gene silencing (e.g. via siRNA) or the presence or absence of inhibitory molecules such as but not limited to protein inhibitors or inhibitory antibodies.

In the context of the present invention it is preferred that a protein (or a segment or a domain or an epitope) being "functionally deleted" refers to the fact that the amino acids or nucleotides of the corresponding sequence are either deleted or present but not fulfilling their biological function.

As used herein, the term "consensus" refers to an amino acid or nucleotide sequence that represents the results of a multiple sequence alignment, wherein related sequences were compared to each other. Such consensus sequence is composed of the amino acids or nucleotides most commonly observed at each position. In the context of the present invention it is preferred that the sequences used in the sequence alignment to obtain the consensus sequence are sequences of different viral subtypes/serotypes strains isolated in various different disease outbreaks worldwide. Each individual sequence used in the sequence alignment is referred to as the sequence of a particular virus "isolate". A more detailed description of the mathematical methods to obtain such consensus is provided in the Example section. In case that for a given position no "consensus nucleotide" or "consensus amino acid" can be determined, e.g. because only two isolates were compared, than it is preferred that the amino acid of each one of the isolates is used. The resulting protein is assessed for its respective B cell and/or T cell inducing ability.

A "peptide linker" (or short: "linker") in the context of the present invention refers to an amino acid sequence of between 1 and 100 amino acids. In preferred embodiments, a peptide linker according to the present invention has a minimum length of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids. In further preferred embodiments, a peptide linker according to the present invention has a maximum length of 100, 95, 90, 85, 80, 75, 70, 65, 60, 55, 50, 45, 40, 35, 34, 33, 32, 31, 30, 29, 28, 27, 26, 25, 24, 23, 22, 21, 20, 19, 18, 17, 16, or 15 amino acids or less. It is preferred that peptide linkers provide flexibility among the two amino acid proteins, fragments, segments, epitopes and/or domains that are linked together. Such flexibility is generally increased if the amino acids are small. Thus, preferably the peptide linker of the present invention has an increased content of small amino acids, in particular of glycins, alanines, serines, threonines, leucines and isoleucines. Preferably, more than 20%, 30%, 40%, 50%, 60% or more of the amino acids of the peptide linker are small amino acids. In a preferred embodiment the amino acids of the linker are selected from glycines and serines. In especially preferred embodiments, the above-indicated preferred minimum and maximum lengths of the peptide linker according to the present invention may be combined, if such a combination makes mathematically sense. In further preferred embodiments, the peptide linker of the present invention is non-immunogenic; in particularly preferred embodiments, the peptide linker is non-immunogenic to humans.

The term "cleavage site" as used herein refers to an amino acid sequence or nucleotide sequence where this sequence directs the division, e.g. because it is recognized by a cleaving enzyme, and/or can be divided. Typically, a polypeptide chain is cleaved by hydrolysis of one or more peptide bonds that link the amino acids and a polynucleotide chain is cleaved by hydrolysis of one or more of the phosphodiester bond between the nucleotides. Cleavage of peptide- or phosphodiester-bonds may originate from chemical or enzymatic cleavage. Enzymatic cleavage refers to such cleavage being attained by proteolytic enzymes including but not limited to restriction endonuclease (e.g. type 1, type II, type II, type IV or artificial restriction enzymes) and endo- or exo-peptidases or -proteases (e.g. serine-proteases, cysteine-proteases, metallo-proteases, threonine proteases, aspartate proteases, glutamic acid proteases). Typically, enzymatic cleavage occurs due to self-cleavage or is effected by an independent proteolytic enzyme. Enzymatic cleavage of a protein or polypeptide can happen either co- or post-translational. Accordingly, the term "endopeptidase cleavage site" used herein, refers to a cleavage cite within the amino acid or nucleotide sequence where this sequence is cleaved or is cleavable by an endopeptidase (e.g. trypsin, pepsin, elastase, thrombin, collagenase, furin, thermolysin, endopeptidase V8, cathepsins). Alternatively or additionally, the polyprotein of the present invention can be cleaved by an autoprotease, i.e. a protease which cleaves peptide bonds in the same protein molecule which also comprises the protease. Examples of such autoproteases are the NS2 protease from flaviviruses or the VP4 protease of birnaviruses.

Alternatively, the term "cleavage site" refers to an amino acid sequence or nucleotide sequence that prevents the formation of peptide- or phosphodiester-bonds between amino acids or nucleotides, respectively. For instance, the bond formation may be prevented due to co-translational self-processing of the polypeptide or polyprotein resulting in two discontinuous translation products being derived from a single translation event of a single open reading frame. Typically, such self-processing is effected by a "ribosomal skip" caused by a pseudo stop-codon sequence that induces the translation complex to move from one codon to the next without forming a peptide bond. Examples of sequences inducing a ribosomal skip include but are not limited to viral 2A peptides or 2A-like peptide (herein both are collectively referred to as "2A peptide" or interchangeably as "2A site" or "2A cleavage site") which are used by several families of viruses, including Picornavirus, insect viruses, Aphtoviridae, Rotaviruses and *Trypanosoma*. Best known are 2A sites of rhinovirus and foot-and-mouth disease virus of the Picornaviridae family which are typically used for producing multiple polypeptides from a single ORF.

Accordingly, the term "self-cleavage site" as used herein refers to a cleavage site within the amino acid or nucleotide sequence where this sequence is cleaved or is cleavable without such cleavage involving any additional molecule or where the peptide- or phosphodiester-bond formation in this sequence is prevented in the first place (e.g. through co-translational self-processing as described above).

It is understood that cleavage sites typically comprise several amino acids or are encoded by several codons (e.g. in those cases, wherein the "cleavage site" is not translated into protein but leads to an interruption of translation). Thus, the cleavage site may also serve the purpose of a peptide linker, i.e. sterically separates two peptides. Thus, in some embodiments a "cleavage site" is both a peptide linker and provides above described cleavage function. In this embodiment the cleavage site may encompass additional N- and/or C-terminal amino acids.

The term "host cell" as used herein refers to a cell that harbours a vector (e.g. a plasmid or virus). Such host cell may either be a prokaryotic (e.g. a bacterial cell) or a eukaryotic cell (e.g. a fungal, plant or animal cell).

"Pharmaceutically acceptable" means approved by a regulatory agency of the Federal or a state government or listed in the U.S. Pharmacopeia or other generally recognized pharmacopeia for use in animals, and more particularly in humans.

The term "carrier", as used herein, refers to a pharmacologically inactive substance such as but not limited to a diluent, excipient, or vehicle with which the therapeutically active ingredient is administered. Such pharmaceutical carriers can be liquid or solid. Liquid carrier include but are not limited to sterile liquids, such as saline solutions in water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. A saline solution is a preferred carrier when the pharmaceutical composition is administered intravenously or intranasally by a nebulizer.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Examples of suitable pharmaceutical carriers are described in "Remington's Pharmaceutical Sciences" by E. W. Martin.

The term "composition" is intended to include the formulation of the active compound with encapsulating material as a carrier providing a capsule in which the active component with or without other carriers, is surrounded by a carrier, which is thus, in association with it.

The term "adjuvant" refers to agents that augment, stimulate, activate, potentiate, or modulate the immune response to the active ingredient of the composition at either the cellular or humoral level, e.g. immunologic adjuvants stimulate the response of the immune system to the actual antigen, but have no immunological effect themselves. Examples of such adjuvants include but are not limited to inorganic adjuvants (e.g. inorganic metal salts such as aluminium phosphate or aluminium hydroxide), organic adjuvants (e.g. saponins or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-γ) particulate adjuvants (e.g. immuno-stimulatory complexes (ISCOMS), liposomes, or biodegradable microspheres), virosomes, bacterial adjuvants (e.g. monophosphoryl lipid A, or muramyl peptides), synthetic adjuvants (e.g. non-ionic block copolymers, muramyl peptide analogues, or synthetic lipid A), or synthetic polynucleotides adjuvants (e.g polyarginine or polylysine).

The term "active ingredient" refers to the substance in a pharmaceutical composition or formulation that is biologically active, i.e. that provides pharmaceutical value. A pharmaceutical composition may comprise one or more active ingredients which may act in conjunction with or independently of each other.

The active ingredient can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as but not limited to those derived from sodium, potassium, ammonium, calcium, ferric hydroxides, isopropylamine, triethylamine, 2-ethylamino ethanol, histidine, procaine, and the like.

As used herein, a "patient" means any mammal, reptile or bird that may benefit from a treatment with a tumour vaccine described herein. Preferably, a "patient" is selected from the group consisting of laboratory animals (e.g. mouse or rat), domestic animals (including e.g. guinea pig, rabbit, horse, donkey, cow, sheep, goat, pig, chicken, camel, cat, dog, turtle, tortoise, snake, or lizard), or primates including chimpanzees, bonobos, gorillas and human beings. It is particularly preferred that the "patient" is a human being.

As used herein, "treat", "treating" or "treatment" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "prevent", "preventing", "prevention", or "prophylaxis" of a disease or disorder means preventing that such disease or disorder occurs in patient.

As used herein, "administering" includes in vivo administration, as well as administration directly to tissue ex vivo, such as vein grafts.

An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

Embodiments of the Invention

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In a first aspect the invention provides an expression system comprising a first polynucleotide encoding at least one protein, peptide or variant thereof, which induces a T cell response and a second polynucleotide encoding at least one protein, which induces an anti-pathogenic B cell response. One of the advantages provided by the present invention is the fact that the B cell response to the protein, peptide or variant thereof inducing an antipathogenic B cell response can be enhanced, if at the same time a protein inducing a T cell response is administered.

In the context of the present invention the term "expression system" preferably refers to one or more polynucleotide sequences comprising in addition to the first and second polynucleotide the elements to direct transcription and translation of the proteins encoded by the first and second or any further polynucleotide, which may be included in the preferred embodiments outlined below. Such elements included promoter and enhancer elements to direct transcription of mRNA in a cell-free or a cell-based based system, preferably a cell-based system. In another embodiment, wherein the polynucleotides are provided as translatable RNAs is envisioned that the expression system comprises those elements that are necessary for translation and/or stabilization of RNAs encoding the T cell and B cell inducing protein, e.g. polyA-tail, IRES, cap structures etc.

According to a preferred embodiment of the first aspect, the first polynucleotide encodes a protein which induces a reaction of the immune system (i.e. immune response) in a host which is mediated by T cells. A T cell response involves the activation of antigen-specific T lymphocyte such as but not limited to cytotoxic T cells (CTLs), T helper cells (Tx cells), central memory T cells (TCM cells), effector memory T cells (TEM cells), and regulatory T cells (Treg cells). A T cell response against a protein is induced, if peptides of the protein are processed within the cell and presented to T cells on the surface of the cell via the MHC I or MHC II pathway. Thus, in the context of the present invention preferably those proteins or parts thereof are used for inducing a T cell response that are normally not exposed to, e.g. non structural or internal proteins or parts of structural or internal proteins of a virus not accessible to B-cells.

The second polynucleotide encodes a protein, peptide or variant thereof that induces an anti-pathogenic B cell response. A B cell response is an immune response based on the activation of B lymphocytes, which produce and secrete antigen specific antibodies. B cells involved in such immune response include but are not limited to plasma B cells, memory B cells and B-1 cells. Thus, in the context of the present invention preferably those pathogenic, e.g. viral, proteins or parts thereof are used for inducing a B cell response that are exposed on the outside of the virus, e.g. structural proteins or at least those parts of structural proteins accessible to B-cells on the outside of the pathogen (virus).

In embodiments of the first aspect of the present invention, the first and the second polynucleotide are comprised on separate vectors or on the same vector. Accordingly, the first polynucleotide may be comprised on one vector and the second polynucleotide may be comprised on a second vector. Alternatively or additionally, the first and the second polynucleotide may be comprised on the same vector. It is preferred that the first and the second polynucleotide are comprised on the same vector. It is particularly preferred that the first and the second polynucleotide comprised on the same vector are linked in such that they are expressed as a polyprotein. Preferably, the first and the second polynucleotide form an open reading frame.

It is preferred that the first and the second polynucleotide are expressed as an artificial polyprotein. In the context of the present invention the term "artificial polyprotein" is directed at polyproteins which are not naturally occurring, e.g. which are generated by using recombinant DNA techniques. Accordingly, the proteins, peptides or variants thereof encoded in this artificial polyprotein are preferably derived from pathogens which genome do not encode a polyprotein comprising the proteins, peptides or variants encoded by the first and second polynucleotide (and, optionally, the third polynucleotide) of the invention. Preferably, the first and second polynucleotides are derived from viruses, encoding no polyprotein or a polyprotein wherein the respective polynucleotides have a different order and/or sequence. More preferably, the first and second polynucleotide are derived from a virus which is selected from the group consisting of a DNA virus, a negative sense single stranded (ssRNA(−)) RNA virus or an ambisense RNA virus. Further preferred, the virus is selected from negative-single stranded (ssRNA(−)) RNA virus. Even more preferred, the virus is selected from enveloped ssRNA(−) viruses, more preferably from the group consisting of paramyxoviruses and orthomyxoviruses.

In preferred embodiments of the first aspect the protein, which induces a T cell response is a non-structural and/or internal protein of a virus, and/or the protein, which induces an anti-pathogenic B cell response is a structural and/or surface protein of a pathogen, preferably a virus, wherein the virus is preferably selected from the group consisting of a DNA virus, a negative-strand RNA virus or an ambisense RNA virus. Even more preferred, the virus is selected from negative-single stranded (ssRNA(−)) RNA virus. Even more preferred, the virus is selected from enveloped ssRNA(−) viruses, more preferably from the group consisting of paramyxoviruses and orthomyxoviruses.

It is preferred that the amino acid sequence of the structural (surface) and/or non-structural (internal) protein comprises consecutive segments or a consensus sequence of one or more different virus isolates.

In the context of the present invention it is preferred that the term "segment" refers to a part of a protein or polyprotein. It is particularly preferred that such segment folds and/or functions independently of the rest of the protein or polyprotein such as but not limited to a domain, an epitope or a fragment thereof. It is understood that a protein variant in the context of the present invention differs in comparison to its parent polypeptide in changes in the amino acid sequence such as amino acid exchanges, insertions, deletions, N-terminal truncations, or C-terminal truncations, or any combination of these changes, which may occur at one or several sites whereby the variant exhibits at least 80% sequence identity to its parent polypeptide.

In preferred embodiments, the structural protein, peptide or a variant thereof is a protein or peptide exposed on the surface of the native pathogen, e.g. a virus. It is preferred that the structural and/or surface protein triggers a T-cell independent immune response such as but not limited to an antibody mediated immune response or an activation of the complement system. In a particularly preferred embodiment, the structural and/or surface protein induces an antibody mediated immune response. Such antibody mediated immune response is based on the activation of B cells which produce and secrete antigen specific antibodies. B cells involved in such immune response include but are not limited to plasma B cells, memory B cells and B-1 cells.

According to a preferred embodiment of the first aspect, the second polynucleotide encodes a protein or variant thereof that induces an anti-pathogenic B cell response. A B cell response is an immune response based on the activation of B lymphocytes, which produce and secrete antigen specific antibodies. B cells involved in such immune response include but are not limited to plasma B cells, memory B cells and B-1 cells. Thus, in the context of the present invention preferably those proteins or parts thereof are used for inducing a B cell response that are exposed on the outside of a virus, e.g. structural and/or surface proteins or at least those parts of structural and/or surface proteins accessible to B-cells on the outside of a virus. An anti-pathogenic B cell response is a B cell response directed against a pathogen which inactivates, eliminates, blocks and/or neutralizes the respective pathogen such that the disease caused by the pathogen does not break out and/or the symptoms are alleviated. In preferred embodiments of the invention, the anti-apthogenic B cell response is effected by antibodies that bind to the surface of a pathogenic organism and attract the first component of the complement cascade with their Fc region and initiate activation of the "classical" complement system. This results in pathogen elimination by two mechanisms. First, the binding of the antibody and complement molecules marks the pathogen for ingestion by phagocytes in a process called opsonization. Secondly, some complement system components form a membrane attack complex to assist antibodies to destroy the pathogen directly. Alternatively, the anti-apthogenic B cell response is effected by antibodies that bind to the pathogen's structural proteins blocking the attachment to cellular receptors. In this way, the antibody can neutralize the infection. As a further atemative, the anti-apthogenic B cell response is effected by antibodies that bind at a specialized region of the pathogen's surface protein, the fusion peptide, which is necessary for the entry of the pathogen into the host cell. The antibody binding results in fixing the protein in a pre-fusion state and blocking infection. The ability of a protein or variant to induce B cell response which is anti-pathogenic can be determined by the skilled person by applying tests and/or assays well known in the art.

In a further preferred embodiment, a membrane attachment domain of the protein exposed on the surface of the native virus or variant thereof is functionally deleted, thus, either being structurally deleted or structurally present but not fulfilling its biological function. In a particularly preferred embodiment, the amino acid sequence corresponding to the membrane attachment domain is deleted. The deletion of the membrane attachment region serves the purpose of ascertaining that the anti-pathogenic B cell response inducing protein is secreted from the cell into which the expression system of the invention has been introduced.

In a further preferred embodiment the anti-pathogenic B cell response inducing protein comprises a secretion signal, which targets the protein to the endoplasmatic reticulum (ER). Such secretion signals are present preferably in the context of a deleted membrane attachment domain. The skilled person is well aware of various such secretion signals, which may be used as heterologous secretion signals, e.g. added to the N-terminus of the anti-pathogenic B cell response inducing protein. Alternatively or additionally a naturally occurring secretion signal may be used, which is, e.g., present in the majority of structural and/or surface viral proteins. Thus, if naturally present in the respective protein it is preferred that the secretion signal is maintained in a modified version of the structural and/or surface protein.

In embodiments of the first aspect, the non-structural protein is a conserved internal protein suitable for inducing a T cell mediated immune response against the pathogen, preferably the viruses, involving the activation of antigen-specific T lymphocyte such as but not limited to cytotoxic T cells (CTLs), T helper cells ($T_H$ cells), central memory T cells (TCM cells), effector memory T cells (TEM cells), and regulatory T cells (Treg cells). Thus, preferably the T cell inducing protein of the pathogen (virus) does not comprise a secretion signal.

In the context of the present invention, the protein, peptide or variant thereof encoded by the first polynucleotide is located either N- or C-terminally with respect to the protein, peptide or variant thereof encoded by the second polynucleotide. In a preferred embodiment, the protein, peptide or variant thereof encoded by the second polynucleotide is located C-terminally with respect to the protein, peptide or variant thereof encoded by the first polynucleotide.

Accordingly, embodiments of the present invention have the formula X-Y or Y-X, wherein "X" depicts the T cell response inducing protein and "Y" depicts the anti-pathogenic B cell response inducing protein and a "dash" depicts a peptide bond.

In preferred embodiments of the first aspect, a polynucleotide encoding a cleavage site is positioned between the first polynucleotide and the second polynucleotide. It is within the scope of the present invention that every protein can be combined with any other protein and that any two proteins can or cannot be connected or linked by a cleavage site.

It is preferred that this cleavage site is either a self-cleaving site (i.e. a cleavage site within the amino acid sequence where this sequence is cleaved or is cleavable without such cleavage involving any additional molecule or where the peptide-bond formation in this sequence is prevented in the first place) or an endopeptidase cleavage site (i.e. a cleavage cite within the amino acid sequence where this sequence is cleaved or is cleavable by an endopeptidase, e.g. trypsin, pepsin, elastase, thrombin, collagenase, furin, thermolysin, endopeptidase V8, cathepsins). More preferably, the self-cleaving site is a 2A cleavage site selected from the group consisting of a viral 2A peptide or 2A-like peptide of Picornavirus, insect viruses, Aphtoviridae, Rotaviruses and *Trypanosoma*, preferably wherein the 2A cleavage site is the 2 A peptide of foot and mouth disease virus. Alternatively or additionally, the polyprotein of the present invention can be cleaved by an autoprotease, i.e. a protease which cleaves peptide bonds in the same protein molecule which also comprises the protease. Examples of such autoproteases are the NS2 protease from flaviviruses or the VP4 protease of birnaviruses In the context of the present invention, the cleavage site can be positioned N-terminally with respect to the protein, peptide or variant thereof encoded by the first polynucleotide and C-terminally with respect to the protein, peptide or variant thereof encoded by the second polynucleotide. Alternatively the cleavage site can be positioned C-terminally with respect to the protein, peptide or variant thereof encoded by the first polynucleotide and N-terminally with respect to the protein, peptide or variant thereof encoded by the second polynucleotide.

Accordingly, embodiments of the present invention have the formula X-C-Y or Y-C-X, wherein X" depicts the T cell response inducing protein and "Y" depicts the anti-pathogenic B cell response inducing protein, "C" depicts a cleavage site, and a "dash" depicts a peptide bond.

In a preferred embodiment of the first aspect, the expression system further comprises a third polynucleotide encoding a protein, peptide or a variant thereof of a pathogen.

It is preferred that the protein, peptide or variant thereof encoded by the third polynucleotide is a protein, peptide or variant thereof inducing a T cell response, preferably the third polynucleotide is a protein, peptide or variant thereof which is a non-structural or internal protein, peptide or variant thereof inducing a T cell response.

It is preferred that the protein, peptide or variant thereof encoded by the third polynucleotide differs from the protein, peptide or variant thereof encoded by the first polynucleotide or the second polynucleotide. Preferably, the proteins, peptides or variants thereof encoded by the first, second and the third polynucleotide differ from each other in that they comprise amino acid sequences of different proteins.

In preferred embodiments a polynucleotide encoding a linker is positioned between the second polynucleotide and the third polynucleotide. It is preferred that the linker is a flexible linker, preferably a flexible linker comprising an amino acid sequence according to SEQ ID NO: 6 (Gly-Gly-Gly-Ser-Gly-Gly-Gly).

In preferred embodiments the third polynucleotide is comprised on a separate or on the same vector as the first polynucleotide and/or the second polynucleotide.

Accordingly, the first polynucleotide is comprised on one vector and the second polynucleotide is comprised on a second vector and the third polynucleotide is comprised on a third vector. Alternatively or additionally, the first and the second polynucleotide are comprised on the same vector and the third polynucleotide is comprised on a separate vector, or the first and the third polynucleotide are comprised on the same vector and the second polynucleotide is comprised on a separate vector, or the second and the third polynucleotide are comprised on the same vector and the first polynucleotide is comprised on a separate vector. Alternatively or additionally, the first and the second and the third polynucleotide are comprised on the same vector. It is preferred that the first and the second and the third polynucleotide may be comprised on the same vector. It is particularly preferred that the first and the second and the third polynucleotide comprised on the same vector are linked in such that they are expressed as a polyprotein. Preferably, the first and the second and the third polynucleotide comprised on the same vector form an open reading frame and, preferably, are expressed as a polyprotein.

In preferred embodiments of this aspect, the protein encoded by the second polynucleotide is located N-terminally with respect to the protein encoded by the first polynucleotide and/or the protein of the optional third polynucleotide, or the protein encoded by the second polynucleotide is located C-terminally with respect to the protein encoded by the first polynucleotide and/or the protein of the optional third polynucleotide.

In even more preferred embodiments of this aspect, the first polynucleotide is located N-terminally with respect to the protein encoded by the second polynucleotide and/or the protein of the optional third polynucleotide is located N-terminally with respect to the protein encoded by the first polynucleotide or is located between the protein encoded by the second polynucleotide and the protein encoded by the first polynucleotide; or the protein encoded by the first polynucleotide is located C-terminally with respect to the protein encoded by the second polynucleotide and/or the protein of the optional third polynucleotide is located C-terminally with respect to the protein encoded by the first polynucleotide or is located between the protein encoded by the second polynucleotide and the protein encoded by the first polynucleotide.

Preferred embodiments of the present invention have the formula X-K-Y, Y-K-X, X-K-Y-Y, Y-Y-K-X, X-Y-K-Y, Y-K-Y-X, X-K-Y-K-Y, Y-K-Y-K-X, X-C-Y, Y-C-X, X-C-Y-Y, Y-Y-C-X, X-Y-C-Y, Y-C-Y-X, X-C-Y-C-Y, Y-C-Y-C-X, X-K-Y-C-Y, Y-C-Y-K-X, X-C-Y-K-Y, or Y-K-Y-C-X, wherein "X" depicts the second polynucleotide encoding at least one protein, peptide or variant thereof, which induces an antipathogenic 13 cell response and "Y" depicts the first polynucleotide encoding at least one protein, peptide or variant thereof, which induces an T cell response, "K" indicates that one or more peptide linkers are present in this position, "C" indicates that one or more cleavage sites are present in this position and a "dash" depicts a peptide bond. Preferred arrangements are Y-K-Y-C-X or X-C-Y-K-Y.

It is further preferred that the non-structural and/or internal protein encoded by the third polynucleotide is a conserved internal protein suitable for inducing a T cell mediated immune response against the virus involving the activation of antigen-specific T lymphocyte such as but not limited to cytotoxic T cells (CTLs), T helper cells ($T_H$ cells), central memory T cells (TCM cells), effector memory T cells (TEM cells), and regulatory T cells (Treg cells).

It is within the scope of the present invention that every protein can be combined with any other protein and that any two proteins can or cannot be connected or linked by either a cleavage site or a linker peptide.

In preferred embodiments, the vector or vectors comprising the first, and the second and/or the third polynucleotide is/are selected from the group consisting of plasmid, cosmid, phage, virus, and artificial chromosome. More preferably, a vector suitable for practicing the present invention is selected from the group consisting of plasmid vectors, cosmid vectors, phage vectors, preferably lambda phage and filamentous phage vectors, viral vectors, adenovirus vectors (e.g., non-replicating Ad5, Ad11, Ad26, Ad35, Ad49, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd 73, ChAd82, ChAd83, ChAd146, ChAd147, PanAd1, PanAd2, and PanAd3 vectors or replication-competent Ad4 and Ad7 vectors), adeno-associated virus (AAV) vectors (e.g., AAV type 5 and type 2), alphavirus vectors (e.g., Venezuelan equine encephalitis virus (VEE), sindbis virus (SIN), semliki forest virus (SFV), and VEE-SIN chimeras), herpes virus vectors (e.g. vectors derived from cytomegaloviruses. like rhesus cytomegalovirus (RhCMV) (14)), arena virus vectors (e.g. lymphocytic choriomeningitis virus (LCMV) vectors (15)), measles virus vectors, pox virus vectors (e.g., vaccinia virus, modified vaccinia virus Ankara (MVA), NYVAC (derived from the Copenhagen strain of vaccinia), and avipox vectors: canarypox (ALVAC) and fowlpox (FPV) vectors), vesicular stomatitis virus vectors, retrovirus, lentivirus, viral like particles, and bacterial spores. The vectors ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63 and ChAd82 are described in detail in WO 2005/071093. The vectors PanAd1, PanAd2, PanAd3, ChAd55, ChAd73, ChAd83, ChAd146, and ChAd147 are described in detail in WO 2010/086189. It is particularly preferred that the vector is selected from the group consisting of MVA, ChAd63 and PanAd3.

In preferred embodiments, the expression system is for use in medicine. In more preferred embodiments, the expression system is for use in the prophylaxis or treatment of an infection and/or in the manufacturing of medicament for use in the prophylaxis or treatment of an infection and/or for use in methods of prophylaxis or treatment of an infection, wherein the infection is preferably a viral infection, particularly preferably for use in the prophylaxis or treatment of a pathogen and/or in the manufacturing of medicament for use in the prophylaxis or treatment of a pathogen and/or for use in methods of prophylaxis or treatment of a pathogen, wherein the pathogen preferably is a virus. Preferably, the expression system is for use in the prophylaxis or treatment of an infection by a virus and/or in the manufacturing of medicament for use in the prophylaxis or treatment of a virus and/or for use in methods of prophylaxis or treatment of a virus, wherein the pathogen selected from the group of a DNA virus, a negative-single stranded (ssRNA(−)) RNA virus or an ambisense RNA virus. Further preferred the expression system is for use in the prophylaxis or treatment and/or in the manufacturing of medicament for use in the prophylaxis or treatment of a virus and/or for use in methods of prophylaxis or treatment of an infection by negative sense single-stranded (ssRNA(−)) RNA virus. Even more preferred, the expression system is for use in the prophylaxis or treatment and/or in the manufacturing of medicament for use in the prophylaxis or treatment of a virus and/or for use in methods of prophylaxis or treatment of an infection by a virus selected from enveloped ssRNA(−) viruses, more preferably from the group consisting of paramyxoviruses and orthomyxoviruses.

In preferred embodiments the expression system is for use in enhancing an immune response. In more preferred embodiments, the expression system is for use in enhancing a B cell immune response against an immunogen, preferably a pathogen, more preferably a virus as defined above.

According to a preferred embodiment of the first aspect, the first polynucleotide encodes a viral protein of a paramyxovirus or variant thereof which induces a reaction of the immune system (i.e. immune response) in a host which is mediated by T cells, and the second polynucleotide encodes a viral protein of a paramyxovirus or variant thereof that induces an anti-pathogenic B cell response against paramyxoviruses. It is preferred that the paramyxovirus whose viral proteins are encoded for by the first and second polynucleotide is selected from the subfamily of Pneumovirinae, Paramyxovirinae, Fer-de-Lance-Virus, Nariva-Virus, Salem-Virus, Tupaia-Paramyxovirus, Beilong-Virus, J-Virus, Menangle-Virus, Mossmann-Virus, and Murayama-Virus. In even more preferred embodiments, the Pneumovirinae is selected from the group consisting of Pneumovirus, preferably human respiratory syncytial virus (RSV), murine pneumonia virus, bovine RSV, ovine RSV, caprine RSV, turkey rinotracheitis virus, and Metapneumovirus, preferably human metapneumovirus (hMPV) and avian metapneumovirus. In even more preferred embodiments, the Paramyxovirinae is selected from the group consisting of Respirovirus, preferably human parainfluenza virus 1 and 3, and Rubulavirus, preferably human parainfluenza virus 2 and 4.

In embodiments of the first aspect of the present invention, the first and the second polynucleotide are comprised on separate vectors or on the same vector. Accordingly, the first polynucleotide may be comprised on one vector and the second polynucleotide may be comprised on a second vector. Alternatively or additionally, the first and the second polynucleotide may be comprised on the same vector. It is preferred that the first and the second polynucleotide are comprised on the same vector. It is particularly preferred that the first and the second polynucleotide comprised on the same vector are linked in such that they are expressed as a polyprotein. Preferably, the first and the second polynucleotide form an open reading frame.

According to preferred embodiments of the first aspect the first polynucleotide encodes a viral protein of a paramyxovirus or variant thereof which induces a reaction of the immune system (i.e. immune response) in a host which is mediated by T cells. A T cell response involves the activation of antigen-specific T lymphocyte such as but not limited to cytotoxic T cells (CTLs), T helper cells ($T_H$ cells), central memory T cells (TCM cells), effector memory T cells (TEM cells), and regulatory T cells (Treg cells). A T cell response against a protein is induced, if peptides of the protein are processed within the cell and presented to T cells on the surface of the cell via the MHC I or MHC II pathway. Thus, in the context of the present invention preferably those viral proteins or parts thereof are used for inducing a T cell response that are normally not exposed on the outside of the virus, e.g. non structural or internal proteins or parts of structural or surface proteins not accessible to B-cells on the outside of the virus.

The second polynucleotide encodes a viral protein of a paramyxovirus or variant thereof that induces an anti-pathogenic B cell response against the paramyxovirus. A B cell response is an immune response based on the activation of B lymphocytes, which produce and secrete antigen specific antibodies. B cells involved in such immune response include but are not limited to plasma B cells, memory B cells and B-1 cells. Thus, in the context of the present invention preferably those viral proteins or parts thereof are used for inducing an anti-pathogenic B cell response that are exposed on the outside of the virus, e.g. structural proteins or at least those parts of structural proteins accessible to B-cells on the outside of the virus.

According to a preferred embodiment of the first aspect, the second polynucleotide encodes a viral protein of a paramyxovirus or variant thereof that induces an anti-pathogenic B cell response. A B cell response is an immune response based on the activation of B lymphocytes, which produce and secrete antigen specific antibodies. B cells involved in such immune response include but are not limited to plasma B cells, memory B cells and B-1 cells. Thus, in the context of the present invention preferably those viral proteins or parts thereof are used for inducing an anti-pathogenic B cell response that are exposed on the outside of the virus, e.g. structural and/or surface proteins or at least those parts of structural and/or surface proteins accessible to B-cells on the outside of the virus.

In preferred embodiments of the first aspect the viral protein of a paramyxovirus, which induces a T cell response is a non-structural and/or internal protein of a paramyxovirus, and/or the viral protein of a paramyxovirus, which induces an anti-pathogenic B cell response is a structural and/or surface protein of a paramyxovirus.

It is preferred that the amino acid sequence of the structural (surface) and/or non-structural (internal) protein comprises consecutive segments or a consensus sequence of one or more different paramyxovirus isolates.

In preferred embodiments, the structural protein is a protein exposed on the surface of the native paramyxovirus or a variant thereof. It is preferred that the structural protein triggers a T-cell independent immune response such as but not limited to an antibody mediated immune response or an activation of the complement system. In a particularly preferred embodiment, the structural and/or surface protein induces an antibody mediated immune response. Such antibody mediated immune response is based on the activation of B cells which produce and secrete antigen specific antibodies. B cells involved in such immune response include but are not limited to plasma B cells, memory B cells and B-1 cells.

In a further preferred embodiment, the membrane attachment domain of the protein exposed on the surface of the native paramyxovirus or variant thereof is functionally deleted, thus, either being structurally deleted or structurally present but not fulfilling its biological function. In a particularly preferred embodiment, the amino acid sequence corresponding to the membrane attachment domain is deleted. The deletion of the membrane attachment region serves the purpose of ascertaining that the anti-pathogenic B cell response inducing protein is secreted from the cell into which the expression system of the invention has been introduced.

In a further preferred embodiment the anti-pathogenic B cell response inducing paramyxovirus protein comprises a secretion signal, which targets the protein to the endoplasmatic reticulum (ER). Thus, if naturally present in the respective structural or surface protein it is preferred that the secretion signal is maintained in a modified version of the structural or surface protein.

It is further preferred that the structural and/or surface protein of the native paramyxovirus is selected from the group consisting of fusion protein (F) and any of the attachment glycoproteins G, H, and HN.

The attachment glycoproteins are found in all enveloped viruses and mediate the initial interaction between the viral envelope and the plasma membrane of the host cell via their binding to carbohydrate moieties or cell adhesion domains of proteins or other molecules on the plasma membrane of the host cell. Thereby, attachment glycoproteins bridge the gap between the virus and the membrane of the host cell. Attachment glycoproteins designated as "H" possess hemagglutinin activity and are found in morbilliviruses and henipaviruses, glycoproteins designated as "HN" possess hemagglutinin and neuraminidase activities and are found in respiroviruses, rubulaviruses and avulaviruses. Attachment glycoproteins are designated as "G" when they have neither haemagglutination nor neuraminidase activity. G attachment glycoproteins can be found in all members of Pneumovirinae.

Fusion protein "F" is found in all enveloped viruses and mediates the fusion of the viral envelope with the plasma membrane of the host cell. F is a type I glycoprotein that recognizes receptors present on the cell surface of the host cell to which it binds. F consists of a fusion peptide adjacent to which the transmembrane domains are located, followed by two heptad repeat (HR) regions, HR1 and HR2, respectively. Upon insertion of the fusion peptide into the plasma membrane of the host cell, the HR1 region forms a trimeric coiled coil structure into whose hydrophobic grooves the HR2 regions folds back. Thereby, a hairpin structure is formed that draws the viral lipid bilayer and cellular plasma membrane even closer together and allows for the formation of a fusion pore and consecutively the complete fusion of both lipid bilayers enabling the virus capsid to enter into the cytoplasm of the host cell. All of these features are common in fusion-mediating proteins of enveloped viruses.

In a preferred embodiment of the first aspect, F comprises, essentially consists of or consists of an amino acid sequence of F of one RSV isolate or a consensus amino acid sequence of two or more different RSV isolates, preferably according to SEQ ID NO: 1, more preferably according to SEQ ID NO: 2 or a variant thereof.

In preferred embodiments of the first aspect, the non-structural protein is a conserved internal protein of paramyxoviruses suitable for inducing a T cell mediated immune response against the paramyxovirus, involving the activation of antigen-specific T lymphocyte such as but not limited to cytotoxic T cells (CTLs), T helper cells (Tx cells), central memory T cells (TCM cells), effector memory T cells (TEM cells), and regulatory T cells (Treg cells). Thus, preferably the T cell inducing protein of the paramyxovirus does not comprise a secretion signal.

Preferably, the non-structural and/or internal protein is selected from the group consisting of nucleoprotein N, Matrix proteins M and M2, Phosphoprotein P, non structural proteins NS1 and NS2, and the catalytic subunit of the polymerase (L).

The nucleoprotein N serves several functions which include the encapsidation of the RNA genome into a RNAase-resistant nucleocapsid. N also interacts with the M protein during virus assembly and interacts with the P-L polymerase during transcription and replication of the genome.

The matrix protein M is the most abundant protein in paramyxovirus and is considered to be the central organizer of viral morphology by interacting with the cytoplasmatic tail of the integral membrane proteins and the nucleocapsid. M2 is a second membrane-associated protein that is not glycosylated and is mainly found in pneumovirus.

Phosphoprotein P binds to the N and L proteins and forms part of the RNA polymerase complex in all paramyxoviruses. Large protein L is the catalytic subunit of RNA-dependent RNA polymerase.

The function of non-structural proteins NS1 and NS2 has not yet been identified; however, there are indications that they are involved in the viral replication cycle.

In preferred embodiments, N comprises an amino acid sequence of N, of one RSV isolate or a consensus amino acid sequence of two or more different RSV isolates, preferably according to SEQ ID NO: 3 and wherein M2 comprises an amino acid sequence of M2 of one RSV isolate or a consensus amino acid sequence of two or more different RSV isolates, preferably according to SEQ ID NO: 5. It is further preferred that wherein N comprises the amino acid sequence according to SEQ ID NO: 4 and M2 comprises the amino acid sequence according to SEQ ID NO: 5.

In the context of the present invention, the structural and/or surface protein encoded by the first polynucleotide is located either N- or C-terminally with respect to the non-structural and/or internal protein encoded by the second polynucleotide. In a preferred embodiment, the non-structural and/or internal protein encoded by the second polynucleotide is located C-terminally with respect to the structural and/or surface protein encoded by the first polynucleotide.

More specifically, N, M, M2, P, NS1, NS2, or L can be located N- or C-terminally of F, G, H, or HN. Preferably, N, M, M2, P, NS1, NS2, or L are located C-terminally of F, G, H, or HN. In a more preferred embodiment N or M2 are located C-terminally of F. In a particularly preferred embodiment N is located C-terminally of F.

Accordingly, embodiments of the present invention have the formula X-Y or Y-X, wherein "X" depicts F, G, H, or HN and "Y" depicts N, M, M2, P, NS1, NS2, or L and a "dash" depicts a peptide bond. Preferred arrangements are the following:

F-N, G-N, H-N, HN-N, F-M, G-M, H-M, HN-M, F-M2, G-M2, H-M2, HN-M2, F-P, G-P, H-P, HN-P, F-NS1, G-NS1, H-NS1, HN-NS1, F-NS2, G-NS2, H-NS2, 14N-NS2, F-L, G-L, H-L, HN-L, N-F, N-G, N-H, N-HN, M-F, M-G, M-H, M-HN, M2-F, M2-G, M2-H, M2-HN, P-F, P-G, P-H, P-HN, NS1-FF, NS1-G, NS1-H, NS1-HN, NS2-F, NS2-G, NS2-H, NS2-HN, L-F, L-G, L-H, or L-HN.

It is within the scope of the present invention that every protein can be combined with any other protein.

In preferred embodiments of the first aspect, a polynucleotide encoding a cleavage site is positioned between the first polynucleotide and the second polynucleotide.

It is preferred that this cleavage site is either a self-cleaving site (i.e. a cleavage site within the amino acid sequence where this sequence is cleaved or is cleavable without such cleavage involving any additional molecule or where the peptide-bond formation in this sequence is prevented in the first place) or an endopeptidase cleavage site (i.e. a cleavage cite within the amino acid sequence where this sequence is cleaved or is cleavable by an endopeptidase, e.g. trypsin, pepsin, elastase, thrombin, collagenase, furin, thermolysin, endopeptidase V8, cathepsins). More preferably, the self-cleaving site is a 2A cleavage site selected from the group consisting of a viral 2A peptide or 2A-like peptide of Picornavirus, insect viruses, Aphtoviridae, Rotaviruses and *Trypanosoma*, preferably wherein the 2A cleavage site is the 2 A peptide of foot and mouth disease virus.

In the context of the present invention, the cleavage site can be positioned N-terminally with respect to the structural and/or surface protein encoded by the first polynucleotide and C-terminally with respect to the non-structural and/or internal protein encoded by the second polynucleotide. Alternatively the cleavage site can be positioned C-terminally with respect to the structural and/or surface protein encoded by the first polynucleotide and N-terminally with respect to the non-structural and/or internal protein encoded by the second polynucleotide. More specifically, the cleavage site can be positioned C- or N-terminally with respect to F, G, H, or HN and C- or N-terminally with respect to N, M, M2, P, NS1, NS2, or L. In a preferred embodiment the cleavage site is located N-terminally with respect to N, M, M2, P, NS1, NS2, or L and C-terminally with respect to F, G, H, or HN. It is particularly preferred that the cleavage site is located N-terminally with respect to N and C-terminally with respect to F.

Accordingly, embodiments of the present invention have the formula X-C-Y or Y-C-X, wherein "X" depicts F, G, H, or HN and "Y" depicts N, M, M2, P, NS1, NS2, or L, "C" depicts a cleavage site, and a "dash" depicts a peptide bond. Preferred arrangements are the following:

F-C-N, G-C-N, H-C-N, HN-C-N, F-C-M, G-C-M, H-C-M, HN-C-M, F-C-M2, G-C-M2, H-C-M2, HN-C-M2, F-C-P, G-C-P, H-C-P, HN-C-P, F-C-NS1, G-C-NS1, H-C-NS1, HN-C-NS1, F-C-NS2, G-C-NS2, H-C-NS2, HN-C-NS2, F-C-L, G-C-L, H-C-L, HN-C-L, N-C-F, N-C-G, N-C-H, N-C-HN, M-C-F, M-C-G, M-C-H, M-C-HN, M2-C-F, M2-C-G, M2-C-H, M2-C-HN, P-C-F, P-C-G, P-C-H, P-C-HN, NS1-C-FF, NS1-C-G, NS1-C-H, NS1-C-HN, NS2-C-F, NS2-C-G, NS2-C-H, NS2-C-HN, L-C-F, L-C-G, L-C-H, or L-C-HN. Particularly, preferred is F-C-N.

It is within the scope of the present invention that every protein can be combined with any other protein and that any two proteins can or cannot be connected or linked by a cleavage site.

In preferred embodiment of the first aspect, the expression system further comprises a third polynucleotide encoding a non-structural and/or internal protein of a paramyxovirus or a variant thereof. Preferably, the non-structural and/or internal protein is of a paramyxovirus selected from the group consisting of Pneumovirinae, Paramyxovirinae, Fer-de-Lance-Virus, Nariva-Virus, Salem-Virus, Tupaia-Paramyxovirus, Beilong-Virus, J-Virus, Menangle-Virus, Mossmann-Virus, and Murayama-Virus, more preferably, the Pneumovirinae is selected from the group consisting of Pneumovirus, preferably human respiratory syncytical virus (RSV), murine pneumonia virus, bovine RSV, ovine RSV, caprine RSV, turkey rinotracheitis and Metapneumovirus, preferably human metapneumovirus, avaian metapneumovirus, more preferably, the Paramyxovirinae is selected from the group consisting of Respirovirus, preferably human parainfluenza virus 1 and 3, and Rubulavirus, preferably human parainfluenza virus 2 and 4.

In preferred embodiments the third polynucleotide is comprised on a separate or on the same vector as the first polynucleotide and/or the second polynucleotide.

Accordingly, the first polynucleotide is comprised on one vector and the second polynucleotide is comprised on a second vector and the third polynucleotide is comprised on a third vector. Alternatively or additionally, the first and the second polynucleotide are comprised on the same vector and the third polynucleotide is comprised on a separate vector, or the first and the third polynucleotide are comprised on the same vector and the second polynucleotide is comprised on a separate vector, or the second and the third polynucleotide are comprised on the same vector and the first polynucleotide is comprised on a separate vector. Alternatively or additionally, the first and the second and the third polynucleotide are comprised on the same vector. It is preferred that the first and the second and the third polynucleotide may be comprised on the same vector. It is particularly preferred that the first and the second and the third polynucleotide comprised on the same vector are linked in such that they are expressed as a viral polyprotein. Preferably, the first and the second and the third polynucleotide comprised on the same vector form an open reading frame.

It is further preferred that the non-structural and/or internal protein encoded by the third polynucleotide is a conserved internal protein suitable for inducing a T cell mediated immune response against the virus involving the activation of antigen-specific T lymphocyte such as but not limited to cytotoxic T cells (CTLs), T helper cells (Tx cells), central memory T cells (TCM cells), effector memory T cells (TEM cells), and regulatory T cells (Treg cells).

Preferably, the non-structural and/or internal protein is selected from the group consisting of nucleoprotein N, Matrix proteins M and M2, Phosphoprotein P, non structural proteins NS1 and NS2, and the catalytic subunit of the polymerase (L).

In preferred embodiments, N comprises an amino acid sequence of N, of one RSV isolate or a consensus amino acid sequence of two or more different RSV isolates, preferably according to SEQ ID NO: 3 and wherein M2 comprises an amino acid sequence of M2 of one RSV isolate or a consensus amino acid sequence of two or more different RSV isolates, preferably according to SEQ ID NO: 5. It is further preferred that wherein N comprises the amino acid sequence according to SEQ ID NO: 4 and M2 comprises the amino acid sequence according to SEQ ID NO: 5.

It is preferred that the non-structural and/or internal protein encoded by the third polynucleotide differs from the non-structural and/or internal protein encoded by the second polynucleotide.

The non-structural and/or internal proteins encoded by the second and the third polynucleotide differ from each other in that they comprise amino acid sequences of different viral proteins. For instance, this means that the non-structural and/or internal protein encoded by the second polynucleotide comprises the amino acid sequence of the N protein whilst the non-structural and/or internal protein encoded by the second polynucleotide comprises the amino acid sequence of the M2 protein or vice versa.

The non-structural and/or internal protein encoded by the third polynucleotide can be located either N- or C-terminally of the non-structural and/or internal protein encoded by the second polynucleotide. In a preferred embodiment of the first aspect, the non-structural and/or internal protein encoded by the third polynucleotide is located C-terminally of the non-structural and/or internal protein encoded by the second polynucleotide. More specifically, N or M2 can be located N- or C-terminally of N or M2, preferably N is located C-terminally of M2.

In preferred embodiments a polynucleotide encoding a linker is positioned between the second polynucleotide and the third polynucleotide. It is preferred that the linker is a flexible linker, preferably a flexible linker comprising an amino acid sequence according to SEQ ID NO: 6.

In embodiments of the first aspect, the protein encoded by the second polynucleotide is located N-terminally with respect to the protein encoded by the first polynucleotide and/or the protein of the optional third polynucleotide, or the protein encoded by the second polynucleotide is located C-terminally with respect to the protein encoded by the first polynucleotide and/or the protein of the optional third polynucleotide.

In even more preferred embodiments of this aspect, the first polynucleotide is located N-terminally with respect to the protein encoded by the second polynucleotide and/or the protein of the optional third polynucleotide is located N-terminally with respect to the protein encoded by the first polynucleotide or is located between the protein encoded by the second polynucleotide and the protein encoded by the first polynucleotide; or the protein encoded by the first polynucleotide is located C-terminally with respect to the protein encoded by the second polynucleotide and/or the protein of the optional third polynucleotide is located C-terminally with respect to the protein encoded by the first polynucleotide or is located between the protein encoded by the second polynucleotide and the protein encoded by the first polynucleotide. More specifically, F, G, H, or HN are located C- or N-terminally with respect to N, M, M2, P, NS1, NS2, or L and N, M, M2, P, NS1, NS2, or L are located C- or N-terminally with respect to N or M2. In a preferred embodiment F is located N-terminally with respect to N and M2 is located C-terminally with respect to N.

Accordingly, preferred embodiments of the present invention have the formula X-K-Y, Y-K-X, X-K-Y-Y, Y-Y-K-X, X-Y-K-Y, Y-K-Y-X, X-K-Y-K-Y, Y-K-Y-K-X, X-C-Y, Y-C-X, X-C-Y-Y, Y-Y-C-X, X-Y-C-Y, Y-C-Y-X, X-C-Y-C-Y, Y-C-Y-C-X, X-K-Y-C-Y, Y-C-Y-K-X, X-C-Y-K-Y, or Y-K-Y-C-X, wherein "X" depicts F, G, H, or HN and "Y" depicts N, M, M2, P, NS1, NS2, or L, "K" indicates that one or more peptide linkers are present in this position, "C" indicates that one or more cleavage sites are present in this position and a "dash" depicts a peptide bond. Preferred arrangements are X-C-Y-K-Y. Even more preferred arrangements are the following:

F-K-N, G-K-N, H-K-N, HN-K-N, F-K-M, G-K-M, H-K-M, HN-K-M, F-K-M2, G-K-M2, H-K-M2, HN-K-M2, F-K-P, G-K-P, H-K-P, HN-K-P, F-K-NS1, G-K-NS1, H-K-NS1, HN-K-NS1, F-K-NS2, G-K-NS2, H-K-NS2, HN-K-NS2, F-K-L, G-K-L, H-K-L, HN-K-L, N-K-F, N-K-G, N-K-H, N-K-HN, M-K-F, M-K-G, M-K-H, M-K-HN, M2-K-F, M2-K-G, M2-K-H, M2-K-HN, P-K-F, P-K-G, P-K-H, P-K-HN, NS1-K-FF, NS1-K-G, NS1-K-H, NS1-K-HN, NS2-K-F, NS2-K-G, NS2-K-H, NS2-K-HN, L-K-F, L-K-G, L-K-H, L-K-HN, F-C-N, G-C-N, H-C-N, HN-C-N, F-C-M, G-C-M, H-C-M, HN-C-M, F-C-M2, G-C-M2, H-C-M2, HN-C-M2, F-C-P, G-C-P, H-C-P, HN-C-P, F-C-NS1, G-C-NS1, H-C-NS1, HN-C-NS1, F-C-NS2, G-C-NS2, H-C-NS2, HN-C-NS2, F-C-L, G-C-L, H-C-L, HN-C-L, N-C-F, N-C-G, N-C-H, N-C-FIN, M-C-F, M-C-G, M-C-H, M-C-HN, M2-C-F, M2-C-G, M2-C-H, M2-C-HN, P-C-F, P-C-G, P-C-H, P-C-HN, NS1-C-FF, NS1-C-G, NS1-C-H, NS1-C-HN, NS2-C-F, NS2-C-G, NS2-C-H, NS2-C-HN, L-C-F, L-C-G, L-C-H, or L-C-HN, F-N-M, G-N-M, H-N-M, HN-N-M, F-N-M2, G-N-M2, H-N-M2, HN-N-M2, F-N-P, G-N-P, H-N-P, HN-N-P, F-N-NS1, G-N-NS1, H-N-NS1, HN-N-NS1, F-N-NS2, G-N-NS2, H-N-NS2, HN-N-NS2, F-N-L, G-N-L, H-N-L, HN-N-L, F-M-N, G-M-N, H-M-N, HN-M-N, F-M-P, G-M-P, H-M-P, HN-M-P, F-M-NS1, G-M-NS1, H-M-NS1, HN-M-NS1, F-M-NS2, G-M-NS2, H-M-NS2, HN-M-NS2, F-M-L, G-M-L, H-M-L, HN-M-L, F-M2-N, G-M2-N, H-M2-N, HN-M2-N, F-M2-P, G-M2-P, H-M2-P, HN-M2-P, F-M2-NS1, G-M2-NS1, H-M2-NS1, HN-M2-NS1, F-M2-NS2, G-M2-NS2, H-M2-NS2, HN-M2-NS2, F-M2-L, G-M2-L, H-M2-L, HN-M2-L, F-P-N, G-P-N, H-P-N, HN-P-N, F-P-M, G-P-M, H-P-M, HN-P-M, F-P-M2, G-P-M2, H-P-M2, HN-P-M2, F-P-NS1, G-P-NS1, H-P-NS1, HN-P-NS1, F-P-NS2, G-P-NS2, H-P-NS2, HN-P-NS2, F-P-L, G-P-L, H-P-L, HN-P-L, F-NS1-N, G-NS1-N, H-NS1-N, HN-NS1-N, F-NS1-M, G-NS1-M. H-NS1-M, HN-NS1-M, F-NS1-M2, G-NS1-M2, H-NS1-M2, HN-NS1-M2, F-NS1-P, G-NS1-P, H-NS1-P, HN-NS1-P, F-NS1-NS2, G-NS1-NS2, H-NS1-NS2, HN-NS1-NS2, F-NS1-L, G-NS1-L, H-NS1-L, HN-NS1-L, F-NS2-N, G-NS2-N, H-NS2-N, HN-NS2-N, F-NS2-M, G-NS2-M, H-NS2-M, HN-NS2-M, F-NS2-M2, G-NS2-M2, H-NS2-M2, HN-NS2-M2, F-NS2-P, G-NS2-P, H-NS2-P, HN-NS2-P, F-NS2-NS1, G-NS2-NS1, H-NS2-NS1, HN-NS2-NS1, F-NS2-L, G-NS2-L, H-NS2-L, HN-NS2-L, F-L-N, G-L-N, H-L-N, HN-L-N, F-L-M, G-L-M, H-L-M, HN-L-M, F-L-P, G-L-P, H-L-P, HN-L-P, F-L-NS1, G-L-NS1, H-L-NS1, HN-L-NS1, F-L-NS2, G-L-NS2, H-L-NS2, HN-L-NS2, M-N-F, M-N-G, M-N-H, M-N-HN, M2-N-F, M2-N-G, M2-N-H, M2-N-HN, P-N-F, P-N-G, P-N-H, P-N-HN, NS1-N-F, NS1-N-G, NS1-N-H, NS1-N-HN, NS2-N-F, NS2-N-G, NS2-N-H, NS2-N-HN, L-N-F, L-N-G, L-N-H, L-N-HN, N-M-F, N-M-G, N-M-H, N-M-HN, P-M-F, P-M-G, P-M-H, P-M-HN, NS1-M-F, NS1-M-G, NS1-M-H, NS1-M-HN, NS2-M-F, NS2-M-G, NS2-M-H, NS2-M-HN, L-M-F, L-M-G, L-M-H, L-M-HN, N-M2-F, N-M2-G, N-M2-H, N-M2-HN, P-M2-F, P-M2-G, P-M2-H, P-M2-HN, NS1-M2-F, NS1-M2-G, NS1-M2-H, NS1-M2-HN, NS2-M2-F, NS2-M2-G, NS2-M2-H, NS2-M2-HN, L-M2-F, L-M2-G, L-M2-H, L-M2-HN, N-P-F, N-P-G, N-P-H, N-P-HN, M-P-F, M-P-G, M-P-H, M-P-HN, M2-P-F, M2-P-G, M2-P-H, M2-P-HN, NS1-P-F, NS1-P-G, NS1-P-H, NS1-P-HN, NS2-P-F, NS2-P-G, NS2-P-H, NS2-P-HN, L-P-F, L-P-G, L-P-H, L-P-HN, N-NS1-F, N-NS1-G, N-NS1-H, N-NS1-HN, M-NS1-F, M-NS1-G, M-NS1-H, M-NS1-HN, M2-NS1-F, M2-NS1-G, M2-NS1-H, M2-NS1-HN, P-NS1-F, P-NS1-G, P-NS1-H, P-NS1-HN, NS2-NS1-F, NS2-NS1-G, NS2-NS1-H, NS2-NS1-HN, L-NS1-F, L-NS1-G, L-NS1-H, L-NS1-HN, N-NS2-F, N-NS2-G, N-NS2-H, N-NS2-HN, M-NS2-F, M-NS2-G, M-NS2-H, M-NS2-HN, M2-NS2-F, M2-NS2-G, M2-NS2-H, M2-NS2-HN, P-NS2-F, P-NS2-G, P-NS2-H, P-NS2-HN, NS1-NS2-F, NS1-NS2-G, NS1-NS2-H, NS1-NS2-1-1N, L-NS2-F, L-NS2-G, L-NS2-H, L-NS2-HN, N-L-F, N-L-G, N-L-H, N-L-HN, M-L-F, M-L-G, M-L-H, M-L-HN, M2-L-F, M2-L-G, M2-L-H, M2-L-HN, P-L-F, P-L-G, P-L-H, P-L-HN, NS1-L-F, NS1-L-G, NS1-L-H, NS1-L-HN, NS2-L-F, NS2-L-G, NS2-L-H, NS2-L-HN, F-K-N-N, G-K-N-N, H-K-N-N, HN-K-N-N, F-K-N-M, G-K-N-M, H-K-N-M, HN-K-N-M, F-K-N-M2, G-K-N-M2, H-K-N-M2, HN-K-N-M2, F-K-N-P, G-K-N-P, H-K-N-P, HN-K-N-P, F-K-N-NS1, G-K-N-NS1, H-K-N-NS1, HN-K-N-NS1, F-K-N-NS2, G-K-N-NS2, H-K-N-NS2, HN-K-N-NS2, F-K-N-L, G-K-N-L, H-K-N-L, HN-K-N-L, F-C-N-N, G-C-N-N, H-C-N-N, HN-C-N-N, F-C-N-M, G-C-N-M, H-C-N-M, HN-C-N-M, F-C-N-M2, G-C-N-M2, H-C-N-M2, HN-C-N-M2, F-C-N-P, G-C-N-P, H-C-N-P, HN-C-N-P, F-C-N-NS1, G-C-N-NS1, H-C-N-NS1, HN-C-N-NS1, F-C-N-NS2, G-C-N-NS2, H-C-N-NS2, HN-C-N-NS2, F-C-N-L, G-C-N-L, H-C-N-L, HN-C-N-L, F-K-M-M, G-K-M-M, H-K-M-M, HN-K-M-M, F-K-M-M2, G-K-M-M2, H-K-M-M2, HN-K-M-M2, F-K-M-N, G-K-M-N, H-K-M-N, HN-K-M-N, F-K-M-P, G-K-M-P, H-K-M-P, HN-K-M-P, F-K-M-NS1, G-K-M-NS1, H-K-M-NS1, HN-K-M-NS1, F-K-M-NS2, G-K-M-NS2, H-K-M-NS2, HN-K-M-NS2, F-K-M-L, G-K-M-L, H-K-M-L, HN-K-M-L, F-K-M2-M, G-K-M2-M, H-K-M2-M, HN-K-M2-M, F-K-M2-N, G-K-M2-N, H-K-M2-N, HN-K-M2-N, F-K-M2-P, G-K-M2-P, H-K-M2-P, HN-K-M2-P, F-K-M2-NS1, G-K-M2-NS1, H-K-M2-NS1, HN-K-M2-NS1, F-K-M2-NS2, G-K-M2-NS2, H-K-M2-NS2, HN-K-M2-NS2, F-K-M2-L, G-K-M2-L, H-K-M2-L, HN-K-M2-L, F-K-P-N, G-K-P-N, H-K-P-N, HN-K-P-N, F-K-P-M, G-K-P-M, H-K-P-M, HN-K-P-M, F-K-P-M2, G-K-P-M2, H-K-P-M2, HN-K-P-M2, F-K-P-P, G-K-P-P, H-K-P-P, HN-K-P-P, F-K-P-NS1, G-K-P-NS1, H-K-P-NS1, HN-K-P-NS1, F-K-P-NS2, G-K-P-NS2, H-K-P-NS2, HN-K-P-NS2, F-K-P-L, G-K-P-L, H-K-P-L, HN-K-P-L, F-K-NS1-N, G-K-NS1-N, H-K-NS1-N, HN-K-NS1-N, F-K-NS1-M, G-K-NS1-M, H-K-NS1-M, HN-K-NS1-M, F-K-NS1-M2, G-K-NS1-M2, H-K-NS1-M2, HN-K-NS1-M2, F-K-NS1-P, G-K-NS1-P, H-K-NS1-P, HN-K-NS1-P, F-K-NS1-NS1, G-K-NS1-NS1, H-K-NS1-NS1, HN-K-NS1-NS1, F-K-NS1-NS2, G-K-NS1-NS2, H-K-NS1-NS2, HN-K-NS1-NS2, F-K-NS1-L, G-K-NS1-L, H-K-NS1-L, F-K-NS2-N, G-K-NS2-N, H-K-NS2-N,

HN-K-NS2-N, F-K-NS2-M, G-K-NS2-M, H-K-NS2-M, HN-K-NS2-M, F-K-NS2-M2, G-K-NS2-M2, H-K-NS2-M2, HN-K-NS2-M2, F-K-NS2-P, G-K-NS2-P, H-K-NS2-P, HN-K-NS2-P, F-K-NS2-NS1, G-K-NS2-NS1, H-K-NS2-NS1, HN-K-NS2-NS1, F-K-NS2-NS2, G-K-NS2-NS2, H-K-NS2-NS2, HN-K-NS2-NS2, F-K-NS2-L, G-K-NS2-L, H-K-NS2-L, HN-K-NS2-L, F-K-L-N, G-K-L-N, H-K-L-N, HN-K-L-N, F-K-L-M, G-K-L-M, H-K-L-M, HN-K-L-M, F-K-L-M2, G-K-L-M2, H-K-L-M2, HN-K-L-M2, F-K-L-P, G-K-L-P, H-K-L-P, HN-K-L-P, F-K-L-NS1, G-K-L-NS1, H-K-L-NS1, HN-K-L-NS1, F-K-L-NS2, G-K-L-NS2, H-K-L-NS2, HN-K-L-NS2, F-K-L-L, G-K-L-L, H-K-L-L, HN-K-L-L, F-N-K-N, G-N-K-N, H-N-K-N, HN-N-K-N, F-N-K-M, G-N-K-M, H-N-K-M, HN-N-K-M, F-N-K-M2, G-N-K-M2, H-N-K-M2, HN-N-K-M2, F-N-K-P, G-N-K-P, H-N-K-P, HN-N-K-P, F-N-K-NS1, G-N-K-NS1, H-N-K-NS1, HN-N-K-NS1, F-N-K-NS2, G-N-K-NS2, H-N-K-NS2, HN-N-K-NS2, F-N-K-L, G-N-K-L, H-N-K-L, HN-N-K-L, F-M-K-N, G-M-K-N, H-M-K-N, HN-M-K-N, F-M-K-M, G-M-K-M, H-M-K-M, HN-M-K-M, F-M-K-M2, G-M-K-M2, H-M-K-M2, HN-M-K-M2, F-M-K-P, G-M-K-P, H-M-K-P HN-M-K-P, F-M-K-NS1, G-M-K-NS1, H-M-K-NS1, HN-M-K-NS1, F-M-K-NS2, G-M-K-NS2, H-M-K-NS2, HN-M-K-NS2, F-M-K-L, G-M-K-L, H-M-K-L, HN-M-K-L, F-M2-K-N, G-M2-K-N, H-M2-K-N, HN-M2-K-N, F-M2-K-M, G-M2-K-M, H-M2-K-M, HN-M2-K-M, F-M2-K-M2, G-M2-K-M2, H-M2-K-M2, HN-M2-K-M2, F-M2-K-P, G-M2-K-P, H-M2-K-P HN-M2-K-P, F-M2-K-NS1, G-M2-K-NS1, H-M2-K-NS1, HN-M2-K-NS1, F-M2-K-NS2, G-M2-K-NS2, H-M2-K-NS2, HN-M2-K-NS2, G-M2-K-L, H-M2-K-L, HN-M2-K-L, F-P-K-N, G-P-K-N, H-P-K-N, HN-P-K-N, F-P-K-M, G-P-K-M, H-P-K-M, HN-P-K-M, F-P-K-M2, G-P-K-M2, H-P-K-M2; HN-P-K-M2, F-P-K-P, G-P-K-P, H-P-K-P, HN-P-K-P, F-P-K-NS1, G-P-K-NS1, H-P-K-NS1, HN-P-K-NS1, F-P-K-NS2, G-P-K-NS2, H-P-K-NS2, HN-P-K-NS2, F-P-K-L, G-P-K-L, H-P-K-L, HN-P-K-L, F-NS1-K-N, G-NS1-K-N, H-NS1-K-N, HN-NS1-K-N, F-NS1-K-M, G-NS1-K-M, H-NS1-K-M: HN-NS1-K-M, F-NS1-K-M2, G-NS1-K-M2, H-NS1-K-M2; HN-NS1-K-M2, F-NS1-K-P, G-NS1-K-P, H-NS1-K-P, HN-NS1-K-P, F-NS1-K-NS1, G-NS1-K-NS1, H-NS1-K-NS1, HN-NS1-K-NS1, F-NS1-K-NS2, G-NS1-K-NS2, H-NS1-K-NS2, HN-NS1-K-NS2, F-NS1-K-L, G-NS1-K-L, H-NS1-K-L, HN-NS1-K-L, F-NS2-K-N, G-NS2-K-N, H-NS2-K-N, HN-NS2-K-N, F-NS2-K-M, G-NS2-K-M, H-NS2-K-M, HN-NS2-K-M, F-NS2-K-M2, G-NS2-K-M2, H-NS2-K-M2, HN-NS2-K-M2, F-NS2-K-P, G-NS2-K-P, H-NS2-K-P, HN-NS2-K-P, F-NS2-K-NS1, G-NS2-K-NS1, H-NS2-K-NS1, HN-NS2-K-NS1, F-NS2-K-NS2, G-NS2-K-NS2, H-NS2-K-NS2, HN-NS2-K-NS2, F-NS2-K-L, G-NS2-K-L, H-NS2-K-L, HN-NS2-K-L, F-C-M-M, G-C-M-M, H-C-M-M, HN-C-M-M, F-C-M-M2, G-C-M-M2, H-C-M-M2, HN-C-M-M2, F-C-M-N, G-C-M-N, H-C-M-N, HN-C-M-N, F-C-M-P, G-C-M-P, H-C-M-P, HN-C-M-P, F-C-M-NS1, G-C-M-NS1, H-C-M-NS1, HN-C-M-NS1, F-C-M-NS2, G-C-M-NS2, H-C-M-NS2, HN-C-M-NS2, F-C-M-L, G-C-M-L, H-C-M-L, HN-C-M-L, F-C-M2-M, G-C-M2-M, H-C-M2-M, HN-C-M2-M, F-C-M2-N, G-C-M2-N, H-C-M2-N, HN-C-M2-N, F-C-M2-P, G-C-M2-P, H-C-M2-P, HN-C-M2-P, F-C-M2-NS1, G-C-M2-NS1, H-C-M2-NS1, HN-C-M2-NS1, F-C-M2-NS2, G-C-M2-NS2, H-C-M2-NS2, HN-C-M2-NS2, F-C-M2-L, G-C-M2-L, H-C-M2-L, HN-C-M2-L, F-C-P-N, G-C-P-N, H-C-P-N, HN-C-P-N, F-C-P-M, G-C-P-M, H-C-P-M, HN-C-P-M, F-C-P-M2, G-C-P-M2, H-C-P-M2, HN-C-P-M2, F-C-P-P, G-C-P-P, H-C-P-P, HN-C-P-P, F-C-P-NS1, G-C-P-NS1, H-C-P-NS1, HN-C-P-NS1, F-C-P-NS2, G-C-P-NS2, H-C-P-NS2, HN-C-P-NS2, F-C-P-L, G-C-P-L, H-C-P-L, HN-C-P-L, F-C-NS1-N, G-C-NS1-N, H-C-NS1-N, HN-C-NS1-N, F-C-NS1-M, G-C-NS1-M, H-C-NS1-M, HN-C-NS1-M, F-C-NS1-M2, G-C-NS1-M2, H-C-NS1-M2, HN-C-NS1-M2, F-C-NS1-P, G-C-NS1-P, H-C-NS1-P, HN-C-NS1-P, F-C-NS1-NS1, G-C-NS1-NS1, H-C-NS1-NS1, HN-C-NS1-NS1, F-C-NS1-NS2, G-C-NS1-NS2, H-C-NS1-NS2, HN-C-NS1-NS2, F-C-NS1-L, G-C-NS1-L, H-C-NS1-L, HN-C-NS1-L, F-C-NS2-N, G-C-NS2-N, H-C-NS2-N, HN-C-NS2-N, F-C-NS2-M, G-C-NS2-M, H-C-NS2-M, HN-C-NS2-M, F-C-NS2-M2, G-C-NS2-M2, H-C-NS2-M2, HN-C-NS2-M2, F-C-NS2-P, G-C-NS2-P, H-C-NS2-P, HN-C-NS2-P, F-C-NS2-NS1, G-C-NS2-NS1, H-C-NS2-NS1, HN-C-NS2-NS1, F-C-NS2-NS2, G-C-NS2-NS2, H-C-NS2-NS2, HN-C-NS2-NS2, F-C-NS2-L, G-C-NS2-L, H-C-NS2-L, HN-C-NS2-L, F-C-L-N, G-C-L-N, H-C-L-N, HN-C-L-N, F-C-L-M, G-C-L-M, H-C-L-M, HN-C-L-M, F-C-L-M2, G-C-L-M2, H-C-L-M2, HN-C-L-M2, F-C-L-P, G-C-L-P, H-C-L-P, HN-C-L-P, F-C-L-NS1, G-C-L-NS1, H-C-L-NS1, HN-C-L-NS1, F-C-L-NS2, G-C-L-NS2, H-C-L-NS2, HN-C-L-NS2, F-C-L-L, G-C-L-L, HN-C-L-L, F-N-C-N, G-N-C-N, H-N-C-N, HN-N-C-N, F-N-C-M, G-N-C-M, H-N-C-M, HN-N-C-M, F-N-C-M2, G-N-C-M2, H-N-C-M2, HN-N-C-M2, F-N-C-P, G-N-C-P, H-N-C-P, HN-N-C-P, F-N-C-NS1, G-N-C-NS1, H-N-C-NS1, HN-N-C-NS1, F-N-C-NS2, G-N-C-NS2, H-N-C-NS2, HN-N-C-NS2, F-N-C-L, G-N-C-L, H-N-C-L, HN-N-C-L, F-M-C-N, G-M-C-N, H-M-C-N, HN-M-C-N, F-M-C-M, G-M-C-M, H-M-C-M, HN-M-C-M, F-M-C-M2, G-M-C-M2, H-M-C-M2, HN-M-C-M2, F-M-C-P, G-M-C-P, H-M-C-P HN-M-C-P, F-M-C-NS1, G-M-C-NS1, H-M-C-NS1, HN-M-C-NS1, F-M-C-NS2, G-M-C-NS2, H-M-C-NS2, HN-M-C-NS2, F-M-C-L, G-M-C-L, H-M-C-L, HN-M-C-L, F-M2-C-N, G-M2-C-N, H-M2-C-N, HN-M2-C-N, F-M2-C-M, G-M2-C-M, H-M2-C-M, HN-M2-C-M, F-M2-C-M2, G-M2-C-M2, H-M2-C-M2, HN-M2-C-M2, F-M2-C-P, G-M2-C-P, H-M2-C-P HN-M2-C-P, F-M2-C-NS1, G-M2-C-NS1, H-M2-C-NS1, HN-M2-C-NS1, F-M2-C-NS2, G-M2-C-NS2, H-M2-C-NS2, HN-M2-C-NS2, F-M2-C-L, G-M2-C-L, H-M2-C-L, HN-M2-C-L, F-P-C-N, G-P-C-N, H-P-C-N, HN-P-C-N, F-P-C-M, G-P-C-M, H-P-C-M, HN-P-C-M, F-P-C-M2, G-P-C-M2, H-P-C-M2; F-P-C-P. G-P-C-P, H-P-C-P, HN-P-C-P, F-P-C-NS1, G-P-C-NS1, H-P-C-NS1, HN-P-C-NS1, F-P-C-NS2, G-P-C-NS2, H-P-C-NS2, HN-P-C-NS2, F-P-C-L, G-P-C-L, H-P-C-L, HN-P-C-L, F-NS1-C-N, G-NS1-C-N, H-NS1-C-N, HN-NS1-C-N, F-NS1-C-M, G-NS1-C-M, H-NS1-C-M; HN-NS1-C-M, F-NS1-C-M2, G-NS1-C-M2, H-NS1-C-M2; HN-NS1-C-M2, F-NS1-C-P, G-NS1-C-P, H-NS1-C-P, HN-NS1-C-P, F-NS1-C-NS1, G-NS1-C-NS1, H-NS1-C-NS1, HN-NS1-C-NS1, F-NS1-C-NS2, G-NS1-C-NS2, H-NS1-C-NS2, HN-NS1-C-NS2, F-NS1-C-L, G-NS1-C-L, H-NS1-C-L, HN-NS1-C-L, F-NS2-C-N, G-NS2-C-N, H-NS2-C-N, HN-NS2-C-N. F-NS2-C-M, G-NS2-C-M, H-NS2-C-M, HN-NS2-C-M, F-NS2-C-M2, G-NS2-C-M2, H-NS2-C-M2, HN-NS2-C-M2, F-NS2-C-P, G-NS2-C-P, H-NS2-C-P, HN-NS2-C-P, F-NS2-C-NS1, G-NS2-C-NS1, H-NS2-C-NS1, HN-NS2-C-NS1, F-NS2-C-NS2, G-NS2-C-NS2, H-NS2-C-NS2, HN-NS2-C-NS2, F-NS2-C-L, G-NS2-C-L, H-NS2-C-L, HN-NS2-C-L, F-L-K-N, G-L-K-N, H-L-K-N, HN-L-K-N, F-L-K-M, G-L-K-M, H-L-K-M, HN-L-K-M, F-L-K-M2, G-L-K-M2, H-L-K-M2, HN-L-K-M2, F-L-K-P, G-L-K-P, H-L-K-P, HN-L-K-P, F-L-K-NS1, G-L-K-NS1, H-L-K-NS1, HN-L-K-NS1, F-L-K-NS2, G-L-K-NS2, H-L-K-NS2, HN-L-K-NS2, F-L-K-L, G-L-K-L, H-L-K-L, HN-L-K-L, F-L-C-N, G-L-C-N, H-L-C-N, HN-L-C-N, F-L-C-M, G-L-C-M, H-L-C-M, HN-L-C-M, F-L-C-M2, G-L-C-M2, H-L-C-M2, HN-L-C-M2, F-L-C-P, G-L-C-P,

H-L-C-P, HN-L-C-P, F-L-C-NS1, G-L-C-NS1, H-L-C-NS1, HN-L-C-NS1, F-L-C-NS2, G-L-C-NS2, H-L-C-NS2, HN-L-C-NS2, F-L-C-L, G-L-C-L, H-L-C-L, HN-L-C-L, F-K-N-K-N, G-K-N-K-N, H-K-N-K-N, HN-K-N-K-N, F-K-M-K-N, G-K-M-K-N, H-K-M-K-N, HN-K-M-K-N, F-K-M2-K-N, G-K-M2-K-N, H-K-M2-K-N, HN-K-M2-K-N, F-K-P-K-N, G-K-P-K-N, H-K-P-K-N, HN-K-P-K-N, F-K-NS1-K-N, G-K-NS1-K-N, H-K-NS1-K-N, HN-K-NS1-K-N, F-K-NS2-K-N, G-K-NS2-K-N, H-K-NS2-K-N, HN-K-NS2-K-N, F-K-L-K-N, G-K-L-K-N, H-K-L-K-N, HN-K-L-K-N, F-K-N-K-M, G-K-N-K-M, H-K-N-K-M, HN-K-N-K-M, F-K-M-K-M, G-K-M-K-M, H-K-M-K-M, HN-K-M-K-M, F-K-M2-K-M, G-K-M2-K-M, H-K-M2-K-M, HN-K-M2-K-M, F-K-P-K-M, G-K-P-K-M, H-K-P-K-M, HN-K-P-K-M, F-K-NS1-K-M, G-K-NS1-K-M, H-K-NS1-K-M, HN-K-NS1-K-M, F-K-NS2-K-M, G-K-NS2-K-M, H-K-NS2-K-M, HN-K-NS2-K-M, F-K-L-K-M, G-K-L-K-M, H-K-L-K-M, HN-K-L-K-M, F-K-N-K-M2, G-K-N-K-M2, H-K-N-K-M2, HN-K-N-K-M2, F-K-M-K-M2, G-K-M-K-M2, H-K-M-K-M2, HN-K-M-K-M2, F-K-M2-K-M2, G-K-M2-K-M2, H-K-M2-K-M2, HN-K-M2-K-M2, F-K-P-K-M2, G-K-P-K-M2, H-K-P-K-M2, HN-K-P-K-M2, F-K-NS1-K-M2, G-K-NS1-K-M2, H-K-NS1-K-M2, HN-K-NS1-K-M2, F-K-NS2-K-M2, G-K-NS2-K-M2, H-K-NS2-K-M2, HN-K-NS2-K-M2, F-K-L-K-M2, G-K-L-K-M2, H-K-L-K-M2, HN-K-L-K-M2, F-K-N-K-P, G-K-N-K-P, H-K-N-K-P, HN-K-N-K-P, F-K-M-K-P, G-K-M-K-P, H-K-M-K-P, HN-K-M-K-P, F-K-M2-K-P, G-K-M2-K-P, H-K-M2-K-P, HN-K-M2-K-P, F-K-P-K-P, G-K-P-K-P, H-K-P-K-P, HN-K-P-K-P, F-K-NS1-K-P, G-K-NS1-K-P, H-K-NS1-K-P, HN-K-NS1-K-P, F-K-NS2-K-P, G-K-NS2-K-P, H-K-NS2-K-P, HN-K-NS2-K-P, F-K-L-K-P, G-K-L-K-P, H-K-L-K-P, HN-K-L-K-P, F-K-N-K-NS1, G-K-N-K-NS1, H-K-N-K-NS1, HN-K-N-K-NS1, F-K-M-K-NS1, G-K-M-K-NS1, H-K-M-K-NS1, HN-K-M-K-NS1, F-K-M2-K-NS1, G-K-M2-K-NS1, H-K-M2-K-NS1, HN-K-M2-K-NS1, F-K-P-K-NS1, G-K-P-K-NS1, H-K-P-K-NS1, HN-K-P-K-NS1, F-K-NS1-K-NS1, G-K-NS1-K-NS1, H-K-NS1-K-NS1, HN-K-NS1-K-NS1, F-K-NS2-K-NS1, G-K-NS2-K-NS1, H-K-NS2-K-NS1, HN-K-NS2-K-NS1, F-K-L-K-NS1, G-K-L-K-NS1, H-K-L-K-NS1, HN-K-L-K-NS1, F-K-N-K-NS2, G-K-N-K-NS2, H-K-N-K-NS2, HN-K-N-K-NS2, F-K-M-K-NS2, G-K-M-K-NS2, H-K-M-K-NS2, HN-K-M-K-NS2, F-K-M2-K-NS2, G-K-M2-K-NS2, H-K-M2-K-NS2, HN-K-M2-K-NS2, F-K-P-K-NS2, G-K-P-K-NS2, H-K-P-K-NS2, HN-K-P-K-NS2, F-K-NS1-K-NS2 G-K-NS1-K-NS2, H-K-NS1-K-NS2, HN-K-NS1-K-NS2, F-K-NS2-K-NS2 G-K-NS2-K-NS2, H-K-NS2-K-NS2, HN-K-NS2-K-NS2, F-K-L-K-NS2, G-K-L-K-NS2, H-K-L-K-NS2, HN-K-L-K-NS2, F-K-N-K-L, G-K-N-K-L, H-K-N-K-L, HN-K-N-K-K, F-K-M-K-L, G-K-M-K-L, H-K-M-K-L, HN-K-M-K-L, F-K-M2-K-L, G-K-M2-K-L, H-K-M2-K-L, HN-K-M2-K-L, F-K-P-K-L, G-K-P-K-L, H-K-P-K-L, HN-K-P-K-L, F-K-NS1-K-L, G-K-NS1-K-L, H-K-NS1-K-L, HN-K-NS1-K-L, F-K-NS2-K-L, G-K-NS2-K-L, H-K-NS2-K-L, HN-K-NS2-K-L, F-K-L-K-L, G-K-L-K-L, H-K-L-K-L, HN-K-L-K-L, N-K-N-F, N-K-N-G, N-K-N-H, N-K-N-HN, M-K-N-F, M-K-N-G, M-K-N-H, M-K-N-HN, M2-K-N-F, M2-K-N-G, M2-K-N-H, M2-K-N-HN, P-K-N-F, P-K-N-G, P-K-N-H, P-K-N-HN, NS1-K-N-F, NS1-K-N-G, NS1-K-N-H, NS1-K-N-HN, NS2-K-N-F, NS2-K-N-G, NS2-K-N-H, NS2-K-N-HN, L-K-N-F, L-K-N-G, L-K-N-H, L-K-N-HN, N-K-M-F, N-K-M-G, N-K-M-H, N-K-M-HN, M-K-M-F, M-K-M-G, M-K-M-H, M-K-M-HN, M2-K-M-F, M2-K-M-G, M2-K-M-H, M2-K-M-HN, P-K-M-F, P-K-M-G, P-K-M-H, P-K-M-HN, NS1-K-M-F, NS1-K-M-G, NS1-K-M-H, NS1-K-M-HN, NS2-K-M-F, NS2-K-M-G, NS2-K-M-H, NS2-K-M-HN, L-K-M-F, L-K-M-G, L-K-M-H, L-K-M-HN, N-K-M2-F, N-K-M2-G, N-K-M2-H, N-K-M2-HN, M-K-M2-F, M-K-M2-G, M-K-M2-H, M-K-M2-HN, M2-K-M2-F, M2-K-M2-G, M2-K-M2-H, M2-K-M2-HN, P-K-M2-F, P-K-M2-G, P-K-M2-H, P-K-M2-HN, NS1-K-M2-F, NS1-K-M2-G, NS1-K-M2-H, NS1-K-M2-HN, NS2-K-M2-F, NS2-K-M2-G, NS2-K-M2-H, NS2-K-M2-HN, L-K-M2-F, L-K-M2-G, L-K-M2-H, L-K-M2-HN, N-K-P-F, N-K-P-G, N-K-P-H, N-K-P-HN, M-K-P-F, M-K-P-G, M-K-P-H, M-K-P-HN, M2-K-P-F, M2-K-P-G, M2-K-P-H, M2-K-P-HN, P-K-P-F, P-K-P-G, P-K-P-H, NS1-K-P-F, NS1-K-P-G, NS1-K-P-H, NS1-K-P-HN, NS2-K-P-F, NS2-K-P-G, NS2-K-P-H, NS2-K-P-HN, L-K-P-F, L-K-P-G, L-K-P-H, N-K-NS1-F, N-K-NS1-G, N-K-NS1-H, N-K-NS1-HN, M-K-NS1-F, M-K-NS1-G, M-K-NS1-H, M-K-NS1-HN, M2-K-NS1-F, M2-K-NS1-G, M2-K-NS1-H, M2-K-NS1-HN, P-K-NS1-F, P-K-NS1-G, P-K-NS1-H, P-K-NS1-HN, NS1-K-NS1-F, NS1-K-NS1-G, NS1-K-NS1-H, NS1-K-NS1-HN, NS2-K-NS1-F, NS2-K-NS1-G, NS2-K-NS1-H, NS2-K-NS1-HN, L-K-NS1-F, L-K-NS1-G, L-K-NS1-H, L-K-NS1-HN, N-K-NS2-F, N-K-NS2-G, N-K-NS2-H, N-K-NS2-HN, M-K-NS2-F, M-K-NS2-G, M-K-NS2-H, M-K-NS2-HN, M2-K-NS2-F, M2-K-NS2-G, M2-K-NS2-H, M2-K-NS2-HN, P-K-NS2-F, P-K-NS2-G, P-K-NS2-H, P-K-NS2-HN, NS1-K-NS2-F, NS1-K-NS2-G, NS1-K-NS2-H, NS1-K-NS2-HN, NS2-K-NS2-F, NS2-K-NS2-G, NS2-K-NS2-H, NS2-K-NS2-HN, L-K-NS2-F, L-K-NS2-G, L-K-NS2-H, L-K-NS2-HN, N-K-L-F, N-K-L-G, N-K-L-H, N-K-L-HN, M-K-L-F, M-K-L-G, M-K-L2-H, M-K-L-HN, M2-K-L-F, M2-K-L-G, M2-K-L-H, M2-K-L-HN, P-K-L-F, P-K-L-G, P-K-L-H, P-K-L-HN, NS1-K-L-F, NS1-K-L-G, NS1-K-L-H, NS2-K-L-F, NS2-K-L-G, NS2-K-L-H, NS2-K-L-HN, L-K-L-F, L-K-L-G, L-K-L-H, L-K-L-HN, N-N-K-F, N-N-K-G, N-N-K-H, N-N-K-HN, N-M-K-F, N-M-K-G, N-M-K-H, N-M-K-HN, N-M2-K-F, N-M2-K-G, N-M2-K-H, N-M2-K-HN, N-P-K-F, N-P-K-G, N-P-K-H, N-NS1-K-F, N-NS1-K-G, N-NS1-K-H, N-NS1-K-HN, N-NS2-K-F, N-NS2-K-G, N-NS2-K-H, N-NS2-K-HN, N-L-K-F, N-L-K-G, N-L-K-H, N-L-K-HN, M-N-K-F, M-N-K-G, M-N-K-H, M-N-K-HN. M-M-K-F, M-M-K-G, M-M-K-H, M-M-K-HN, M-M2-K-F, M-M2-K-G, M-M2-K-H, M-M2-K-HN, M-P-K-F, M-P-K-G, M-P-K-H, M-P-K-HN, M-NS1-K-F, M-NS1-K-G, M-NS1-K-H, M-NS1-K-HN, M-NS2-K-F, M-NS2-K-G, M-NS2-K-H, M-NS2-K-HN, M-L-K-F, M-L-K-G, M-L-K-H, M-L-K-HN, M2-N-K-F, M2-N-K-G, M2-N-K-H, M2-N-K-HN, M2-M-K-F, M2-M-K-G, M2-M-K-H, M2-M-K-HN, M2-M2-K-F, M2-M2-K-G, M2-M2-K-H, M2-M2-K-HN, M2-P-K-F, M2-P-K-G, M2-P-K-H, M2-P-K-HN, M2-NS1-K-F, M2-NS1-K-G, M2-NS1-K-H, M2-NS1-K-HN, M2-NS2-K-F, M2-NS2-K-G, M2-NS2-K-H, M2-NS2-K-HN, M2-L-K-F, M2-L-K-G, M2-L-K-H, M2-L-K-HN, P-N-K-F, P-N-K-G, P-N-K-H, P-N-K-HN, P-M-K-F, P-M-K-G, P-M-K-H, P-M-K-HN, P-M2-K-F, P-M2-K-G, P-M2-K-H, P-M2-K-HN, P-P-K-F, P-P-K-G, P-P-K-H, P-P-K-HN, P-NS1-K-F, P-NS1-K-G, P-NS1-K-H, P-NS1-K-HN, P-NS2-K-F, P-NS2-K-G, P-NS2-K-H, P-NS2-K-HN, P-L-K-F, P-L-K-G, P-L-K-H, P-L-K-HN, NS1-N-K-F, NS1-N-K-G, NS1-N-K-H, NS1-N-K-HN, NS1-M-K-F, NS1-M-K-G, NS1-M-K-H, NS1-M-K-HN, NS1-M2-K-F, NS1-M2-K-G, NS1-M2-K-H, NS1-M2-K-HN, NS1-P-K-F, NS1-P-K-G, NS1-P-K-H, NS1-P-K-HN, NS1-NS1-K-F, NS1-NS1-K-G, NS1-NS1-K-H, NS1-NS1-K-HN, NS1-NS2-K-F, NS1-NS2-K-G, NS1-NS2-K-H, NS1-NS2-K-HN, NS1-L-K-F, NS1-L-K-G, NS1-L-K-H, NS1-L-K-HN, NS2-N-K-F, NS2-N-K-G, NS2-N-K-H, NS2-N-K-HN, NS2-M-K-F, NS2-M-K-G, NS2-M-K-H, NS2-M-K-HN, NS2-M2-K-F, NS2-M2-K-G, NS2-M2-K-H, NS2-M2-K-HN, NS2-P-K-F, NS2-P-

K-G, NS2-P-K-H, NS2-NS1-K-F, NS2-NS1-K-G, NS2-NS1-K-H, NS2-NS1-K-HN, NS2-NS2-K-F, NS2-NS2-K-G, NS2-NS2-K-H, NS2-NS2-K-HN, NS2-L-K-F, NS2-L-K-G, NS2-L-K-H, NS2-L-K-HN, L-N-K-F, L-N-K-G, L-N-K-H, L-N-K-HN, L-M-K-F, L-M-K-G, L-M-K-H, L-M-K-HN, L-M2-K-F, L-M2-K-G, L-M2-K-H, L-M2-K-HN, L-L-K-F, L-P-K-G, L-P-K-H, L-P-K-HN, L-NS1-K-F, L-NS1-K-G, L-NS1-K-H, L-NS1-K-HN, L-NS2-K-F, L-NS2-K-G, L-NS2-K-H, L-NS2-K-HN, L-L-K-F, L-L-K-G, L-L-K-H, L-L-K-HN, N-K-N-K-F, N-K-N-K-G, N-K-N-K-H, N-K-N-K-HN, N-K-M-K-F, N-K-M-K-G, N-K-M-K-H, N-K-M-K-HN, N-K-M2-K-F, N-K-M2-K-G, N-K-M2-K-H, N-K-M2-K-HN, N-K-P-K-F, N-K-P-K-G, N-K-P-K-H, N-K-P-K-HN, N-K-NS1-K-F, N-K-NS1-K-G, N-K-NS1-K-H, N-K-NS1-K-HN, N-K-NS2-K-F, N-K-NS2-K-G, N-K-NS2-K-H, N-K-NS2-K-HN, N-K-L-K-F, N-K-L-K-G, N-K-L-K-H, N-K-L-K-HN, M-K-N-K-F, M-K-N-K-G, M-K-N-K-H, M-K-N-K-HN, M-K-M-K-F, M-K-M-K-G, M-K-M-K-H, M-K-M-K-HN, M-K-M2-K-F, M-K-M2-K-G, M-K-M2-K-H, M-K-M2-K-HN, M-K-P-K-F, M-K-P-K-G, M-K-P-K-H, M-K-P-K-HN, M-K-NS1-K-F, M-K-NS1-K-G, M-K-NS1-K-H, M-K-NS1-K-HN, M-K-NS2-K-F, M-K-NS2-K-G, M-K-NS2-K-H, M-K-NS2-K-HN, M-K-L-K-F, M-K-L-K-G, M-K-L-K-H, M-K-L-K-HN, M2-K-N-K-F, M2-K-N-K-G, M2-K-N-K-H, M2-K-N-K-HN, M2-K-M-K-F, M2-K-M-K-G, M2-K-M-K-H, M2-K-M-K-HN, M2-K-M2-K-F, M2-K-M2-K-G, M2-K-M2-K-H, M2-K-M2-K-HN, M2-K-P-K-F, M2-K-P-K-G, M2-K-P-K-H, M2-K-P-K-HN, M2-K-NS1-K-F, M2-K-NS1-K-G, M2-K-NS1-K-H, M2-K-NS1-K-HN, M2-K-NS2-K-F, M2-K-NS2-K-G, M2-K-NS2-K-H, M2-K-NS2-K-HN, M2-K-L-K-F, M2-K-L-K-G, M2-K-L-K-H, M2-K-L-K-HN, P-K-N-K-F, P-K-N-K-G, P-K-N-K-H, P-K-N-K-HN, P-K-M-K-F, P-K-M-K-G, P-K-M-K-H, P-K-M-K-HN, P-K-M2-K-F, P-K-M2-K-G, P-K-M2-K-H, P-K-M2-K-HN, P-K-P-K-F, P-K-P-K-G, P-K-P-K-H, P-K-P-K-HN, P-K-NS1-K-F, P-K-NS1-K-G, P-K-NS1-K-H, P-K-NS1-K-HN, P-K-NS2-K-F, P-K-NS2-K-G, P-K-NS2-K-H, P-K-NS2-K-HN, P-K-L-K-F, P-K-L-K-G, P-K-L-K-H, P-K-L-K-HN, NS1-K-N-K-F, NS1-K-N-K-G, NS1-K-N-K-H, NS1-K-N-K-HN, NS1-K-M-K-F, NS1-K-M-K-G, NS1-K-M-K-H, NS1-K-M-K-HN, NS1-K-M2-K-F, NS1-K-M2-K-G, NS1-K-M2-K-H, NS1-K-M2-K-HN, NS1-K-P-K-F, NS1-K-P-K-G, NS1-K-P-K-H, NS1-K-P-K-HN, NS1-K-NS1-K-F, NS1-K-NS1-K-G, NS1-K-NS1-K-H, NS1-K-NS1-K-HN, NS1-K-NS2-K-F, NS1-K-NS2-K-G, NS1-K-NS2-K-H, NS1-K-NS2-K-HN, NS1-K-L-K-F, NS1-K-L-K-G, NS1-K-L-K-H, NS1-K-L-K-HN, NS2-K-N-K-F, NS2-K-N-K-G, NS2-K-N-K-H, NS2-K-N-K-HN, NS2-K-M-K-F, NS2-K-M-K-G, NS2-K-M-K-H, NS2-K-M-K-HN, NS2-K-M2-K-F, NS2-K-M2-K-G, NS2-K-M2-K-H, NS2-K-M2-K-HN, NS2-K-P-K-F, NS2-K-P-K-G, NS2-K-P-K-H, NS2-K-P-K-HN, NS2-K-NS1-K-F, NS2-K-NS1-K-G, NS2-K-NS1-K-H, NS2-K-NS1-K-HN, NS2-K-NS2-K-F, NS2-K-NS2-K-G, NS2-K-NS2-K-H, NS2-K-NS2-K-HN, NS2-K-L-K-F, NS2-K-L-K-G, NS2-K-L-K-H, NS2-K-L-K-HN, L-K-N-K-F, L-K-N-K-G, L-K-N-K-H, L-K-N-K-HN, L-K-M-K-F, L-K-M-K-G, L-K-M-K-H, L-K-M-K-HN, L-K-M2-K-F, L-K-M2-K-G, L-K-M2-K-H, L-K-M2-K-HN, L-K-P-K-F, L-K-P-K-G, L-K-P-K-H, L-K-P-K-HN, L-K-NS1-K-F, L-K-NS1-K-G, L-K-NS1-K-H, L-K-NS1-K-HN, L-K-NS2-K-F, L-K-NS2-K-G, L-K-NS2-K-H, L-K-NS2-K-HN, L-K-L-K-F, L-K-L-K-G, L-K-L-K-H, or L-K-L-K-HN, F-C-N-K-N, G-C-N-K-N, H-C-N-K-N, HN-C-N-K-N, F-C-M-K-N, G-C-M-K-N, H-C-M-K-N, HN-C-M-K-N, F-C-M2-K-N, G-C-M2-K-N, H-C-M2-K-N, HN-C-M2-K-N, F-C-P-K-N, G-C-P-K-N, H-C-P-K-N, HN-C-P-K-N, F-C-NS1-K-N, G-C-NS1-K-N, H-C-NS1-K-N, HN-C-NS1-K-N, F-C-NS2-K-N, G-C-NS2-K-N, H-C-NS2-K-N, HN-C-NS2-K-N, F-C-L-K-N, G-C-L-K-N, H-C-L-K-N, HN-C-L-K-N, F-C-N-K-M, G-C-N-K-M, H-C-N-K-M, HN-C-N-K-M, F-C-M-K-M, G-C-M-K-M, H-C-M-K-M, HN-C-M-K-M, F-C-M2-K-M, G-C-M2-K-M, H-C-M2-K-M, HN-C-M2-K-M, F-C-P-K-M, G-C-P-K-M, H-C-P-K-M, HN-C-P-K-M, F-C-NS1-K-M, G-C-NS1-K-M, H-C-NS1-K-M, HN-C-NS1-K-M, F-C-NS2-K-M, G-C-NS2-K-M, H-C-NS2-K-M, HN-C-NS2-K-M, F-C-L-K-M, G-C-L-K-M, H-C-L-K-M, HN-C-L-K-M, F-C-N-K-M2, G-C-N-K-M2, H-C-N-K-M2, HN-C-N-K-M2, F-C-M-K-M2, G-C-M-K-M2, H-C-M-K-M2, HN-C-M-K-M2, F-C-M2-K-M2, G-C-M2-K-M2, H-C-M2-K-M2, HN-C-M2-K-M2, F-C-P-K-M2, G-C-P-K-M2, H-C-P-K-M2, HN-C-P-K-M2, F-C-NS1-K-M2, G-C-NS1-K-M2, H-C-NS1-K-M2, HN-C-NS1-K-M2, F-C-NS2-K-M2, G-C-NS2-K-M2, H-C-NS2-K-M2, HN-C-NS2-K-M2, F-C-L-K-M2, G-C-L-K-M2, H-C-L-K-M2, HN-C-L-K-M2, F-C-N-K-P, G-C-N-K-P, H-C-N-K-P, HN-C-N-K-P, F-C-M-K-P, G-C-M-K-P, H-C-M-K-P, HN-C-M-K-P, F-C-M2-K-P, G-C-M2-K-P, H-C-M2-K-P, HN-C-M2-K-P, F-C-P-K-P, G-C-P-K-P, H-C-P-K-P, HN-C-P-K-P, F-C-NS1-K-P, G-C-NS1-K-P, H-C-NS1-K-P, HN-C-NS1-K-P, F-C-NS2-K-P, G-C-NS2-K-P, H-C-NS2-K-P, HN-C-NS2-K-P, F-C-L-K-P, G-C-L-K-P, H-C-L-K-P, HN-C-L-K-P, F-C-N-K-NS1, G-C-N-K-NS1, H-C-N-K-NS1, HN-C-N-K-NS1, F-C-M-K-NS1, G-C-M-K-NS1, H-C-M-K-NS1, HN-C-M-K-NS1, F-C-M2-K-NS1, G-C-M2-K-NS1, H-C-M2-K-NS1, HN-C-M2-K-NS1, F-C-P-K-NS1, G-C-P-K-NS1, H-C-P-K-NS1, HN-C-P-K-NS1, F-C-NS1-K-NS1, G-C-NS1-K-NS1, H-C-NS1-K-NS1, HN-C-NS1-K-NS1, F-C-NS2-K-NS1, G-C-NS2-K-NS1, H-C-NS2-K-NS1, HN-C-NS2-K-NS1, F-C-L-K-NS1, G-C-L-K-NS1, H-C-L-K-NS1, HN-C-L-K-NS1, F-C-N-K-NS2, G-C-N-K-NS2, H-C-N-K-NS2, HN-C-N-K-NS2, F-C-M-K-NS2, G-C-M-K-NS2, H-C-M-K-NS2, HN-C-M-K-NS2, F-C-M2-K-NS2, G-C-M2-K-NS2, H-C-M2-K-NS2, HN-C-M2-K-NS2, F-C-P-K-NS2, G-C-P-K-NS2, H-C-P-K-NS2, HN-C-P-K-NS2, F-C-NS1-K-NS2 G-C-NS1-K-NS2, H-C-NS1-K-NS2, HN-C-NS1-K-NS2, F-C-NS2-K-NS2 G-C-NS2-K-NS2, H-C-NS2-K-NS2, HN-C-NS2-K-NS2, F-C-L-K-NS2, G-C-L-K-NS2, H-C-L-K-NS2, HN-C-L-K-NS2, F-C-N-K-L, G-C-N-K-L, H-C-N-K-L, HN-C-N-K-L, F-C-M-K-L, G-C-M-K-L, H-C-M-K-L, HN-C-M-K-L, F-C-M2-K-L, G-C-M2-K-L, H-C-M2-K-L, HN-C-M2-K-L, F-C-P-K-L, G-C-P-K-L, H-C-P-K-L, HN-C-P-K-L, F-C-NS1-K-L, G-C-NS1-K-L, H-C-NS1-K-L, HN-C-NS1-K-L, F-C-NS2-K-L, G-C-NS2-K-L, H-C-NS2-K-L, HN-C-NS2-K-L, F-C-L-K-L, G-C-L-K-L, H-C-L-K-L, HN-C-L-K-L, N-C-N-F, N-C-N-G, N-C-N-H, N-C-N-HN, M-C-N-F, M-C-N-G, M-C-N-H, M-C-N-HN, M2-C-N-F, M2-C-N-G, M2-C-N-H, M2-C-N-HN, P-C-N-F, P-C-N-G, P-C-N-H, P-C-N-HN, NS1-C-N-F, NS1-C-N-G, NS1-C-N-H, NS1-C-N-HN, NS2-C-N-F, NS2-C-N-G, NS2-C-N-H, NS2-C-N-HN, L-C-N-F, L-C-N-G, L-C-N-H, L-C-N-HN, N-C-M-F, N-C-M-G, N-C-M-H, N-C-M-HN, M-C-M-F, M-C-M-G, M-C-M-H, M-C-M-HN, M2-C-M-F, M2-C-M-G, M2-C-M-H, M2-C-M-HN, P-C-M-F, P-C-M-G, P-C-M-H, P-C-M-HN, NS1-C-M-F, NS1-C-M-G, NS1-C-M-H, NS1-C-M-FIN, NS2-C-M-F, NS2-C-M-G, NS2-C-M-H, NS2-C-M-HN, L-C-M-F, L-C-M-G, L-C-M-H, L-C-M-HN, N-C-M2-F, N-C-M2-G, N-C-M2-H, N-C-M2-HN, M-C-M2-F, M-C-M2-G, M-C-M2-H, M-C-M2-HN, M2-C-M2-F, M2-C-M2-G, M2-C-M2-H, M2-C-M2-HN, P-C-M2-F, P-C-M2-G, P-C-M2-H, P-C-M2-HN, NS1-C-M2-F, NS1-C-M2-G, NS1-C-M2-H, NS1-C-M2-HN, NS2-C-M2-F, NS2-C-M2-G, NS2-C-M2-H, NS2-C-M2-HN, L-C-M2-F, L-C-M2-G, L-C-M2-H, L-C-M2-HN, N-C-P-F, N-C-P-G, N-C-P-H, N-C-P-HN, M-C-P-

F, M-C-P-G, M-C-P-H, M-C-P-HN, M2-C-P-F, M2-C-P-G, M2-C-P-H, M2-C-P-HN, P-C-P-F, P-C-P-G, P-C-P-H, P-C-P-HN, NS1-C-P-F, NS1-C-P-G, NS1-C-P-H, NS1-C-P-HN, NS2-C-P-F, NS2-C-P-G, NS2-C-P-H, NS2-C-P-HN, L-C-P-F, L-C-P-G, L-C-P-H, L-C-P-HN, N-C-NS1-F, N-C-NS1-G, N-C-NS1-H, N-C-NS1-HN, M-C-NS1-F, M-C-NS1-G, M-C-NS1-H, M-C-NS1-HN, M2-C-NS1-F, M2-C-NS1-G, M2-C-NS1-H, M2-C-NS1-HN, P-C-NS1-F, P-C-NS1-G, P-C-NS1-H, P-C-NS1-HN, NS1-C-NS1-F, NS1-C-NS1-G, NS1-C-NS1-H, NS1-C-NS1-HN, NS2-C-NS1-F, NS2-C-NS1-G, NS2-C-NS1-H, NS2-C-NS1-HN, L-C-NS1-F, L-C-NS1-G, L-C-NS1-H, L-C-NS1-HN, N-C-NS2-F, N-C-NS2-G, N-C-NS2-H, N-C-NS2-HN, M-C-NS2-F, M-C-NS2-G, M-C-NS2-H, M-C-NS2-HN, M2-C-NS2-F, M2-C-NS2-G, M2-C-NS2-H, M2-C-NS2-HN, P-C-NS2-F, P-C-NS2-G, P-C-NS2-H, P-C-NS2-HN, NS1-C-NS2-F, NS1-C-NS2-G, NS1-C-NS2-H, NS1-C-NS2-HN, NS2-C-NS2-F, NS2-C-NS2-G, NS2-C-NS2-H, NS2-C-NS2-HN, L-C-NS2-F, L-C-NS2-G, L-C-NS2-H, L-C-NS2-HN, N-C-L-F, N-C-L-G, N-C-L-H, N-C-L-HN, M-C-L-F, M-C-L-G, M-C-L2-H, M-C-L-HN, M2-C-L-F, M2-C-L-G, M2-C-L-H, M2-C-L-HN, P-C-L-F, P-C-L-G, P-C-L-H, P-C-L-HN, NS1-C-L-F, NS1-C-L-G, NS1-C-L-H, NS1-C-L-HN, NS2-C-L-F, NS2-C-L-G, NS2-C-L-H, NS2-C-L-HN, L-C-L-F, L-C-L-G, L-C-L-H, L-C-L-HN, N-N-C-F, N-N-C-G, N-N-C-H, N-N-C-HN, N-M-C-F, N-M-C-G, N-M-C-H, N-M-C-HN, N-M2-C-F, N-M2-C-G, N-M2-C-H, N-M2-C-HN, N-P-C-F, N-P-C-G, N-P-C-H, N-P-C-HN, N-NS1-C-F, N-NS1-C-G, N-NS1-C-H, N-NS1-C-HN, N-NS2-C-F, N-NS2-C-G, N-NS2-C-H, N-NS2-C-HN, N-L-C-F, N-L-C-G, N-L-C-H, N-L-C-HN, M-N-C-F, M-N-C-G, M-N-C-H, M-N-C-HN, M-M-C-F, M-M-C-G, M-M-C-H, M-M-C-HN, M-M2-C-F, M-M2-C-G, M-M2-C-H, M-M2-C-HN, M-P-C-F, M-P-C-G, M-P-C-H, M-P-C-HN, M-NS1-C-F, M-NS1-C-G, M-NS1-C-H, M-NS1-C-HN, M-NS2-C-F, M-NS2-C-G, M-NS2-C-H, M-NS2-C-HN, M-L-C-F, M-L-C-G, M-L-C-H, M-L-C-HN, M2-N-C-F, M2-N-C-G, M2-N-C-H, M2-N-C-HN, M2-M-C-F, M2-M-C-G, M2-M-C-H, M2-M-C-HN, M2-M2-C-F, M2-M2-C-G, M2-M2-C-H, M2-M2-C-HN, M2-P-C-F, M2-P-C-G, M2-P-C-H, M2-P-C-HN, M2-NS1-C-F, M2-NS1-C-G, M2-NS1-C-H, M2-NS1-C-HN, M2-NS2-C-F, M2-NS2-C-G, M2-NS2-C-H, M2-NS2-C-HN, M2-L-C-F, M2-L-C-G, M2-L-C-H, M2-L-C-HN, P-N-C-F, P-N-C-G, P-N-C-H, P-N-C-HN, P-M-C-F, P-M-C-G, P-M-C-H, P-M-C-HN, P-M2-C-F, P-M2-C-G, P-M2-C-H, P-M2-C-HN, P-P-C-F, P-P-C-G, P-P-C-H, P-P-C-HN, P-NS1-C-F, P-NS1-C-G, P-NS1-C-H, P-NS1-C-HN, P-NS2-C-F, P-NS2-C-G, P-NS2-C-H, P-NS2-C-HN, P-L-C-F, P-L-C-G, P-L-C-H, P-L-C-HN, NS1-N-C-F, NS1-N-C-G, NS1-N-C-H, NS1-N-C-HN, NS1-M-C-F, NS1-M-C-G, NS1-M-C-H, NS1-M-C-HN, NS1-M2-C-F, NS1-M2-C-G, NS1-M2-C-H, NS1-M2-C-HN, NS1-P-C-F, NS1-P-C-G, NS1-P-C-H, NS1-P-C-HN, NS1-NS1-C-F, NS1-NS1-C-G, NS1-NS1-C-H, NS1-NS1-C-HN, NS1-NS2-C-F, NS1-NS2-C-G, NS1-NS2-C-H, NS1-NS2-C-HN, NS1-L-C-F, NS1-L-C-G, NS1-L-C-H, NS1-L-C-HN, NS2-N-C-F, NS2-N-C-G, NS2-N-C-H, NS2-N-C-HN, NS2-M-C-F, NS2-M-C-G, NS2-M-C-H, NS2-M-C-HN, NS2-M2-C-F, NS2-M2-C-G, NS2-M2-C-H, NS2-M2-C-HN, NS2-P-C-F, NS2-P-C-G, NS2-P-C-H, NS2-P-C-HN, NS2-NS1-C-F, NS2-NS1-C-G, NS2-NS1-C-H, NS2-NS1-C-HN, NS2-NS2-C-F, NS2-NS2-C-G, NS2-NS2-C-H, NS2-NS2-C-HN, NS2-L-C-F, NS2-L-C-G, NS2-L-C-H, NS2-L-C-HN, L-N-C-F, L-N-C-G, L-N-C-H, L-N-C-HN, L-M-C-F, L-M-C-G, L-M-C-H, L-M-C-HN, L-M2-C-F, L-M2-C-G, L-M2-C-H, L-M2-C-HN, L-L-C-F, L-P-C-G, L-P-C-H, L-P-C-HN, L-NS1-C-F, L-NS1-C-G, L-NS1-C-H, L-NS1-C-HN, L-NS2-C-F, L-NS2-C-G, L-NS2-C-H, L-NS2-C-HN, L-L-C-F, L-L-C-G, L-L-C-H, L-L-C-HN, N-C-N-K-F, N-C-N-K-G, N-C-N-K-H, N-C-N-K-HN, N-C-M-K-F, N-C-M-K-G, N-C-M-K-H, N-C-M-K-HN, N-C-M2-K-F, N-C-M2-K-G, N-C-M2-K-H, N-C-M2-K-HN, N-C-P-K-F, N-C-P-K-G, N-C-P-K-H, N-C-P-K-HN, N-C-NS1-K-F, N-C-NS1-K-G, N-C-NS1-K-H, N-C-NS1-K-HN, N-C-NS2-K-F, N-C-NS2-K-G, N-C-NS2-K-H, N-C-NS2-K-HN, N-C-L-K-F, N-C-L-K-G, N-C-L-K-H, N-C-L-K-HN, M-C-N-K-F, M-C-N-K-G, M-C-N-K-H, M-C-N-K-HN, M-C-M-K-F, M-C-M-K-G, M-C-M-K-H, M-C-M-K-HN, M-C-M2-K-F, M-C-M2-K-G, M-C-M2-K-H, M-C-M2-K-HN, M-C-P-K-F, M-C-P-K-G, M-C-P-K-H, M-C-P-K-HN, M-C-NS1-K-F, M-C-NS1-K-G, M-C-NS1-K-H, M-C-NS1-K-HN, M-C-NS2-K-F, M-C-NS2-K-G, M-C-NS2-K-H, M-C-NS2-K-HN, M-C-L-K-F, M-C-L-K-G, M-C-L-K-H, M-C-L-K-HN, M2-C-N-K-F, M2-C-N-K-G, M2-C-N-K-H, M2-C-N-K-HN, M2-C-M-K-F, M2-C-M-K-G, M2-C-M-K-H, M2-C-M-K-HN, M2-C-M2-K-F, M2-C-M2-K-G, M2-C-M2-K-H, M2-C-M2-K-HN, M2-C-P-K-F, M2-C-P-K-G, M2-C-P-K-H, M2-C-P-K-HN, M2-C-NS1-K-F, M2-C-NS1-K-G, M2-C-NS1-K-H, M2-C-NS1-K-HN, M2-C-NS2-K-F, M2-C-NS2-K-G, M2-C-NS2-K-H, M2-C-NS2-K-HN, M2-C-L-K-F, M2-C-L-K-G, M2-C-L-K-H, M2-C-L-K-HN, P-C-N-K-F, P-C-N-K-G, P-C-N-K-H, P-C-N-K-HN, P-C-M-K-F, P-C-M-K-G, P-C-M-K-H, P-C-M-K-HN, P-C-M2-K-F, P-C-M2-K-G, P-C-M2-K-H, P-C-M2-K-HN, P-C-P-K-F, P-C-P-K-G, P-C-P-K-H, P-C-P-K-HN, P-C-NS1-K-F, P-C-NS1-K-G, P-C-NS1-K-H, P-C-NS1-K-HN, P-C-NS2-K-F, P-C-NS2-K-G, P-C-NS2-K-H, P-C-NS2-K-HN, P-C-L-K-F, P-C-L-K-G, P-C-L-K-H, P-C-L-K-HN, NS1-C-N-K-F, NS1-C-N-K-G, NS1-C-N-K-H, NS1-C-N-K-HN, NS1-C-M-K-F, NS1-C-M-K-G, NS1-C-M-K-H, NS1-C-M-K-HN, NS1-C-M2-K-F, NS1-C-M2-K-G, NS1-C-M2-K-H, NS1-C-M2-K-HN, NS1-C-P-K-F, NS1-C-P-K-G, NS1-C-P-K-H, NS1-C-P-K-HN, NS1-C-NS1-K-F, NS1-C-NS1-K-G, NS1-C-NS1-K-H, NS1-C-NS1-K-HN, NS1-C-NS2-K-F, NS1-C-NS2-K-G, NS1-C-NS2-K-H, NS1-C-NS2-K-HN, NS1-C-L-K-F, NS1-C-L-K-G, NS1-C-L-K-H, NS1-C-L-K-HN, NS2-C-N-K-F, NS2-C-N-K-G, NS2-C-N-K-H, NS2-C-N-K-HN, NS2-C-M-K-NS2-C-M-K-G, NS2-C-M-K-H, NS2-C-M-K-HN, NS2-C-M2-K-F, NS2-C-M2-K-G, NS2-C-M2-K-H, NS2-C-M2-K-HN, NS2-C-P-K-F, NS2-C-P-K-G, NS2-C-P-K-H, NS2-C-P-K-HN, NS2-C-NS1-K-F, NS2-C-NS1-K-G, NS2-C-NS1-K-H, NS2-C-NS1-K-HN, NS2-C-NS2-K-F, NS2-C-NS2-K-G, NS2-C-NS2-K-H, NS2-C-NS2-K-HN, NS2-C-L-K-F, NS2-C-L-K-G, NS2-C-L-K-H, NS2-C-L-K-HN, L-C-N-K-F, L-C-N-K-G, L-C-N-K-H, L-C-N-K-HN, L-C-M-K-F, L-C-M-K-G, L-C-M-K-H, L-C-M-K-HN, L-C-M2-K-F, L-C-M2-K-G, L-C-M2-K-H, L-C-M2-K-L-C-P-K-F, L-C-P-K-G, L-C-P-K-H, L-C-P-K-HN, L-C-NS1-K-F, L-C-NS1-K-G, L-C-NS1-K-H, L-C-NS2-K-F, L-C-NS2-K-G, L-C-NS2-K-H, L-C-NS2-K-HN, L-C-L-K-F, L-C-L-K-G, L-C-L-K-H, or L-C-L-K-HN. Most preferably the arrangement is F-C-N-K-M2.

In preferred embodiments, the expression system is for use in the prophylaxis or treatment of viral infection, particularly preferably for use in the prophylaxis or treatment of a paramyxovirus infection, preferably a RSV infection and/or in the manufacturing of medicament for use in the prophylaxis or treatment of a paramyxovirus infection, preferably a RSV infection, and/or for use in methods of prophylaxis or treatment of an of a paramyxovirus infection, preferably a RSV infection.

In preferred embodiments, the expression system is for use in enhancing an immune response, preferably a B cell immune response against a paramyxovirus infection, preferably a RSV infection.

According to a preferred embodiment of the first aspect, the first polynucleotide encodes a viral protein of a orthomyxovirus or variant thereof which induces a reaction of the immune system (i.e. immune response) in a host which is mediated by T cells, and the second polynucleotide encodes a viral protein of a orthomyxovirus or variant thereof that induces an anti-pathogenic B cell response against the orthomyxovirus. It is preferred that the orthomyxovirus whose viral proteins are encoded for by the first and second polynucleotide is selected from the genus of Influenzavirus A, Influenzavirus B, Influenzavirus C, Thogotoviris and Isavirus. In even more preferred embodiments, the orthomyxovirus is Influenzavirus A, preferably selected from the subtypes H1N1, H1N2, H2N2, H3N1, H3N2, H3N8, H5N1, H5N2, H5N3, H5N8, H5N9, H7N1, H7N2, H7N3, H7N4, H7N7, H9N2, H10N7. According to a preferred embodiment of the first aspect, the second polynucleotide encodes a viral protein of an orthomyxovirus or variant thereof that induces an anti-pathogenic B cell response against the orthomyxovirus.

According to preferred embodiments of the first aspect first polynucleotide encodes a viral protein of a orthomyxovirus or variant thereof which induces a reaction of the immune system (i.e. immune response) in a host which is mediated by T cells. A T cell response involves the activation of antigen-specific T lymphocyte such as but not limited to cytotoxic T cells (CTLs), T helper cells (Tx cells), central memory T cells (TCM cells), effector memory T cells (TEM cells), and regulatory T cells (Treg cells). A T cell response against a protein is induced, if peptides of the protein are processed within the cell and presented to T cells on the surface of the cell via the MHC I or MHC II pathway. Thus, in the context of the present invention preferably those viral proteins or parts thereof are used for inducing a T cell response that are normally not exposed on the outside of the virus, e.g. non structural or internal proteins or parts of structural or surface proteins not accessible to B-cells on the outside of the virus.

According to a preferred embodiment of the first aspect, the second polynucleotide encodes a viral protein of an orthomyxovirus or variant thereof that induces an anti-pathogenic B cell response. A B cell response is an immune response based on the activation of B lymphocytes, which produce and secrete antigen specific antibodies. B cells involved in such immune response include but are not limited to plasma B cells, memory B cells and B-1 cells. Thus, in the context of the present invention preferably those viral proteins or parts thereof are used for inducing a B cell response that are exposed on the outside of the virus, e.g. structural and/or surface proteins or at least those parts of structural and/or surface proteins accessible to B-cells on the outside of the virus.

In a preferred embodiment of the first aspect the viral protein of an orthomyxovirus, which induces a T cell response is a non-structural and/or internal protein of an orthomyxovirus, and/or the viral protein of a orthomyxovirus, which induces an anti-pathogenic B cell response is a structural and/or surface protein of a orthomyxovirus.

It is preferred that the amino acid sequence of the structural (surface) and/or non-structural and/or internal protein comprises consecutive segments or a consensus sequence of one or more different orthomyxovirus isolates.

In preferred embodiments, the structural protein is a protein exposed on the surface of the native orthomyxovirus or a variant thereof. It is preferred that the structural and/or surface protein triggers a T-cell independent immune response such as but not limited to an antibody mediated immune response or an activation of the complement system. In a particularly preferred embodiment, the structural and/or surface protein induces an antibody mediated immune response. Such antibody mediated immune response is based on the activation of B cells which produce and secrete antigen specific antibodies. B cells involved in such immune response include but are not limited to plasma B cells, memory B cells and B-1 cells.

In a further preferred embodiment, the membrane attachment domain of the protein exposed on the surface of the native orthomyxovirus or variant thereof is functionally deleted, thus, either being structurally deleted or structurally present but not fulfilling its biological function. In a particularly preferred embodiment, the amino acid sequence corresponding to the membrane attachment domain is deleted. The deletion of the membrane attachment region serves the purpose of ascertaining that the anti-pathogenic B cell response inducing protein is secreted from the cell into which the expression system of the invention has been introduced.

It is further preferred that the viral surface proteins of the native orthomyxovirus is selected from the group consisting of hemagglutinin (HA) and neuraminidase (NA). It is more preferred that the viral surface protein of the native orthomyxovirus is hemagglutinin (HA).

In a preferred embodiment of the first aspect, HA comprises, essentially consists of or consists of an amino acid sequence of HA of one influenza A virus isolate or a consensus amino acid sequence of two or more different influenza A virus isolates, preferably according to SEQ ID NO: 8 or SEQ ID NO: 20, more preferably according to SEQ ID NO: 9, SEQ ID NO: 10, SEQ ID NO: 21 or a variant of one of these sequences.

In preferred embodiments of the first aspect, the non-structural protein is a conserved internal protein of orthomyxoviruses suitable for inducing a T cell mediated immune response against the paramyxovirus, involving the activation of antigen-specific T lymphocyte such as but not limited to cytotoxic T cells (CTLs), T helper cells (Tx cells), central memory T cells (TCM cells), effector memory T cells (TEM cells), and regulatory T cells (Treg cells). Thus, preferably the T cell inducing protein of the orthomyxovirus does not comprise a secretion signal.

Preferably, the non-structural and/or internal protein is selected from the group consisting of nucleoprotein NP, Matrix proteins M1 and M2, non structural proteins NS1 and NS2/NEP, and the RNA polymerases PA, PB1, PB2 and the protein PB1-F2 (PB1F2).

The nucleoprotein NP is a structural protein which encapsidates the negative strand viral RNA. NP is one of the main determinants of species specificity.

The protein M1 is a matrix protein of the influenza virus. It forms a coat inside the viral envelope. The M1 protein binds to the viral RNA. It also has multiple regulatory functions, performed by interaction with the components of the host cell. The mechanisms regulated include a role in the export of the viral ribonucleoproteins from the host cell nucleus, inhibition of viral transcription, and a role in the virus assembly and budding. The M1 protein forms a layer under the patches of host cell membrane that are rich with the viral hemagglutinin, neuraminidase and M2 transmembrane proteins, and facilitates budding of the mature viruses.

The non-structural NS1 protein is created by the internal protein encoding, linear negative-sense, single stranded RNA, NS gene segment and which also codes for the nuclear export protein or NEP, formerly referred to as the NS2 protein, which mediates the export of vRNPs. NS1 also binds dsRNA. As a consequence of its binding to dsRNA, the NS1 protein blocks the activation of the dsRNA-activated protein kinase (PKR) in vitro. This kinase phosphorylates the alpha subunit of eukaryotic translation initiation factor 2 (eIF-2 alpha), leading to a decrease in the rate of initiation of translation. In the absence of NS1, this pathway is inhibited during anti-viral response to halt all protein translation—thus stopping the synthesis of viral proteins; however, the influenza virus' NS1 protein is an agent that circumvents host defenses to allow viral gene transcription to occur.

In preferred embodiments, HA comprises an amino acid sequence of HA of one influenza A virus isolate or a consensus amino acid sequence of two or more different influenza A virus isolates, preferably according to SEQ ID NO: 9 or SEQ ID NO: 21, NP comprises an amino acid sequence of NP of one influenza A virus isolate or a consensus amino acid sequence of two or more different influenza A virus isolates, preferably according to SEQ ID NO: 11, and/or M1 comprises an amino acid sequence of M1 of one influenza A virus isolate or a consensus amino acid sequence of two or more different influenza A virus isolates, preferably according to SEQ ID NO: 12. It is further preferred that when NP comprises the amino acid sequence according to SEQ ID NO: 11 and M1 comprises the amino acid sequence according to SEQ ID NO: 12.

In the context of the present invention, the structural and/or surface protein encoded by the first polynucleotide is located either N- or C-terminally with respect to the non-structural and/or internal protein encoded by the second polynucleotide. In a preferred embodiment, the non-structural and/or internal protein encoded by the second polynucleotide is located C-terminally with respect to the structural and/or surface protein encoded by the first polynucleotide.

More specifically, HA or NA can be located N- or C-terminally of NP, M1, M2, NS1, NS2/NEP, PA, PB1, PB2 or PB1-F2 (PB1F2). In a preferred embodiment M1 is located N-terminally of HA.

Accordingly, embodiments of the present invention have the formula X-Y or Y-X, wherein "X" depicts HA or NA, preferably HA, and "Y" depicts NP, M1, M2, NS1, NS2/NEP, PA, PB1, PB2 or PB1-F2 (PB1F2), preferably NP or M1, and a "dash" depicts a peptide bond. Preferred arrangements are the following:

HA-NP, HA-M1, HA-M2, HA-NS1, HA-NS2/NEP, HA-PA, HA-PB1, HA-PB2, HA-PB1F2, NP-HA, M1-HA, M2-HA, NS1-HA, NS2/NEP-HA, PA-HA, PB1-HA, PB2-HA, PB1F2-HA, NA-NP, NA-M1, NA-M2, NA-NS1, NA-NS2/NEP, NA-PA, NA-PB1, NA-PB2, NA-PB1F2, NP-NA, M1-NA, M2-NA, NS1-NA, NS2/NEP-NA, PA-NA, PB1-NA, PB2-NA or PB1F2-NA. A particulary preferred arrangement is M1-HA.

It is within the scope of the present invention that every protein can be combined with any other protein.

In preferred embodiments of the first aspect, a polynucleotide encoding a cleavage site is positioned between the first polynucleotide and the second polynucleotide.

It is preferred that this cleavage site is either a self-cleaving site (i.e. a cleavage site within the amino acid sequence where this sequence is cleaved or is cleavable without such cleavage involving any additional molecule or where the peptide-bond formation in this sequence is prevented in the first place) or an endopeptidase cleavage site (i.e. a cleavage cite within the amino acid sequence where this sequence is cleaved or is cleavable by an endopeptidase, e.g. trypsin, pepsin, elastase, thrombin, collagenase, furin, thermolysin, endopeptidase V8, cathepsins). More preferably, the self-cleaving site is a 2A cleavage site selected from the group consisting of a viral 2A peptide or 2A-like peptide of Picornavirus, insect viruses, Aphtoviridae, Rotaviruses and *Trypanosoma*, preferably wherein the 2A cleavage site is the 2 A peptide of foot and mouth disease virus. Alternatively or additionally, the polyprotein of the present invention can be cleaved by an autoprotease, i.e. a protease which cleaves peptide bonds in the same protein molecule which also comprises the protease. Examples of such autoproteases are the NS2 protease from flaviviruses or the VP4 protease of birnaviruses.

In the context of the present invention, the cleavage site can be positioned N-terminally with respect to the structural and/or surface protein encoded by the first polynucleotide and C-terminally with respect to the non-structural and/or internal protein encoded by the second polynucleotide. Alternatively the cleavage site can be positioned C-terminally with respect to the structural and/or surface protein encoded by the first polynucleotide and N-terminally with respect to the non-structural and/or internal protein encoded by the second polynucleotide. More specifically, the cleavage site can be positioned C- or N-terminally with respect to HA or NA and C- or N-terminally with respect to NP, M1, M2, NS1, NS2/NEP, PA, PB1, PB2 or PB1-F2 (PB1F2). In a preferred embodiment the cleavage site is located C-terminally with respect to NP M2, NS1, NS2/NEP, PA, PB1, PB2 or PB1-F2 (PB1F2) and N-terminally with respect to HA or NA. It is particularly preferred that the cleavage site is located N-terminally with respect to HA and C-terminally with respect to M1.

Accordingly, embodiments of the present invention have the formula X-C-Y or Y-C-X, wherein "X" depicts HA or NA, preferably, HA and "Y" depicts NP, M1, M2, NS1, NS2/NEP, PA, PB1, PB2 or PB1-F2 (PB1F2), preferably NP or M1, "C" depicts a cleavage site, and a "dash" depicts a peptide bond.

Preferred arrangements are the following: HA-C-NP, HA-C-M1, HA-C-M2, HA-C-NS1, HA-C-NS2/NEP, HA-C-PA, HA-C-PB1, HA-C-PB2, HA-C-PB1F2, NP-C-HA, M1-C-HA, M2-C-HA, NS1-C-HA, NS2/NEP-C-HA, PA-C-HA, PB1-C-HA, PB2-C-HA, PB1F2-C-HA, NA-C-NP, NA-C-M1, NA-C-M2, NA-C-NS1, NA-C-NS2/NEP, NA-C-PA, NA-C-PB1, NA-C-PB2, NA-C-PB1F2, NP-C-NA, M1-C-NA, M2-C-NA, NS1-C-NA, NS2/NEP-C-NA, PA-C-NA, PB1-C-NA, PB2-C-NA or PB1F2-C-NA. A particulary preferred arrangement is M1-C-HA.

It is within the scope of the present invention that every protein can be combined with any other protein and that any two proteins can or cannot be connected or linked by a cleavage site.

In preferred embodiment of the first aspect, the expression system further comprises a third polynucleotide encoding a non-structural and/or internal protein of an orthomyxovirus or a variant thereof. Preferably, the non-structural and/or internal protein is of a orthomyxovirus selected from the genus of Influenzavirus A, Influenzavirus B, Influenzavirus C, Thogotoviris and Isavirus. In even more preferred embodiments, the orthomxyovirus is Influenzavirus A, preferably selected from the influenza A virus subtypes H1N1, H1N2, H2N2, H3N1, H3N2, H3N8, H5N1, H5N2, H5N3, H5N8, H5N9, H7N1, H7N2, H7N3, H7N4, H7N7, H9N2, H10N7, more preferably the influenza A virus subtype H1N1.

In preferred embodiments the third polynucleotide is comprised on a separate or on the same vector as the first polynucleotide and/or the second polynucleotide.

Accordingly, the first polynucleotide is comprised on one vector and the second polynucleotide is comprised on a second vector and the third polynucleotide is comprised on a third vector. Alternatively or additionally, the first and the second polynucleotide are comprised on the same vector and the third polynucleotide is comprised on a separate vector, or the first and the third polynucleotide are comprised on the same vector and the second polynucleotide is comprised on a separate vector, or the second and the third polynucleotide are comprised on the same vector and the first polynucleotide is comprised on a separate vector. Alternatively or additionally, the first and the second and the third polynucleotide are comprised on the same vector. It is preferred that the first and the second and the third polynucleotide may be comprised on the same vector. It is particularly preferred that the first and the second and the third polynucleotide comprised on the same vector are linked in such that they are expressed as a viral polyprotein. Preferably, the first and the second and the third polynucleotide comprised on the same vector form an open reading frame.

It is further preferred that the non-structural and/or internal protein encoded by the third polynucleotide is a conserved internal protein suitable for inducing a T cell mediated immune response against the virus involving the activation of antigen-specific T lymphocyte such as but not limited to cytotoxic T cells (CTLs), T helper cells ($T_H$ cells), central memory T cells (TCM cells), effector memory T cells (TEM cells), and regulatory T cells (Treg cells).

Preferably, the non-structural and/or internal protein is selected from the group consisting of NP, M1, M2, NS1, NS2/NEP, PA, PB1, PB2 or PB1-F2 (PB1F2), more preferably NP or M1.

It is preferred that the non-structural and/or internal protein encoded by the third polynucleotide differs from the non-structural and/or internal protein encoded by the second polynucleotide.

The non-structural and/or internal proteins encoded by the second and the third polynucleotide differ from each other in that they comprise amino acid sequences of different viral proteins. For instance, this means that the non-structural and/or internal protein encoded by the second polynucleotide comprises the amino acid sequence of the M1 protein whilst the non-structural and/or internal protein encoded by the third polynucleotide comprises the amino acid sequence of the NP protein or vice versa.

The non-structural and/or internal protein encoded by the third polynucleotide can be located either N- or C-terminally of the non-structural and/or internal protein encoded by the second polynucleotide. In a preferred embodiment of the first aspect, the non-structural and/or internal protein encoded by the third polynucleotide is located C-terminally of the non-structural and/or internal protein encoded by the second polynucleotide.

In preferred embodiments a polynucleotide encoding a linker is positioned between the second polynucleotide and the third polynucleotide. It is preferred that the linker is a flexible linker, preferably a flexible linker comprising an amino acid sequence according to SEQ ID NO: 6.

In embodiments of the first aspect, the protein encoded by the second polynucleotide is located N-terminally with respect to the protein encoded by the first polynucleotide and/or the protein of the optional third polynucleotide, or the protein encoded by the second polynucleotide is located C-terminally with respect to the protein encoded by the first polynucleotide and/or the protein of the optional third polynucleotide.

In even more preferred embodiments of this aspect, the first polynucleotide is located N-terminally with respect to the protein encoded by the second polynucleotide and/or the protein of the optional third polynucleotide is located N-terminally with respect to the protein encoded by the first polynucleotide or is located between the protein encoded by the second polynucleotide and the protein encoded by the first polynucleotide; or the protein encoded by the first polynucleotide is located C-terminally with respect to the protein encoded by the second polynucleotide and/or the protein of the optional third polynucleotide is located C-terminally with respect to the protein encoded by the first polynucleotide or is located between the protein encoded by the second polynucleotide and the protein encoded by the first polynucleotide. More specifically, HA, or NA are located C- or N-terminally with respect to NP, M1, M2, NS1, NS2/NEP, PA, PB1, PB2 or PB1-F2 (PB1F2).

In a preferred embodiment HA is located C-terminally with respect to M1 and NP is located N-terminally with respect to M1.

Accordingly, preferred embodiments of the present invention have the formula X-K-Y, Y-K-X, X-K-Y-Y, Y-Y-K-X, X-Y-K-Y, Y-K-Y-X, X-K-Y-K-Y, Y-K-Y-K-X, X-C-Y, Y-C-X, X-C-Y-Y, Y-Y-C-X, X-Y-C-Y, Y-C-Y-X, X-C-Y-C-Y, Y-C-Y-C-X, X-K-Y-C-Y, Y-C-Y-K-X, X-C-Y-K-Y, or Y-K-Y-C-X, wherein "X" depicts HA, or NA, preferably HA, and "Y" depicts NP, M1, M2, NS1, NS2/NEP, PA, PB1, PB2 or PB1-F2 (PB1F2), preferably NP or M1, "K" indicates that one or more peptide linkers are present in this position, "C" indicates that one or more cleavage sites are present in this position and a "dash" depicts a peptide bond. Preferred arrangements are Y-K-Y-C-X. Even more preferred arrangements are the following: HA-K-NP, NP-K-HA, HA-K-NP-NP, NP-NP-K-HA, HA-NP-K-NP, NV-K-NP-HA, HA-K-NP-K-NP, NP-K-NP-K-HA, HA-C-NP, NP-C-HA, HA-C-NP-NP, NP-NP-C-HA, HA-NP-C-NP, NP-C-NP-HA, HA-C-NP-C-NP, NP-C-NP-C-HA, HA-K-NP-C-NP, NP-C-NP-K-HA, HA-C-NP-K-NP, NP-K-NP-C-HA, HA-K-NP-M1, HA-K-M1-NP, NP-M1-K-HA, M1-NP-K-HA, HA-NP-K-M1, HA-M1-K-NP, NP-K-M1-HA, M1-K-NP-HA, HA-K-NP-K-M1, HA-K-M1-K-NP, NP-K-M1-K-HA, M1-K-NP-K-HA, HA-C-NP-M1, HA-C-M1-NP, NP-M1-C-HA, M1-NP-C-HA, HA-NP-C-M1, HA-M1-C-NP, NP-C-M1-HA, M1-C-NP-HA, HA-C-NP-C-M1, HA-C-M1-C-NP, NP-C-M1-C-HA, M1-C-NP-C-HA, HA-K-NP-C-M1, HA-K-M1-C-NP, NP-C-M1-K-HA, M1-C-NP-K-HA, HA-C-NP-K-M1, HA-C-M1-K-NP, NP-K-M1-C-HA, M1-K-NP-C-HA, HA-K-NP-M2, HA-K-M2-NP, NP-M2-K-HA, M2-NP-K-HA, HA-NP-K-M2, HA-M2-K-NP, NP-K-M2-HA, M2-K-NP-HA, HA-K-NP-K-M2, HA-K-M2-K-NP, NP-K-M2-K-HA, M2-K-NP-K-HA, HA-C-NP-M2, HA-C-M2-NP, NP-M2-C-HA, M2-NP-C-HA, HA-NP-C-M2, HA-M2-C-NP, NP-C-M2-HA, M2-C-NP-HA, HA-C-NP-C-M2, HA-C-M2-C-NP, NP-C-M2-C-HA, M2-C-NP-C-HA, HA-K-NP-C-M2, HA-K-M2-C-NP, NP-C-M2-K-HA, M2-C-NP-K-HA, HA-C-NP-K-M2, HA-C-M2-K-NP, NP-K-M2-C-HA, M2-K-NP-C-HA, HA-K-NP-NS1, HA-K-NS1-NP, NP-NS1-K-HA, NS1-NP-K-HA, HA-NP-K-NS1, HA-NS1-K-NP, NP-K-NS1-HA, NS1-K-NP-HA, HA-K-NP-K-NS1, HA-K-NS1-K-NP, NP-K-NS1-K-HA, NS1-K-NP-K-HA, HA-C-NP-NS1, HA-C-NS1-NP, NP-NS1-C-HA, NS1-NP-C-HA, HA-NP-C-NS1,

HA-NS1-C-NP, NP-C-NS1-HA, NS1-C-NP-HA, HA-C-NP-C-NS1, HA-C-NS1-C-NP, NP-C-NS1-C-HA, NS1-C-NP-C-HA, HA-K-NP-C-NS1, HA-K-NS1-C-NP, NP-C-NS1-K-HA, NS1-C-NP-K-HA, HA-C-NP-K-NS1, HA-C-NS1-K-NP, NP-K-NS1-C-HA, NS1-K-NP-C-HA, HA-K-NP-NS2/NEP, HA-K-NS2/NEP-NP, NP-NS2/NEP-K-HA, NS2/NEP-NP-K-HA, HA-NP-K-NS2/NEP, HA-NS2/NEP-K-NP, NP-K-NS2/NEP-HA, NS2/NEP-K-NP-HA, HA-K-NP-K-NS2/NEP, HA-K-NS2/NEP-K-NP, NP-K-NS2/NEP-K-HA, NS2/NEP-K-NP-K-HA, HA-C-NP-NS2/NEP, HA-C-NS2/NEP-NP, NP-NS2/NEP-C-HA, NS2/NEP-NP-C-HA, HA-NP-C-NS2/NEP, HA-NS2/NEP-C-NP, NP-C-NS2/NEP-HA, NS2/NEP-C-NP-HA, HA-C-NP-C-NS2/NEP, HA-C-NS2/NEP-C-NP, NP-C-NS2/NEP-C-HA, NS2/NEP-C-NP-C-HA, HA-K-NP-C-NS2/NEP, HA-K-NS2/NEP-C-NP, NP-C-NS2/NEP-K-HA, NS2/NEP-C-NP-K-HA, HA-C-NP-K-NS2/NEP, HA-C-NS2/NEP-K-NP, NP-K-NS2/NEP-C-HA, NS2/NEP-K-NP-C-HA, HA-K-NP-PA, HA-K-PA-NP, NP-PA-K-HA, PA-NP-K-HA, HA-NP-K-PA, HA-PA-K-NP, NP-K-PA-HA, PA-K-NP-HA, HA-K-NP-K-PA, HA-K-PA-K-NP, NP-K-PA-K-HA, PA-K-NP-K-HA, HA-C-NP-PA, HA-C-PA-NP, NP-PA-C-HA, PA-NP-C-HA, HA-NP-C-PA, HA-PA-C-NP, NP-C-PA-HA, PA-C-NP-HA, HA-C-NP-C-PA, HA-C-PA-C-NP, NP-C-PA-C-HA, PA-C-NP-C-HA, HA-K-NP-C-PA, HA-K-PA-C-NP, NP-C-PA-K-HA, PA-C-NP-K-HA, HA-C-NP-K-PA, HA-C-PA-K-NP, NP-K-PA-C-HA, PA-K-NP-C-HA, HA-K-NP-PB1, HA-K-PB1-NP, NP-PB1-K-HA, PB1-NP-K-HA, HA-NP-K-PB1, HA-PB1-K-NP, NP-K-PB1-HA, PB1-K-NP-HA, HA-K-NP-K-PB1, HA-K-PB1-K-NP, NP-K-PB1-K-HA, PB1-K-NP-K-HA, HA-C-NP-PB1, HA-C-PB1-NP, NP-PB1-C-HA, PB1-NP-C-HA, HA-NP-C-PB1, HA-PB1-C-NP, NP-C-PB1-HA, PB1-C-NP-HA, HA-C-NP-C-PB1, HA-C-PB1-C-NP, NP-C-PB1-C-HA, PB1-C-NP-C-HA, HA-K-NP-C-PB1, HA-K-PB1-C-NP, NP-C-PB1-K-HA, PB1-C-NP-K-HA, HA-C-NP-K-PB1, HA-C-PB1-K-NP, NP-K-PB1-C-HA, PB1-K-NP-C-HA, HA-K-NP-PB2, HA-K-PB2-NP, NP-PB2-K-HA, PB2-NP-K-HA, HA-NP-K-PB2, HA-PB2-K-NP, NP-K-PB2-HA, PB2-K-NP-HA, HA-K-NP-K-PB2, HA-K-PB2-K-NP, NP-K-PB2-K-HA, PB2-K-NP-K-HA, HA-C-NP-PB2, HA-C-PB2-NP, NP-PB2-C-HA, PB2-NP-C-HA, HA-NP-C-PB2, HA-PB2-C-NP, NP-C-PB2-HA, PB2-C-NP-HA, HA-C-NP-C-PB2, HA-C-PB2-C-NP, NP-C-PB2-C-HA, PB2-C-NP-C-HA, HA-K-NP-C-PB2, HA-K-PB2-C-NP, NP-C-PB2-K-HA, PB2-C-NP-K-HA, HA-C-NP-K-PB2, HA-C-PB2-K-NP, NP-K-PB2-C-HA, PB2-K-NP-C-HA, HA-K-NP-PB1F2, HA-K-PB1F2-NP, NP-PB1F2-K-HA, PB1F2-NP-K-HA, HA-NP-K-PB1F2, HA-PB1F2-K-NP, NP-K-PB1F2-HA, PB1F2-K-NP-HA, HA-K-NP-K-PB1F2, HA-K-PB1F2-K-NP, NP-K-PB1F2-K-HA, PB1F2-K-NP-K-HA, HA-C-NP-PB1F2, HA-C-PB1F2-NP, NP-PB1F2-C-HA, PB1F2-NP-C-HA, HA-NP-C-PB1F2, HA-PB1F2-C-NP, NP-C-PB1F2-HA, PB1F2-C-NP-HA, HA-C-NP-C-PB1F2, HA-C-PB1F2-C-NP, NP-C-PB1F2-C-HA, PB1F2-C-NP-C-HA, HA-K-NP-C-PB1F2, HA-K-PB1F2-C-NP, NP-C-PB1F2-K-HA, PB1F2-C-NP-K-HA, HA-C-NP-K-PB1F2, HA-C-PB1F2-K-NP, NP-K-PB1F2-C-HA, PB1F2-K-NP-C-HA, HA-K-M1, M1-K-HA, HA-K-M1-M1, M1-M1-K-HA, HA-M1-K-M1, M1-K-M1-HA, HA-K-M1-K-M1, M1-K-M1-K-HA, HA-C-M1, M1-C-HA, HA-C-M1-M1, M1-M1-C-HA, HA-M1-C-M1, M1-C-M1-HA, HA-C-M1-C-M1, M1-C-M1-C-HA, HA-K-M1-C-M1, M1-C-M1-K-HA, HA-C-M1-K-M1, M1-K-M1-C-HA, HA-K-M1-M2, HA-K-M2-M1, M1-M2-K-HA, M2-M1-K-HA, HA-M1-K-M2, HA-M2-K-M1, M1-K-M2-HA, M2-K-M1-HA, HA-K-M1-K-M2, HA-K-M2-K-M1, M1-K-M2-K-HA, M2-K-M1-K-HA, HA-C-M1-M2, HA-C-M2-M1, M1-M2-C-HA, M2-M1-C-HA, HA-M1-C-M2, HA-M2-C-M1, M1-C-M2-HA, M2-C-M1-HA, HA-C-M1-C-M2, HA-C-M2-C-M1, M1-C-M2-C-HA, M2-C-M1-C-HA, HA-K-M1-C-M2, HA-K-M2-C-M1, M1-C-M2-K-HA, M2-C-M1-K-HA, HA-C-M1-K-M2, HA-C-M2-K-M1, M1-K-M2-C-HA, M2-K-M1-C-HA, HA-K-M1-NS1, HA-K-NS1-M1, M1-NS1-K-HA, NS1-M1-K-HA, HA-M1-K-NS1, HA-NS1-K-M1, M1-K-NS1-HA, NS1-K-M1-HA, HA-K-M1-K-NS1, HA-K-NS1-K-M1, M1-K-NS1-K-HA, NS1-K-M1-K-HA, HA-C-M1-NS1, HA-C-NS1-M1, M1-NS1-C-HA, NS1-M1-C-HA, HA-M1-C-NS1, HA-NS1-C-M1, M1-C-NS1-HA, NS1-C-M1-HA, HA-C-M1-C-NS1, HA-C-NS1-C-M1, M1-C-NS1-C-HA, NS1-C-M1-C-HA, HA-K-M1-C-NS1, HA-K-NS1-C-M1, M1-C-NS1-K-HA, NS1-C-M1-K-HA, HA-C-M1-K-NS1, HA-C-NS1-K-M1, M1-K-NS1-C-HA, NS1-K-M1-C-HA, HA-K-M1-NS2/NEP, HA-K-NS2/NEP-M1, M1-NS2/NEP-K-HA, NS2/NEP-M1-K-HA, HA-M1-K-NS2/NEP, HA-NS2/NEP-K-M1, M1-K-NS2/NEP-HA, NS2/NEP-K-M1-HA, HA-K-M1-K-NS2/NEP, HA-K-NS2/NEP-K-M1, M1-K-NS2/NEP-K-HA, NS2/NEP-K-M1-K-HA, HA-C-M1-NS2/NEP, HA-C-NS2/NEP-M1, M1-NS2/NEP-C-HA, NS2/NEP-M1-C-HA, HA-M1-C-NS2/NEP, HA-NS2/NEP-C-M1, M1-C-NS2/NEP-HA, NS2/NEP-C-M1-HA, HA-C-M1-C-NS2/NEP, HA-C-NS2/NEP-C-M1, M1-C-NS2/NEP-C-HA, NS2/NEP-C-M1-C-HA, HA-K-M1-C-NS2/NEP, HA-K-NS2/NEP-C-M1, M1-C-NS2/NEP-K-HA, NS2/NEP-C-M1-K-HA, HA-C-M1-K-NS2/NEP, HA-C-NS2/NEP-K-M1, M1-K-NS2/NEP-C-HA, NS2/NEP-K-M1-C-HA, HA-K-M1-PA, HA-K-PA-M1, M1-PA-K-HA, PA-M1-K-HA, HA-M1-K-PA, HA-PA-K-M1, M1-K-PA-HA, PA-K-M1-HA, HA-K-M1-K-PA, HA-K-PA-K-M1, M1-K-PA-K-HA, PA-K-M1-K-HA, HA-C-M1-PA, HA-C-PA-M1, M1-PA-C-HA, PA-M1-C-HA, HA-M1-C-PA, HA-PA-C-M1, M1-C-PA-HA, PA-C-M1-HA, HA-C-M1-C-PA, HA-C-PA-C-M1, M1-C-PA-C-HA, PA-C-M1-C-HA, HA-K-M1-C-PA, HA-K-PA-C-M1, M1-C-PA-K-HA, PA-C-M1-K-HA, HA-C-M1-K-PA, HA-C-PA-K-M1, M1-K-PA-C-HA, PA-K-M1-C-HA, HA-K-M1-PB1, HA-K-PB1-M1, M1-PB1-K-HA, PB1-M1-K-HA, HA-M1-K-PB1, HA-PB1-K-M1, M1-K-PB1-HA, PB1-K-M1-HA, HA-K-M1-K-PB1, HA-K-PB1-K-M1, M1-K-PB1-K-HA, PB1-K-M1-K-HA, HA-C-M1-PB1, HA-C-PB1-M1, M1-PB1-C-HA, PB1-M1-C-HA, HA-M1-C-PB1, HA-PB1-C-M1, M1-C-PB1-HA, PB1-C-M1-HA, HA-C-M1-C-PB1, HA-C-PB1-C-M1, M1-C-PB1-C-HA, PB1-C-M1-C-HA, HA-K-M1-C-PB1, HA-K-PB1-C-M1, M1-C-PB1-K-HA, PB1-C-M1-K-HA, HA-C-M1-K-PB1, HA-C-PB1-K-M1, M1-K-PB1-C-HA, PB1-K-M1-C-HA, HA-K-M1-PB2, HA-K-PB2-M1, M1-PB2-K-HA, PB2-M1-K-HA, HA-M1-K-PB2, HA-PB2-K-M1, M1-K-PB2-HA, PB2-K-M1-HA, HA-K-M1-K-PB2, HA-K-PB2-K-M1, M1-K-PB2-K-HA, PB2-K-M1-K-HA, HA-C-M1-PB2, HA-C-PB2-M1, M1-PB2-C-HA, PB2-M1-C-HA, HA-M1-C-PB2, HA-PB2-C-M1, M1-C-PB2-HA, PB2-C-M1-HA, HA-C-M1-C-PB2, HA-C-PB2-C-M1, M1-C-PB2-C-HA, PB2-C-M1-C-HA, HA-K-M1-C-PB2, HA-K-PB2-C-M1, M1-C-PB2-K-HA, PB2-C-M1-K-HA, HA-C-M1-K-PB2, HA-C-PB2-K-M1, M1-K-PB2-C-HA, PB2-K-M1-C-HA, HA-K-M1-PB1F2, HA-K-PB1F2-M1, M1-PB1F2-K-HA, PB1F2-M1-K-HA, HA-M1-K-PB1F2, HA-PB1F2-K-M1, M1-K-PB1F2-HA, PB1F2-K-M1-HA, HA-K-M1-K-PB1F2, HA-K-PB1F2-K-M 1, M1-K-PB1F2-K-HA, PB1F2-K-M1-K-HA, HA-C-M1-PB1F2, HA-C-PB1F2-M1, M1-PB1F2-C-HA, PB1F2-M1-C-HA, HA-M1-C-PB1F2, HA-PB1F2-C-M1, M1-C-PB1F2-HA, PB1F2-C-M1-HA, HA-C-M1-C-PB1F2, HA-C-PB1F2-C-M1, M1-C-

PB1F2-C-HA, PB1F2-C-M1-C-HA, HA-K-M1-C-PB1F2, HA-K-PB1F2-C-M 1, M1-C-PB1F2-K-HA, PB1F2-C-M1-K-HA, HA-C-M1-K-PB1F2, HA-C-PB1F2-K-M1, M1-K-PB1F2-C-HA, PB1F2-K-M1-C-HA, HA-K-M2, M2-K-HA, HA-K-M2-M2, M2-M2-K-HA, HA-M2-K-M2, M2-K-M2-HA, HA-K-M2-K-M2, M2-K-M2-K-HA, HA-C-M2, M2-C-HA, HA-C-M2-M2, M2-M2-C-HA, HA-M2-C-M2, M2-C-M2-HA, HA-C-M2-C-M2, M2-C-M2-C-HA, HA-K-M2-C-M2, M2-C-M2-K-HA, HA-C-M2-K-M2, M2-K-M2-C-HA, HA-K-M2-NS1, HA-K-NS1-M2, M2-NS1-K-HA, NS1-M2-K-HA, HA-M2-K-NS1, HA-NS1-K-M2, M2-K-NS1-HA, NS1-K-M2-HA, HA-K-M2-K-NS1, HA-K-NS1-K-M2, M2-K-NS1-K-HA, NS1-K-M2-K-HA. HA-C-M2-NS1, HA-C-NS1-M2, M2-NS1-C-HA, NS1-M2-C-HA, HA-M2-C-NS1, HA-NS1-C-M2, M2-C-NS1-HA, NS1-C-M2-HA, HA-C-M2-C-NS1, HA-C-NS1-C-M2, M2-C-NS1-C-HA, NS1-C-M2-C-HA, HA-K-M2-C-NS1, HA-K-NS1-C-M2, M2-C-NS1-K-HA, NS1-C-M2-K-H A, HA-C-M2-K-NS1, HA-C-NS1-K-M2, M2-K-NS1-C-HA, NS1-K-M2-C-HA, HA-K-M2-NS2/NEP, HA-K-NS2/NEP-M2, M2-NS2/NEP-K-HA, NS2/NEP-M2-K-HA, HA-M2-K-NS2/NEP, HA-NS2/NEP-K-M2, M2-K-NS2/NEP-HA, NS2/NEP-K-M2-HA, HA-K-M2-K-NS2/NEP, HA-K-NS2/NEP-K-M2, M2-K-NS2/NEP-K-HA, NS2/NEP-K-M2-K-HA, HA-C-M2-NS2/NEP, HA-C-NS2/NEP-M2, M2-NS2/NEP-C-HA, NS2/NEP-M2-C-HA, HA-M2-C-NS2/NEP, HA-NS2/NEP-C-M2, M2-C-NS2/NEP-HA, NS2/NEP-C-M2-HA, HA-C-M2-C-NS2/NEP, HA-C-NS2/NEP-C-M2, M2-C-NS2/NEP-C-HA, NS2/NEP-C-M2-C-HA, HA-K-M2-C-NS2/NEP, HA-K-NS2/NEP-C-M2, M2-C-NS2/NEP-K-HA, NS2/NEP-C-M2-K-HA, HA-C-M2-K-NS2/NEP, HA-C-NS2/NEP-K-M2, M2-K-NS2/NEP-C-HA, NS2/NEP-K-M2-C-HA, HA-K-M2-PA, HA-K-PA-M2, M2-PA-K-HA, PA-M2-K-HA, HA-M2-K-PA, HA-PA-K-M2, M2-K-PA-HA, PA-K-M2-HA, HA-K-M2-K-PA, HA-K-PA-K-M2, M2-K-PA-K-HA, PA-K-M2-K-HA, HA-C-M2-PA, HA-C-PA-M2, M2-PA-C-HA, PA-M2-C-HA, HA-M2-C-PA, HA-PA-C-M2, M2-C-PA-HA, PA-C-M2-HA, HA-C-M2-C-PA, HA-C-PA-C-M2, M2-C-PA-C-HA, PA-C-M2-C-HA, HA-K-M2-C-PA, HA-K-PA-C-M2, M2-C-PA-K-HA, PA-C-M2-K-HA, HA-C-M2-K-PA, HA-C-PA-K-M2, M2-K-PA-C-HA, PA-K-M2-C-HA, HA-K-M2-PB1, HA-K-PB1-M2, M2-PB1-K-HA, PB1-M2-K-HA, HA-M2-K-PB1, HA-PB1-K-M2, M2-K-PB1-HA, PB1-K-M2-HA, HA-K-M2-K-PB1, HA-K-PB1-K-M2, M2-K-PB1-K-HA, PB1-K-M2-K-HA, HA-C-M2-PB1, HA-C-PB1-M2, M2-PB1-C-HA, PB1-M2-C-HA, HA-M2-C-PB1, HA-PB1-C-M2, M2-C-PB1-HA, PB1-C-M2-HA, HA-C-M2-C-PB1, HA-C-PB1-C-M2, M2-C-PB1-C-HA, PB1-C-M2-C-HA, HA-K-M2-C-PB1, HA-K-PB1-C-M2, M2-C-PB1-K-HA, PB1-C-M2-K-HA, HA-C-M2-K-PB1, HA-C-PB1-K-M2, M2-K-PB1-C-HA, PB1-K-M2-C-HA. HA-K-M2-PB2, HA-K-PB2-M2, M2-PB2-K-HA, PB2-M2-K-HA, HA-M2-K-PB2, HA-PB2-K-M2, M2-K-PB2-HA, PB2-K-M2-HA, HA-K-M2-K-PB2, HA-K-PB2-K-M2, M2-K-PB2-K-HA, PB2-K-M2-K-HA, HA-C-M2-PB2, HA-C-PB2-M2, M2-PB2-C-HA, PB2-M2-C-HA, HA-M2-C-PB2, HA-PB2-C-M2, M2-C-PB2-HA, PB2-C-M2-HA, HA-C-M2-C-PB2, HA-C-PB2-C-M2, M2-C-PB2-C-HA, PB2-C-M2-C-HA, HA-K-M2-C-PB2, HA-K-PB2-C-M2, M2-C-PB2-K-HA, PB2-C-M2-K-HA, HA-C-M2-K-PB2, HA-C-PB2-K-M2, M2-K-PB2-C-HA, PB2-K-M2-C-HA, HA-K-M2-PB1F2, HA-K-PB1F2-M2, M2-PB1F2-K-HA, PB1F2-M2-K-HA, HA-M2-K-PB1F2, HA-PB1F2-K-M2, M2-K-PB1F2-HA, PB1F2-K-M2-HA, HA-K-M2-K-PB1F2, HA-K-PB1F2-K-M2, M2-K-PB1F2-K-HA, PB1F2-K-M2-K-HA, HA-C-M2-PB1F2, HA-C-PB1F2-M2, M2-PB1F2-C-HA, PB1F2-M2-C-HA, HA-M2-C-PB1F2, HA-PB1F2-C-M2, M2-C-PB1F2-HA, PB1F2-C-M2-HA, HA-C-M2-C-PB1F2, HA-C-PB1F2-C-M2, M2-C-PB1F2-C-HA, PB1F2-C-M2-C-HA, HA-K-M2-C-PB1F2, HA-K-PB1F2-C-M2, M2-C-PB1F2-K-HA, PB1F2-C-M2-K-HA, HA-C-M2-K-PB1F2, HA-C-PB1F2-K-M2, M2-K-PB1F2-C-HA, PB1F2-K-M2-C-HA, HA-K-NS1, NS1-K-HA, HA-K-NS1-NS1, NS1-NS1-K-HA, HA-NS1-K-NS1, NS1-K-NS1-HA, HA-K-NS1-K-NS1, NS1-K-NS1-K-HA, HA-C-NS1, NS1-C-HA, HA-C-NS1-NS1, NS1-NS1-C-HA, HA-NS1-C-NS1, NS1-C-NS1-HA, HA-C-NS1-C-NS1, NS1-C-NS1-C-HA, HA-K-NS1-C-NS1, NS1-C-NS1-K-HA, HA-C-NS1-K-NS1, NS1-K-NS1-C-HA, HA-K-NS1-NS2/NEP, HA-K-NS2/NEP-NS1, NS1-NS2/NEP-K-HA, NS2/NEP-NS1-K-HA, HA-NS1-K-NS2/NEP, HA-NS2/NEP-K-NS1, NS1-K-NS2/NEP-HA, NS2/NEP-K-NS1-HA, HA-K-NS1-K-NS2/NEP, H A-K-NS2/NEP-K-NS1, NS1-K-NS2/NEP-K-HA, NS2/NEP-K-NS1-K-HA, HA-C-NS1-NS2/NEP, HA-C-NS2/NEP-NS1, NS1-NS2/NEP-C-HA, NS2/NEP-NS1-C-HA, HA-NS1-C-NS2/NEP, HA-NS2/NEP-C-NS1, NS1-C-NS2/NEP-HA, NS2/NEP-C-NS1-HA, HA-C-NS1-C-NS2/NEP, HA-C-NS2/NEP-C-NS1, NS1-C-NS2/NEP-C-HA, NS2/NEP-C-NS1-C-HA, HA-K-NS1-C-NS2/NEP, HA-K-NS2/NEP-C-NS1, NS1-C-NS2/NEP-K-HA, NS2/NEP-C-NS1-K-HA, HA-C-NS1-K-NS2/NEP, HA-C-NS2/NEP-K-NS1, NS1-K-NS2/NEP-C-HA, NS2/NEP-K-NS1-C-HA, HA-K-NS1-PA, HA-K-PA-NS1, NS1-PA-K-HA, PA-NS1-K-HA, HA-NS1-K-PA, HA-PA-K-NS1, NS1-K-PA-HA, PA-K-NS1-HA, HA-K-NS1-K-PA, HA-K-PA-K-NS1, NS1-K-PA-K-HA, PA-K-NS1-K-HA, HA-C-NS1-PA, HA-C-PA-NS1, NS1-PA-C-HA, PA-NS1-C-HA, HA-NS1-C-PA, HA-PA-C-NS1, NS1-C-PA-HA, PA-C-NS1-HA, HA-C-NS1-C-PA, HA-C-PA-C-NS1, NS1-C-PA-C-HA, PA-C-NS1-C-HA, HA-K-NS1-C-PA, HA-K-PA-C-NS1, NS1-C-PA-K-HA, PA-C-NS1-K-HA, HA-C-NS1-K-PA, HA-C-PA-K-NS1, NS1-K-PA-C-HA, PA-K-NS1-C-HA, HA-K-NS1-PB1, HA-K-PB1-NS1, NS1-PB1-K-HA, PB1-NS1-K-HA, HA-NS1-K-PB1, HA-PB1-K-NS1, NS1-K-PB1-HA, PB1-K-NS1-HA, HA-K-NS1-K-PB1, HA-K-PB1-K-NS1, NS1-K-PB1-K-HA, PB1-K-NS1-K-HA, HA-C-NS1-PB1, HA-C-PB1-NS1, NS1-PB1-C-HA, PB1-NS1-C-HA, HA-NS1-C-PB1, HA-PB1-C-NS1, NS1-C-PB1-HA, PB1-C-NS1-HA, HA-C-NS1-C-PB1, HA-C-PB1-C-NS1, NS1-C-PB1-C-HA, PB1-C-NS1-C-HA, HA-K-NS1-C-PB1, HA-K-PB1-C-NS1, NS1-C-PB1-K-HA, PB1-C-NS1-K-HA, HA-C-NS1-K-PB1, HA-C-PB1-K-NS1, NS1-K-PB1-C-HA, PB1-K-NS1-C-HA, HA-K-NS1-PB2, HA-K-PB2-NS1, NS1-PB2-K-HA, PB2-NS1-K-HA, HA-NS1-K-PB2, HA-PB2-K-NS1, NS1-K-PB2-HA, PB2-K-NS1-HA, HA-K-NS1-K-PB2, HA-K-PB2-K-NS1, NS1-K-PB2-K-HA, PB2-K-NS1-K-HA, HA-C-NS1-PB2, HA-C-PB2-NS1, NS1-PB2-C-HA, PB2-NS1-C-HA, HA-NS1-C-PB2, HA-PB2-C-NS1, NS1-C-PB2-HA, PB2-C-NS1-HA, HA-C-NS1-C-PB2, HA-C-PB2-C-NS1, NS1-C-PB2-C-HA, PB2-C-NS1-C-HA, HA-K-NS1-C-PB2, HA-K-PB2-C-NS1, NS1-C-PB2-K-HA, PB2-C-NS1-K-HA, HA-C-NS1-K-PB2, HA-C-PB2-K-NS1, NS1-K-PB2-C-HA, PB2-K-NS1-C-HA, HA-K-NS1-PB1F2, HA-K-PB1F2-NS1, NS1-PB1F2-K-HA, PB1F2-NS1-K-HA, HA-NS1-K-PB1F2, HA-PB1F2-K-NS1, NS1-K-PB1F2-HA, PB1F2-K-NS1-HA, HA-K-NS1-K-PB1F2, HA-K-PB1F2-K-NS1, NS1-K-PB1F2-K-HA, PB1F2-K-NS1-K-HA, HA-C-NS1-PB1F2, HA-C-PB1F2-NS1, NS1-PB1F2-C-HA, PB1F2-NS1-C-HA, HA-NS1-C-PB1F2, HA-PB1F2-C-NS1, NS1-C-PB1F2-HA, PB1F2-C-NS1-HA, HA-C-NS1-C-PB1F2, HA-C-PB1F2-C-NS1, NS1-C-PB1F2-C-HA, PB1F2-C-NS1-C-HA, HA-K-NS1-C-PB1F2, HA-K-PB1F2-C-NS1,

NS1-C-PB1F2-K-HA, PB1F2-C-NS1-K-HA, HA-C-NS1-K-PB1F2, HA-C-PB1F2-K-NS1, NS1-K-PB1F2-C-HA, PB1F2-K-NS1-C-HA, HA-K-NS2/NEP, NS2/NEP-K-HA, HA-K-NS2/NEP-NS2/NEP, NS2/NEP-NS2/NEP-K-HA, HA-NS2/NEP-K-NS2/NEP, NS2/NEP-K-NS2/NEP-HA, HA-K-NS2/NEP-K-NS2/NEP, NS2/NEP-K-NS2/NEP-K-HA, HA-C-NS2/NEP, NS2/NEP-C-HA, HA-C-NS2/NEP-NS2/NEP, NS2/NEP-NS2/NEP-C-HA, HA-NS2/NEP-C-NS2/NEP, NS2/NEP-C-NS2/NEP-HA, HA-C-NS2/NEP-C-NS2/NEP, NS2/NEP-C-NS2/NEP-C-HA, HA-K-NS2/NEP-C-NS2/NEP, NS2/NEP-C-NS2/NEP-K-HA, HA-C-NS2/NEP-K-NS2/NEP, NS2/NEP-K-NS2/NEP-C-HA, HA-K-NS2/NEP-PA, HA-K-PA-NS2/NEP, NS2/NEP-PA-K-HA, PA-NS2/NEP-K-HA, HA-NS2/NEP-K-PA, HA-PA-K-NS2/NEP, NS2/NEP-K-PA-HA, PA-K-NS2/NEP-HA, HA-K-NS2/NEP-K-PA, HA-K-PA-K-NS2/NEP, NS2/NEP-K-PA-K-HA, PA-K-NS2/NEP-K-HA, HA-C-NS2/NEP-PA, HA-C-PA-NS2/NEP, NS2/NEP-PA-C-HA, PA-NS2/NEP-C-HA, HA-NS2/NEP-C-PA, HA-PA-C-NS2/NEP, NS2/NEP-C-PA-HA, PA-C-NS2/NEP-HA, HA-C-NS2/NEP-C-PA, HA-C-PA-C-NS2/NEP, NS2/NEP-C-PA-C-HA, PA-C-NS2/NEP-C-HA, HA-K-NS2/NEP-C-PA, HA-K-PA-C-NS2/NEP, NS2/NEP-C-PA-K-HA, PA-C-NS2/NEP-K-HA, HA-C-NS2/NEP-K-PA, HA-C-PA-K-NS2/NEP, NS2/NEP-K-PA-C-HA, PA-K-NS2/NEP-C-HA, HA-K-NS2/NEP-PB1, HA-K-PB1-NS2/NEP, NS2/NEP-PB1-K-HA, PB1-NS2/NEP-K-HA, HA-NS2/NEP-K-PB1, HA-PB1-K-NS2/NEP, NS2/NEP-K-PB1-HA, PB1-K-NS2/NEP-HA, HA-K-NS2/NEP-K-PB1, HA-K-PB1-K-NS2/NEP, NS2/NEP-K-PB1-K-HA, PB1-K-NS2/NEP-K-HA, HA-C-NS2/NEP-PB1, HA-C-PB1-NS2/NEP, NS2/NEP-PB1-C-HA, PB1-NS2/NEP-C-HA, HA-NS2/NEP-C-PB1, HA-PB1-C-NS2/NEP, NS2/NEP-C-PB1-HA, PB1-C-NS2/NEP-HA, HA-C-NS2/NEP-C-PB1, HA-C-PB1-C-NS2/NEP, NS2/NEP-C-PB1-C-HA, PB1-C-NS2/NEP-C-HA, HA-K-NS2/NEP-C-PB1, HA-K-PB1-C-NS2/NEP, NS2/NEP-C-PB1-K-HA, PB1-C-NS2/NEP-K-HA, HA-C-NS2/NEP-K-PB1, HA-C-PB1-K-NS2/NEP, NS2/NEP-K-PB1-C-HA, PB1-K-NS2/NEP-C-HA, HA-K-NS2/NEP-PB2, HA-K-PB2-NS2/NEP, NS2/NEP-PB2-K-HA, PB2-NS2/NEP-K-HA, HA-NS2/NEP-K-PB2, HA-PB2-K-NS2/NEP, NS2/NEP-K-PB2-HA, PB2-K-NS2/NEP-HA, HA-K-NS2/NEP-K-PB2, HA-K-PB2-K-NS2/NEP, NS2/NEP-K-PB2-K-HA, PB2-K-NS2/NEP-K-HA, HA-C-NS2/NEP-PB2, HA-C-PB2-NS2/NEP, NS2/NEP-PB2-C-HA, PB2-NS2/NEP-C-HA, HA-NS2/NEP-C-PB2, HA-PB2-C-NS2/NEP, NS2/NEP-C-PB2-HA, PB2-C-NS2/NEP-HA, HA-C-NS2/NEP-C-PB2, HA-C-PB2-C-NS2/NEP, NS2/NEP-C-PB2-C-HA, PB2-C-NS2/NEP-C-HA, HA-K-NS2/NEP-C-PB2, HA-K-PB2-C-NS2/NEP, NS2/NEP-C-PB2-K-HA, PB2-C-NS2/NEP-K-HA, HA-C-NS2/NEP-K-PB2, HA-C-PB2-K-NS2/NEP, NS2/NEP-K-PB2-C-HA, PB2-K-NS2/NEP-C-HA, HA-K-NS2/NEP-PB1F2, HA-K-PB1F2-NS2/NEP, NS2/NEP-PB1F2-K-HA, PB1F2-NS2/NEP-K-HA, HA-NS2/NEP-K-PB1F2, HA-PB1F2-K-NS2/NEP, NS2/NEP-K-PB1F2-HA, PB1F2-K-NS2/NEP-HA, HA-K-NS2/NEP-K-PB1F2, HA-K-PB1F2-K-NS2/NEP, NS2/NEP-K-PB1F2-K-HA, PB1F2-K-NS2/NEP-K-HA, HA-C-NS2/NEP-PB1F2, HA-C-PB1F2-NS2/NEP, NS2/NEP-PB1F2-C-HA, PB1F2-NS2/NEP-C-HA, HA-NS2/NEP-C-PB1F2, HA-PB1F2-C-NS2/NEP, NS2/NEP-C-PB1F2-HA, PB1F2-C-NS2/NEP-HA, HA-C-NS2/NEP-C-PB1F2, HA-C-PB1F2-C-NS2/NEP, NS2/NEP-C-PB1F2-C-HA, PB1F2-C-NS2/NEP-C-HA, HA-K-NS2/NEP-C-PB1F2, HA-K-PB1F2-C-NS2/NEP, NS2/NEP-C-PB1F2-K-HA, PB1F2-C-NS2/NEP-K-HA, HA-C-NS2/NEP-K-PB1F2, HA-C-PB1F2-K-NS2/NEP, NS2/NEP-K-PB1F2-C-HA, PB1F2-K-NS2/NEP-C-HA, HA-K-PA, PA-K-HA, HA-K-PA-PA, PA-PA-K-HA, HA-PA-K-PA, PA-K-PA-HA, HA-K-PA-K-PA, PA-K-PA-K-HA, HA-C-PA, PA-C-HA, HA-C-PA-PA, PA-PA-C-HA, HA-PA-C-PA, PA-C-PA-HA, HA-C-PA-C-PA, PA-C-PA-C-HA, HA-K-PA-C-PA, PA-C-PA-K-HA, HA-C-PA-K-PA, PA-K-PA-C-HA, HA-K-PA-PB1, HA-K-PB1-PA, PA-PB1-K-HA, PB1-PA-K-HA, HA-PA-K-PB1, HA-PB1-K-PA, PA-K-PB1-HA, PB1-K-PA-HA, HA-K-PA-K-PB1, HA-K-PB1-K-PA, PA-K-PB1-K-HA, PB1-K-PA-K-HA, HA-C-PA-PB1, HA-C-PB1-PA, PA-PB1-C-HA, PB1-PA-C-HA, HA-PA-C-PB1, HA-PB1-C-PA, PA-C-PB1-HA, PB1-C-PA-HA, HA-C-PA-C-PB1, HA-C-PB1-C-PA, PA-C-PB1-C-HA, PB1-C-PA-C-HA, HA-K-PA-C-PB1, HA-K-PB1-C-PA, PA-C-PB1-K-HA, PB1-C-PA-K-HA, HA-C-PA-K-PB1, HA-C-PB1-K-PA, PA-K-PB1-C-HA, PB1-K-PA-C-HA, HA-K-PA-PB2, HA-K-PB2-PA, PA-PB2-K-HA, PB2-PA-K-HA, HA-PA-K-PB2, HA-PB2-K-PA, PA-K-PB2-HA, PB2-K-PA-HA, HA-K-PA-K-PB2, HA-K-PB2-K-PA, PA-K-PB2-K-HA, PB2-K-PA-K-HA, HA-C-PA-PB2, HA-C-PB2-PA, PA-PB2-C-HA, PB2-PA-C-HA, HA-PA-C-PB2, HA-PB2-C-PA, PA-C-PB2-HA, PB2-C-PA-HA, HA-C-PA-C-PB2, HA-C-PB2-C-PA, PA-C-PB2-C-HA, PB2-C-PA-C-HA, HA-K-PA-C-PB2, HA-K-PB2-C-PA, PA-C-PB2-K-HA, PB2-C-PA-K-HA, HA-C-PA-K-PB2, HA-C-PB2-K-PA, PA-K-PB2-C-HA, PB2-K-PA-C-HA, HA-K-PA-PB1F2, HA-K-PB1F2-PA, PA-PB1F2-K-HA, PB1F2-PA-K-HA, HA-PA-K-PB1F2, HA-PB1F2-K-PA, PA-K-PB1F2-HA, PB1F2-K-PA-HA, HA-K-PA-K-PB1F2, HA-K-PB1F2-K-PA, PA-K-PB1F2-K-HA, PB1F2-K-PA-K-HA, HA-C-PA-PB1F2, HA-C-PB1F2-PA, PA-PB1F2-C-HA, PB1F2-PA-C-HA, HA-PA-C-PB1F2, HA-PB1F2-C-PA, PA-C-PB1F2-HA, PB1F2-C-PA-HA, HA-C-PA-C-PB1F2, HA-C-PB1F2-C-PA, PA-C-PB1F2-C-HA, PB1F2-C-PA-C-HA, HA-K-PA-C-PB1F2, HA-K-PB1F2-C-PA, PA-C-PB1F2-K-HA, PB1F2-C-PA-K-HA, HA-C-PA-K-PB1F2, HA-C-PB1F2-K-PA, PA-K-PB1F2-C-HA, PB1F2-K-PA-C-HA, HA-K-PB1, PB1-K-HA, HA-K-PB1-PB1, PB1-PB1-K-HA, HA-PB1-K-PB1, PB1-K-PB1-HA, HA-K-PB1-K-PB1, PB1-K-PB1-K-HA, HA-C-PB1, PB1-C-HA, HA-C-PB1-PB1, PB1-PB1-C-HA, HA-PB1-C-PB1, PB1-C-PB1-HA, HA-C-PB1-C-PB1, PB1-C-PB1-C-HA, HA-K-PB1-C-PB1, PB1-C-PB1-K-HA, HA-C-PB1-K-PB1, PB1-K-PB1-C-HA, HA-K-PB1-PB2, HA-K-PB2-PB1, PB1-PB2-K-HA, PB2-PB1-K-HA, HA-PB1-K-PB2, HA-PB2-K-PB1, PB1-K-PB2-HA, PB2-K-PB1-HA, HA-K-PB1-K-PB2, HA-K-PB2-K-PB1, PB1-K-PB2-K-HA, PB2-K-PB1-K-HA, HA-C-PB1-PB2, HA-C-PB2-PB1, PB1-PB2-C-HA, PB2-PB1-C-HA, HA-PB1-C-PB2, HA-PB2-C-PB1, PB1-C-PB2-HA, PB2-C-PB1-HA, HA-C-PB1-C-PB2, HA-C-PB2-C-PB1, PB1-C-PB2-C-HA, PB2-C-PB1-C-HA, HA-K-PB1-C-PB2, HA-K-PB2-C-PB1, PB1-C-PB2-K-HA, PB2-C-PB1-K-HA, HA-C-PB1-K-PB2, HA-C-PB2-K-PB1, PB1-K-PB2-C-HA, PB2-K-PB1-C-HA, HA-K-PB1-PB1F2, HA-K-PB1F2-PB1, PB1-PB1F2-K-HA, PB1F2-PB1-K-HA, HA-PB1-K-PB1F2, HA-PB1F2-K-PB1, PB1-K-PB1F2-HA, PB1F2-K-PB1-HA, HA-K-PB1-K-PB1F2, HA-K-PB1F2-K-PB1, PB1-K-PB1F2-K-HA, PB1F2-K-PB1-K-HA, HA-C-PB1-PB1F2, HA-C-PB1F2-PB1, PB1-PB1F2-C-HA, PB1F2-PB1-C-HA, HA-PB1-C-PB1F2, HA-PB1F2-C-PB1, PB1-C-PB1F2-HA, PB1F2-C-PB1-HA, HA-C-PB1-C-PB1F2, HA-C-PB1F2-C-PB1, PB1-C-PB1F2-C-HA, PB1F2-C-PB1-C-HA, HA-K-PB1-C-PB1F2, HA-K-PB1F2-C-PB1, PB1-C-PB1F2-K-HA, PB1F2-C-PB1-K-HA, HA-C-PB1-K-PB1F2, HA-C-PB1F2-K-PB1, PB1-K-PB1F2-C-HA, PB1F2-K-PB1-C-HA, HA-K-PB2, PB2-K-HA, HA-K-PB2-PB2, PB2-PB2-K-HA, HA-PB2-K-PB2, PB2-K-PB2-

HA, HA-K-PB2-K-PB2, PB2-K-PB2-K-HA, HA-C-PB2, PB2-C-PB2-HA, HA-C-PB2-PB2, PB2-PB2-C-HA, HA-PB2-C-PB2, PB2-C-PB2-HA, HA-C-PB2-C-PB2, PB2-C-PB2-C-HA, HA-K-PB2-C-PB2, PB2-C-PB2-K-HA, HA-C-PB2-K-PB2, PB2-K-PB2-C-HA, HA-K-PB2-PB1F2, HA-K-PB1F2-PB2, PB2-PB1F2-K-HA, PB1F2-PB2-K-HA, HA-PB2-K-PB1F2, HA-PB1F2-K-PB2, PB2-K-PB1F2-HA, PB1F2-K-PB2-HA, HA-K-PB2-K-PB1F2, HA-K-PB1F2-K-PB2, PB2-K-PB1F2-K-HA, PB1F2-K-PB2-K-HA, HA-C-PB2-PB1F2, HA-C-PB1F2-PB2, PB2-PB1F2-C-HA, PB1F2-PB2-C-HA, HA-PB2-C-PB1F2, HA-PB1F2-C-PB2, PB2-C-PB1F2-HA, PB1F2-C-PB2-HA, HA-C-PB2-C-PB1F2, HA-C-PB1F2-C-PB2, PB2-C-PB1F2-C-HA, PB1F2-C-PB2-C-HA, HA-K-PB2-C-PB1F2, HA-K-PB1F2-C-PB2, PB2-C-PB1F2-K-HA, PB1F2-C-PB2-K-HA, HA-C-PB2-K-PB1F2, HA-C-PB1F2-K-PB2, PB2-K-PB1F2-C-HA, PB1F2-K-PB2-C-HA, HA-K-PB1F2, PB1F2-K-HA, HA-K-PB1F2-PB1F2, PB1F2-PB1F2-K-HA, HA-PB1F2-K-PB1F2, PB1F2-K-PB1F2-HA, HA-K-PB1F2-K-PB1F2, PB1F2-K-PB1F2-K-HA, HA-C-PB1F2, PB1F2-C-HA, HA-C-PB1F2-PB1F2, PB1F2-PB1F2-C-HA, HA-PB1F2-C-PB1F2, PB1F2-C-PB1F2-HA, HA-C-PB1F2-C-PB1F2, PB1F2-C-PB1F2-C-HA, HA-K-PB1F2-C-PB1F2, PB1F2-C-PB1F2-K-HA, HA-C-PB1F2-K-PB1F2, PB1F2-K-PB1F2-C-HA, NA-K-NP, NP-K-NA, NA-K-NP-NP, NP-NP-K-NA, NA-NP-K-NP, NP-K-NP-NA, NA-K-NP-K-NP, NP-K-NP-K-NA, NA-C-NP, NP-C-NA, NA-C-NP-NP, NP-NP-C-NA, NA-NP-C-NP, NP-C-NP-NA, NA-C-NP-C-NP, NP-C-NP-C-NA, NA-K-NP-C-NP, NP-C-NP-K-NA, NA-C-NP-K-NP, NP-K-NP-C-NA, NA-K-NP-M 1, NA-K-M1-NP, NP-M1-K-NA, M1-NP-K-NA, NA-NP-K-M1, NA-M1-K-NP, NP-K-M1-NA, M1-K-NP-NA, NA-K-NP-K-M1, NA-K-M1-K-NP, NP-K-M1-K-NA, M1-K-NP-K-NA, NA-C-NP-M 1, NA-C-M1-NP, NP-M1-C-NA, M1-NP-C-NA, NA-NP-C-M1, NA-M1-C-NP, NP-C-M1-NA, M1-C-NP-NA, NA-C-NP-C-M1, NA-C-M1-C-NP, NP-C-M1-C-NA, M1-C-NP-C-NA, NA-K-NP-C-M1, NA-K-M1-C-NP, NP-C-M1-K-NA, M1-C-NP-K-NA, NA-C-NP-K-M1, NA-C-M1-K-NP, NP-K-M1-C-NA, M1-K-NP-C-NA, NA-K-NP-M2, NA-K-M2-NP, NP-M2-K-NA, M2-NP-K-NA, NA-NP-K-M2, NA-M2-K-NP, NP-K-M2-NA, M2-K-NP-NA, NA-K-NP-K-M2, NA-K-M2-K-NP, NP-K-M2-K-NA, M2-K-NP-K-NA, NA-C-NP-M2, NA-C-M2-NP, NP-M2-C-NA, M2-NP-C-NA, NA-NP-C-M2, NA-M2-C-NP, NP-C-M2-NA, M2-C-NP-NA, NA-C-NP-C-M2, NA-C-M2-C-NP, NP-C-M2-C-NA, M2-C-NP-C-NA, NA-K-NP-C-M2, NA-K-M2-C-NP, NP-C-M2-K-NA, M2-C-NP-K-NA, NA-C-NP-K-M2, NA-C-M2-K-NP, NP-K-M2-C-NA, M2-K-NP-C-NA, NA-K-NP-NS1, NA-K-NS1-NP, NP-NS1-K-NA, NS1-NP-K-NA, NA-NP-K-NS1, NA-NS1-K-NP, NP-K-NS1-NA, NS1-K-NP-NA, NA-K-NP-K-NS1, NA-K-NS1-K-NP, NP-K-NS1-K-NA, NS1-K-NP-K-NA, NA-C-NP-NS1, NA-C-NS1-NP, NP-NS1-C-NA, NS1-NP-C-NA, NA-NP-C-NS1, NA-NS1-C-NP, NP-C-NS1-NA, NS1-C-NP-NA, NA-C-NP-C-NS1, NA-C-NS1-C-NP, NP-C-NS1-C-NA, NS1-C-NP-C-NA, NA-K-NP-C-NS1, NA-K-NS1-C-NP, NP-C-NS1-K-NA, NS1-C-NP-K-NA, NA-C-NP-K-NS1, NA-C-NS1-K-NP, NP-K-NS1-C-NA, NS1-K-NP-C-NA, NA-K-NP-NS2/NEP, NA-K-NS2/NEP-NP, NP-NS2/NEP-K-NA, NS2/NEP-NP-K-NA, NA-NP-K-NS2/NEP, NA-NS2/NEP-K-NP, NP-K-NS2/NEP-NA, NS2/NEP-K-NP-NA, NA-K-NP-K-NS2/NEP, NA-K-NS2/NEP-K-NP, NP-K-NS2/NEP-K-NA, NS2/NEP-K-NP-K-NA, NA-C-NP-NS2/NEP, NA-C-NS2/NEP-NP, NP-NS2/NEP-C-NA, NS2/NEP-NP-C-NA, NA-NP-C-NS2/NEP, NA-NS2/NEP-C-NP, NP-C-NS2/NEP-NA, NS2/NEP-C-NP-NA, NA-C-NP-C-NS2/NEP, NA-C-NS2/NEP-C-NP, NP-C-NS2/NEP-C-NA, NS2/NEP-C-NP-C-NA, NA-K-NP-C-NS2/NEP, NA-K-NS2/NEP-C-NP, NP-C-NS2/NEP-K-NA, NS2/NEP-C-NP-K-NA, NA-C-NP-K-NS2/NEP, NA-C-NS2/NEP-K-NP, NP-K-NS2/NEP-C-NA, NS2/NEP-K-NP-C-NA, NA-K-NP-PA, NA-K-PA-NP, NP-PA-K-NA, PA-NP-K-NA, NA-NP-K-PA, NA-PA-K-NP, NP-K-PA-NA, PA-K-NP-NA, NA-K-NP-K-PA, NA-K-PA-K-NP, NP-K-PA-K-NA, PA-K-NP-K-NA, NA-C-NP-PA, NA-C-PA-NP, NP-PA-C-NA, PA-NP-C-NA, NA-NP-C-PA, NA-PA-C-NP, NP-C-PA-NA, PA-C-NP-NA, NA-C-NP-C-PA, NA-C-PA-C-NP, NP-C-PA-C-NA, PA-C-NP-C-NA, NA-K-NP-C-PA, NA-K-PA-C-NP, NP-C-PA-K-NA, PA-C-NP-K-NA, NA-C-NP-K-PA, NA-C-PA-K-NP, NP-K-PA-C-NA, PA-K-NP-C-NA, NA-K-NP-PB1, NA-K-PB1-NP, NP-PB1-K-NA, PB1-NP-K-NA, NA-NP-K-PB1, NA-PB1-K-NP, NP-K-PB1-NA, PB1-K-NP-NA, NA-K-NP-K-PB1, NA-K-PB1-K-NP, NP-K-PB1-K-NA, PB1-K-NP-K-NA, NA-C-NP-PB1, NA-C-PB1-NP, NP-PB1-C-NA, PB1-NP-C-NA, NA-NP-C-PB1, NA-PB1-C-NP, NP-C-PB1-NA, PB1-C-NP-NA, NA-C-NP-C-PB1, NA-C-PB1-C-NP, NP-C-PB1-C-NA, PB1-C-NP-C-NA, NA-K-NP-C-PB1, NA-K-PB1-C-NP, NP-C-PB1-K-NA, PB1-C-NP-K-NA, NA-C-NP-K-PB1, NA-C-PB1-K-NP, NP-K-PB1-C-NA, PB1-K-NP-C-NA, NA-K-NP-PB2, NA-K-PB2-NP, NP-PB2-K-NA, PB2-NP-K-NA, NA-NP-K-PB2, NA-PB2-K-NP, NP-K-PB2-NA, PB2-K-NP-NA, NA-K-NP-K-PB2, NA-K-PB2-K-NP, NP-K-PB2-K-NA, PB2-K-NP-K-NA, NA-C-NP-PB2, NA-C-PB2-NP, NP-PB2-C-NA, PB2-NP-C-NA, NA-NP-C-PB2, NA-PB2-C-NP, NP-C-PB2-NA, PB2-C-NP-NA, NA-C-NP-C-PB2, NA-C-PB2-C-NP, NP-C-PB2-C-NA, PB2-C-NP-C-NA, NA-K-NP-C-PB2, NA-K-PB2-C-NP, NP-C-PB2-K-NA, PB2-C-NP-K-NA, NA-C-NP-K-PB2, NA-C-PB2-K-NP, NP-K-PB2-C-NA, PB2-K-NP-C-NA, NA-K-NP-PB1F2, NA-K-PB1F2-NP, NP-PB1F2-K-NA, PB1F2-NP-K-NA, NA-NP-K-PB1F2, NA-PB1F2-K-NP, NP-K-PB1F2-NA, PB1F2-K-NP-NA, NA-K-NP-K-PB1F2, NA-K-PB1F2-K-NP, NP-K-PB1F2-K-NA, PB1F2-K-NP-K-NA, NA-C-NP-PB1F2, NA-C-PB1F2-NP, NP-PB1F2-C-NA, PB1F2-NP-C-NA, NA-NP-C-PB1F2, NA-PB1F2-C-NP, NP-C-PB1F2-NA, PB1F2-C-NP-NA, NA-C-NP-C-PB1F2, NA-C-PB1F2-C-NP, NP-C-PB1F2-C-NA, PB1F2-C-NP-C-NA, NA-K-NP-C-PB1F2, NA-K-PB1F2-C-NP, NP-C-PB1F2-K-NA, PB1F2-C-NP-K-NA, NA-C-NP-K-PB1F2, NA-C-PB1F2-K-NP, NP-K-PB1F2-C-NA, PB1F2-K-NP-C-NA, NA-K-M1, M1-K-NA, NA-K-M1-M1, M1-M1-K-NA, NA-M1-K-M1, M1-K-M1-NA, NA-K-M1-K-M1, M1-K-M1-K-NA, NA-C-M1, M1-C-NA, NA-C-M1-M1, M1-M1-C-NA, NA-M1-C-M1, M1-C-M1-NA, NA-C-M1-C-M1, M1-C-M1-C-NA, NA-K-M1-C-M1, M1-C-M1-K-NA, NA-C-M1-K-M1, M1-K-M1-C-NA, NA-K-M1-M2, NA-K-M2-M1, M1-M2-K-NA, M2-M1-K-NA, NA-M1-K-M2, NA-M2-K-M1, M1-K-M2-NA, M2-K-M1-NA, NA-K-M1-K-M2, NA-K-M2-K-M1, M1-K-M2-K-NA, M2-K-M1-K-NA, NA-C-M1-M2, NA-C-M2-M1, M1-M2-C-NA, M2-M1-C-NA, NA-M1-C-M2, NA-M2-C-M1, M1-C-M2-NA, M2-C-M1-NA, NA-C-M1-C-M2, NA-C-M2-C-M1, M1-C-M2-C-NA, M2-C-M1-C-NA, NA-K-M1-C-M2, NA-K-M2-C-M1, M1-C-M2-K-NA, M2-C-M1-K-NA, NA-C-M1-K-M2, NA-C-M2-K-M1, M1-K-M2-C-NA, M2-K-M1-C-NA, NA-K-M1-NS1, NA-K-NS1-M1, M1-NS1-K-NA, NS1-M1-K-NA, NA-M1-K-NS1, NA-NS1-K-M1, M1-K-NS1-NA, NS1-K-M1-NA, NA-K-M1-K-NS1, NA-K-NS1-K-M1, M1-K-NS1-K-NA, NS1-K-M1-K-NA, NA-C-M1-NS1, NA-C-NS1-M1, M1-NS1-C-NA, NS1-M1-C-NA, NA-M1-C-NS1, NA-NS1-C-M1, M1-C-NS1-NA, NS1-C-M1-NA, NA-C-M1-C-NS1, NA-C-

NS1-C-M1, M1-C-NS1-C-NA, NS1-C-M1-C-NA, NA-K-M1-C-NS1, NA-K-NS1-C-M1, M1-C-NS1-K-NA, NS1-C-M1-K-NA, NA-C-M1-K-NS1, NA-C-NS1-K-M1, M1-K-NS1-C-NA, NS1-K-M1-C-NA, NA-K-M1-NS2/NEP, NA-K-NS2/NEP-M1, M1-NS2/NEP-K-NA, NS2/NEP-M1-K-NA, NA-M1-K-NS2/NEP, NA-NS2/NEP-K-M1, M1-K-NS2/NEP-NA, NS2/NEP-K-M1-NA, NA-K-M1-K-NS2/NEP, NA-K-NS2/NEP-K-M1, M1-K-NS2/NEP-K-NA, NS2/NEP-K-M1-K-NA, NA-C-M1-NS2/NEP, NA-C-NS2/NEP-M1, M1-NS2/NEP-C-NA, NS2/NEP-M1-C-NA, NA-M1-C-NS2/NEP, NA-NS2/NEP-C-M1, M1-C-NS2/NEP-NA, NS2/NEP-C-M1-NA, NA-C-M1-C-NS2/NEP, NA-C-NS2/NEP-C-M1, M1-C-NS2/NEP-C-NA, NS2/NEP-C-M1-C-NA, NA-K-M1-C-NS2/NEP, NA-K-NS2/NEP-C-M1, M1-C-NS2/NEP-K-NA, NS2/NEP-C-M1-K-NA, NA-C-M1-K-NS2/NEP, NA-C-NS2/NEP-K-M1, M1-K-NS2/NEP-C-NA, NS2/NEP-K-M1-C-NA, NA-K-M1-PA, NA-K-PA-M1, M1-PA-K-NA, PA-M1-K-NA, NA-M1-K-PA, NA-PA-K-M1, M1-K-PA-NA, PA-K-M1-NA, NA-K-M1-K-PA, NA-K-PA-K-M1, M1-K-PA-K-NA, PA-K-M1-K-NA, NA-C-M1-PA, NA-C-PA-M1, M1-PA-C-NA, PA-M1-C-NA, NA-M1-C-PA, NA-PA-C-M1, M1-C-PA-NA, PA-C-M1-NA, NA-C-M1-C-PA, NA-C-PA-C-M1, M1-C-PA-C-NA, PA-C-M1-C-NA, NA-K-M1-C-PA, NA-K-PA-C-M1, M1-C-PA-K-NA, PA-C-M1-K-NA, NA-C-M1-K-PA, NA-C-PA-K-M 1, M1-K-PA-C-NA, PA-K-M1-C-NA, NA-K-M1-PB1, NA-K-PB1-M1, M1-PB1-K-NA, PB1-M1-K-NA, NA-M1-K-PB1, NA-PB1-K-M1, M1-K-PB1-NA, PB1-K-M1-NA, NA-K-M1-K-PB1, NA-K-PB1-K-M1, M1-K-PB1-K-NA, PB1-K-M1-K-NA, NA-C-M1-PB1, NA-C-PB1-M1, M1-PB1-C-NA, PB1-M1-C-NA, NA-M1-C-PB1, NA-PB1-C-M1, M1-C-PB1-NA, PB1-C-M1-NA, NA-C-M1-C-PB1, NA-C-PB1-C-M1, M1-C-PB1-C-NA, PB1-C-M1-C-NA, NA-K-M1-C-PB1, NA-K-PB1-C-M1, M1-C-PB1-K-NA, PB1-C-M1-K-NA, NA-C-M1-K-PB1, NA-C-PB1-K-M1, M1-K-PB1-C-NA, PB1-K-M1-C-NA, NA-K-M1-PB2, NA-K-PB2-M1, M1-PB2-K-NA, PB2-M1-K-NA, NA-M1-K-PB2, NA-PB2-K-M1, M1-K-PB2-NA, PB2-K-M1-NA, NA-K-M1-K-PB2, NA-K-PB2-K-M1, M1-K-PB2-K-NA, PB2-K-M1-K-NA, NA-C-M1-PB2, NA-C-PB2-M1, M1-PB2-C-NA, PB2-M1-C-NA, NA-M1-C-PB2, NA-PB2-C-M1, M1-C-PB2-NA, PB2-C-M1-NA, NA-C-M1-C-PB2, NA-C-PB2-C-M1, M1-C-PB2-C-NA, PB2-C-M1-C-NA, NA-K-M1-C-PB2, NA-K-PB2-C-M1, M1-C-PB2-K-NA, PB2-C-M1-K-NA, NA-C-M1-K-PB2, NA-C-PB2-K-M1, M1-K-PB2-C-NA, PB2-K-M1-C-NA, NA-K-M1-PB1F2, NA-K-PB1F2-M1, M1-PB1F2-K-NA, PB1F2-M1-K-NA, NA-M1-K-PB1F2, NA-PB1F2-K-M1, M1-K-PB1F2-NA, PB1F2-K-M1-NA, NA-K-M1-K-PB1F2, NA-K-PB1F2-K-M1, M1-K-PB1F2-K-NA, PB1F2-K-M1-K-NA, NA-C-M1-PB1F2, NA-C-PB1F2-M1, M1-PB1F2-C-NA, PB1F2-M1-C-NA, NA-M1-C-PB1F2, NA-PB1F2-C-M1, M1-C-PB1F2-NA, PB1F2-C-M1-NA, NA-C-M1-C-PB1F2, NA-C-PB1F2-C-M1, M1-C-PB1F2-C-NA, PB1F2-C-M1-C-NA, NA-K-M1-C-PB1F2, NA-K-PB1F2-C-M1, M1-C-PB1F2-K-NA, PB1F2-C-M1-K-NA, NA-C-M1-K-PB1F2, NA-C-PB1F2-K-M1, M1-K-PB1F2-C-NA, PB1F2-K-M1-C-NA, NA-K-M2, M2-K-NA, NA-K-M2-M2, M2-M2-K-NA, NA-M2-K-M2, M2-K-M2-NA, NA-K-M2-K-M2, M2-K-M2-K-NA, NA-C-M2, M2-C-NA, NA-C-M2-M2, M2-M2-C-NA, NA-M2-C-M2, M2-C-M2-NA, NA-C-M2-C-M2, M2-C-M2-C-NA, NA-K-M2-C-M2, M2-C-M2-K-NA, NA-C-M2-K-M2, M2-K-M2-C-NA, NA-K-M2-NS1, NA-K-NS1-M2, M2-NS1-K-NA, NS1-M2-K-NA, NA-M2-K-NS1, NA-NS1-K-M2, M2-K-NS1-NA, NS1-K-M2-NA, NA-K-M2-K-NS1, NA-K-NS1-K-M2, M2-K-NS1-K-NA, NS1-K-M2-K-NA, NA-C-M2-NS1, NA-C-NS1-M2, M2-NS1-C-NA, NS1-M2-C-NA, NA-M2-C-NS1, NA-NS1-C-M2, M2-C-NS1-NA, NS1-C-M2-NA, NA-C-M2-C-NS1, NA-C-NS1-C-M2, M2-C-NS1-C-NA, NS1-C-M2-C-NA, NA-K-M2-C-NS1, NA-K-NS1-C-M2, M2-C-NS1-K-NA, NS1-C-M2-K-NA, NA-C-M2-K-NS1, NA-C-NS1-K-M2, M2-K-NS1-C-NA, NS1-K-M2-C-NA, NA-K-M2-NS2/NEP, NA-K-NS2/NEP-M2, M2-NS2/NEP-K-NA, NS2/NEP-M2-K-NA, NA-M2-K-NS2/NEP, NA-NS2/NEP-K-M2, M2-K-NS2/NEP-NA, NS2/NEP-K-M2-NA, NA-K-M2-K-NS2/NEP, NA-K-NS2/NEP-K-M2, M2-K-NS2/NEP-K-NA, NS2/NEP-K-M2-K-NA, NA-C-M2-NS2/NEP, NA-C-NS2/NEP-M2, M2-NS2/NEP-C-NA, NS2/NEP-M2-C-NA, NA-M2-C-NS2/NEP, NA-NS2/NEP-C-M2, M2-C-NS2/NEP-NA, NS2/NEP-C-M2-NA, NA-C-M2-C-NS2/NEP, NA-C-NS2/NEP-C-M2, M2-C-NS2/NEP-C-NA, NS2/NEP-C-M2-C-NA, NA-K-M2-C-NS2/NEP, NA-K-NS2/NEP-C-M2, M2-C-NS2/NEP-K-NA, NS2/NEP-C-M2-K-NA, NA-C-M2-K-NS2/NEP, NA-C-NS2/NEP-K-M2, M2-K-NS2/NEP-C-NA, NS2/NEP-K-M2-C-NA, NA-K-M2-PA, NA-K-PA-M2, M2-PA-K-NA, PA-M2-K-NA, NA-M2-K-PA, NA-PA-K-M2, M2-K-PA-NA, PA-K-M2-NA, NA-K-M2-K-PA, NA-K-PA-K-M2, M2-K-PA-K-NA, PA-K-M2-K-NA, NA-C-M2-PA, NA-C-PA-M2, M2-PA-C-NA, PA-M2-C-NA, NA-M2-C-PA, NA-PA-C-M2, M2-C-PA-NA, PA-C-M2-NA, NA-C-M2-C-PA, NA-C-PA-C-M2, M2-C-PA-C-NA, PA-C-M2-C-NA, NA-K-M2-C-PA, NA-K-PA-C-M2, M2-C-PA-K-NA, PA-C-M2-K-NA, NA-C-M2-K-PA, NA-C-PA-K-M2, M2-K-PA-C-NA, PA-K-M2-C-NA, NA-K-M2-PB1, NA-K-PB1-M2, M2-PB1-K-NA, PB1-M2-K-NA, NA-M2-K-PB1, NA-PB1-K-M2, M2-K-PB1-NA, PB1-K-M2-NA, NA-K-M2-K-PB1, NA-K-PB1-K-M2, M2-K-PB1-K-NA, PB1-K-M2-K-NA, NA-C-M2-PB1, NA-C-PB1-M2, M2-PB1-C-NA, PB1-M2-C-NA, NA-M2-C-PB1, NA-PB1-C-M2, M2-C-PB1-NA, PB1-C-M2-NA, NA-C-M2-C-PB1, NA-C-PB1-C-M2, M2-C-PB1-C-NA, PB1-C-M2-C-NA, NA-K-M2-C-PB1, NA-K-PB1-C-M2, M2-C-PB1-K-NA, PB1-C-M2-K-NA, NA-C-M2-K-PB1, NA-C-PB1-K-M2, M2-K-PB1-C-NA, PB1-K-M2-C-NA, NA-K-M2-PB2, NA-K-PB2-M2, M2-PB2-K-NA, PB2-M2-K-NA, NA-M2-K-PB2, NA-PB2-K-M2, M2-K-PB2-NA, PB2-K-M2-NA, NA-K-M2-K-PB2, NA-K-PB2-K-M2, M2-K-PB2-K-NA, PB2-K-M2-K-NA, NA-C-M2-PB2, NA-C-PB2-M2, M2-PB2-C-NA, PB2-M2-C-NA, NA-M2-C-PB2, NA-PB2-C-M2, M2-C-PB2-NA, PB2-C-M2-NA, NA-C-M2-C-PB2, NA-C-PB2-C-M2, M2-C-PB2-C-NA, PB2-C-M2-C-NA, NA-K-M2-C-PB2, NA-K-PB2-C-M2, M2-C-PB2-K-NA, PB2-C-M2-K-NA, NA-C-M2-K-PB2, NA-C-PB2-K-M2, M2-K-PB2-C-NA, PB2-K-M2-C-NA, NA-K-M2-PB1F2, NA-K-PB1F2-M2, M2-PB1F2-K-NA, PB1F2-M2-K-NA, NA-M2-K-PB1F2, NA-PB1F2-K-M2, M2-K-PB1F2-NA, PB1F2-K-M2-NA, NA-K-M2-K-PB1F2, NA-K-PB1F2-K-M2, M2-K-PB1F2-K-NA, PB1F2-K-M2-K-NA, NA-C-M2-PB1F2, NA-C-PB1F2-M2, M2-PB1F2-C-NA, PB1F2-M2-C-NA, NA-M2-C-PB1F2, NA-PB1F2-C-M2, M2-C-PB1F2-NA, PB1F2-C-M2-NA, NA-C-M2-C-PB1F2, NA-C-PB1F2-C-M2, M2-C-PB1F2-C-NA, PB1F2-C-M2-C-NA, NA-K-M2-C-PB1F2, NA-K-PB1F2-C-M2, M2-C-PB1F2-K-NA, PB1F2-C-M2-K-NA, NA-C-M2-K-PB1F2, NA-C-PB1F2-K-M2, M2-K-PB1F2-C-NA, PB1F2-K-M2-C-NA, NA-K-NS1, NS1-K-NA, NA-K-NS1-NS1, NS1-NS1-K-NA, NA-NS1-K-NS1, NS1-K-NS1-NA, NA-K-NS1-K-NS1, NS1-K-NS1-K-NA, NA-C-NS1, NS1-C-NA, NA-C-NS1-NS1, NS1-NS1-C-NA, NA-NS1-C-NS1, NS1-C-NS1-NA, NA-C-NS1-C-NS1, NS1-C-NS1-C-NA, NA-K-NS1-C-NS1, NS1-C-NS1-K-NA, NA-C-NS1-K-NS1, NS1-K-NS I-C-NA, NA-K-NS1-NS2/NEP, NA-K-

NS2/NEP-NS1, NS1-NS2/NEP-K-NA, NS2/NEP-NS1-K-NA, NA-NS1-K-NS2/NEP, NA-NS2/NEP-K-NS1, NS1-K-NS2/NEP-NA, NS2/NEP-K-NS1-NA, NA-K-NS1-K-NS2/NEP, NA-K-NS2/NEP-K-NS1, NS1-K-NS2/NEP-K-NA, NS2/NEP-K-NS1-K-NA, NA-C-NS1-NS2/NEP, NA-C-NS2/NEP-NS1, NS1-NS2/NEP-C-NA, NS2/NEP-NS1-C-NA, NA-NS1-C-NS2/NEP, NA-NS2/NEP-C-NS1, NS1-C-NS2/NEP-NA, NS2/NEP-C-NS1-NA, NA-C-NS1-C-NS2/NEP, NA-C-NS2/NEP-C-NS1, NS1-C-NS2/NEP-C-NA, NS2/NEP-C-NS1-C-NA, NA-K-NS1-C-NS2/NEP, NA-K-NS2/NEP-C-NS1, NS1-C-NS2/NEP-K-NA, NS2/NEP-C-NS1-K-NA, NA-C-NS1-K-NS2/NEP, NA-C-NS2/NEP-K-NS1, NS1-K-NS2/NEP-C-NA, NS2/NEP-K-NS1-C-NA, NA-K-NS1-PA, NA-K-PA-NS1, NS1-PA-K-NA, PA-NS1-K-NA, NA-NS1-K-PA, NA-PA-K-NS1, NS1-K-PA-NA, PA-K-NS1-NA, NA-K-N S 1-K-PA, NA-K-PA-K-NS1, NS1-K-PA-K-NA, PA-K-NS1-K-NA, NA-C-NS1-PA, NA-C-PA-NS1, NS1-PA-C-NA, PA-NS1-C-NA, NA-NS1-C-PA, NA-PA-C-NS1, NS1-C-PA-NA, PA-C-NS1-NA, NA-C-NS1-C-PA, NA-C-PA-C-NS1, NS1-C-PA-C-NA, PA-C-NS1-C-NA, NA-K-NS1-C-PA, NA-K-PA-C-NS1, NS1-C-PA-K-NA, PA-C-NS1-K-NA, NA-C-NS1-K-PA, NA-C-PA-K-NS1, NS1-K-PA-C-NA, P A-K-NS1-C-NA, NA-K-NS1-PB1, NA-K-PB1-NS1, NS1-PB1-K-NA, PB1-NS1-K-NA, NA-NS1-K-PB1, NA-PB1-K-NS1, NS1-K-PB1-NA, PB1-K-NS1-NA, NA-K-NS1-K-PB1, NA-K-PB1-K-NS1, NS1-K-PB1-K-NA, PB1-K-NS1-K-NA, NA-C-NS1-PB1, NA-C-PB1-NS1, NS1-PB1-C-NA, PB1-NS1-C-NA, NA-NS1-C-PB1, NA-PB1-C-NS1, NS1-C-PB1-NA, PB1-C-NS1-NA. NA-C-NS1-C-PB1, NA-C-PB1-C-NS1, NS1-C-PB1-C-NA, PB1-C-NS1-C-NA, NA-K-NS1-C-PB1, NA-K-PB1-C-NS1, NS1-C-PB1-K-NA, PB1-C-NS1-K-NA, NA-C-NS1-K-PB1, NA-C-PB1-K-NS1, NS1-K-PB1-C-NA, PB1-K-NS1-C-NA, NA-K-NS1-PB2, NA-K-PB2-NS1, NS1-PB2-K-NA, PB2-NS1-K-NA, NA-NS1-K-PB2, NA-PB2-K-NS1, NS1-K-PB2-NA, PB2-K-NS1-NA, NA-K-NS1-K-PB2, NA-K-PB2-K-NS1, NS1-K-PB2-K-NA, PB2-K-NS1-K-NA, NA-C-NS1-PB2, NA-C-PB2-NS1, NS1-PB2-C-NA, PB2-NS1-C-NA, NA-NS1-C-PB2, NA-PB2-C-NS1, NS1-C-PB2-NA, PB2-C-NS1-NA, NA-C-NS1-C-PB2, NA-C-PB2-C-NS1, NS1-C-PB2-C-NA, PB2-C-NS1-C-NA, NA-K-NS1-C-PB2, NA-K-PB2-C-NS1, NS1-C-PB2-K-NA, PB2-C-NS1-K-NA, NA-C-NS1-K-PB2, NA-C-PB2-K-NS1, NS1-K-PB2-C-NA, PB2-K-NS1-C-NA, NA-K-NS1-PB1F2, NA-K-PB1F2-NS1, NS1-PB1F2-K-NA, PB1F2-NS1-K-NA, NA-NS1-K-PB1F2, NA-PB1F2-K-NS1, NS1-K-PB1F2-NA, PB1F2-K-NS1-NA, NA-K-NS1-K-PB1F2, NA-K-PB1F2-K-NS1, NS1-K-PB1F2-K-NA, PB1F2-K-NS1-K-NA, NA-C-NS1-PB1F2, NA-C-PB1F2-NS1, NS1-PB1F2-C-NA, PB1F2-NS1-C-NA, NA-NS1-C-PB1F2, NA-PB1F2-C-NS1, NS1-C-PB1F2-NA, PB1F2-C-NS1-NA, NA-C-NS1-C-PB1F2, NA-C-PB1F2-C-NS1, NS1-C-PB1F2-C-NA, PB1F2-C-NS1-C-NA, NA-K-NS1-C-PB1F2, NA-K-PB1F2-C-NS1, NS1-C-PB1F2-K-NA, PB1F2-C-NS1-K-NA, NA-C-NS1-K-PB1F2, NA-C-PB1F2-K-NS1, NS1-K-PB1F2-C-NA, PB1F2-K-NS1-C-NA, NA-K-NS2/NEP, NS2/NEP-K-NA, NA-K-NS2/NEP-NS2/NEP, NS2/NEP-NS2/NEP-K-NA, NA-NS2/NEP-K-NS2/NEP, NS2/NEP-K-NS2/NEP-NA, NA-K-NS2/NEP-K-NS2/NEP, NS2/NEP-K-NS2/NEP-K-NA, NA-C-NS2/NEP, NS2/NEP-C-NA, NA-C-NS2/NEP-NS2/NEP, NS2/NEP-NS2/NEP-C-NA, NA-NS2/NEP-C-NS2/NEP, NS2/NEP-C-NS2/NEP-NA, NA-C-NS2/NEP-C-NS2/NEP, NS2/NEP-C-NS2/NEP-C-NA, NA-K-NS2/NEP-C-NS2/NEP, NS2/NEP-C-NS2/NEP-K-NA, NA-C-NS2/NEP-K-NS2/NEP, NS2/NEP-K-NS2/NEP-C-NA, NA-K-NS2/NEP-PA, NA-K-PA-NS2/NEP, NS2/NEP-PA-K-NA, PA-NS2/NEP-K-NA, NA-NS2/NEP-K-PA, NA-PA-K-NS2/NEP, NS2/NEP-K-PA-NA, PA-K-NS2/NEP-NA, NA-K-NS2/NEP-K-PA, NA-K-PA-K-NS2/NEP, NS2/NEP-K-PA-K-NA, PA-K-NS2/NEP-K-NA, NA-C-NS2/NEP-PA, NA-C-PA-NS2/NEP, NS2/NEP-PA-C-NA, PA-NS2/NEP-C-NA, NA-NS2/NEP-C-PA, NA-PA-C-NS2/NEP, NS2/NEP-C-PA-NA, PA-C-NS2/NEP-NA, NA-C-NS2/NEP-C-PA, NA-C-PA-C-NS2/NEP, NS2/NEP-C-PA-C-NA, PA-C-NS2/NEP-C-NA, NA-K-NS2/NEP-C-PA, NA-K-PA-C-NS2/NEP, NS2/NEP-C-PA-K-NA, PA-C-NS2/NEP-K-NA, NA-C-NS2/NEP-K-PA, NA-C-PA-K-NS2/NEP, NS2/NEP-K-PA-C-NA, PA-K-NS2/NEP-C-NA, NA-K-NS2/NEP-PB1, NA-K-PB1-NS2/NEP, NS2/NEP-PB1-K-NA, PB1-NS2/NEP-K-NA, NA-NS2/NEP-K-PB1, NA-PB1-K-NS2/NEP, NS2/NEP-K-PB1-NA, PB1-K-NS2/NEP-NA, NA-K-NS2/NEP-K-PB1, NA-K-PB1-K-NS2/NEP, NS2/NEP-K-PB1-K-NA, PB1-K-NS2/NEP-K-NA, NA-C-NS2/NEP-PB1, NA-C-PB1-NS2/NEP, NS2/NEP-PB1-C-NA, PB1-NS2/NEP-C-NA, NA-NS2/NEP-C-PB1, NA-PB1-C-NS2/NEP, NS2/NEP-C-PB1-NA, PB1-C-NS2/NEP-NA, NA-C-NS2/NEP-C-PB1, NA-C-PB1-C-NS2/NEP, NS2/NEP-C-PB1-C-NA, PB1-C-NS2/NEP-C-NA, NA-K-NS2/NEP-C-PB1, NA-K-PB1-C-NS2/NEP, NS2/NEP-C-PB1-K-NA, PB1-C-NS2/NEP-K-NA, NA-C-NS2/NEP-K-PB1, NA-C-PB1-K-NS2/NEP, NS2/NEP-K-PB1-C-NA, PB1-K-NS2/NEP-C-NA, NA-K-NS2/NEP-PB2, NA-K-PB2-NS2/NEP, NS2/NEP-PB2-K-NA, PB2-NS2/NEP-K-NA, NA-NS2/NEP-K-PB2, NA-PB2-K-NS2/NEP, NS2/NEP-K-PB2-NA, PB2-K-NS2/NEP-NA, NA-K-NS2/NEP-K-PB2, NA-K-PB2-K-NS2/NEP, NS2/NEP-K-PB2-K-NA, PB2-K-NS2/NEP-K-NA, NA-C-NS2/NEP-PB2, NA-C-PB2-NS2/NEP, NS2/NEP-PB2-C-NA, PB2-NS2/NEP-C-NA, NA-NS2/NEP-C-PB2, NA-PB2-C-NS2/NEP, NS2/NEP-C-PB2-NA, PB2-C-NS2/NEP-NA, NA-C-NS2/NEP-C-PB2, NA-C-PB2-C-NS2/NEP, NS2/NEP-C-PB2-C-NA, PB2-C-NS2/NEP-C-NA, NA-K-NS2/NEP-C-PB2, NA-K-PB2-C-NS2/NEP, NS2/NEP-C-PB2-K-NA, PB2-C-NS2/NEP-K-NA, NA-C-NS2/NEP-K-PB2, NA-C-PB2-K-NS2/NEP, NS2/NEP-K-PB2-C-NA, PB2-K-NS2/NEP-C-NA, NA-K-NS2/NEP-PB1F2, NA-K-PB1F2-NS2/NEP, NS2/NEP-PB1F2-K-NA, PB1F2-NS2/NEP-K-NA, NA-NS2/NEP-K-PB1F2, NA-PB1F2-K-NS2/NEP, NS2/NEP-K-PB1F2-NA, PB1F2-K-NS2/NEP-NA, NA-K-NS2/NEP-K-PB1F2, NA-K-PB1F2-K-NS2/NEP, NS2/NEP-K-PB1F2-K-NA, PB1F2-K-NS2/NEP-K-NA, NA-C-NS2/NEP-PB1F2, NA-C-PB1F2-NS2/NEP, NS2/NEP-PB1F2-C-NA, PB1F2-NS2/NEP-C-NA, NA-NS2/NEP-C-PB1F2, NA-PB1F2-C-NS2/NEP, NS2/NEP-C-PB1F2-NA, PB1F2-C-NS2/NEP-NA, NA-C-NS2/NEP-C-PB1F2, NA-C-PB1F2-C-NS2/NEP, NS2/NEP-C-PB1F2-C-NA, PB1F2-C-NS2/NEP-C-NA, NA-K-NS2/NEP-C-PB1F2, NA-K-PB1F2-C-NS2/NEP, NS2/NEP-C-PB1F2-K-NA, PB1F2-C-NS2/NEP-K-NA, NA-C-NS2/NEP-K-PB1F2, NA-C-PB1F2-K-NS2/NEP, NS2/NEP-K-PB1F2-C-NA, PB1F2-K-NS2/NEP-C-NA, NA-K-PA, PA-K-NA, NA-K-PA-PA, PA-PA-K-NA, NA-PA-K-PA, PA-K-PA-NA, NA-K-PA-K-PA, PA-K-PA-K-NA, NA-C-PA, PA-C-NA, NA-C-PA-PA, PA-PA-C-NA, NA-PA-C-PA, PA-C-PA-NA, NA-C-PA-C-PA, PA-C-PA-C-NA, NA-K-PA-C-PA, PA-C-PA-K-NA, NA-C-PA-K-PA, PA-K-PA-C-NA, NA-K-PA-PB1, NA-K-PB1-PA, PA-PB1-K-NA, PB1-PA-K-NA, NA-PA-K-PB1, NA-PB1-K-PA, PA-K-PB1-NA, PB1-K-PA-NA, NA-K-PA-K-PB1, NA-K-PB1-K-PA, PA-K-PB1-K-NA, PB1-K-PA-K-NA, NA-C-PA-PB1, NA-C-PB1-PA, PA-PB1-C-NA, PB1-PA-C-NA, NA-PA-C-PB1, NA-PB1-C-PA, PA-C-PB1-NA, PB1-C-PA-NA, NA-C-PA-C-PB1, NA-C-PB1-C-PA, PA-C-PB1-C-NA, PB1-C-PA-C-NA, NA-K-PA-C-PB1, NA-K-PB1-C-

PA, PA-C-PB1-K-NA, PB1-C-PA-K-NA, NA-C-PA-K-PB1, NA-C-PB1-K-PA, PA-K-PB1-C-NA, PB1-K-PA-C-NA, NA-K-PA-PB2, NA-K-PB2-PA, PA-PB2-K-NA, PB2-PA-K-NA, NA-PA-K-PB2, NA-PB2-K-PA, PA-K-PB2-NA, PB2-K-PA-NA, NA-K-PA-K-PB2, NA-K-PB2-K-PA, PA-K-PB2-K-NA, PB2-K-PA-K-NA, NA-C-PA-PB2, NA-C-PB2-PA, PA-PB2-C-NA, PB2-PA-C-NA, NA-PA-C-PB2, NA-PB2-C-PA, PA-C-PB2-NA, PB2-C-PA-NA, NA-C-PA-C-PB2, NA-C-PB2-C-PA, PA-C-PB2-C-NA, PB2-C-PA-C-NA, NA-K-PA-C-PB2, NA-K-PB2-C-PA, PA-C-PB2-K-NA, PB2-C-PA-K-NA, NA-C-PA-K-PB2, NA-C-PB2-K-PA, PA-K-PB2-C-NA, PB2-K-PA-C-NA, NA-K-PA-PB1F2, NA-K-PB1F2-PA, PA-PB1F2-K-NA, PB1F2-PA-K-NA, NA-PA-K-PB1F2, NA-PB1F2-K-PA, PA-K-PB1F2-NA, PB1F2-K-PA-NA, NA-K-PA-K-PB1F2, NA-K-PB1F2-K-PA, PA-K-PB1F2-K-NA, PB1F2-K-PA-K-NA, NA-C-PA-PB1F2, NA-C-PB1F2-PA, PA-PB1F2-C-NA, PB1F2-PA-C-NA, NA-PA-C-PB1F2, NA-PB1F2-C-PA, PA-C-PB1F2-NA, PB1F2-C-PA-NA, NA-C-PA-C-PB1F2, NA-C-PB1F2-C-PA, PA-C-PB1F2-C-NA, PB1F2-C-PA-C-NA, NA-K-PA-C-PB1F2, NA-K-PB1F2-C-PA, PA-C-PB1F2-K-NA, PB1F2-C-PA-K-NA, NA-C-PA-K-PB1F2, NA-C-PB1F2-K-PA, PA-K-PB1F2-C-NA, PB1F2-K-PA-C-NA, NA-K-PB1, PB1-K-NA, NA-K-PB1-PB1, PB1-PB1-K-NA, NA-PB1-K-PB1, PB1-K-PB1-NA, NA-K-PB1-K-PB1, PB1-K-PB1-K-NA, NA-C-PB1, PB1-C-NA, NA-C-PB1-PB1, PB1-PB1-C-NA, NA-PB1-C-PB1, PB1-C-PB1-NA, NA-C-PB1-C-PB1, PB1-C-PB1-C-NA, NA-K-PB1-C-PB1, PB1-C-PB1-K-NA, NA-C-PB1-K-PB1, PB1-K-PB1-C-NA, NA-K-PB1-PB2, NA-K-PB2-PB1, PB1-PB2-K-NA, PB2-PB1-K-NA, NA-PB1-K-PB2, NA-PB2-K-PB1, PB1-K-PB2-NA, PB2-K-PB1-NA, NA-K-PB1-K-PB2, NA-K-PB2-K-PB1, PB1-K-PB2-K-NA, PB2-K-PB1-K-NA, NA-C-PB1-PB2, NA-C-PB2-PB1, PB1-PB2-C-NA, PB2-PB1-C-NA, NA-PB1-C-PB2, NA-PB2-C-PB1, PB1-C-PB2-NA, PB2-C-PB1-NA, NA-C-PB1-C-PB2, NA-C-PB2-C-PB1, PB1-C-PB2-C-NA, PB2-C-PB1-C-NA, NA-K-PB1-C-PB2, NA-K-PB2-C-PB1, PB1-C-PB2-K-NA, PB2-C-PB1-K-NA, NA-C-PB1-K-PB2, NA-C-PB2-K-PB1, PB1-K-PB2-C-NA, PB2-K-PB1-C-NA, NA-K-PB1-PB1F2, NA-K-PB1F2-PB1, PB1-PB1F2-K-NA, PB1F2-PB1-K-NA, NA-PB1-K-PB1F2, NA-PB1F2-K-PB1, PB1-K-PB1F2-NA, PB1F2-K-PB1-NA, NA-K-PB1-K-PB1F2, NA-K-PB1F2-K-PB1, PB1-K-PB1F2-K-NA, PB1F2-K-PB1-K-NA, NA-C-PB1-PB1F2, NA-C-PB1F2-PB1, PB1-PB1F2-C-NA, PB1F2-PB1-C-NA, NA-PB1-C-PB1F2, NA-PB1F2-C-PB1, PB1-C-PB1F2-NA, PB1F2-C-PB1-NA, NA-C-PB1-C-PB1F2, NA-C-PB1F2-C-PB1, PB1-C-PB1F2-C-NA, PB1F2-C-PB1-C-NA, NA-K-PB1-C-PB1F2, NA-K-PB1F2-C-PB1, PB1-C-PB1F2-K-NA, PB1F2-C-PB1-K-NA, NA-C-PB1-K-PB1F2, NA-C-PB1F2-K-PB1, PB1-K-PB1F2-C-NA, PB1F2-K-PB1-C-NA, NA-K-PB2, PB2-K-NA, NA-K-PB2-PB2, PB2-PB2-K-NA, NA-PB2-K-PB2, PB2-K-PB2-NA, NA-K-PB2-K-PB2, PB2-K-PB2-K-NA, NA-C-PB2, PB2-C-NA, NA-C-PB2-PB2, PB2-PB2-C-NA, NA-C-PB2-PB2, PB2-C-PB2-NA, NA-C-PB2-C-PB2, PB2-C-PB2-C-NA, NA-K-PB2-C-PB2, PB2-C-PB2-K-NA, NA-C-PB2-K-PB2, PB2-K-PB2-C-NA, NA-K-PB2-PB1F2, NA-K-PB1F2-PB2, PB2-PB1F2-K-NA, PB1F2-PB2-K-NA, NA-PB2-K-PB1F2, NA-PB1F2-K-PB2, PB2-K-PB1F2-NA, PB1F2-K-PB2-NA, NA-K-PB2-K-PB1F2, NA-K-PB1F2-K-PB2, PB2-K-PB1F2-K-NA, PB1F2-K-PB2-K-NA, NA-C-PB2-PB1F2, NA-C-PB1F2-PB2, PB2-PB1F2-C-NA, PB1F2-PB2-C-NA, NA-PB2-C-PB1F2, NA-PB1F2-C-PB2, PB2-C-PB1F2-NA, PB1F2-C-PB2-NA, NA-C-PB2-C-PB1F2, NA-C-PB1F2-C-PB2, PB2-C-PB1F2-C-NA, PB1F2-C-PB2-C-NA, NA-K-PB2-C-PB1F2, NA-K-PB1F2-C-PB2, PB2-C-PB1F2-K-NA, PB1F2-C-PB2-K-NA, NA-C-PB2-K-PB1F2, NA-C-PB1F2-K-PB2, PB2-K-PB1F2-C-NA, PB1F2-K-PB2-C-NA, NA-K-PB1F2, PB1F2-K-NA, NA-K-PB1F2-PB1F2, PB1F2-PB1F2-K-NA, NA-PB1F2-K-PB1F2, PB1F2-K-PB1F2-NA, NA-K-PB1F2-K-PB1F2, PB1F2-K-PB1F2-K-NA, NA-C-PB1F2, PB1F2-C-NA, NA-C-PB1F2-PB1F2, PB1F2-PB1F2-C-NA, NA-C-PB1F2-C-PB1F2, PB1F2-C-PB1F2-NA, NA-C-PB1F2-C-PB1F2, PB1F2-C-PB1F2-C-NA, NA-K-PB1F2-C-PB1F2, PB1F2-C-PB1F2-K-NA, NA-C-PB1F2-K-PB1F2 or PB1F2-K-PB1F2-C-NA. Most preferably, the arrangement is NP-K-M1-C-HA.

It is within the scope of the present invention that every protein can be combined with any other protein and that any two proteins can or cannot be connected or linked by either a cleavage site or a linker peptide.

In preferred embodiments, the expression system is for use in the prophylaxis or treatment of viral infection, particularly preferably for use in the prophylaxis or treatment of an orthomyxovirus infection, preferably an influenza virus infection, more preferably an influenza A virus infection, and/or in the manufacturing of medicament for use in the prophylaxis or treatment of an orthomyxovirus infection, preferably an influenza virus infection, more preferably an influenza A virus infection, and/or for use in methods of prophylaxis or treatment of an orthomyxovirus infection, preferably an influenza virus infection, more preferably an influenza A virus infection, preferably an influenza virus infection, more preferably an influenza A virus infection.

In preferred embodiments, the expression system is for use in enhancing an immune response, preferably a B cell immune response an orthomyxovirus infection, preferably an influenza virus infection, more preferably an influenza A virus infection.

In a preferred embodiment of this aspect, HA is defined according to the eighth aspect.

It is particularly preferred that the viral polyprotein encoded by the first, the second and the third polynucleotide has an amino acid according to SEQ ID NO: 13 or a variant thereof and/or is encoded by a polynucleotide having the nucleic acid sequence of SEQ ID NO: 14 or a variant thereof. Preferably, the encoded triple antigen protein NP-M1-H1p is processed into a cytoplasmic NP-M1 fusion protein and a membrane spanning H1p protein by the 2A sequence.

In preferred embodiments, the expression system is for use in the prophylaxis or treatment of an orthomyxovirus infection, preferably an influenza A virus infection.

In more preferred embodiments, the expression system is for use in enhancing an immune response, preferably a B cell immune response against a an orthomyxovirus protein, preferably an influenza A virus protein.

In preferred embodiments, the vector or vectors comprising the first, and the second and/or the third polynucleotide is/are selected from the group consisting of plasmid, cosmid, phage, virus, and artificial chromosome. More preferably, a vector suitable for practicing the present invention is selected from the group consisting of plasmid vectors, cosmid vectors, phage vectors, preferably lambda phage and filamentous phage vectors, viral vectors, adenovirus vectors (e.g., non-replicating Ad5, Ad11, Ad26, Ad35, Ad49, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd 73, ChAd82, ChAd83, ChAd146, ChAd147, PanAd1, PanAd2, and PanAd3 vectors or replication-competent Ad4 and Ad7 vectors), adeno-associated virus (AAV) vectors (e.g., AAV type 5 and type 2), alphavirus vectors (e.g., Venezuelan equine encephalitis virus (VEE), sindbis virus (SIN), semliki forest virus (SFV), and VEE-SIN chimeras), herpes virus vectors (e.g. vectors derived from cytomegaloviruses, like rhesus cytomegalovirus (RhCMV) (14)), arena virus vectors (e.g. lymphocytic choriomeningitis virus (LCMV) vectors (15)), measles virus vectors, pox virus vectors (e.g., vaccinia virus, modified vaccinia virus Ankara (MVA), NYVAC (derived from the Copenhagen strain of vaccinia), and avipox vectors: canarypox (ALVAC) and fowlpox (FPV) vectors), vesicular stomatitis virus vectors, retrovirus, lentivirus, viral like particles, and bacterial spores. The vectors ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63 and ChAd82 are described in detail in WO 2005/071093. The vectors PanAd1, PanAd2, PanAd3, ChAd55, ChAd73, ChAd83, ChAd146, and ChAd147 are described in detail in WO 2010/086189. It is particularly preferred that the vector is selected from the group consisting of MVA, ChAd63 and PanAd3.

In preferred embodiments, the expression system is for use in medicine. In more preferred embodiments, the expression system is for use in the prophylaxis or treatment of viral infection, particularly preferably for use in the prophylaxis or treatment of RSV infection.

In a second aspect, the present invention provides an isolated protein mixture encoded by the expression system of the first aspect. Preferably, the isolated protein mixture contains, essentially contains or comprises one or more of the viral proteins encoded by the expression system of the first aspect.

In preferred embodiments, the isolated protein mixture is for use in medicine. In particularly preferred embodiments, the isolated protein mixture is for use in the prophylaxis or treatment of viral infection, particularly preferably for use in the prophylaxis or treatment of RSV infection or in the prophylaxis or treatment of influenza A infection.

In a third aspect, the present invention provides an isolated host cell containing the expression system of the first aspect and/or the protein mixture of the second aspect. It is understood that such host cell includes but is not limited to prokaryotic (e.g. a bacterial cell) or eukaryotic cells (e.g. a fungal, plant or animal cell).

In preferred embodiments, the host cell is for use in medicine. In particularly preferred embodiments, the host cell is for use in the prophylaxis or treatment of viral infection, particularly preferably for use in the prophylaxis or treatment of RSV infection or in the prophylaxis or treatment of influenza A infection.

In a fourth aspect, the present invention provides a composition comprising the expression system of the first aspect or the protein mixture of the second aspect and a pharmaceutical acceptable carrier and/or excipient. Preferably, such composition is a pharmaceutical composition.

The composition of the fourth aspect contains a therapeutically effective amount of the compound, preferably in purified form, together with a suitable amount of carrier so as to provide the form for proper administration to the patient. The formulation should suit the mode of administration.

The compositions can take the form of solutions, suspensions, emulsion, tablets, pills, capsules, powders, sustained-release formulations and the like. The composition can be formulated as a suppository, with traditional binders and carriers such as triglycerides.

For preparing pharmaceutical compositions of the present invention, pharmaceutically acceptable carriers can be either solid or liquid.

Solid form compositions include powders, tablets, pills, capsules, lozenges, cachets, suppositories, and dispersible granules. A solid excipient can be one or more substances, which may also act as diluents, flavoring agents, binders, preservatives, tablet disintegrating agents, or an encapsulating material. In powders, the excipient is preferably a finely divided solid, which is in a mixture with the finely divided inhibitor of the present invention. In tablets, the active ingredient is mixed with the carrier having the necessary binding properties in suitable proportions and compacted in the shape and size desired. Suitable excipients are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify. Tablets, powders, capsules, pills, cachets, and lozenges can be used as solid dosage forms suitable for oral administration.

Liquid form composition include solutions, suspensions, and emulsions, for example, water, saline solutions, aqueous dextrose, glycerol solutions or water/propylene glycol solutions. A saline solution is a preferred carrier when the pharmaceutical composition is administered intravenously or intranasally by a nebulizer. For parenteral injection, liquid preparations can be formulated in solution in, e.g. aqueous polyethylene glycol solution.

In a particularly preferred embodiment of this aspect, the pharmaceutical composition is in the form of a solution, suspension, or emulsion and is administered intranasally by a nebulizer.

Preferably, the pharmaceutical composition is in unit dosage form. In such form the composition may be subdivided into unit doses containing appropriate quantities of the active component. The unit dosage form can be a packaged composition, the package containing discrete quantities of the composition, such as packeted tablets, capsules, and powders in vials or ampoules. Also, the unit dosage form can be a capsule, an injection vial, a tablet, a cachet, or a lozenge itself, or it can be the appropriate number of any of these in packaged form.

The composition, if desired, can also contain minor amounts of wetting or emulsifying agents, or pH buffering agents.

Furthermore, such composition may also comprise other pharmacologically active substance such as but not limited to adjuvants and/or additional active ingredients.

Adjuvants in the context of the present invention include but are not limited to Examples of such adjuvants include but are not limited to inorganic adjuvants, organic adjuvants, oil-based adjuvants, cytokines, particulate adjuvants, virosomes, bacterial adjuvants, synthetic adjuvants, or synthetic polynucleotides adjuvants.

Additional active ingredients include but are not limited to other vaccine compounds or compositions. Preferably, the additional active ingredient is another viral vaccine, more preferably a vaccine against a DNA virus, a negative sense single stranded (ssRNA(−)) RNA virus or an ambisense RNA virus. Further preferred, the virus is selected from negative-single stranded (ssRNA(−)) RNA virus. Even more preferred, the virus is selected from enveloped ssRNA(−) viruses, more preferably from the group consisting of paramyxoviruses and orthomyxoviruses. Preferably, the additional active ingredient is a vaccine against paramyxoviruses, preferably selected from the group consisting of Pneumovirinae, Paramyxovirinae, Fer-de-Lance-Virus, Nariva-Virus, Salem-Virus, Tupaia-Paramyxovirus, Beilong-Virus, J-Virus, Menangle-Virus, Mossmann-Virus, and Murayama-Virus. It is particularly preferred that the Pneumovirinae is selected from the group consisting of Pneumovirus, (e.g. human respiratory syncytical virus (RSV), murine pneumonia virus, bovine RSV, ovine RSV, caprine RSV) and Metapneumovirus, (e.g. human metapneumovirus, avaian metapneumovirus). It is particularly preferred that the Paramyxovirinae is selected from the group consisting of Respirovirus (e.g. human parainfluenza virus 1 and 3), and Rubulavirus, (e.g. human parainfluenza virus 2 and 4). Alternatively or additionally, the additional active ingredient is preferably another viral vaccine against an orthomyxovirus, more preferably selected from the genus of Influenzavirus A, Influenzavirus B, Influenzavirus C, Thogotoviris and Isavirus. In even more preferred embodiments, the orthomxyovirus is Influenzavirus A, preferably selected from the influenza A virus subtypes H1N1, H1N2, H2N2, H3N1, H3N2, H3N8, H5N1, H5N2, H5N3, H5N8, H5N9, H7N1, H7N2, H7N3, H7N4, H7N7, H9N2, H10N7, more preferably the influenza A virus subtype H1N1.

In a fifth aspect the present invention provides for an expression system of the first aspect, the isolated protein mixture of the second aspect, the isolated host cell of the third aspect or the composition of the fourth aspect, for the use in the treatment or prevention of a viral disease.

In preferred embodiments of this aspect, the viral disease is caused by a DNA virus, a negative sense single stranded (ssRNA(−)) RNA virus or an ambisense RNA virus. Further preferred, the virus is selected from negative-single stranded (ssRNA(−)) RNA virus. Even more preferred, the virus is selected from enveloped ssRNA(−) viruses, more preferably from the group consisting of paramyxoviruses and orthomyxoviruses. The paramyxovirus is preferably selected from the group consisting of Pneumovirinae, Paramyxovirinae, Fer-de-Lance-Virus, Nariva-Virus, Salem-Virus, Tupaia-Paramyxovirus, Beilong-Virus, J-Virus, Menangle-Virus, Mossmann-Virus, and Murayama-Virus. Even more preferably, the Pneumovirinae is selected from the group consisting of Pneumovirus, (e.g. human respiratory syncytical virus (RSV), murine pneumonia virus, bovine RSV, ovine RSV, caprine RSV) and Metapneumovirus, (e.g. human metapneumovirus, avaian metapneumovirus). Even more preferably, the Paramyxovirinae is selected from the group consisting of Respirovirus (e.g. human parainfluenza virus 1 and 3), and Rubulavirus, (e.g. human parainfluenza virus 2 and 4).Alternatively or additionally, the viral disease is preferably caused by an orthomyxovirus, more preferably selected from the genus of Influenzavirus A, Influenzavirus B, Influenzavirus C, Thogotoviris and Isavirus. In even more preferred embodiments, the orthomxyovirus is Influenzavirus A, preferably selected from the influenza A virus subtypes H1N1, H1N2, H2N2, H3N1, H3N2, H3N8, H5N1, H5N2, H5N3, H5N8, H5N9, H7N1, H7N2, H7N3, H7N4, H7N7, H9N2, H10N7, more preferably the influenza A virus subtype H1N1.

In a sixth aspect, the present invention provides for a method of treatment or prevention of a viral disease comprising the administration of effective amounts of the expression system of the first aspect, the isolated protein mixture of the second aspect, the isolated host cell of the third aspect or the composition of the fourth aspect for the use in the treatment or prevention of a viral disease.

In preferred embodiments of this aspect, the viral disease is caused by a DNA virus, a negative sense single stranded (ssRNA(−)) RNA virus or an ambisense RNA virus. Further preferred, the virus is selected from negative-single stranded (ssRNA(−)) RNA virus. Even more preferred, the virus is selected from enveloped ssRNA(−) viruses, more preferably from the group consisting of paramyxoviruses and orthomyxoviruses. The paramyxovirus is preferably selected from the group consisting of Pneumovirinae, Paramyxovirinae, Fer-de-Lance-Virus, Nariva-Virus, Salem-Virus, Tupaia-Paramyxovirus, Beilong-Virus, J-Virus, Menangle-Virus, Mossmann-Virus, and Murayaina-Virus. Even more preferably, the Pneumovirinae is selected from the group consisting of Pneumovirus, (e.g. human respiratory syncytical virus (RSV), murine pneumonia virus, bovine RSV, ovine RSV, caprine RSV) and Metapneumovirus, (e.g. human metapneumovirus, avaian metapneumovirus). Even more preferably, the Paramyxovirinae is selected from the group consisting of Respirovirus (e.g. human parainfluenza virus 1 and 3), and Rubulavirus, (e.g. human parainfluenza virus 2 and 4). Alternatively or additionally, the viral disease is preferably caused by an orthomyxovirus, more preferably selected from the genus of Influenzavirus A, Influenzavirus B, Influenzavirus C, Thogotoviris and Isavirus. In even more preferred embodiments, the orthomxyovirus is Influenzavirus A, preferably selected from the influenza A virus subtypes H1N1, H1N2, H2N2, H3N1, H3N2, H3N8, H5N1, H5N2, H5N3, 14.5N8, H5N9, H7N1, H7N2, H7N3, H7N4, H7N7, H9N2, H10N7, more preferably the influenza A virus subtype H1N1.

In a seventh aspect, the present invention provides for a method of enhancing an immune response against an immunogen comprising the administration of the expression system of the first aspect, the protein mixture of the second aspect, the cell of the third aspect and the composition of the fourth aspect.

In preferred embodiments of this aspect, the immunogen is a pathogen, more preferred the immunogen is a virus. Preferably, the virus is selected from the group consisting of a DNA virus, a negative sense single stranded (ssRNA(−)) RNA virus or an ambisense RNA virus. Further preferred, the virus is selected from negative-single stranded (ssRNA(−)) RNA virus. Even more preferred, the virus is selected from enveloped ssRNA(−) viruses, more preferably from the group consisting of paramyxoviruses and orthomyxoviruses. The paramyxovirus is preferably selected from the group consisting of Pneumovirinae, Paramyxovirinae, Fer-de-Lance-Virus, Nariva-Virus, Salem-Virus, Tupaia-Paramyxovirus, Beilong-Virus, J-Virus, Menangle-Virus, Mossmann-Virus, and Murayama-Virus. Even more preferably, the Pneumovirinae is selected from the group consisting of Pneumovirus, (e.g. human respiratory syncytical virus (RSV), murine pneumonia virus, bovine RSV, ovine RSV, caprine RSV) and Metapneumovirus, (e.g. human metapneumovirus, avaian metapneumovirus). Even more preferably, the Paramyxovirinae is selected from the group consisting of Respirovirus (e.g. human parainfluenza virus 1 and 3), and Rubulavirus, (e.g. human parainfluenza virus 2 and 4). Alternatively or additionally, the viral disease is preferably caused by an orthomyxovirus, more preferably selected from the genus of Influenzavirus A, Influenzavirus B, Influenzavirus C, Thogotoviris and Isavirus. In even more preferred embodiments, the orthomxyovirus is Influenzavirus A, preferably selected from the influenza A virus subtypes H1N1, H1N2, H2N2, H3N1, H3N2, H3N8, H5N1, H5N2, H5N3, H5N8, H5N9, H7N1, H7N2, H7N3, H7N4, H7N7, H9N2, H10N7, more preferably the influenza A virus subtype H1N1.

In an eighth aspect, the present invention provides nucleotide constructs encoding influenza hemagglutinin (HA), an expression system comprising these nucleotide constructs, and proteins or polyproteins encoded by the nucleotide constructs, wherein the HA0 cleavage site has a multibasic sequence.

The nucleic acid construct of this aspect comprises, essentially consists or consists of a polynucleotide encoding a modified influenza hemagglutinin (HA), wherein the HA0 cleavage site is modified by introducing one or more basic amino acids. Preferably, in the modified HA, the HA0 cleavage site of the consensus HA gene was substituted with the multibasic cleavage site of H5N1 that is cleaved by ubiquitous proteases to obtain a fully processed HA (H1p).

Influenza hemagglutinin (HA) is a protein belonging to the group of viral hemagglutinins found on the surface of the influenza viruses. It is an antigenic glycoprotein which is responsible for binding the virus to the cell that is being infected. HA proteins like influenza hemagglutinin bind to cells with sialic acid on the membranes, such as cells in the upper respiratory tract or erythrocytes. There are at least 16 different HA antigens. These serotypes or subtypes are named H1 through H16.

HA has two functions:

1. Recognition of target cells by binding to sialic acid-containing receptors.

2. Mediating the entry of the viral genome into the target cells by causing the fusion of host endosomal membrane with the viral membrane (envelop) In detail, HA binds to the monosaccharide sialic acid which is present on the surface of its target cells. The cell membrane then engulfs the virus and the portion of the membrane that encloses the virus forms an endosome. Then the endosome is acidified and being transformed it into a lysosome. As soon as the pH within the endosome drops to about 6.0, the original folded structure of the HA molecule becomes unstable, causing it to partially unfold, releasing a hydrophobic portion of its peptide chain. This fusion peptide acts inserts into the endosomal membrane. Then, the rest of the HA molecule refolds into a new structure and causes the fusion of the viral membrane with the endosomal membrane such that the contents of the virus, including its RNA genome, are released into the cytoplasm of the cell.

To acquire its membrane fusion potential, HA0 must be cleaved into HA1 and HA2 by host cell proteases. Cleavage occurs at a linker sequence connecting the HA1 and HA2 subunits, which is located on a partially surface exposed loop. The H0 cleavage site of the influenza HA is located at about aa 340 in the H1N1 subtype (aa 339 to 344 of SEQ ID NO: 8), the H5N1 subtype (aa 337 to 346 of SEQ ID NO: 10) and H3N2 (aa 340 to 350 of SEQ ID NO: 20). The position of the H0 cleavage site in other subtypes of Influenza virus HA can be determined by the skilled person by conducting sequence alignments and analysing the homology of the sequences by methods well-known in this technical field. Influenza A virus HA of subtype H1N1 and H3N2 require cleavage by host cell proteases to transit into a fusion-competent state. Proteolytic activation of influenza viruses can occur in the Golgi apparatus or at the plasma membrane of infected cells, as well as in the extracellular space and in target cell vesicles, so the nature of the cleavage site and the respective activating proteases have important implications for the biological properties of influenza virus as well as for therapeutic intervention. HA of subtype H5N1 were shown to harbour several arginine and lysine residues at the cleavage site, with an R-X-R/K-R consensus sequence being indispensable for efficient cleavage. In addition, evidence was obtained that cleavage of HA might occur in the trans-Golgi network (TGN). It has been demonstrated that these viruses are activated by furin.

The amino acid sequence of SEQ ID NO: 8 is a consensus sequence derived from the alignment of 829 sequences of the H1N1 subtype annotated in the NCBI Influenza Virus Resource Database, circulating worldwide from April to September 2009. The amino acid sequence of SEQ ID NO: 9 is identical to SEQ ID NO: 8 with the exception that the natural H0 protease cleavage site has been substituted with a multibasic site derived from H5N1. The amino acid sequence of SEQ ID NO: 10 is a consensus derived from the alignment of 259 sequences of the H5N1 subtype annotated in the NCBI Influenza Virus Resource Database, infecting humans worldwide from 1990 to 2009. The amino acid sequence SEQ ID NO: 20 is the sequence of HA of influenza A virus subtype H3N2, strain A/Wellington/01/2004(H3N2). The amino acid sequence of SEQ ID NO: 21 is based on SEQ ID NO: 20 wherein the natural H0 protease cleavage site has been substituted with a multibasic site derived from H5N1

The amino acid sequence of SEQ ID NO: 11 is a NP consensus sequence which was designed on the basis of the alignment of the different influenza subtype consensus sequences. Further, the NP sequence of SEQ ID NO: 11 lacks the Nuclear Localization Signal residing in aa 6-8 (TRK to AAA) to increase cytoplasmic expression.

The amino acid sequence of SEQ ID NO: 12 is a M1 consensus sequence which was derived by alignment of different consensus sequences which were aligned and the most common amino acid at each position was chosen.

In a preferred embodiment of this aspect, the nucleic acid construct and/or the expression system comprising this nucleic acid construct, comprises elements to direct transcription and translation of the HA and the optional further proteins encoded by the nucleic acid construct and/or the expression system, which may be included in the preferred embodiments outlined below. Such elements included promoter and enhancer elements to direct transcription of mRNA in a cell-free or a cell-based based system, preferably a cell-based system. In another embodiment, wherein the polynucleotides are provided as translatable RNAs is envisioned that the expression system comprises those elements that are necessary for translation and/or stabilization of RNAs encoding the HA and/or the T cell inducing protein (s), e.g. polyA-tail, IRES, cap structures etc.

In a preferred embodiment of this aspect, the nucleic acid construct encodes a HA protein, peptide or variant thereof comprising a modified H0 cleavage site, wherein the HA is selected from the group of HA subtypes consisting of H1, H2, H3, H4, H6, H7, H8, H9, H10, H11, H12, H13, H14, H15, H16 or a variant thereof or a consensus sequence thereof, or a variant thereof or a consensus sequence of one or more of the HA subtypes selected from the group of HA subtypes consisting of H1, H2, H3, H4, H5, H6, H7, H8, H9, H10, H11, H12, H13, H14, H15, H16. Preferably, the HA subtypes are selected from the group consisting of H1, H2, H3, H7, H9, H10, or a variant thereof or a consensus sequence thereof, or a variant thereof or a consensus sequence of one or more of the HA subtypes selected from the group of HA subtypes consisting of H1, H2, H3, H5, H7, H9, H10. More preferred, the HA protein, peptide or variant thereof which comprises a modified H0 cleavage site, is a HA from subtype H1 or a variant thereof. Most preferred, the polynucleotide encoding the HA of the nucleotide construct has the sequence of SEQ ID NO: 9.

In a preferred embodiment of this aspect, the nucleic acid construct encodes a HA protein, peptide or variant thereof, wherein H0 cleavage site is modified by substituting at least one non-basic amino acid by a basic amino acid and/or by introducing at least one basic amino acid into the sequence of the H0 cleavage site. Preferably, the basic amino acid is selected from the group consisting of arginine (Arg; R), lysine (Lys; K) and histidine (His, H). More preferably, the basic amino acid is selected from the group consisting of arginine (Arg; R) and lysine (Lys; K).

Preferably, the cleavage site comprises a sequence of 6 to 12 amino acids, more preferably 10-12 amino-acids.

Preferably, at least 20%, at least 30%, at least 40%, at least 50%, at least 60%, at least 70%, at least 80%, at least 90%, or 100% to the amino acids of the polypeptide forming the H0 cleavage site are basic amino acids.

Preferably, the HA0 cleavage site of has a sequence selected from the group consisting of PQRERRRKKR (SEQ ID NO: 15), PQRESRRKKR (SEQ ID NO: 16), PQGERRRKKR (SEQ ID NO: 17), PLRERRRKR (SEQ ID NO: 18) and PQRETR (SEQ ID NO: 19). Most preferred, the HA0 cleavage site of has the sequence PQRERRRKKR (SEQ ID NO: 15).

In Table 1 the sequences of the H0 cleavage site of H1N1 strain and the sequences of the H0 cleavage site of H5N1 strain are compared in their respective context of the HA amino acid chain. In the first line, the consensus sequence of the H0 polybasic cleavage site of the highly pathogenic H5N1 subtype is indicated. In the second line, the amino acid sequence of the H0 cleavage site of the HA of the H1N1 wild-type strain is indicated. In the third line the engineered sequence of the polybasic cleavage site in the H1p protein, replacing the natural sequence.

TABLE 1

| | | |
|---|---|---|
| H5N1 cleavage site | LATGLRNS PQRERRRKKR GLFGAIA...... | Amino acids 329-353 of SEQ ID NO: 10 |
| H1N1 cleavage site | LATGLRNV PSIQSR GLFGAIA...... | Amino acids 331-351 of SEQ ID NO: 8 |
| H1p cleavage site | LATGLRNI PQRERRRKKR GLFGAIA...... | Amino acids 1118-1142 of SEQ ID NO: 13 |

In embodiments of the eighth aspect of the present invention, the nucleic acid construct is part of an expression system encoding the modified HA and a second polynucleotide. In this expression system the polynucleotide encoding the modified HA and the second polynucleotide are comprised on separate vectors or on the same vector. Accordingly, the polynucleotide encoding the modified HA may be comprised on one vector and the second polynucleotide may be comprised on a second vector. Alternatively or additionally, the polynucleotide encoding the modified HA and the second polynucleotide may be comprised on the same vector. It is preferred that the polynucleotide encoding the modified HA and the second polynucleotide are comprised on the same vector. It is particularly preferred that the polynucleotide encoding the modified HA and the second polynucleotide comprised on the same vector are linked in such that they are expressed as a polyprotein. Preferably, the polynucleotide encoding the modified HA and the second polynucleotide form an open reading frame.

It is preferred that the polynucleotide encoding the modified HA and the second polynucleotide are expressed as an artificial polyprotein. In the context of the present invention the term "artificial polyprotein" is directed at polyproteins which are not naturally occurring, e.g. which are generated by using recombinant DNA techniques. Accordingly, the proteins, peptides or variants thereof encoded in this artificial polyprotein are preferably derived from pathogens which genome do not encode a polyprotein comprising the proteins, peptides or variants encoded by the polynucleotide encoding the modified HA and second polynucleotide of the invention. Preferably, the polynucleotide encoding the modified HA and the second polynucleotide are both derived from influenza A viruses.

In preferred embodiments of the eighth aspect, the second polynucleotide encodes a protein or variant thereof, which induces a T cell response, and which is, preferably, a non-structural and/or internal protein of influenza A virus. Preferably, the non-structural and/or internal protein encoded by the second polynucleotide is selected from the group consisting of NP, M1, M2, NS1, NS2/NEP, PA, PB1, PB2 or PB1-F2 (PB1F2).

It is preferred that the amino acid sequence of the modified HA and/or the non-structural (internal) protein encoded by the second polynucleotide comprises consecutive segments or a consensus sequence of one or more different virus isolates.

In the context of the present invention it is preferred that the term "segment" refers to a part of a protein or polyprotein. It is particularly preferred that such segment folds and/or functions independently of the rest of the protein or polyprotein such as but not limited to a domain, an epitope or a fragment thereof. It is understood that a protein variant in the context of the present invention differs in comparison to its parent polypeptide in changes in the amino acid sequence such as amino acid exchanges, insertions, deletions, N-terminal truncations, or C-terminal truncations, or any combination of these changes, which may occur at one or several sites whereby the variant exhibits at least 80% sequence identity to its parent polypeptide.

In a further preferred embodiment, a membrane attachment domain of the modified HA or a variant thereof is functionally deleted, thus, either being structurally deleted or structurally present but not fulfilling its biological function. In a particularly preferred embodiment, the amino acid sequence corresponding to the membrane attachment domain is deleted. The deletion of the membrane attachment region serves the purpose of ascertaining that the anti-pathogenic B cell response inducing protein is secreted from the cell into which the expression system of the invention has been introduced.

In a further preferred embodiment of this aspect the modified HA comprises a secretion signal, which targets the protein to the endoplasmatic reticulum (ER). Such secretion signals are present preferably in the context of a deleted membrane attachment domain. The skilled person is well aware of various such secretion signals, which may be used as heterologous secretion signals, e.g. added to the N-terminus of the modified HA. Alternatively or additionally a naturally occurring secretion signal may be used, which is, e.g., present in the majority of structural and/or surface viral proteins. Thus, if naturally present in the respective protein, it is preferred that the secretion signal is maintained in a modified version of the structural and/or surface protein.

In embodiments of the eighth aspect, the non-structural protein is a conserved internal protein suitable for inducing a T cell mediated immune response against the pathogen involving the activation of antigen-specific T lymphocyte such as but not limited to cytotoxic T cells (CTLs), T helper cells (T$_H$ cells), central memory T cells (TCM cells), effector memory T cells (TEM cells), and regulatory T cells (Treg cells). Thus, preferably the T cell inducing protein of the pathogen does not comprise a secretion signal.

In the context of the present invention, the modified HA or variant thereof is located either N- or C-terminally with respect to the protein, peptide or variant thereof encoded by the second polynucleotide. In a preferred embodiment, the protein, peptide or variant thereof encoded by the second polynucleotide is located N-terminally with respect to the modified HA or variant thereof.

In preferred embodiments of the eighth aspect, a polynucleotide encoding a cleavage site is positioned between the modified HA or variant thereof and the second polynucleotide. It is within the scope of the present invention that that any two proteins can or cannot be connected or linked by a cleavage site.

It is preferred that this cleavage site is either a self-cleaving site (i.e. a cleavage site within the amino acid sequence where this sequence is cleaved or is cleavable without such cleavage involving any additional molecule or where the peptide-bond formation in this sequence is prevented in the first place) or an endopeptidase cleavage site (i.e. a cleavage cite within the amino acid sequence where this sequence is cleaved or is cleavable by an endopeptidase, e.g. trypsin, pepsin, elastase, thrombin, collagenase, furin, thermolysin, endopeptidase V8, cathepsins). More preferably, the self-cleaving site is a 2A cleavage site selected from the group consisting of a viral 2A peptide or 2A-like peptide of Picornavirus, insect viruses, Aphtoviridae, Rotaviruses and *Trypanosoma*, preferably wherein the 2A cleavage site is the 2 A peptide of foot and mouth disease virus. Alternatively or additionally, the polyprotein of the present invention can be cleaved by an autoprotease, i.e. a protease which cleaves peptide bonds in the same protein molecule which also comprises the protease. Examples of such autoproteases are the NS2 protease from flaviviruses or the VP4 protease of birnaviruses In the context of the present invention, the cleavage site can be positioned N-terminally with respect to the modified HA or variant thereof and C-terminally with respect to the protein, peptide or variant thereof encoded by the second polynucleotide. Alternatively the cleavage site can be positioned C-terminally with respect to the modified HA or variant thereof and N-terminally with respect to the protein, peptide or variant thereof encoded by the second polynucleotide.

In preferred embodiment of the eighth aspect, the expression system further comprises a third polynucleotide encoding a protein, peptide or a variant thereof of a pathogen.

It is preferred that the protein, peptide or variant thereof encoded by the third polynucleotide differs from the modified HA or variant thereof or from the protein, peptide or variant thereof encoded by the second polynucleotide. Preferably, the proteins, peptides or variants thereof encoded by the first, second and the third polynucleotide differ from each other. in that they comprise amino acid sequences of different proteins.

In preferred embodiments of the eighth aspect, the third polynucleotide encodes a protein or variant thereof, which induces a T cell response, and which is, preferably, a non-structural and/or internal protein of influenza A virus. Preferably, the non-structural and/or internal protein encoded by the third polynucleotide is selected from the group consisting of NP, M1, M2, NS1, NS2/NEP, PA, PB1, PB2 or PB1-F2 (PB1F2).

In preferred embodiments a polynucleotide encoding a linker is positioned between the second polynucleotide and the third polynucleotide. It is preferred that the linker is a flexible linker, preferably a flexible linker comprising an amino acid sequence according to SEQ ID NO: 6 (Gly-Gly-Gly-Ser-Gly-Gly-Gly).

In preferred embodiments the third polynucleotide is comprised on a separate or on the same vector as the polynucleotide encoding the modified HA or variant thereof and/or the second polynucleotide.

Accordingly, the polynucleotide encoding the modified HA or variant thereof is comprised on one vector and the second polynucleotide is comprised on a second vector and the third polynucleotide is comprised on a third vector. Alternatively or additionally, the polynucleotide encoding the modified HA or variant thereof and the second polynucleotide are comprised on the same vector and the third polynucleotide is comprised on a separate vector, or the polynucleotide encoding the modified HA or variant thereof and the third polynucleotide are comprised on the same vector and the second polynucleotide is comprised on a separate vector, or the second and the third polynucleotide are comprised on the same vector and the polynucleotide encoding the modified HA or variant thereof is comprised on a separate vector. Alternatively or additionally, the polynucleotide encoding the modified HA or variant thereof and the second and the third polynucleotide are comprised on the same vector. It is preferred that the polynucleotide encoding the modified HA or variant thereof and the second and the third polynucleotide may be comprised on the same vector. It is particularly preferred that the polynucleotide encoding the modified HA or variant thereof and the second and the third polynucleotide comprised on the same vector are linked in such that they are expressed as a polyprotein. Preferably, the polynucleotide encoding the modified HA or variant thereof and the second and the third polynucleotide comprised on the same vector form an open reading frame.

In preferred embodiments of this aspect, the vector or vectors comprising the polynucleotide encoding the modified HA or variant thereof, and the second and/or the third polynucleotide is/are selected from the group consisting of plasmid, cosmid, phage, virus, and artificial chromosome. More preferably, a vector suitable for practicing the present invention is selected from the group consisting of plasmid vectors, cosmid vectors, phage vectors, preferably lambda phage and filamentous phage vectors, viral vectors, adenovirus vectors (e.g., non-replicating Ad5, Ad11, Ad26, Ad35, Ad49, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd 73, ChAd82, ChAd83, ChAd146, ChAd147, PanAd1, PanAd2, and PanAd3 vectors or replication-competent Ad4 and Ad7 vectors), adeno-associated virus (AAV) vectors (e.g., AAV type 5 and type 2), alphavirus vectors (e.g., Venezuelan equine encephalitis virus (VEE), sindbis virus (SIN), semliki forest virus (SFV), and VEE-SIN chimeras), herpes virus vectors (e.g. vectors derived from cytomegaloviruses, like rhesus cytomegalovirus (RhCMV) (14)), arena virus vectors (e.g. lymphocytic choriomeningitis virus (LCMV) vectors (15)), measles virus vectors, pox virus vectors (e.g., vaccinia virus, modified vaccinia virus Ankara (MVA), NYVAC (derived from the Copenhagen strain of vaccinia), and avipox vectors: canarypox (ALVAC) and fowlpox (FPV) vectors), vesicular stomatitis virus vectors, retrovirus, lentivirus, viral like particles, and bacterial spores. The vectors ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63 and ChAd82 are described in detail in WO 2005/071093. The vectors PanAd1, PanAd2, PanAd3, ChAd55, ChAd73, ChAd83, ChAd146, and ChAd147 are described in detail in WO 2010/086189. It is particularly preferred that the vector is selected from the group consisting of MVA, ChAd63 and PanAd3.

In preferred embodiments of this aspect, the nucleotide construct or the expression system or the vector or vectors comprising the polynucleotide of the nucleotide construct or the expression system may encompass "expression control sequences" that regulate the expression of the gene of interest. Typically, expression control sequences are polypeptides or polynucleotides such as but not limited to promoters, enhancers, silencers, insulators, or repressors.

In a particularly preferred embodiment of this aspect, the expression system is defined according to the embodiments of the first aspect of the present invention directed at expressing systems comprising polynucleotides encoding proteins, peptides or variants thereof from orthomyxovirus, preferably proteins, peptides or variants from influenza A viruses.

In preferred embodiments, the nucleic acid construct and/or the expression system of the eighth aspect is for use in medicine. In more preferred embodiments, the nucleic acid constructs, the expression systems or the proteins of this aspect are for use in the prophylaxis or treatment of an influenza A virus infection and/or in the manufacturing of medicament for use in the prophylaxis or treatment of an influenza A virus infection and/or for use in methods of prophylaxis or treatment of an influenza A virus infection.

In preferred embodiments the expression system is for use in enhancing an immune response. In more preferred embodiments, the expression system is for use in enhancing an anti-pathogenic B cell immune response against an influenza A virus infection, more preferably an influenza A virus as defined in the first aspect of the invention.

In a ninth aspect, the present invention provides the use of the multibasic HA0 cleavage site as defined in the eighth aspect for constructing a nucleic acid construct or an expression systems capable of expressing the modified influenza hemagglutinin (HA) of the eighth aspect in vitro and/or in vivo. Furthermore, this aspect provides the isolated protein mixture, the protein and/or polyprotein encoded by the nucleic acid construct or expression system constructed according to this aspect.

In a tenth aspect, the invention provides an isolated protein mixture encoded by the expression system of the eighth aspect. Preferably, the isolated protein mixture contains, essentially contains or comprises one or more of the proteins or polyproteins encoded by the nucleic acid construct or the expression system of the eighth aspect. In preferred embodiments, the isolated protein mixture is for use in medicine. In particularly preferred embodiments, the isolated protein mixture is for use in the prophylaxis or treatment of a viral infection, particularly preferably for use in the prophylaxis or treatment of an influenza A virus infection and/or in the manufacturing of medicament for use in the prophylaxis or treatment of an influenza A virus infection and/or for use in methods of prophylaxis or treatment of an influenza A virus infection.

In an eleventh aspect, the invention provides an isolated host cell containing the nucleotide constructs, the expression system or the proteins or polyproteins of the eighth aspect and/or the protein mixture of the tenth aspect. It is understood that such host cell includes but is not limited to prokaryotic (e.g. a bacterial cell) or eukaryotic cells (e.g. a fungal, plant or animal cell). In preferred embodiments of this aspect, the host cell is for use in medicine. In particularly preferred embodiments, the host cell is for use in the prophylaxis or treatment of an influenza A virus infection and/or in the manufacturing of medicament for use in the prophylaxis or treatment of an influenza A virus infection and/or for use in methods of prophylaxis or treatment of an influenza A virus infection.

In a twelfth aspect, the present invention provides a composition comprising the nucleotide constructs, the expression system or the proteins or polyproteins of the eighth aspect, or the protein mixture of the tenth aspect, and a pharmaceutical acceptable carrier and/or excipient. Preferably, such composition is a pharmaceutical composition.

The composition of the twelfth aspect contains a therapeutically effective amount of the compound, preferably in purified form, together with a suitable amount of carrier so as to provide the form for proper administration to the patient. The formulation should suit the mode of administration.

The compositions can take the form of solutions, suspensions, emulsion, tablets, pills, capsules, powders, sustained-release formulations and the like. The composition can be formulated as a suppository, with traditional binders and carriers such as triglycerides.

For preparing pharmaceutical compositions of the present invention, pharmaceutically acceptable carriers can be either solid or liquid.

Solid form compositions include powders, tablets, pills, capsules, lozenges, cachets, suppositories, and dispersible granules. A solid excipient can be one or more substances, which may also act as diluents, flavoring agents, binders, preservatives, tablet disintegrating agents, or an encapsulating material. In powders, the excipient is preferably a finely divided solid, which is in a mixture with the finely divided inhibitor of the present invention. In tablets, the active ingredient is mixed with the carrier having the necessary binding properties in suitable proportions and compacted in the shape and size desired. Suitable excipients are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify. Tablets, powders, capsules, pills, cachets, and lozenges can be used as solid dosage forms suitable for oral administration.

Liquid form composition include solutions, suspensions, and emulsions, for example, water, saline solutions, aqueous dextrose, glycerol solutions or water/propylene glycol solutions. A saline solution is a preferred carrier when the pharmaceutical composition is administered intravenously or intranasally by a nebulizer. For parenteral injection, liquid preparations can be formulated in solution in, e.g. aqueous polyethylene glycol solution.

In a particularly preferred embodiment of this aspect, the pharmaceutical composition is in the form of a solution, suspension, or emulsion and is administered intranasally by a nebulizer.

Preferably, the pharmaceutical composition is in unit dosage form. In such form the composition may be subdivided into unit doses containing appropriate quantities of the active component. The unit dosage form can be a packaged composition, the package containing discrete quantities of the composition, such as packeted tablets, capsules, and powders in vials or ampoules. Also, the unit dosage form can be a capsule, an injection vial, a tablet, a cachet, or a lozenge itself, or it can be the appropriate number of any of these in packaged form.

The composition, if desired, can also contain minor amounts of wetting or emulsifying agents, or pH buffering agents.

Furthermore, such composition may also comprise other pharmacologically active substance such as but not limited to adjuvants and/or additional active ingredients.

Adjuvants in the context of the present invention include but are not limited to Examples of such adjuvants include but are not limited to inorganic adjuvants, organic adjuvants, oil-based adjuvants, cytokines, particulate adjuvants, virosomes, bacterial adjuvants, synthetic adjuvants, or synthetic polynucleotides adjuvants.

Additional active ingredients include but are not limited to other vaccine compounds or compositions. Preferably, the additional active ingredient is another viral vaccine, more preferably a vaccine against a DNA virus, a negative sense single stranded (ssRNA(-)) RNA virus or an ambisense RNA virus. Further preferred, the virus is selected from negative-single stranded (ssRNA(-)) RNA virus. Even more preferred, the virus is selected from enveloped ssRNA(-) viruses, more preferably from the group consisting of paramyxoviruses and orthomyxoviruses. Preferably, the additional active ingredient is a vaccine against paramyxoviruses, preferably selected from the group consisting of Pneumovirinae, Paramyxovirinae, Fer-de-Lance-Virus, Nariva-Virus, Salem-Virus, Tupaia-Paramyxovirus, Beilong-Virus, J-Virus, Menangle-Virus, Mossmann-Virus, and Murayama-Virus. It is particularly preferred that the Pneumovirinae is selected from the group consisting of Pneumovirus, (e.g. human respiratory syncytical virus (RSV), murine pneumonia virus, bovine RSV, ovine RSV, caprine RSV) and Metapneumovirus, (e.g. human metapneumovirus, avaian metapneumovirus). It is particularly preferred that the Paramyxovirinae is selected from the group consisting of Respirovirus (e.g. human parainfluenza virus 1 and 3), and Rubulavirus, (e.g. human parainfluenza virus 2 and 4). Alternatively or additionally, the additional active ingredient is preferably another viral vaccine against an orthomyxovirus, more preferably selected from the genus of Influenzavirus A, Influenzavirus B, Influenzavirus C, Thogotoviris and Isavirus. In even more preferred embodiments, the orthomxyovirus is Influenzavirus A, preferably selected from the influenza A virus subtypes H1N1, H1N2, H2N2, H3N1, H3N2, H3N8, H5N1, H5N2, H5N3, H5N8, H5N9, H7N1, H7N2, H7N3, H7N4, H7N7, H9N2, H10N7, more preferably the influenza A virus subtype H1N1.

In a thirteenth aspect, the present invention provides the nucleotide constructs, the expression system or the proteins or polyproteins of the eighth aspect, the protein mixture of the tenth aspect, the cell of the eleventh aspect and the composition of the twelfth aspect, for the use in medicine in particular in the treatment or prevention of influenza A virus infections. The influenza A virus is preferably selected from the influenza A virus subtypes H1N1, H1N2, H2N2, H3N1, H3N2, H3N8, H5N1, H5N2, H5N3, H5N8, H5N9, H7N1, H7N2, H7N3, H7N4, H7N7, H9N2, H10N7, more preferably the influenza A virus subtype H1N1.

In a fourteenth aspect, the present invention provides for a method of treatment or prevention of an influenza A virus infections comprising the administration of an effective amount of the nucleotide constructs, the expression system or the proteins or polyproteins of the eighth aspect, the protein mixture of the tenth aspect, the cell of the eleventh aspect and the composition of the twelfth aspect. The influenza A virus is preferably selected from the influenza A virus subtypes H1N1, H1N2, H2N2, H3N1, H3N2, H3N8, H5N1, H5N2, H5N3, H5N8, H5N9, H7N1, H7N2, H7N3, H7N4, H7N7, H9N2, H10N7, more preferably the influenza A virus subtype H1N1.

In a fifteenth aspect, the present invention provides for a method of enhancing an immune response comprising the administration of the nucleotide constructs or the expression system or the proteins or polyproteins of the eighth aspect, the protein mixture of the tenth aspect, the cell of the eleventh aspect and the composition of the twelfth aspect. In a preferred embodiment of this aspect, the method enhances an immune response against influenza A virus. The influenza A virus is preferably selected from the influenza A virus subtypes H1N1, H1N2, H2N2, H3N1, H3N2, H3N8, H5N1, H5N2, H5N3, H5N8, H5N9, H7N1, H7N2, H7N3, H7N4, H7N7, H9N2, H10N7, more preferably the influenza A virus subtype H1N1.

The following examples are merely illustrative of the present invention and should not be construed to limit the scope of the invention as indicated by the appended claims in any way.

EXAMPLES

Example 1: Design and Synthesis of DNA Encoding Optimised RSV Antigen

Consensus Vaccine

Several computational alternatives to isolate-based vaccine design exist. One approach is reconstruction of the most recent common ancestor (MRCA) sequence (9). In this type of analysis, the ancestral state is an estimate of the actual sequence that existed in the past (i.e., it comes directly from the reconstructed history). Another type of computational analysis is a center of the tree (COT) approach. The COT approach identifies a point on the unrooted phylogeny, where the average evolutionary distance from that point to each tip on the phylogeny is minimized. Advocates of this approach state that because the COT is a point on the phylogeny, the estimated COT sequence will have the same advantages as the estimated ancestral sequence. See, for example, U.S. Application 2005/0137387 A1. However, this COT approach is sufficiently complex that reducing it to practice for a large and heterologous data set such as the Influenza sequence database is not practical with technology. Overall, the MRCA and COT approaches are impractical for application to the complex Influenza sequence database.

A third type of computational analysis is the consensus sequence approach. Because the consensus sequence is composed of the amino acid most commonly observed at each position, it likely represents the most-fit state of the virus. Thus, effective evasion of the immune response by selection of a sequence divergent from consensus may result in a less fit virus from a replicative standpoint. The consensus sequence approach favors heavily sampled sublineages and deemphasizes outliers. As such, the approaches utilized herein are far more straightforward than the other types of computational analyses. Furthermore, these approaches can use the entire data set for RSV. One advantage of the consensus sequence is that it minimizes the genetic differences between vaccine strains and contemporary isolates, effectively reducing the extent of diversity by half, and thus it may have enhanced potential for eliciting cross-reactive responses.

Vaccine Design

To design the vaccine antigen of the present invention, protein sequences of the F0-, N-, and M2-1-proteins of RSV were retrieved from the National Center for Biotechnology Information (NCBI) RSV Resource database (on the world wibe web at ncbi.nlm.nih.gov). Protein sequences were chosen from different RSV subtype A strains.

A F0 consensus sequence was derived by alignment of all non-identical sequences of the F-protein using MUSCLE version 3.6 and applying the majority rule. The vaccine's F0 consensus sequence was designed on the basis of the alignment of the different RSV sequences. The sequence similarity of the vaccine consensus F0 sequence was measured performing BLAST analysis, which stands for Basic Local Alignment Search Tool and is publicly available through the NCBI. The highest average similarity of the consensus sequence, calculated compared to all RSV sequences in the database, was 100% with respect to the human respiratory syncytial virus A2 strain.

Further, the vaccine's F0 sequence lacks the transmembrane region residing in amino acids 525 to 574 to allow for the secretion of F0ΔTM.

Finally, the vaccine F0ΔTM sequence was codon-optimized for expression in eukaryotic cells.

The vaccine's N consensus sequence was derived by alignment of all non-identical sequences of the N-protein using MUSCLE version 3.6 and applying the majority rule. BLAST analysis of the N consensus sequence found the best alignment with the human respiratory syncytial virus A2 strain. The vaccine's N sequence was then codon-optimized for expression in eukaryotic cells.

A M2-1 consensus sequence was derived by alignment of all non-identical sequences of the M2-1-protein using MUSCLE version 3.6 and applying the majority rule. BLAST analysis of the M2-1 consensus sequence found the best alignment with the human respiratory syncytial virus A2 strain. Finally, the vaccine M2-1 sequence was codon-optimized for expression in eukaryotic cells.

The vaccines F0ΔTM sequence and N sequence were spaced by the cleavage sequence 2A of the Foot and Mouth Disease virus. The vaccines N sequence and M2-1 sequence were separated by a flexible linker (GGGSGGG; SEQ ID NO: 6).

Finally, the codon-optimized viral genes were cloned as the single open reading frame F0ΔTM-N-M2-1. A schematic diagram of the antigen composition is given in FIG. 1.

Generation of DNA Plasmids Encoding F0ΔTM and F0ΔTM-N-M2-1

Consensus F0ΔTM, N and M2-1 sequences were optimized for mammalian expression, including the addition of a Kozak sequence and codon optimization. The DNA sequence encoding the multi-antigen vaccine was chemically synthesized and then sub-cloned by suitable restriction enzymes EcoRV and NotI into the pVJTetOCMV shuttle vector under the control of the CMV promoter.

Generation of PanAd3 Viral-Vectored RSV Vaccine

A viral-vectored RSV vaccine PanAd3/F0ΔTM-N-M2-1 was generated which contains a 809 aa polyprotein coding for the consensus F0ΔTM, N and M2-1 proteins fused by a flexible linker.

Bonobo Adenovirus type 3 (PanAd3) is a novel adenovirus strain with improved seroprevalence and has been described previously.

Cloning of F0ΔTM-N-M2-1 from the plasmid vector pVJTetOCMV/F0ΔTM-N-M2-1 into the PanAd3 pre-Adeno vector was performed by cutting out the antigen sequences flanked by homologous regions and enzymatic in vitro recombination.

Analysis of Antigen Expression in Mammalian Cells

To control that the unique combination of viral antigens was efficiently expressed and correctly processed into mammalian cells, Hela cells were transfected with 10 μg of DNA plasmid encoding the F0ΔTM-N-M2-1 antigen. Cells were cultured for 36 hours before the supernatant was collected and cell lysates were prepared. Proteins were separated by SDS-PAGE and blotted onto nylon filters. A mouse monoclonal antibody (mAb8) raised against the M viral protein (gift from Dr. Geraldine Taylor) was used to reveal the expressed proteins.

Figure 2:
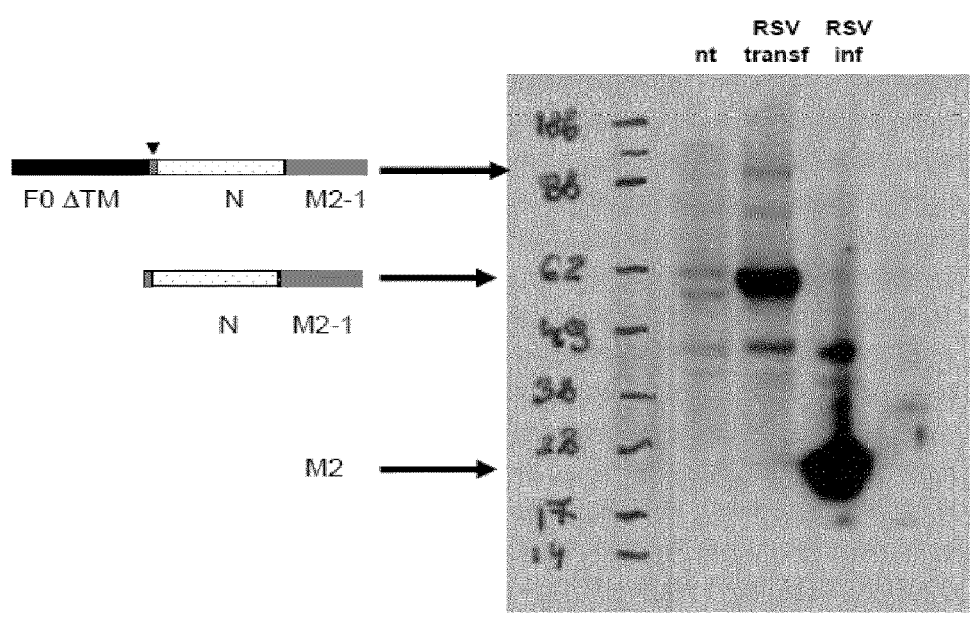
FIG. 2: The vaccine antigen F0ΔTM-N-M2-1 is efficiently processed in mammalian cells. Western Blot analysis of lysates from HeLa cells; nt: not transfected Hela. RSV transf: HeLa cells transfected with F0ΔTM-N-M2-1. RSV inf: Hep2 cells infected with RSV strain A
Figure 3:
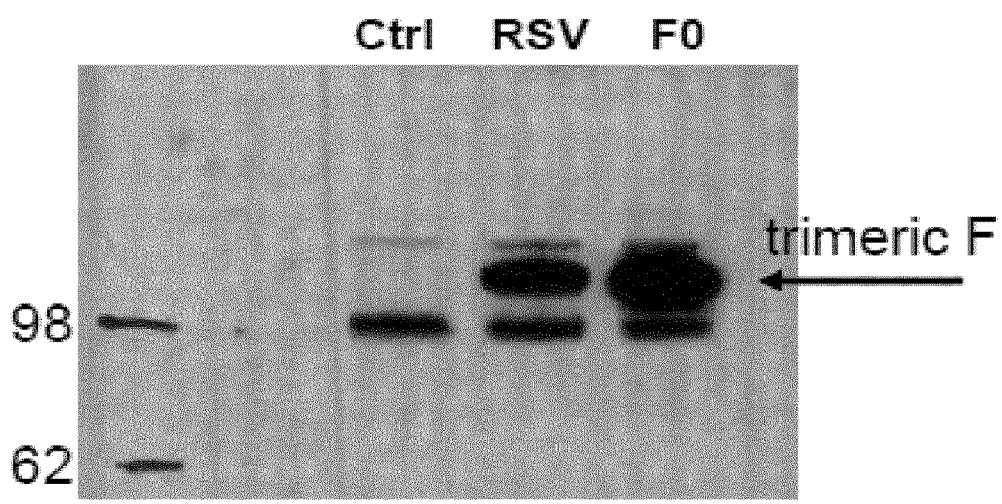
FIG. 3: The secreted F protein forms a homotrimer. Western Blot analysis of supernatant from transfected HeLa cells; RSV: F0ΔTM-N-M2-1 transfected, F0: F0ΔTM transfected, Ctrl: empty plasmid transfected

As shown in FIGS. 2 and 3, the fused viral protein N-M2-1 is very efficiently released from the polyprotein by the 2A cleavage site and recognized as a major band by mAb8. Very few high molecular weight precursor is present at steady-state in the cells. Lysates of Hep2-cells infected with RSV strain A were used as control.

Non-Reducing SDS-PAGE and Western blot analysis of the cell culture medium showed that the F-protein deleted of the trans-membrane region is secreted into the supernatant (see FIG. 3, lane RSV). The molecular weight of the F-protein in the supernatant is consistent with homotrimeric F-protein, which is its native configuration.

Example 2: Vaccine Immunogenicity in Mice

Anti-F Antibodies by DNA Immunization

DNA plasmids encoding F0ΔTM-N-M2-1 or F0ΔTM alone were used to immunize mice by DNA plasmid injection and electroporation (GET) with a regimen of priming and boosting at three weeks post prime. Sera of immunized mice were collected two weeks after boosting and pooled.

Supernatants from Hela cells infected with PanAd3/F0ΔTM-N-M2-1 at MOI 250 were separated on non-reducing SDS-PAGE, blotted onto nylon filters and probed with different dilutions of sera from mice immunized with F0ΔTM or F0ΔTM-N-M2-1.

Figure 4:
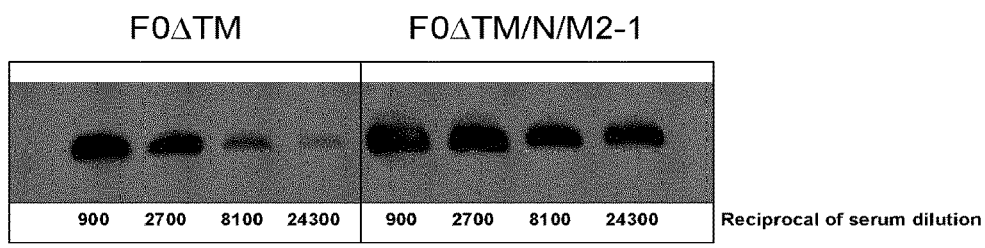
FIG. 4: The F protein expressed from the vaccine polyprotein is a better immunogen than the F protein alone. A. Western Blot analysis of supernatant from HeLa cells infected with PanAd3/F0ΔTM-N-M2-1 which was probed with different dilutions of sera from mice immunized with F0ΔTM or F0ΔTM-N-M2-1 B. densitometric scanning of the Western Blot on panel A. Data are expressed as Relative Intensity of the area corresponding to the protein band.
Figure 4:
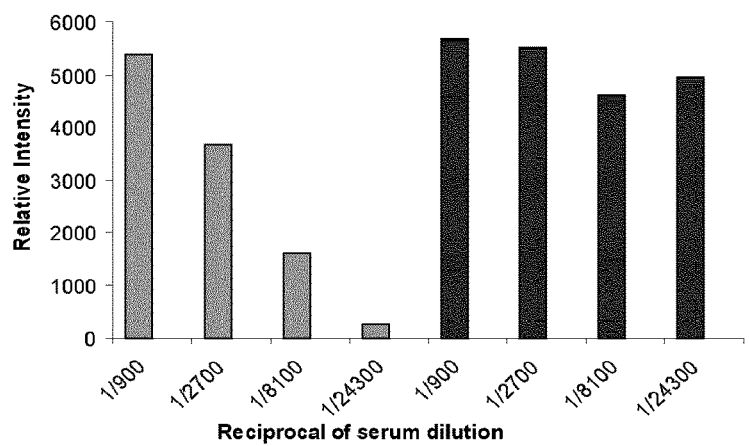

As shown in FIGS. 4A and B, the antibody titers raised by the F-protein expressed in the context of the vaccine antigen are at least 30 times higher than those elicited by the F-protein alone. Thus, the F0ΔTM-N-M2-1 antigen has superior immunogenic properties in inducing B-cell responses in mice.

T Cell Response

The immunological potency of the chimpanzee adenoviral vector PanAd3 bearing the RSV vaccine antigen F0ΔTM-N-M2-1 was evaluated in mice.

Groups of Balb/C mice were immunized by intramuscular injection in the quadriceps with increasing dose of PanAd3/F0ΔTM-N-M2-1. 4 weeks after vaccination mice were sacrificed and splenocytes were subjected to IFNγ-Elispot assay using mapped immunodominant peptides from RSV F- and M-proteins (peptide GWYTSVITIELSNIKE (F aa 51-66 of SEQ ID NO:2) peptide KYKNAVTEL (F aa 85-93 of SEQ ID NO:2) and peptide SYIGSINNI (M aa 282-290; aa 82-90 of SEQ ID NO:5)).

Figure 5:
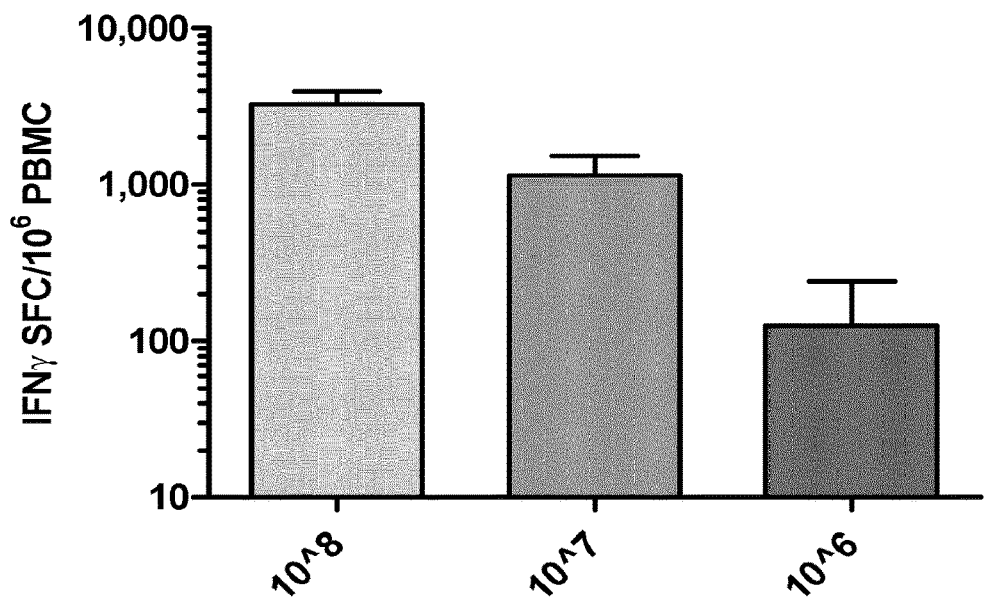
FIG. 5: The RSV vaccine induced potent systemic T cell immunity in mice by a single intramuscular injection. IFNg-Elispot assay of splenocytes of PanAd3/F0ΔTM-N-M2-1 immunized Balb/C mice using mapped immunodominant peptides from RSV F and M proteins.
Figure 6:
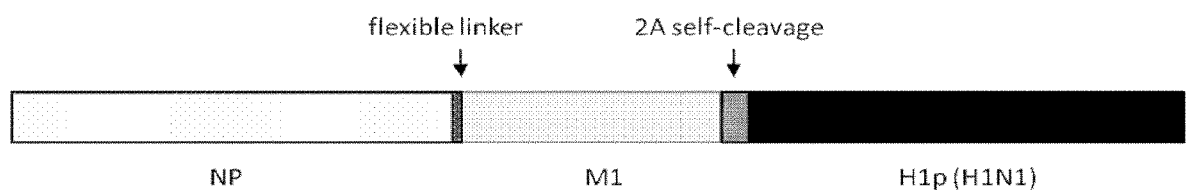
FIG. 6: Schematic diagram of the Influenza vaccine polyprotein. NP=consensus sequence of the NP protein, M1=consensus sequence of M1 protein, 2A=translational cleavage site of the Foot and Mouth Disease virus, H1p=consensus sequence of the HA protein from H1N12009.

As shown in FIG. 5, a potent T cell response was observed against known Balb/C immunodominant epitopes against RSV F and M proteins.

Example 3: Induction of Neutralizing Antibodies by H1p

Figure 7:
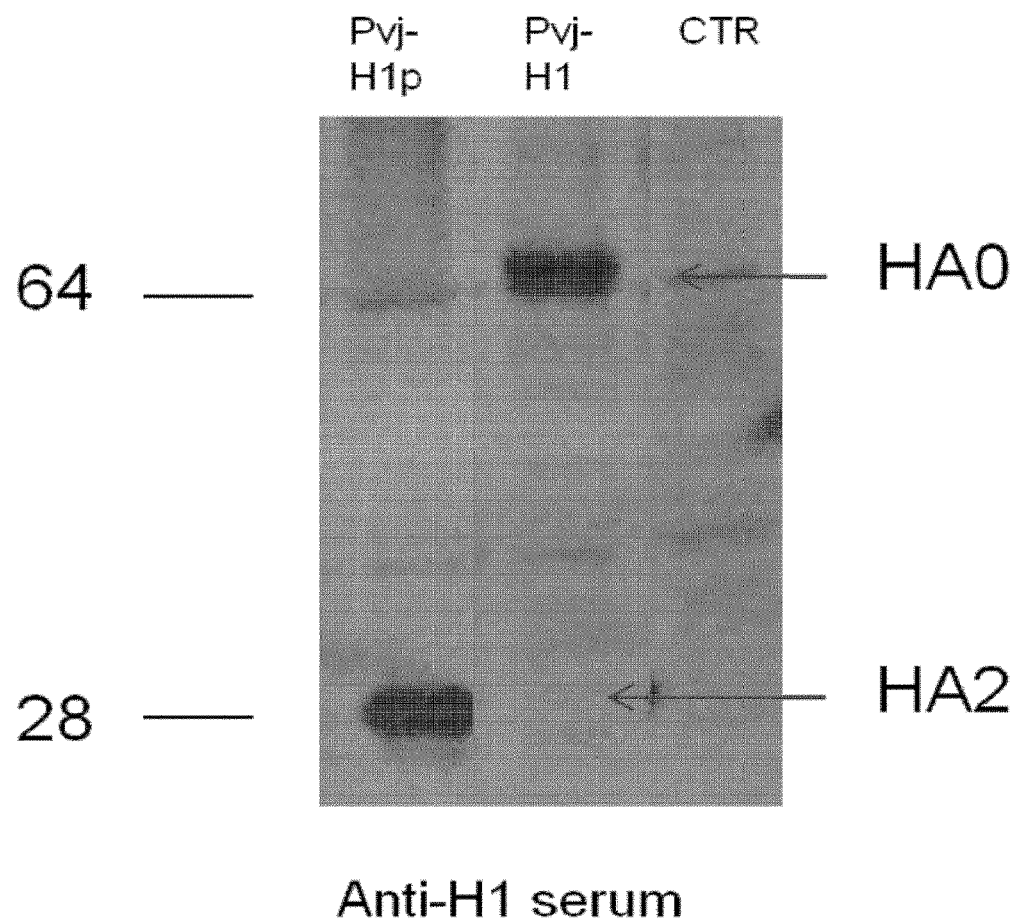
FIG. 7 Western Blot analysis of H1p expression in transfected HeLa cells. Total lysate of HeLa cells transfected with PVJ-H1p (Lane 1), with PVJ-H1 (Lane 2) and not transfected CTR (Lane 3). The arrows show the bands corresponding to the uncleaved (70 kD) HA0 form and the cleaved (28 Kd) HA2. The polyclonal anti-HA serum recognize epitopes in the HA2 protein fragment. It is shown that theH1p protein is fully processed.

The novel chimeric H1p protein engineered to contain the multibasic HA0 cleavage site from H5N1 is efficiently expressed and fully cleaved in transfected HeLa cells. The equivalent protein with the wild type cleavage site, H1, is not cleaved in HeLa cells, as shown in FIG. 7.

Figure 8:
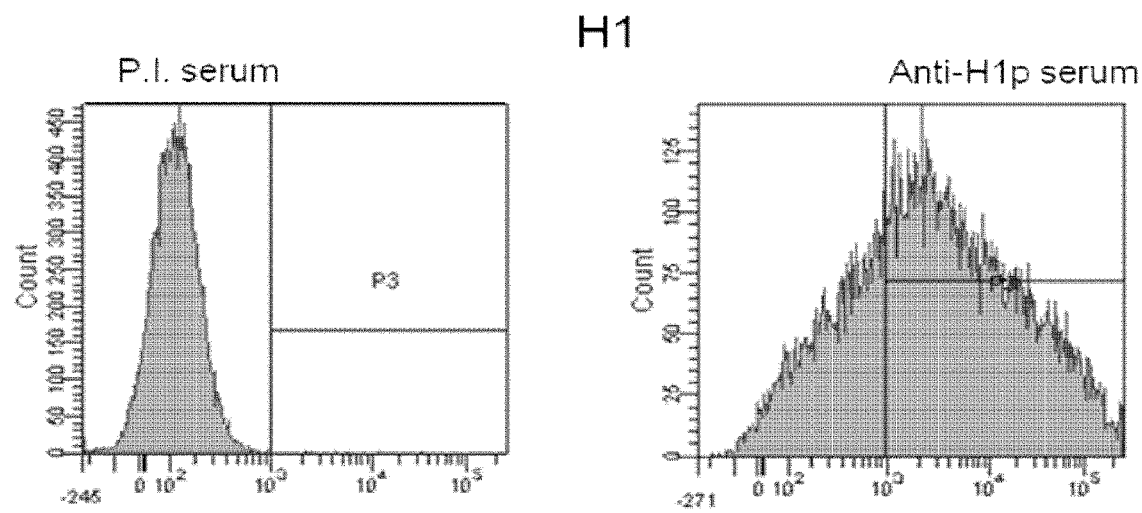
FIG. 8 Whole-cell FACS analysis of membrane-displayed HA proteins. The histograms represent the median fluorescence analysis of HeLa cells transfected with wild type HA (right upper panel) and H1 (right lower panel). Cells were incubated with hyperimmune mouse polyclonal serum raised against H1p and then with a secondary anti-mouse antibody PE-conjugated. In the left upper and lower panels, cells were incubated with mouse pre-immune serum to set the background fluorescence level.
Figure 8:
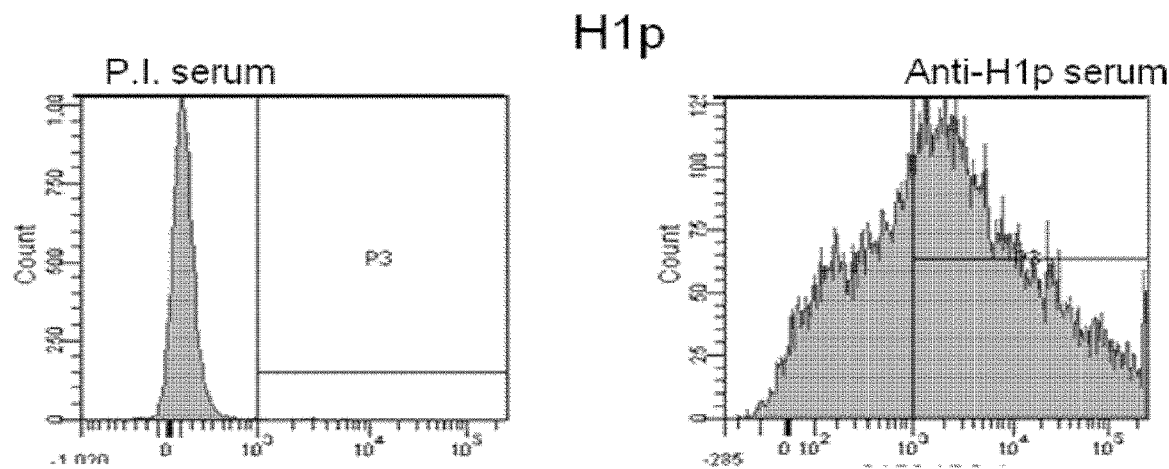

In order to control that the chimeric H1p protein is correctly displayed on the cell membrane, a whole-cell FACS binding assay has been performed using a polyclonal anti-HA serum to reveal the transfected protein on the cell surface. As shown in FIG. 8, H1p is exposed on the cell membrane as efficiently as the corresponding wild type HA protein.

Figure 9:
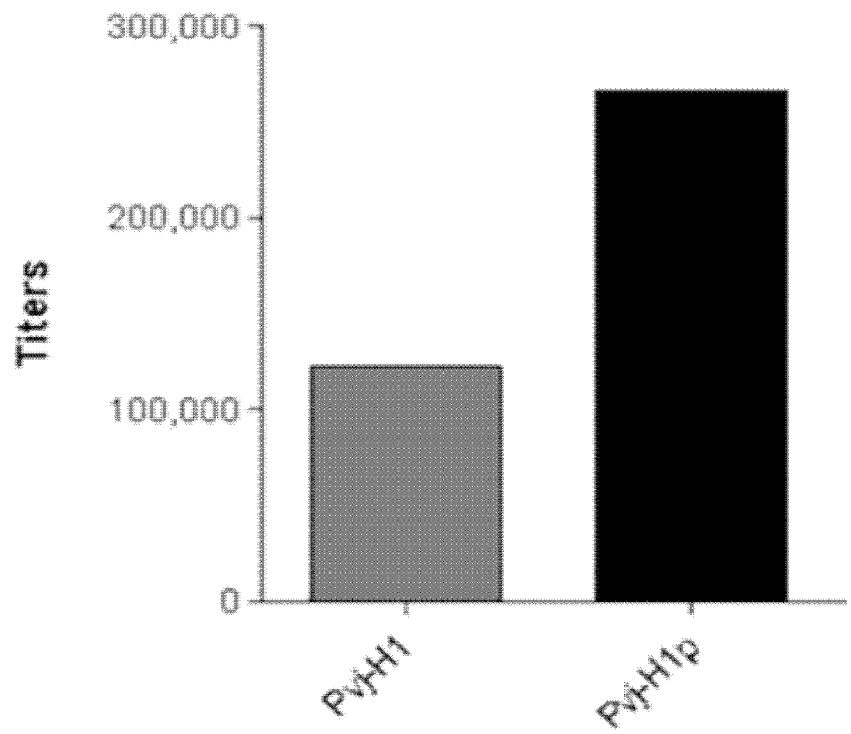
FIG. 9 H1p is able to induce higher antibody titers. ELISA assay on coated recombinant HA (H1N1California 2009). Antibody titers were measured on sera from animals immunized with H1 and H1p. Titers were calculated by serial dilution of the sera and represents the dilution giving an OD value three times higher than the background.

To measure the immunological potency of H1p, Balb/C mice were immunized with plasmid DNA vectors encoding the modified H1p and the unmodified H1 (PVJ-H1p and PVJ-H1, respectively). The sera from immunized animals have been analyzed by ELISA on purified recombinant HA protein (H1N1California2009). The anti-HA titers elicited by the engineered H1p protein were surprisingly higher than those elicited by the HA bearing the wild type protease cleavage site (FIG. 9).

Figure 10:
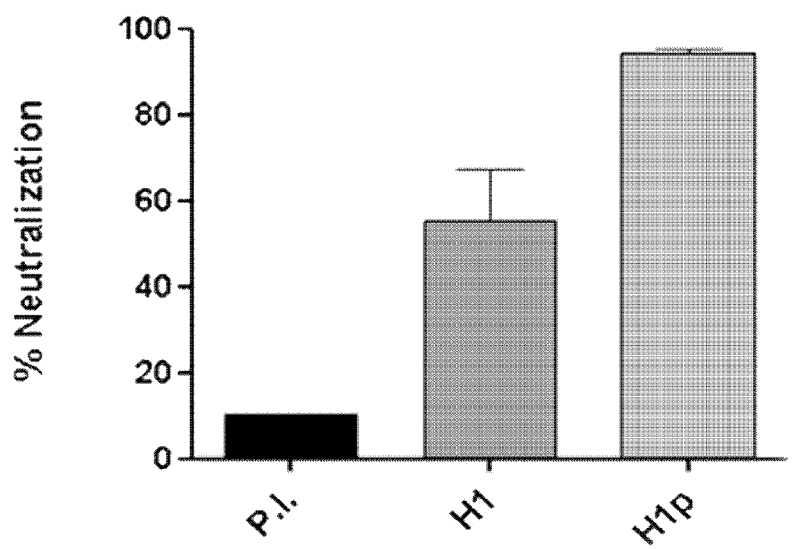
FIG. 10 HA (H1N1Mexico2009) pseudotyped virus infection of MDCK cells is more potently neutralized by the serum of animals immunized with H1p. Results of an ELISA assay on coated recombinant HA (H1N1California 2009) with the sera of animals immunized with H1p and NPM1H1p.

To confirm and expand these results, the sera from H1 and H1p immunized animals were tested for their capacity to neutralize the infection of retroviral vectors pseudotyped with the Flu HA protein in a cell culture based assay. Pseudovirions are infectious for a single cycle of infection in which they express the reporter gene luciferase. FIG. 10 shows the serum neutralization capacity in a HA (H1N1Mexico2009) pseudotyped virus particles infection assay on MDCK cells. The result confirms that the antibodies elicited by H1p have greater neutralizing activity than those induced by H1 protein.

Example 4: Enhanced Antibody Titer by a Polyprotein Comprising NP, M1 and H1p

Figure 11:
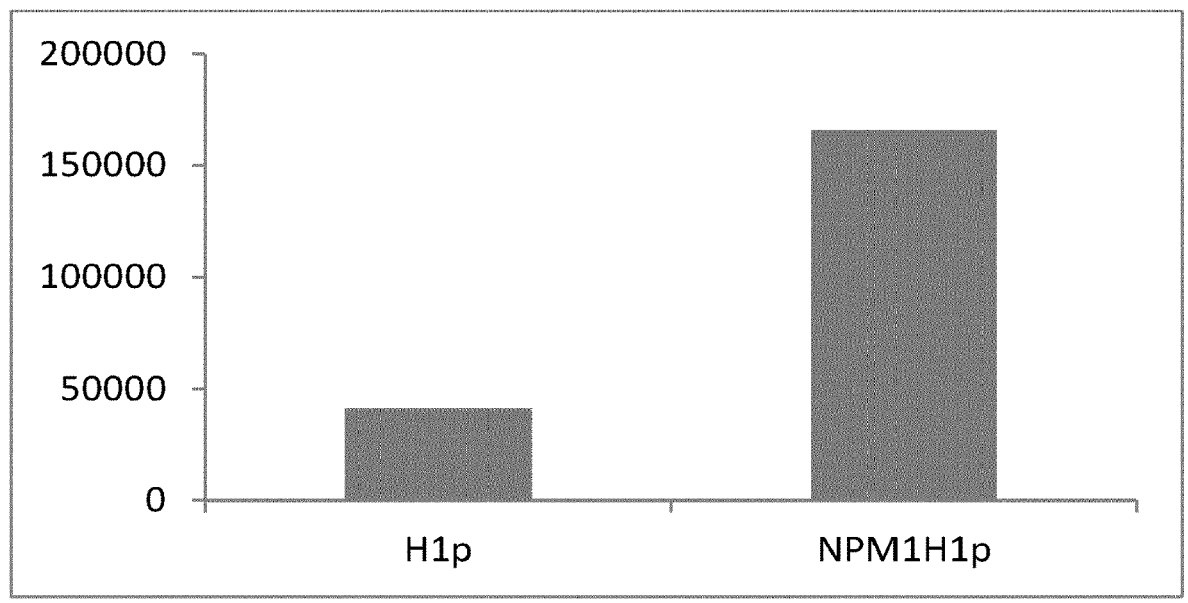
FIG. 11 H1p expressed in the context of the triple antigen is able to induce higher antibody titers. ELISA assay on coated recombinant HA (H1N1California 2009). Antibody titers were measured on sera from animals immunized with H1p and NPM1H1p. Titers were calculated by serial dilution of the sera and represent the dilution giving an OD value three times higher than the background.

Head to head comparison of the immunological potency of the H1p and NPM1H1p revealed that the HA protein expressed in the context of the triple antigen induces higher antibody titer than HA alone. FIG. 11 shows the results of an ELISA assay where a recombinant HA (H1N1California 2009) was coated on the bottom of 96 well plate. Serial dilutions of sera of animals immunized with H1p and NPM1H1p were put on the plate and the bound IgG were revealed with an anti-mouse IgG secondary antibody. As already observed for the RSV antigen, the co-expression of internal antigens (NP and M1) with the surface exposed antigen (HA) improves the humoral response directed to the latter protein.

Example 5: Processing of the Novel FLU Antigen Composed of NP, M1 and H1p

Figure 12:
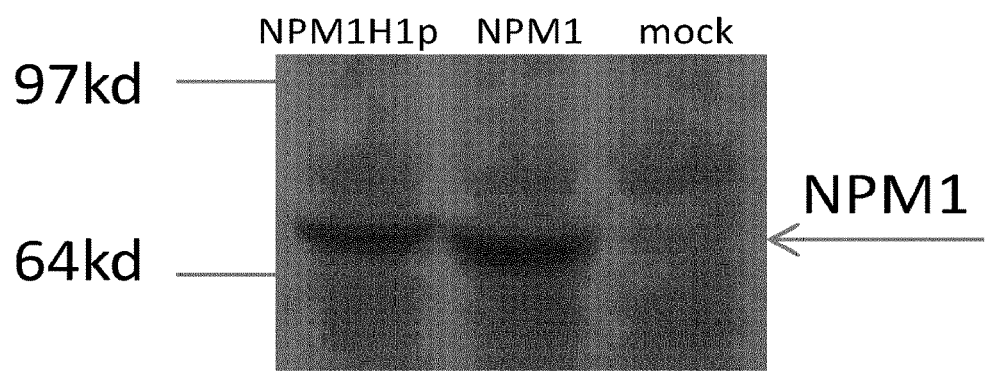
FIG. 12 Western Blot analysis of NPM1H1p antigen expression in transfected HeLa cells shows that the protein is fully processed. Total lysate of HeLa cells transfected with pNEB-NPM1H1p (Lane 1), with pNEB-NPM1 (Lane 2) and mock transfected (Lane 3). The arrow shows the band corresponding to the fusion protein NPM1 (70 kD. A monoclonal anti-NP antibody has been used to detect the intracellular protein.
Figure 13:
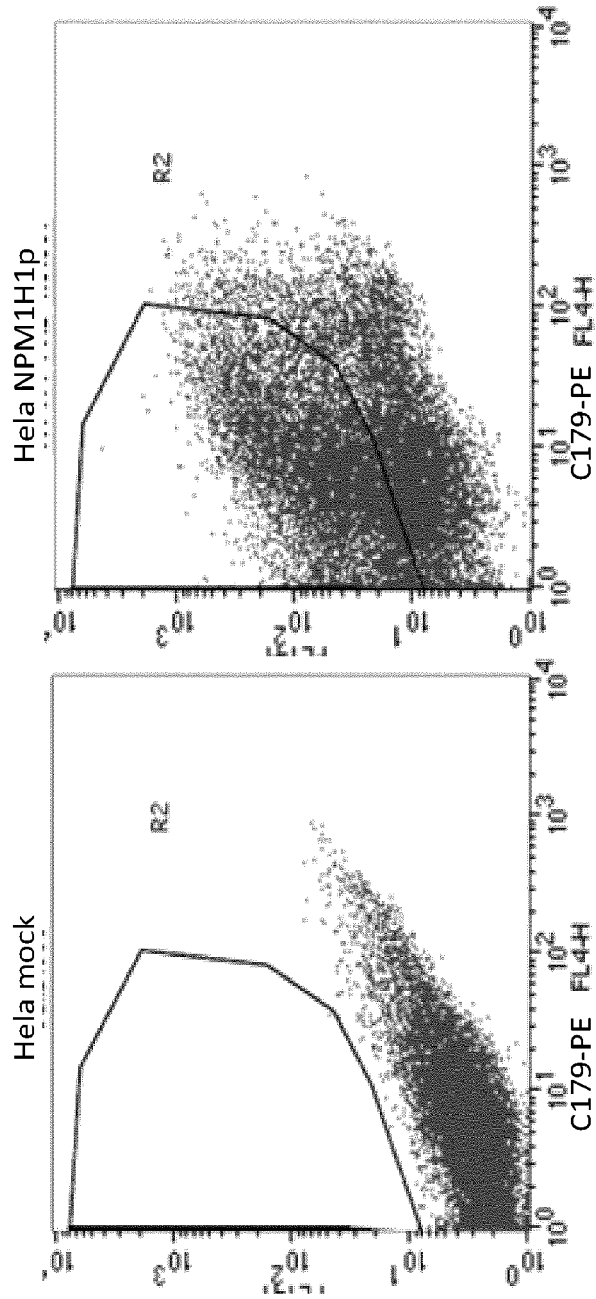
FIG. 13 H1p derived from processing of NPM1H1p is displayed on the cell membrane and correctly folded. Whole-cell FACS analysis of HeLa cells mock transfected (left panel) or transfected with NPM1H1p (right panel). Cells were incubated with the mouse mAb C179 which binds to a conformational epitope in the HA stem region and then with a secondary anti-mouse antibody PE-conjugated.

To control the expression and processing of the vaccine antigen proteins, HeLa cells have been transfected with an expression plasmid containing NPM1H1p under the control of the CMV promoter. Cells were harvested 48 hours after transfection. Half cells were lysed for Western Blot analysis (FIG. 12) and half were incubated with a commercially available antibody C179 (Okuno Y, JVI 1994), which binds the stem region of the HA protein (FIG. 13) and analysed by FACS. Western blot analysis of the total cell lysate shows a unique 70 kDa band which correspond to the NPM1 fusion protein (FIG. 12). This indicates that the antigen is fully and correctly processed out of the 2A cleavage site. FIG. 13 shows that the released H1p protein is then displayed on the cell membrane and correctly folded, as detected by the use of a conformation-dependent antibody C179 which binds to the HA stem region. Accordingly, the novel FLU antigen composed of NP, M1 and H1p is correctly processed and the released HA protein is displayed on the cell surface and recognized by a conformational antibody.

REFERENCES

1) Ono & Freed, (2005), Adv. Virus Res., 273:5419-5442
2) Collins P et al., (1996). Parainfluenza viruses, 1205-1241. In Fields et al. (ed.), Fields Virology. Lippincot-Raven Publishers, Philadelphia (Pa.) USA
3) Shay D K et al., (1999), Bronchiolitis-Associated Hospitalizations Among US Children, 1980-1996. JAMA 282:1440-1446
4) Simoes E A & Carbonell-Estrany X (2003), Pediatr Infect Dis J 22:S13-8; discussion S18-20.
5) Collins P L & Graham B S (2008), J Virol 82:2040-55
6) Falsey A R et al., (2005), N Engl J Med 352:1749-59
7) Fleming D M & Elliot A J (2007), Eur Respir J 30:1029-31
8) Cardenas S et al., (2005), Expert Rev Anti Infect Ther 3:719-26
9) Kim H W et al., (1969), Amer J Epidemiol 89:422-434
10) Delgado M F et al., (2009), Nat Med 15:34-41
11) Graham B S et al., (1993), J Immunol 151:2032-2040
12) Polack F P et al., (2002), J Exp Med 196:859-865
13) Castilow E M & Varga S M, (2008), Future Virol 3:445-454
14) Hansen S et al., (2011), Nature 473:523-527
15) Flatz, L et al. (2010), Nature Med 16:339-345

Sequence Listing—Free Text Information

SEQ ID NO: 1 F protein minimal sequence
SEQ ID NO: 2 F0ΔTM
SEQ ID NO: 3 N protein minimal sequence
SEQ ID NO: 4 N protein of RSV
SEQ ID NO: 5 M2-1 protein of RSV
SEQ ID NO: 6 peptide linker
SEQ ID NO: 7 F0ΔTM-N-M2-1
SEQ ID NO: 8 HA subtype H1 consensus sequence
SEQ ID NO: 9 HA subtype H1 consensus sequence modified H0 cleavage site
SEQ ID NO: 10 HA subtype H5 consensus sequence
SEQ ID NO: 11 NP consensus sequence
SEQ ID NO: 12 M1 consensus sequence
SEQ ID NO: 13 NP-M1-HA (amino acid sequence)
SEQ ID NO: 14 NP-M1-HA (nucleic acid sequence)
SEQ ID NO: 15 H0 cleavage site sequence
SEQ ID NO: 16 H0 cleavage site sequence
SEQ ID NO: 17 H0 cleavage site sequence
SEQ ID NO: 18 H0 cleavage site sequence
SEQ ID NO: 19 H0 cleavage site sequence
SEQ ID NO: 20 HA subtype H3 strain A/Wellington/01/2004(H3N2)
SEQ ID NO: 21 HA subtype H3 strain A/Wellington/01/2004(H3N2) modified H0 cleavage site

The invention claimed is:

1. A pharmaceutical composition comprising an adenovirus vector and a pharmaceutically acceptable excipient wherein the adenovirus vector comprises:
    (a) a first polynucleotide encoding at least one protein that induces a T cell response directed to a respiratory syncytial virus (RSV) protein, wherein the at least one protein that induces a T cell response is a non-structural or internal protein of RSV that is protein M2, wherein the protein comprises the amino acid sequence of SEQ ID NO: 5;
    (b) a second polynucleotide encoding at least one protein, wherein the at least one protein is a fusion protein F surface protein of RSV, which induces an anti-pathogenic B cell response, wherein the protein comprises the amino acid sequence of SEQ ID NO: 1 or 2; and
    (c) a third polynucleotide encoding at least one protein, which is a non-structural and internal protein of RSV that is protein N, which induces a T cell response, wherein the protein comprises the amino acid sequence of SEQ ID NO: 3 or 4, wherein the first, the second, and the third polynucleotides are located on the same adenovirus vector.

2. The pharmaceutical composition of claim 1, wherein the first and second polynucleotides form an open reading frame and are linked such that they are expressed as an artificial polyprotein.

3. The pharmaceutical composition of claim 2, wherein a polynucleotide which encodes a cleavage site is positioned between the first and the second polynucleotide.

4. The pharmaceutical composition of claim 3, wherein the cleavage site is a self-cleaving site or an endopeptidase cleavage site.

5. The pharmaceutical composition of claim 4, wherein the self-cleaving site is selected from the group consisting of a viral 2A peptide or 2A-like peptide of Picornavirus, insect viruses, Aphtoviridae, Rotaviruses, and *Trypanosoma*.

6. The pharmaceutical composition of claim 1, wherein the adenovirus vector is selected from the group consisting of PanAd3, ChAd3, ChAd63, and ChAd83.

7. The pharmaceutical composition of claim 1, wherein the adenovirus vector is replication competent.

8. The pharmaceutical composition of claim 1, wherein the adenovirus vector is replication defective.

9. A pharmaceutical composition comprising a simian adenovirus vector and a pharmaceutically acceptable excipient, wherein the simian adenovirus vector comprises nucleic acid sequences encoding a simian adenoviral hexon, a simian adenoviral fiber and a simian adenoviral penton, wherein the adenovirus vector comprises:
    (a) a first polynucleotide encoding at least one protein that induces a T cell response directed to a respiratory syncytial virus (RSV) protein, wherein the at least one protein or peptide that induces a T cell response is a non-structural or internal protein of RSV that is protein M2, wherein the protein comprises the amino acid sequence of SEQ ID NO: 5; and
    (b) a second polynucleotide encoding at least one protein, wherein the at least one protein is a fusion protein F surface protein of RSV, which induces an anti-pathogenic B cell response, wherein the protein comprises the amino acid sequence of SEQ ID NO: 1 or 2; and
    (c) a third polynucleotide encoding at least one protein, which is a non-structural and internal protein of RSV that is protein N, which induces a T cell response, wherein the protein comprises the amino acid sequence of SEQ ID NO: 3 or 4, wherein the first, the second, and the third polynucleotides are located on the same adenovirus vector.

10. An isolated host cell comprising the adenovirus vector of claim 9.

11. A method of treatment of a respiratory syncytial viral disease comprising administering of an effective amount of the pharmaceutical composition of claim 1.

12. The pharmaceutical composition of claim 5, wherein the 2A cleavage site is the 2A peptide of foot and mouth disease virus.

13. The pharmaceutical composition of claim 1, wherein the adenovirus vector comprises a polynucleotide encoding an amino acid according to SEQ ID NO: 7.

14. The pharmaceutical composition of claim 1, wherein the composition enhances an immune response against an RSV infection in a subject.

15. The pharmaceutical composition of claim 1, wherein a polynucleotide encoding a linker is positioned between the second polynucleotide and the third polynucleotide.

16. The pharmaceutical composition of claim 1, further comprising an adjuvant.

* * * * *

SEQUENCE LISTING

<160> NUMBER OF SEQ ID NOS: 21

<210> SEQ ID NO 1
<211> LENGTH: 360
<212> TYPE: PRT
<213> ORGANISM: Artificial Sequence
<220> FEATURE:
<223> OTHER INFORMATION: Synthetic Polypeptide

<400> SEQUENCE: 1

```
Val Leu His Leu Glu Gly Glu Val Asn Lys Ile Lys Ser Ala Leu Leu
1               5                   10                  15

Ser Thr Asn Lys Ala Val Val Ser Leu Ser Asn Gly Val Ser Val Leu
            20                  25                  30

Thr Ser Lys Val Leu Asp Leu Lys Asn Tyr Ile Asp Lys Gln Leu Leu
        35                  40                  45

Pro Ile Val Asn Lys Gln Ser Cys Ser Ile Ser Asn Ile Glu Thr Val
    50                  55                  60

Ile Glu Phe Gln Gln Lys Asn Asn Arg Leu Leu Glu Ile Thr Arg Glu
65                  70                  75                  80

Phe Ser Val Asn Ala Gly Val Thr Thr Pro Val Ser Thr Tyr Met Leu
                85                  90                  95

Thr Asn Ser Glu Leu Leu Ser Leu Ile Asn Asp Met Pro Ile Thr Asn
            100                 105                 110

Asp Gln Lys Lys Leu Met Ser Asn Asn Val Gln Ile Val Arg Gln Gln
        115                 120                 125

Ser Tyr Ser Ile Met Ser Ile Ile Lys Glu Glu Val Leu Ala Tyr Val
    130                 135                 140

Val Gln Leu Pro Leu Tyr Gly Val Ile Asp Thr Pro Cys Trp Lys Leu
145                 150                 155                 160

His Thr Ser Pro Leu Cys Thr Thr Asn Thr Lys Glu Gly Ser Asn Ile
                165                 170                 175

Cys Leu Thr Arg Thr Asp Arg Gly Trp Tyr Cys Asp Asn Ala Gly Ser
            180                 185                 190

Val Ser Phe Phe Pro Gln Ala Glu Thr Cys Lys Val Gln Ser Asn Arg
        195                 200                 205

Val Phe Cys Asp Thr Met Asn Ser Leu Thr Leu Pro Ser Glu Val Asn
    210                 215                 220

Leu Cys Asn Val Asp Ile Phe Asn Pro Lys Tyr Asp Cys Lys Ile Met
225                 230                 235                 240

Thr Ser Lys Thr Asp Val Ser Ser Val Ile Thr Ser Leu Gly Ala
                245                 250                 255

Ile Val Ser Cys Tyr Gly Lys Thr Lys Cys Thr Ala Ser Asn Lys Asn
            260                 265                 270

Arg Gly Ile Ile Lys Thr Phe Ser Asn Gly Cys Asp Tyr Val Ser Asn
        275                 280                 285

Lys Gly Val Asp Thr Val Ser Val Gly Asn Thr Leu Tyr Tyr Val Asn
    290                 295                 300

Lys Gln Glu Gly Lys Ser Leu Tyr Val Lys Gly Glu Pro Ile Ile Asn
305                 310                 315                 320

Phe Tyr Asp Pro Leu Val Phe Pro Ser Asp Glu Phe Asp Ala Ser Ile
                325                 330                 335

Ser Gln Val Asn Glu Lys Ile Asn Gln Ser Leu Ala Phe Ile Arg Lys
            340                 345                 350

Ser Asp Glu Leu Leu His Asn Val
```

<210> SEQ ID NO 2
<211> LENGTH: 524
<212> TYPE: PRT
<213> ORGANISM: Artificial Sequence
<220> FEATURE:
<223> OTHER INFORMATION: Synthetic Polypeptide

<400> SEQUENCE: 2

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
```

```
                355                 360                 365
Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn
        515                 520
```

<210> SEQ ID NO 3
<211> LENGTH: 170
<212> TYPE: PRT
<213> ORGANISM: Artificial Sequence
<220> FEATURE:
<223> OTHER INFORMATION: Synthetic Polypeptide

<400> SEQUENCE: 3

```
Ile Lys Ile Leu Arg Asp Ala Gly Tyr His Val Lys Ala Asn Gly Val
1               5                   10                  15

Asp Val Thr Thr His Arg Gln Asp Ile Asn Gly Lys Glu Met Lys Phe
            20                  25                  30

Glu Val Leu Thr Leu Ala Ser Leu Thr Thr Glu Ile Gln Ile Asn Ile
        35                  40                  45

Glu Ile Glu Ser Arg Lys Ser Tyr Lys Lys Met Leu Lys Glu Met Gly
50                  55                  60

Glu Val Ala Pro Glu Tyr Arg His Asp Ser Pro Asp Cys Gly Met Ile
65                  70                  75                  80

Ile Leu Cys Ile Ala Ala Leu Val Ile Thr Lys Leu Ala Ala Gly Asp
                85                  90                  95

Arg Ser Gly Leu Thr Ala Val Ile Arg Arg Ala Asn Asn Val Leu Lys
            100                 105                 110

Asn Glu Met Lys Arg Tyr Lys Gly Leu Leu Pro Lys Asp Ile Ala Asn
        115                 120                 125

Ser Phe Tyr Glu Val Phe Glu Lys Tyr Pro His Phe Ile Asp Val Phe
    130                 135                 140

Val His Phe Gly Ile Ala Gln Ser Ser Thr Arg Gly Gly Ser Arg Val
145                 150                 155                 160

Glu Gly Ile Phe Ala Gly Leu Phe Met Asn
                165                 170
```

<210> SEQ ID NO 4
<211> LENGTH: 391
<212> TYPE: PRT

<213> ORGANISM: Artificial Sequence
<220> FEATURE:
<223> OTHER INFORMATION: Synthetic Polypeptide

<400> SEQUENCE: 4

Met Ala Leu Ser Lys Val Lys Leu Asn Asp Thr Leu Asn Lys Asp Gln
1               5                   10                  15

Leu Leu Ser Ser Ser Lys Tyr Thr Ile Gln Arg Ser Thr Gly Asp Ser
                20                  25                  30

Ile Asp Thr Pro Asn Tyr Asp Val Gln Lys His Ile Asn Lys Leu Cys
            35                  40                  45

Gly Met Leu Leu Ile Thr Glu Asp Ala Asn His Lys Phe Thr Gly Leu
    50                  55                  60

Ile Gly Met Leu Tyr Ala Met Ser Arg Leu Gly Arg Glu Asp Thr Ile
65                  70                  75                  80

Lys Ile Leu Arg Asp Ala Gly Tyr His Val Lys Ala Asn Gly Val Asp
                85                  90                  95

Val Thr Thr His Arg Gln Asp Ile Asn Gly Lys Glu Met Lys Phe Glu
            100                 105                 110

Val Leu Thr Leu Ala Ser Leu Thr Thr Glu Ile Gln Ile Asn Ile Glu
        115                 120                 125

Ile Glu Ser Arg Lys Ser Tyr Lys Lys Met Leu Lys Glu Met Gly Glu
    130                 135                 140

Val Ala Pro Glu Tyr Arg His Asp Ser Pro Asp Cys Gly Met Ile Ile
145                 150                 155                 160

Leu Cys Ile Ala Ala Leu Val Ile Thr Lys Leu Ala Ala Gly Asp Arg
                165                 170                 175

Ser Gly Leu Thr Ala Val Ile Arg Arg Ala Asn Asn Val Leu Lys Asn
            180                 185                 190

Glu Met Lys Arg Tyr Lys Gly Leu Leu Pro Lys Asp Ile Ala Asn Ser
        195                 200                 205

Phe Tyr Glu Val Phe Glu Lys Tyr Pro His Phe Ile Asp Val Phe Val
    210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ala Gly Gln Val
                245                 250                 255

Met Leu Arg Trp Gly Val Leu Ala Lys Ser Val Lys Asn Ile Met Leu
            260                 265                 270

Gly His Ala Ser Val Gln Ala Glu Met Glu Gln Val Glu Val Tyr
        275                 280                 285

Glu Tyr Ala Gln Lys Leu Gly Gly Glu Ala Gly Phe Tyr His Ile Leu
    290                 295                 300

Asn Asn Pro Lys Ala Ser Leu Leu Ser Leu Thr Gln Phe Pro His Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
            340                 345                 350

Tyr Ala Glu Gln Leu Lys Glu Asn Gly Val Ile Asn Tyr Ser Val Leu
        355                 360                 365

Asp Leu Thr Ala Glu Glu Leu Glu Ala Ile Lys His Gln Leu Asn Pro
    370                 375                 380

Lys Asp Asn Asp Val Glu Leu

<210> SEQ ID NO 5
<211> LENGTH: 194
<212> TYPE: PRT
<213> ORGANISM: Artificial Sequence
<220> FEATURE:
<223> OTHER INFORMATION: Synthetic Polypeptide

<400> SEQUENCE: 5

```
Met Ser Arg Arg Asn Pro Cys Lys Phe Glu Ile Arg Gly His Cys Leu
1               5                   10                  15
Asn Gly Lys Arg Cys His Phe Ser His Asn Tyr Phe Glu Trp Pro Pro
            20                  25                  30
His Ala Leu Leu Val Arg Gln Asn Phe Met Leu Asn Arg Ile Leu Lys
        35                  40                  45
Ser Met Asp Lys Ser Ile Asp Thr Leu Ser Glu Ile Ser Gly Ala Ala
    50                  55                  60
Glu Leu Asp Arg Thr Glu Glu Tyr Ala Leu Gly Val Val Gly Val Leu
65                  70                  75                  80
Glu Ser Tyr Ile Gly Ser Ile Asn Asn Ile Thr Lys Gln Ser Ala Cys
                85                  90                  95
Val Ala Met Ser Lys Leu Leu Thr Glu Leu Asn Ser Asp Asp Ile Lys
            100                 105                 110
Lys Leu Arg Asp Asn Glu Glu Leu Asn Ser Pro Lys Ile Arg Val Tyr
        115                 120                 125
Asn Thr Val Ile Ser Tyr Ile Glu Ser Asn Arg Lys Asn Asn Lys Gln
    130                 135                 140
Thr Ile His Leu Leu Lys Arg Leu Pro Ala Asp Val Leu Lys Lys Thr
145                 150                 155                 160
Ile Lys Asn Thr Leu Asp Ile His Lys Ser Ile Thr Ile Asn Asn Pro
                165                 170                 175
Lys Glu Ser Thr Val Ser Asp Thr Asn Asp His Ala Lys Asn Asn Asp
            180                 185                 190
Thr Thr
```

<210> SEQ ID NO 6
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 6

```
Gly Gly Gly Ser Gly Gly Gly
1               5
```

<210> SEQ ID NO 7
<211> LENGTH: 1146
<212> TYPE: PRT
<213> ORGANISM: Artificial Sequence
<220> FEATURE:
<223> OTHER INFORMATION: Synthetic Polypeptide

<400> SEQUENCE: 7

```
Met Glu Leu Leu Ile Leu Lys Ala Asn Ala Ile Thr Thr Ile Leu Thr
1               5                   10                  15
Ala Val Thr Phe Cys Phe Ala Ser Gly Gln Asn Ile Thr Glu Glu Phe
            20                  25                  30
```

```
Tyr Gln Ser Thr Cys Ser Ala Val Ser Lys Gly Tyr Leu Ser Ala Leu
             35                  40                  45
Arg Thr Gly Trp Tyr Thr Ser Val Ile Thr Ile Glu Leu Ser Asn Ile
 50                  55                  60
Lys Glu Asn Lys Cys Asn Gly Thr Asp Ala Lys Val Lys Leu Ile Lys
 65                  70                  75                  80
Gln Glu Leu Asp Lys Tyr Lys Asn Ala Val Thr Glu Leu Gln Leu Leu
                 85                  90                  95
Met Gln Ser Thr Pro Ala Thr Asn Asn Arg Ala Arg Glu Leu Pro
                100                 105                 110
Arg Phe Met Asn Tyr Thr Leu Asn Asn Ala Lys Lys Thr Asn Val Thr
             115                 120                 125
Leu Ser Lys Lys Arg Lys Arg Arg Phe Leu Gly Phe Leu Leu Gly Val
130                 135                 140
Gly Ser Ala Ile Ala Ser Gly Val Ala Val Ser Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Ser Lys Val
                180                 185                 190
Leu Asp Leu Lys Asn Tyr Ile Asp Lys Gln Leu Leu Pro Ile Val Asn
                195                 200                 205
Lys Gln Ser Cys Ser Ile Ser Asn Ile Glu Thr Val Ile Glu Phe Gln
                210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
                260                 265                 270
Leu Met Ser Asn Asn Val Gln Ile Val Arg Gln Gln Ser Tyr Ser Ile
                275                 280                 285
Met Ser Ile Ile Lys Glu Glu Val Leu Ala Tyr Val Val Gln Leu Pro
                290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
                340                 345                 350
Pro Gln Ala Glu Thr Cys Lys Val Gln Ser Asn Arg Val Phe Cys Asp
                355                 360                 365
Thr Met Asn Ser Leu Thr Leu Pro Ser Glu Val Asn Leu Cys Asn Val
                370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
                435                 440                 445
Thr Val Ser Val Gly Asn Thr Leu Tyr Tyr Val Asn Lys Gln Glu Gly
```

```
                450             455             460
    Lys Ser Leu Tyr Val Lys Gly Glu Pro Ile Ile Asn Phe Tyr Asp Pro
    465                 470                 475                 480

Leu Val Phe Pro Ser Asp Glu Phe Asp Ala Ser Ile Ser Gln Val Asn
                        485                 490                 495

Glu Lys Ile Asn Gln Ser Leu Ala Phe Ile Arg Lys Ser Asp Glu Leu
                    500                 505                 510

Leu His Asn Val Asn Ala Gly Lys Ser Thr Thr Asn Arg Lys Arg Arg
                    515                 520                 525

Ala Pro Val Lys Gln Thr Leu Asn Phe Asp Leu Leu Lys Leu Ala Gly
                530                 535                 540

Asp Val Glu Ser Asn Pro Gly Pro Met Ala Leu Ser Lys Val Lys Leu
    545                 550                 555                 560

Asn Asp Thr Leu Asn Lys Asp Gln Leu Leu Ser Ser Lys Tyr Thr
                        565                 570                 575

Ile Gln Arg Ser Thr Gly Asp Ser Ile Asp Thr Pro Asn Tyr Asp Val
                    580                 585                 590

Gln Lys His Ile Asn Lys Leu Cys Gly Met Leu Leu Ile Thr Glu Asp
                    595                 600                 605

Ala Asn His Lys Phe Thr Gly Leu Ile Gly Met Leu Tyr Ala Met Ser
                610                 615                 620

Arg Leu Gly Arg Glu Asp Thr Ile Lys Ile Leu Arg Asp Ala Gly Tyr
    625                 630                 635                 640

His Val Lys Ala Asn Gly Val Asp Val Thr Thr His Arg Gln Asp Ile
                        645                 650                 655

Asn Gly Lys Glu Met Lys Phe Glu Val Leu Thr Leu Ala Ser Leu Thr
                    660                 665                 670

Thr Glu Ile Gln Ile Asn Ile Glu Ile Glu Ser Arg Lys Ser Tyr Lys
                    675                 680                 685

Lys Met Leu Lys Glu Met Gly Glu Val Ala Pro Glu Tyr Arg His Asp
                690                 695                 700

Ser Pro Asp Cys Gly Met Ile Ile Leu Cys Ile Ala Ala Leu Val Ile
    705                 710                 715                 720

Thr Lys Leu Ala Ala Gly Asp Arg Ser Gly Leu Thr Ala Val Ile Arg
                        725                 730                 735

Arg Ala Asn Asn Val Leu Lys Asn Glu Met Lys Arg Tyr Lys Gly Leu
                    740                 745                 750

Leu Pro Lys Asp Ile Ala Asn Ser Phe Tyr Glu Val Phe Glu Lys Tyr
                755                 760                 765

Pro His Phe Ile Asp Val Phe Val His Phe Gly Ile Ala Gln Ser Ser
                770                 775                 780

Thr Arg Gly Gly Ser Arg Val Glu Gly Ile Phe Ala Gly Leu Phe Met
    785                 790                 795                 800

Asn Ala Tyr Gly Ala Gly Gln Val Met Leu Arg Trp Gly Val Leu Ala
                        805                 810                 815

Lys Ser Val Lys Asn Ile Met Leu Gly His Ala Ser Val Gln Ala Glu
                    820                 825                 830

Met Glu Gln Val Val Glu Val Tyr Glu Tyr Ala Gln Lys Leu Gly Gly
                    835                 840                 845

Glu Ala Gly Phe Tyr His Ile Leu Asn Asn Pro Lys Ala Ser Leu Leu
                850                 855                 860

Ser Leu Thr Gln Phe Pro His Phe Ser Ser Val Val Leu Gly Asn Ala
    865                 870                 875                 880
```

```
Ala Gly Leu Gly Ile Met Gly Glu Tyr Arg Gly Thr Pro Arg Asn Gln
                885                 890                 895

Asp Leu Tyr Asp Ala Ala Lys Ala Tyr Ala Glu Gln Leu Lys Glu Asn
            900                 905                 910

Gly Val Ile Asn Tyr Ser Val Leu Asp Leu Thr Ala Glu Glu Leu Glu
        915                 920                 925

Ala Ile Lys His Gln Leu Asn Pro Lys Asp Asn Asp Val Glu Leu Gly
    930                 935                 940

Gly Gly Gly Ser Gly Gly Gly Met Ser Arg Arg Asn Pro Cys Lys
945                 950                 955                 960

Phe Glu Ile Arg Gly His Cys Leu Asn Gly Lys Arg Cys His Phe Ser
                965                 970                 975

His Asn Tyr Phe Glu Trp Pro Pro His Ala Leu Leu Val Arg Gln Asn
            980                 985                 990

Phe Met Leu Asn Arg Ile Leu Lys Ser Met Asp Lys Ser Ile Asp Thr
        995                 1000                1005

Leu Ser Glu Ile Ser Gly Ala Ala Glu Leu Asp Arg Thr Glu Glu
    1010                1015                1020

Tyr Ala Leu Gly Val Val Gly Val Leu Glu Ser Tyr Ile Gly Ser
    1025                1030                1035

Ile Asn Asn Ile Thr Lys Gln Ser Ala Cys Val Ala Met Ser Lys
    1040                1045                1050

Leu Leu Thr Glu Leu Asn Ser Asp Asp Ile Lys Lys Leu Arg Asp
    1055                1060                1065

Asn Glu Glu Leu Asn Ser Pro Lys Ile Arg Val Tyr Asn Thr Val
    1070                1075                1080

Ile Ser Tyr Ile Glu Ser Asn Arg Lys Asn Asn Lys Gln Thr Ile
    1085                1090                1095

His Leu Leu Lys Arg Leu Pro Ala Asp Val Leu Lys Lys Thr Ile
    1100                1105                1110

Lys Asn Thr Leu Asp Ile His Lys Ser Ile Thr Ile Asn Asn Pro
    1115                1120                1125

Lys Glu Ser Thr Val Ser Asp Thr Asn Asp His Ala Lys Asn Asn
    1130                1135                1140

Asp Thr Thr
    1145

<210> SEQ ID NO 8
<211> LENGTH: 566
<212> TYPE: PRT
<213> ORGANISM: Artificial Sequence
<220> FEATURE:
<223> OTHER INFORMATION: Artificial Sequence

<400> SEQUENCE: 8

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80
```

```
Asn Pro Glu Cys Glu Ser Leu Ser Thr Ala Ser Ser Trp Ser Tyr Ile
                85                  90                  95
Val Glu Thr Ser Ser Ser Asp Asn Gly Thr Cys Tyr Pro Gly Asp Phe
            100                 105                 110
Ile Asp Tyr Glu Glu Leu Arg Glu Gln Leu Ser Ser Val Ser Ser Phe
            115                 120                 125
Glu Arg Phe Glu Ile Phe Pro Lys Thr Ser Ser Trp Pro Asn His Asp
130                 135                 140
Ser Asn Lys Gly Val Thr Ala Ala Cys Pro His Ala Gly Ala Lys Ser
145                 150                 155                 160
Phe Tyr Lys Asn Leu Ile Trp Leu Val Lys Lys Gly Asn Ser Tyr Pro
                165                 170                 175
Lys Leu Ser Lys Ser Tyr Ile Asn Asp Lys Gly Lys Glu Val Leu Val
            180                 185                 190
Leu Trp Gly Ile His His Pro Ser Thr Ser Ala Asp Gln Gln Ser Leu
            195                 200                 205
Tyr Gln Asn Ala Asp Ala Tyr Val Phe Val Gly Ser Ser Arg Tyr Ser
210                 215                 220
Lys Lys Phe Lys Pro Glu Ile Ala Ile Arg Pro Lys Val Arg Asp Gln
225                 230                 235                 240
Glu Gly Arg Met Asn Tyr Tyr Trp Thr Leu Val Glu Pro Gly Asp Lys
                245                 250                 255
Ile Thr Phe Glu Ala Thr Gly Asn Leu Val Val Pro Arg Tyr Ala Phe
            260                 265                 270
Ala Met Glu Arg Asn Ala Gly Ser Gly Ile Ile Ile Ser Asp Thr Pro
            275                 280                 285
Val His Asp Cys Asn Thr Thr Cys Gln Thr Pro Lys Gly Ala Ile Asn
290                 295                 300
Thr Ser Leu Pro Phe Gln Asn Ile His Pro Ile Thr Ile Gly Lys Cys
305                 310                 315                 320
Pro Lys Tyr Val Lys Ser Thr Lys Leu Arg Leu Ala Thr Gly Leu Arg
                325                 330                 335
Asn Val Pro Ser Ile Gln Ser Arg Gly Leu Phe Gly Ala Ile Ala Gly
            340                 345                 350
Phe Ile Glu Gly Gly Trp Thr Gly Met Val Asp Gly Trp Tyr Gly Tyr
            355                 360                 365
His His Gln Asn Glu Gln Gly Ser Gly Tyr Ala Ala Asp Leu Lys Ser
370                 375                 380
Thr Gln Asn Ala Ile Asp Glu Ile Thr Asn Lys Val Asn Ser Val Ile
385                 390                 395                 400
Glu Lys Met Asn Thr Gln Phe Thr Ala Val Gly Lys Glu Phe Asn His
                405                 410                 415
Leu Glu Lys Arg Ile Glu Asn Leu Asn Lys Lys Val Asp Asp Gly Phe
            420                 425                 430
Leu Asp Ile Trp Thr Tyr Asn Ala Glu Leu Leu Val Leu Leu Glu Asn
            435                 440                 445
Glu Arg Thr Leu Asp Tyr His Asp Ser Asn Val Lys Asn Leu Tyr Glu
450                 455                 460
Lys Val Arg Ser Gln Leu Lys Asn Asn Ala Lys Glu Ile Gly Asn Gly
465                 470                 475                 480
Cys Phe Glu Phe Tyr His Lys Cys Asp Asn Thr Cys Met Glu Ser Val
                485                 490                 495
```

```
Lys Asn Gly Thr Tyr Asp Tyr Pro Lys Tyr Ser Glu Glu Ala Lys Leu
                500                 505                 510

Asn Arg Glu Glu Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Val
        530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 9
<211> LENGTH: 570
<212> TYPE: PRT
<213> ORGANISM: Artificial Sequence
<220> FEATURE:
<223> OTHER INFORMATION: Synthetic Polypeptide

<400> SEQUENCE: 9

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285
```

Val His Asp Cys Asn Thr Thr Cys Gln Thr Pro Lys Gly Ala Ile Asn
290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Gln Arg Glu Arg Arg Lys Lys Arg Gly Leu Phe Gly
                340                 345                 350

Ala Ile Ala Gly Phe Ile Glu Gly Gly Trp Thr Gly Met Val Asp Gly
                355                 360                 365

Trp Tyr Gly Tyr His His Gln Asn Glu Gln Gly Ser Gly Tyr Ala Ala
370                 375                 380

Asp Leu Lys Ser Thr Gln Asn Ala Ile Asp Glu Ile Thr Asn Lys Val
385                 390                 395                 400

Asn Ser Val Ile Glu Lys Met Asn Thr Gln Phe Thr Ala Val Gly Lys
                405                 410                 415

Glu Phe Asn His Leu Glu Lys Arg Ile Glu Asn Leu Asn Lys Lys Val
                420                 425                 430

Asp Asp Gly Phe Leu Asp Ile Trp Thr Tyr Asn Ala Glu Leu Leu Val
                435                 440                 445

Leu Leu Glu Asn Glu Arg Thr Leu Asp Tyr His Asp Ser Asn Val Lys
450                 455                 460

Asn Leu Tyr Glu Lys Val Arg Ser Gln Leu Lys Asn Asn Ala Lys Glu
465                 470                 475                 480

Ile Gly Asn Gly Cys Phe Glu Phe Tyr His Lys Cys Asp Asn Thr Cys
                485                 490                 495

Met Glu Ser Val Lys Asn Gly Thr Tyr Asp Tyr Pro Lys Tyr Ser Glu
                500                 505                 510

Glu Ala Lys Leu Asn Arg Glu Glu Ile Asp Gly Val Lys Leu Glu Ser
                515                 520                 525

Thr Arg Ile Tyr Gln Ile Leu Ala Ile Tyr Ser Thr Val Ala Ser Ser
                530                 535                 540

Leu Val Leu Val Val Ser Leu Gly Ala Ile Ser Phe Trp Met Cys Ser
545                 550                 555                 560

Asn Gly Ser Leu Gln Cys Arg Ile Cys Ile
                565                 570

<210> SEQ ID NO 10
<211> LENGTH: 568
<212> TYPE: PRT
<213> ORGANISM: Artificial Sequence
<220> FEATURE:
<223> OTHER INFORMATION: Synthetic Polypeptide

<400> SEQUENCE: 10

Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Leu Asp Gly Val Lys
        50                  55                  60

Pro Leu Ile Leu Arg Asp Cys Ser Val Ala Gly Trp Leu Leu Gly Asn
65                  70                  75                  80

```
Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Arg Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
    275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
```

```
                        500                 505                 510
Arg Leu Lys Arg Glu Ile Ser Gly Val Lys Leu Glu Ser Ile Gly
            515                 520                 525

Thr Tyr Gln Ile Leu Ser Ile Tyr Ser Thr Val Ala Ser Ser Leu Ala
            530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
            565

<210> SEQ ID NO 11
<211> LENGTH: 498
<212> TYPE: PRT
<213> ORGANISM: Artificial Sequence
<220> FEATURE:
<223> OTHER INFORMATION: Synthetic Polypeptide

<400> SEQUENCE: 11

Met Ala Ser Gln Gly Ala Ala Ser Tyr Glu Gln Met Glu Thr Asp
1               5                   10                  15

Gly Asp Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Lys Met Val Leu Ser Ala Phe Asp Glu Arg Arg Asn Arg Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Met Met Ile Trp His Ser Asn Leu Asn
130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Lys Glu Gly Tyr Ser Leu Val Gly Ile Asp Pro Phe
```

```
                290                 295                 300
Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Ser Ser Phe Ile Arg Gly Thr Lys Val
                340                 345                 350

Ser Pro Arg Gly Lys Leu Ser Thr Arg Gly Val Gln Ile Ala Ser Asn
                355                 360                 365

Glu Asn Met Asp Asn Met Gly Ser Ser Thr Leu Glu Leu Arg Ser Arg
                370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Lys Ser Thr Ile Met Ala Ala Phe Thr Gly Asn
                420                 425                 430

Thr Glu Gly Arg Thr Ser Asp Met Arg Ala Glu Ile Ile Arg Met Met
                435                 440                 445

Glu Ser Ala Lys Pro Glu Glu Val Ser Phe Arg Gly Arg Gly Val Phe
                450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 12
<211> LENGTH: 252
<212> TYPE: PRT
<213> ORGANISM: Artificial Sequence
<220> FEATURE:
<223> OTHER INFORMATION: Synthetic Polypeptide

<400> SEQUENCE: 12

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
                20                  25                  30

Ala Gly Lys Asn Thr Asp Leu Glu Ala Leu Met Glu Trp Leu Lys Thr
                35                  40                  45

Arg Pro Ile Leu Ser Pro Leu Thr Lys Gly Ile Leu Gly Phe Val Phe
        50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
                100                 105                 110

Lys Glu Ile Ala Leu Ser Tyr Ser Ala Gly Ala Leu Ala Ser Cys Met
            115                 120                 125

Gly Leu Ile Tyr Asn Arg Met Gly Ala Val Thr Thr Glu Val Ala Phe
        130                 135                 140

Gly Leu Val Cys Ala Thr Cys Glu Gln Ile Ala Asp Ser Gln His Arg
145                 150                 155                 160
```

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Ile Ala Ser Gln
        195                 200                 205

Ala Arg Gln Met Val Gln Ala Met Arg Thr Ile Gly Thr His Pro Ser
    210                 215                 220

Ser Ser Thr Gly Leu Arg Asp Asp Leu Leu Glu Asn Leu Gln Thr Tyr
225                 230                 235                 240

Gln Lys Arg Met Gly Val Gln Met Gln Arg Phe Lys
                245                 250

<210> SEQ ID NO 13
<211> LENGTH: 1357
<212> TYPE: PRT
<213> ORGANISM: Artificial Sequence
<220> FEATURE:
<223> OTHER INFORMATION: Synthetic Polypeptide

<400> SEQUENCE: 13

Met Ala Ser Gln Gly Ala Ala Ala Ser Tyr Glu Gln Met Glu Thr Asp
1               5                   10                  15

Gly Asp Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Lys Met Val Leu Ser Ala Phe Asp Glu Arg Arg Asn Arg Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Val Leu Tyr Asp
                100                 105                 110

Lys Glu Glu Ile Arg Arg Ile Trp Arg Gln Ala Asn Asn Gly Glu Asp
            115                 120                 125

Ala Thr Ala Gly Leu Thr His Met Met Ile Trp His Ser Asn Leu Asn
        130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
                260                 265                 270

```
Lys Ser Cys Leu Pro Ala Cys Val Tyr Gly Pro Ala Val Ala Ser Gly
        275                 280                 285

Tyr Asp Phe Glu Lys Glu Gly Tyr Ser Leu Val Gly Ile Asp Pro Phe
    290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Ser Ser Phe Ile Arg Gly Thr Lys Val
            340                 345                 350

Ser Pro Arg Gly Lys Leu Ser Thr Arg Gly Val Gln Ile Ala Ser Asn
        355                 360                 365

Glu Asn Met Asp Asn Met Gly Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Lys Ser Thr Ile Met Ala Ala Phe Thr Gly Asn
            420                 425                 430

Thr Glu Gly Arg Thr Ser Asp Met Arg Ala Glu Ile Ile Arg Met Met
        435                 440                 445

Glu Ser Ala Lys Pro Glu Glu Val Ser Phe Arg Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn Gly Gly Gly Gly Ser Gly Gly Gly Met Ser Leu Leu Thr
            500                 505                 510

Glu Val Glu Thr Tyr Val Leu Ser Ile Val Pro Ser Gly Pro Leu Lys
    515                 520                 525

Ala Glu Ile Ala Gln Arg Leu Glu Asp Val Phe Ala Gly Lys Asn Thr
530                 535                 540

Asp Leu Glu Ala Leu Met Glu Trp Leu Lys Thr Arg Pro Ile Leu Ser
545                 550                 555                 560

Pro Leu Thr Lys Gly Ile Leu Gly Phe Val Phe Thr Leu Thr Val Pro
                565                 570                 575

Ser Glu Arg Gly Leu Gln Arg Arg Phe Val Gln Asn Ala Leu Asn
            580                 585                 590

Gly Asn Gly Asp Pro Asn Asn Met Asp Lys Ala Val Lys Leu Tyr Arg
        595                 600                 605

Lys Leu Lys Arg Glu Ile Thr Phe His Gly Ala Lys Glu Ile Ala Leu
    610                 615                 620

Ser Tyr Ser Ala Gly Ala Leu Ala Ser Cys Met Gly Leu Ile Tyr Asn
625                 630                 635                 640

Arg Met Gly Ala Val Thr Thr Glu Val Ala Phe Gly Leu Val Cys Ala
                645                 650                 655

Thr Cys Glu Gln Ile Ala Asp Ser Gln His Arg Ser His Arg Gln Met
            660                 665                 670

Val Thr Thr Thr Asn Pro Leu Ile Arg His Glu Asn Arg Met Val Leu
        675                 680                 685
```

```
Ala Ser Thr Thr Ala Lys Ala Met Glu Gln Met Ala Gly Ser Ser Glu
690                 695                 700
Gln Ala Ala Glu Ala Met Glu Ile Ala Ser Gln Ala Arg Gln Met Val
705                 710                 715                 720
Gln Ala Met Arg Thr Ile Gly Thr His Pro Ser Ser Ser Thr Gly Leu
            725                 730                 735
Arg Asp Asp Leu Leu Glu Asn Leu Gln Thr Tyr Gln Lys Arg Met Gly
            740                 745                 750
Val Gln Met Gln Arg Phe Lys Arg Lys Arg Arg Ala Pro Val Lys Gln
            755                 760                 765
Thr Leu Asn Phe Asp Leu Leu Lys Leu Ala Gly Asp Val Glu Ser Asn
770                 775                 780
Pro Gly Pro Met Lys Ala Ile Leu Val Val Leu Leu Tyr Thr Phe Ala
785                 790                 795                 800
Thr Ala Asn Ala Asp Thr Leu Cys Ile Gly Tyr His Ala Asn Asn Ser
            805                 810                 815
Thr Asp Thr Val Asp Thr Val Leu Glu Lys Asn Val Thr Val Thr His
            820                 825                 830
Ser Val Asn Leu Leu Glu Asp Lys His Asn Gly Lys Leu Cys Lys Leu
835                 840                 845
Arg Gly Val Ala Pro Leu His Leu Gly Lys Cys Asn Ile Ala Gly Trp
850                 855                 860
Ile Leu Gly Asn Pro Glu Cys Glu Ser Leu Ser Thr Ala Ser Ser Trp
865                 870                 875                 880
Ser Tyr Ile Val Glu Thr Ser Ser Ser Asp Asn Gly Thr Cys Tyr Pro
            885                 890                 895
Gly Asp Phe Ile Asp Tyr Glu Glu Leu Arg Glu Gln Leu Ser Ser Val
            900                 905                 910
Ser Ser Phe Glu Arg Phe Glu Ile Phe Pro Lys Thr Ser Ser Trp Pro
            915                 920                 925
Asn His Asp Ser Asn Lys Gly Val Thr Ala Ala Cys Pro His Ala Gly
930                 935                 940
Ala Lys Ser Phe Tyr Lys Asn Leu Ile Trp Leu Val Lys Lys Gly Asn
945                 950                 955                 960
Ser Tyr Pro Lys Leu Ser Lys Ser Tyr Ile Asn Asp Lys Gly Lys Glu
            965                 970                 975
Val Leu Val Leu Trp Gly Ile His His Pro Ser Thr Ser Ala Asp Gln
            980                 985                 990
Gln Ser Leu Tyr Gln Asn Ala Asp Ala Tyr Val Phe Val Gly Ser Ser
    995                 1000                1005
Arg Tyr Ser Lys Lys Phe Lys Pro Glu Ile Ala Ile Arg Pro Lys
    1010                1015                1020
Val Arg Asp Gln Glu Gly Arg Met Asn Tyr Tyr Trp Thr Leu Val
    1025                1030                1035
Glu Pro Gly Asp Lys Ile Thr Phe Glu Ala Thr Gly Asn Leu Val
    1040                1045                1050
Val Pro Arg Tyr Ala Phe Ala Met Glu Arg Asn Ala Gly Ser Gly
    1055                1060                1065
Ile Ile Ile Ser Asp Thr Pro Val His Asp Cys Asn Thr Thr Cys
    1070                1075                1080
Gln Thr Pro Lys Gly Ala Ile Asn Thr Ser Leu Pro Phe Gln Asn
    1085                1090                1095
Ile His Pro Ile Thr Ile Gly Lys Cys Pro Lys Tyr Val Lys Ser
```

```
                  1100                1105                 1110
Thr Lys Leu Arg Leu Ala Thr Gly Leu Arg Asn Ile Pro Gln Arg
    1115                1120                 1125

Glu Arg Arg Arg Lys Lys Arg Gly Leu Phe Gly Ala Ile Ala Gly
    1130                1135                 1140

Phe Ile Glu Gly Gly Trp Thr Gly Met Val Asp Gly Trp Tyr Gly
    1145                1150                 1155

Tyr His His Gln Asn Glu Gln Gly Ser Gly Tyr Ala Ala Asp Leu
    1160                1165                 1170

Lys Ser Thr Gln Asn Ala Ile Asp Glu Ile Thr Asn Lys Val Asn
    1175                1180                 1185

Ser Val Ile Glu Lys Met Asn Thr Gln Phe Thr Ala Val Gly Lys
    1190                1195                 1200

Glu Phe Asn His Leu Glu Lys Arg Ile Glu Asn Leu Asn Lys Lys
    1205                1210                 1215

Val Asp Asp Gly Phe Leu Asp Ile Trp Thr Tyr Asn Ala Glu Leu
    1220                1225                 1230

Leu Val Leu Leu Glu Asn Glu Arg Thr Leu Asp Tyr His Asp Ser
    1235                1240                 1245

Asn Val Lys Asn Leu Tyr Glu Lys Val Arg Ser Gln Leu Lys Asn
    1250                1255                 1260

Asn Ala Lys Glu Ile Gly Asn Gly Cys Phe Glu Phe Tyr His Lys
    1265                1270                 1275

Cys Asp Asn Thr Cys Met Glu Ser Val Lys Asn Gly Thr Tyr Asp
    1280                1285                 1290

Tyr Pro Lys Tyr Ser Glu Glu Ala Lys Leu Asn Arg Glu Glu Ile
    1295                1300                 1305

Asp Gly Val Lys Leu Glu Ser Thr Arg Ile Tyr Gln Ile Leu Ala
    1310                1315                 1320

Ile Tyr Ser Thr Val Ala Ser Ser Leu Val Leu Val Val Ser Leu
    1325                1330                 1335

Gly Ala Ile Ser Phe Trp Met Cys Ser Asn Gly Ser Leu Gln Cys
    1340                1345                 1350

Arg Ile Cys Ile
    1355

<210> SEQ ID NO 14
<211> LENGTH: 4079
<212> TYPE: DNA
<213> ORGANISM: Artificial Sequence
<220> FEATURE:
<223> OTHER INFORMATION: Synthetic Oligonucleotide

<400> SEQUENCE: 14
atggcctctc agggcgcagc cgccagctac gagcagatgg aaaccgacgg cgacagacag      60
aacgccaccg agatcagagc cagcgtgggc aagatgatcg acggcatcgg ccggttctac     120
atccagatgt gcaccgagct gaagctgtcc gactacgagg ccggctgat ccagaacagc      180 ctgaccatcg agaagatggt gctgtccgcc ttcgacgagc ggcggaatag atacctggaa     240
gaacacccca gcgccggcaa ggaccctaag aaaccggcg acccatcta gacgggtg         300 gacggcaagt ggatgcggga gctggtgctg tacgacaaag aggaaatcag aagaatctgg     360
cggcaggcca acaatggcga ggatgccaca gccggcctga cccacatgat gatctggcac     420
agcaacctga cgacaccac ctaccagcgg acaagagccc tcgtgcggac cggcatggac     480
```

```
cccccggatgt gcagcctgat gcagggcagc acactgccta agaagatctgg cgccgctggc    540
gctgccgtga agggcatcgg caccatggtc atggaactga tccggatgat caagcggggc    600
atcaacgacc ggaacttttg agagggcgag aacggcagaa agaccagatc cgcctacgag    660
cggatgtgca acatcctgaa gggcaagttc cagacagccg cccagagggc aatgatggac    720
caggtccggg agagcagaaa ccccggcaac gccgagatcg aggacctgat cttcctggcc    780
agaagcgccc tgatcctgag aggcagcgtg gcccacaaga gctgcctgcc cgcctgtgtg    840
tatggaccag ccgtggctag cggctacgac ttcgagaaag agggctacag cctcgtcggc    900
atcgaccct tcaagctgct gcagaacagc caggtgtaca gcctgatccg gcccaacgag    960
aaccctgccc acaagtccca gctcgtgtgg atggcctgcc acagcgccgc cttcgaggat   1020
ctgcggctgt ccagcttcat ccggggcacc aaggtgtccc ccagaggcaa gctgtctacc   1080
agaggcgtgc agatcgccag caacgagaac atggacaaca tgggcagcag caccctggaa   1140
ctgcggagcc ggtactgggc catcagaacc agaagcggcg gcaacaccaa ccagcagaga   1200
gccagcgccg acagatcag cgtgcagccc accttctccg tgcagcggaa tctgcccttc   1260
gagaagtcca ccatcatggc cgccttcacc ggcaataccg agggccggac cagcgacatg   1320
cgggccgaga tcatcagaat gatggaaagc gccaagcccg aggaagtgtc cttccggggc   1380
agaggcgtgt cgagctgtc cgatgagaag gccaccaacc ccatcgtgcc cagcttcgac   1440
atgagcaacg agggcagcta cttcttcggc gacaacgccg aggaatacga caatggcggc   1500
ggaggatctg ggggcggagg catgagtctg ctgactgaag tcgagacata cgtgctgtcc   1560
atcgtgccta gcgccctct gaaggccgag atcgcccagc ggctggaaga tgtgttcgcc   1620
ggcaagaaca ccgacctgga agccctgatg gaatggctga aaacccggcc catcctgagc   1680
cctctgacca agggcatcct gggcttcgtg ttcaccctga ccgtgccctc tgagcggggc   1740
ctgcagcgga gaagattcgt gcagaacgcc ctgaacggca acggcgaccc caacaacatg   1800
gataaggccc tgaagctgta ccggaagctg aagcgggaga tcaccttcca cggcgccaaa   1860
gagatcgccc tgtcctactc tgccggcgct ctggccagct gcatgggcct catctacaac   1920
cggatgggcc ccgtgaccac agaggtggcc ttcggcctcg tgtgtgccac ttgcgagcag   1980
atcgccgaca gccagcaccg gtcccacaga cagatggtca ccaccaccaa ccctctgatc   2040
cggcacgaga accggatggt gctcgcctct accaccgcca aggccatgga acagatggcc   2100
ggcagcagcg aacaggccgc cgaagccatg gaaatcgcca gccaggccag gcagatggtc   2160
caggccatgc ggaccatcgg cacccacccct agcagctcca ccggcctgcg ggacgatctg   2220
ctggaaaatc tgcagaccta tcagaaacgg atgggggtgc agatgcagcg gttcaagagg   2280
aaaagacgtg cgccagtaaa gcagacatta aactttgatt tgctgaaact tgcaggtgat   2340
gtagagtcaa atccaggtcc aatgaaggcc atcctggtgg tgctgctgta caccttcgcc   2400
accgccaacg ccgacacccct gtgcattggg tatcatgcca caactccac cgacaccgtg   2460
gataccgtgc tggaaaagaa tgtgacagtc acccacagcg tgaacctgct ggaagataag   2520
cacaatggga agctgtgcaa gctgcggggc gtggccctc tgcacctggg caagtgcaat   2580
atcgccggct ggatcctggg aaatcctgag tgcgagagcc tgagcaccgc cagcagctgg   2640
tcttacatcg tcgagacaag cagcagcgac aacggcacct gttaccccgg cgatttcatt   2700
gattatgagg aactgcgcga gcagctgtcc tccgtgtcca gcttcgagag attcgagatc   2760
ttccctaaga ccagctcctg gcccaaccac gactccaaca agggcgtgac cgccgcctgt   2820
cctcacgctg gcgccaagag cttctacaag aacctgatct ggctcgtcaa gaagggcaac   2880
```

```
tcctacccca agctgagcaa gagctacatc aacgacaagg gcaaagaggt cctcgtcctc    2940
tggggaattc atcaccctag caccagcgcc gaccagcaga gcctgtatca gaacgccgac    3000
gcctacgtgt tcgtgggcag cagccggtac agcaagaagt tcaagcctga gatcgccatc    3060
agacccaaag tgcgggacca ggaaggccgg atgaactact actggaccct ggtggaaccc    3120
ggcgacaaga tcaccttcga ggccaccggc aatctggtgg tgcccagata cgccttcgcc    3180
atggaacgga acgccggcag cggcatcatc atcagcgaca cccccgtgca cgactgcaat    3240
accacctgtc agacacctaa gggggccatc aacacctccc tgccttttcca gaatatccac    3300 cctatcacca tcgggaagtg tcctaaatat gtcaagagca ccaagctgcg gctggccaca    3360
ggactgagaa acatccccca gagagagcgg agacggaaga agcggggcct gttcggcgct    3420
atcgctggat tcattgaggg cggatggacc ggcatggtcg atgggtggta tgggtatcat    3480
caccagaatg agcagggctc cggatatgcc gccgatctga agtccactca gaacgccatc    3540
gacgagatca caaacaaagt caactccgtg atcgagaaaa tgaatactca gttcaccgcc    3600
gtcgggaaag agttcaatca cctggagaag cgcatcgaga atctcaacaa aaaggtcgac    3660
gacggcttcc tcgacatctg gacatacaat gctgaactgc tcgtgctgct ggagaatgag    3720
agaaccctgg attaccacga ttccaacgtc aagaatctct atgagaaagt gcggagccag    3780
ctgaagaaca atgccaaaga aatcgggaat ggctgttttg agttttatca caagtgtgat    3840
aacacctgta tggaatccgt gaagaatggc acatacgatt accctaagta ctccgaagag    3900
gccaagctga acagaagaa gatcgacggg gtcaagctgg aaagcacccg gatctatcag    3960
atcctggcca tctattctac cgtggcctcc tccctggtgc tggtggtgtc cctgggcgct    4020
atcagcttct ggatgtgctc caatggctcc ctgcagtgca gaatctgtat ttgataatt    4079
```

<210> SEQ ID NO 15
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 15

Pro Gln Arg Glu Arg Arg Arg Lys Lys Arg
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 16

Pro Gln Arg Glu Ser Arg Arg Lys Lys Arg
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 17

Pro Gln Gly Glu Arg Arg Arg Lys Lys Arg
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 18

Pro Leu Arg Glu Arg Arg Arg Lys Arg
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 19

Pro Gln Arg Glu Thr Arg
1               5

<210> SEQ ID NO 20
<211> LENGTH: 566
<212> TYPE: PRT
<213> ORGANISM: Artificial Sequence
<220> FEATURE:
<223> OTHER INFORMATION: Synthetic Polypeptide

<400> SEQUENCE: 20

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Lys Arg Arg Ser Asn
145                 150                 155                 160

Lys Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Ser Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asp Val Pro Ser Arg Ile Ser Ile Tyr Trp Thr Ile Val Lys Pro Gly
            245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
            325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
            405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
            485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540

Val Ala Leu Leu Gly Phe Ile Met Trp Ala Cys Gln Lys Gly Asn Ile
545                 550                 555                 560

Arg Cys Asn Ile Cys Ile
            565

<210> SEQ ID NO 21
<211> LENGTH: 566
<212> TYPE: PRT
<213> ORGANISM: Artificial Sequence
<220> FEATURE:
<223> OTHER INFORMATION: Synthetic Polypeptide

<400> SEQUENCE: 21

Met Lys Thr Ile Ile Ala Leu Ser Tyr Ile Leu Cys Leu Val Phe Ala
1               5                   10                  15

-continued

Gln Lys Leu Pro Gly Asn Asp Asn Ser Thr Ala Thr Leu Cys Leu Gly
           20                  25                  30

His His Ala Val Pro Asn Gly Thr Ile Val Lys Thr Ile Thr Asn Asp
       35                  40                  45

Gln Ile Glu Val Thr Asn Ala Thr Glu Leu Val Gln Ser Ser Ser Thr
 50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
               100                 105                 110

Cys Tyr Pro Tyr Asp Val Pro Asp Tyr Ala Ser Leu Arg Ser Leu Val
           115                 120                 125

Ala Ser Ser Gly Thr Leu Glu Phe Asn Asn Glu Ser Phe Asn Trp Thr
130                 135                 140

Gly Val Thr Gln Asn Gly Thr Ser Ser Ala Cys Lys Arg Arg Ser Asn
145                 150                 155                 160

Lys Ser Phe Phe Ser Arg Leu Asn Trp Leu Thr His Leu Lys Phe Lys
               165                 170                 175

Tyr Pro Ala Leu Asn Val Thr Met Pro Asn Asn Glu Lys Phe Asp Lys
           180                 185                 190

Leu Tyr Ile Trp Gly Val His His Pro Gly Thr Asp Asn Asp Gln Ile
               195                 200                 205

Ser Leu Tyr Ala Gln Ala Ser Gly Arg Ile Thr Val Ser Thr Lys Arg
210                 215                 220

Ser Gln Gln Thr Val Ile Pro Asn Ile Gly Ser Arg Pro Arg Val Arg
225                 230                 235                 240

Asp Val Pro Ser Arg Ile Ser Ile Tyr Trp Thr Ile Val Lys Pro Gly
               245                 250                 255

Asp Ile Leu Leu Ile Asn Ser Thr Gly Asn Leu Ile Ala Pro Arg Gly
               260                 265                 270

Tyr Phe Lys Ile Arg Ser Gly Lys Ser Ser Ile Met Arg Ser Asp Ala
   275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
               325                 330                 335

Arg Asn Val Ile Pro Gln Arg Glu Arg Arg Arg Lys Lys Arg Ile Ala
               340                 345                 350

Gly Phe Ile Glu Asn Gly Trp Glu Gly Met Val Asp Gly Trp Tyr Gly
       355                 360                 365

Phe Arg His Gln Asn Ser Glu Gly Thr Gly Gln Ala Ala Asp Leu Lys
       370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                   405                 410                 415

Glu Val Glu Gly Arg Ile Gln Asp Leu Glu Lys Tyr Val Glu Asp Thr
           420                 425                 430

Lys Ile Asp Leu Trp Ser Tyr Asn Ala Glu Leu Leu Val Ala Leu Glu

```
                435                 440                 445
Asn Gln His Thr Ile Asp Leu Thr Asp Ser Glu Met Asn Lys Leu Phe
            450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
            530                 535                 540

Val Ala Leu Leu Gly Phe Ile Met Trp Ala Cys Gln Lys Gly Asn Ile
545                 550                 555                 560

Arg Cys Asn Ile Cys Ile
                565
```